US009206479B2

(12) United States Patent
Maquat et al.

(10) Patent No.: US 9,206,479 B2
(45) Date of Patent: Dec. 8, 2015

(54) METHODS AND COMPOSITIONS RELATED TO STAUFEN 1 BINDING SITES FORMED BY DUPLEXING ALU ELEMENTS

(75) Inventors: Lynne E. Maquat, Rochester, NY (US); Chenguang Gong, Rochester, NY (US)

(73) Assignee: University of Rochester, Rochester, NY (US)

( * ) Notice: Subject to any disclaimer, the term of this patent is extended or adjusted under 35 U.S.C. 154(b) by 105 days.

(21) Appl. No.: 13/984,709

(22) PCT Filed: Feb. 9, 2012

(86) PCT No.: PCT/US2012/024534
§ 371 (c)(1),
(2), (4) Date: Aug. 9, 2013

(87) PCT Pub. No.: WO2012/109476
PCT Pub. Date: Aug. 16, 2012

(65) Prior Publication Data
US 2013/0317087 A1    Nov. 28, 2013

Related U.S. Application Data

(60) Provisional application No. 61/440,967, filed on Feb. 9, 2011.

(51) Int. Cl.
*C12Q 1/68* (2006.01)
*A61K 48/00* (2006.01)
*C07H 21/02* (2006.01)
*C07K 14/47* (2006.01)

(52) U.S. Cl.
CPC .............. *C12Q 1/6883* (2013.01); *C07K 14/47* (2013.01); *C12Q 1/6881* (2013.01); *C12Q 2600/178* (2013.01)

(58) Field of Classification Search
CPC .............................. C12N 15/113; A61K 48/00
See application file for complete search history.

(56) References Cited

FOREIGN PATENT DOCUMENTS

WO        2006039399        4/2006

OTHER PUBLICATIONS

Miki et al., The role of mammalian Staufen on mRNA traffic: a view from its nucleocytoplasmic shuttling function, Cell Struct.Funct., vol. 30, 2005, pp. 51-56.
Mohr et al., The RNA-binding protein Tsunagi interacts with Mago Nashi to establish polarity and localize oskar mRNA during Drosophila oogenesis, Genes Dev., vol. 15, 2001, pp. 2886-2899.
Monshausen et al., Two rat brain staufen isoforms differentially bind RNA, J. Neurochem., vol. 76, 2001, pp. 155-165.
Moriarty et al., Selenium deficiency reduces the abundance of mRNA for Se-dependent glutathione peroxidase 1 by a UGA-dependent mechanism likely to be nonsense codon-mediated decay of cytoplasmic mRNA, Mol. Cell. Biol., vol. 18, 1998, pp. 2932-2939.
Mouland et al., The double-stranded RNA-binding protein Staufen is incorporated in human immunodeficiency virus type 1: evidence for a role in genomic RNA encapsidation, J. Virol., vol. 74, 2000, pp. 5441-5451.
Nagy et al., A rule for termination-codon position within intron-containing genes: when nonsense affects RNA abundance, Trends Biochem. Sci., vol. 23, 1998, pp. 198-199.
Ohashi et al., Identification of mRNA/protein (mRNP) complexes containing Puralpha, mStaufen, fragile X protein, and myosin Va and their association with rough endoplasmic reticulum equipped with a kinesin motor, J. Biol. Chem., vol. 277, 2002, pp. 37804-37810.
Otwinowski et al., Processing of X-ray Diffraction Data Collected in Oscillation Mode, Method.Enzymol., vol. 276, 1997, pp. 307-326.
Pal et al., Evidence that phosphorylation of human Upf1 protein varies with intracellular location and is mediated by a wortmannin-sensitive and rapamycin-sensitive PI 3-kinase-related kinase signaling pathway, RNA, vol. 7, 2001, pp. 5-15.
Palacios et al., an eIF4AIII-containing complex required for mRNA localization and nonsense-mediated mRNA decay, Nature, vol. 427, 2004, pp. 753-757.
Pang et al., RNAdb 2.0—an expanded database of mammalian non-coding RNAs, Nucleic Acids Res., vol. 35, 2007, pp. D178-182.
Papworth et al., Site directed mutagenesis in one day with >80% efficiency, Strategies, vol. 3, 1996, pp. 3-4.
Parker et al., dsRNA binding properties of RDE-4 and TRBP reflect their distinct roles in RNAi, J. Mol. Biol., vol. 384, 2008, pp. 967-979.
International Application No. PCT/US2012/024534, International Preliminary Report on Patentability mailed on Aug. 22, 2013, 8 pages.
International Application No. PCT/US2012/024534, International Search Report and Written Opinion mailed on Jul. 27, 2012, 11 pages.
Peng et al., Functional characterization of a non-AUUUA AU-rich element from the c-jun proto-oncogene mRNA: evidence for a novel class of AU-rich elements, Mol. Cell. Biol., vol. 16, 1996, pp. 1490-1499.
Philo et al., A method for directly fitting the time derivative of sedimentation velocity data and an alternative algorithm for calculating sedimentation coefficient distribution functions, Anal Biochem, vol. 279, 2000, pp. 151-163.
Philo et al., Improved methods for fitting sedimentation coefficient distributions derived by time-derivative techniques, Anal Biochem, vol. 354, 2006, pp. 238-246.
Piecyk et al., TIA-1 is a translational silencer that selectively regulates the expression of TNF-alpha, EMBO J., vol. 19, 2000, pp. 4154-4163.

(Continued)

*Primary Examiner* — Amy Bowman
(74) *Attorney, Agent, or Firm* — Kilpatrick Townsend & Stockton, LLP

(57) ABSTRACT

Disclosed are compositions and methods for identifying binding sites of targets of Stau1-mediated mRNA decay; methods and compositions for treating subjects with conditions resulting from Stau1-mediated mRNA decay, and method of screening for therapeutic agents. Also disclosed is the new pathway as a means for cells to down-regulate the expression of Stau1-binding mRNAs.

4 Claims, 39 Drawing Sheets

(56) References Cited

OTHER PUBLICATIONS

Figure 1:
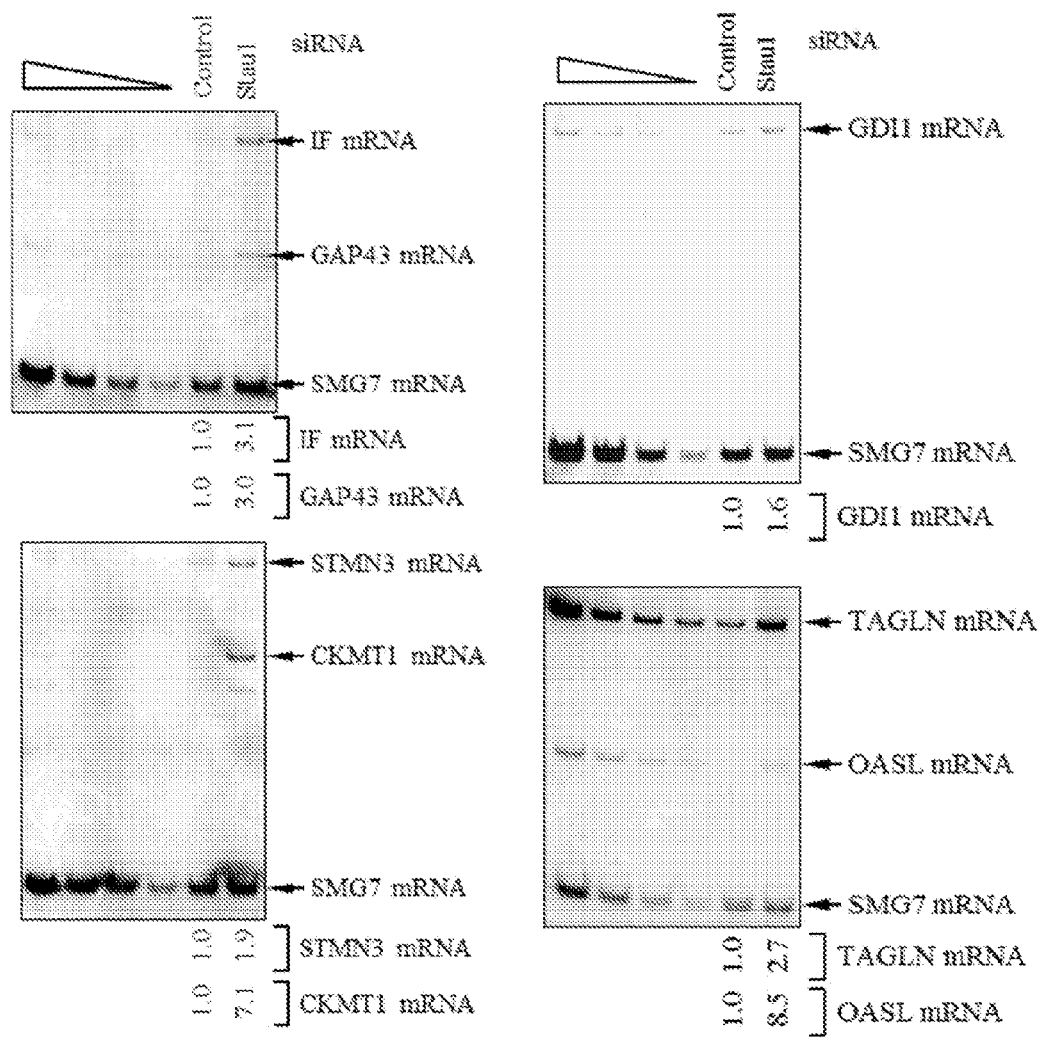

Providence et al., SERPINE1 (PAI-1) is deposited into keratinocyte migration "trails" and required for optimal monolayer wound repair, Arch. Dermatol. Res., vol. 300, 2008, pp. 303-310.
Ramos et al., RNA recognition by a Staufen double-stranded RNA-binding domain, EMBO J., vol. 19, 2000, pp. 997-1009.
Roy et al., I-TASSEr: a unified platform for automated protein structure and function prediction, Nat. Protoc., vol. 5, 2010, pp. 725-738.
Ryter et al., Molecular basis of double-stranded RNA-protein interactions: structure of a dsRNA-binding domain complexed with dsRNA, EMBO J., vol. 17, 1998, pp. 7505-7513.
Schuck, Size-distribution analysis of macromolecules by sedimentation velocity ultracentrifugation and lamm equation modeling, Biophys J, vol. 78, 2000, pp. 1606-1619.
Schuldt et al., Miranda mediates asymmetric protein and RNA localization in the developing nervous system, Genes Dev., vol. 12, 1998, pp. 1847-1857.
Serin et al., Identification and characterization of human orthologues to Saccharomyces cerevisiae Upf2 protein and Upf3 protein (Caenorhabditis elegans SMG-4), Mol. Cell. Biol., vol. 21, 2001, pp. 209-223.
Shcherbo et al., Bright far-red fluorescent protein for whole-body imaging, Nat Methods, vol. 4, 2007, pp. 741-746.
Shen et al., Miranda as a multidomain adapter linking apically localized Inscuteable and basally localized Staufen and Prospero during asymmetric cell division in Drosophila, Genes Dev., vol. 12, 1998, pp. 1837-1846.
Shetty et al., Posttranscriptional regulation of plasminogen activator inhibitor-1 in human lung carcinoma cells in vitro, Am. J. Physiol. Lung Cell Mol. Physiol., vol. 278, 2000, pp. L148-156.
Shibuya et al., eIF4AIII binds spliced mRNA in the exon junction complex and is essential for nonsense-mediated decay, Nat. Struct. Mol. Biol., vol. 11, 2004, pp. 346-351.
Siebel et al., Regulation of tissue-specific P-element pre-mRNA splicing requires the RNA-binding protein PSI, Genes Dev, vol. 8, 1994, pp. 1713-1725.
Slabinski et al., XtalPred: a web server for prediction of protein crystallizability, Bioinformatics, vol. 23, 2007, pp. 3403-3405.
St Johnston et al., A conserved double-stranded RNA-binding domain, Proc. Natl. Acad. Sci., vol. 89, 1992, pp. 10979-10983.
St Johnston et al., Staufen, a gene required to localize maternal RNAs in the Drosophila egg, Cell, vol. 66, 1991, pp. 51-63.
St Johnston, The intracellular localization of messenger RNAs, Cell, vol. 81, 1995, pp. 161-170.
Stafford et al., Analysis of heterologous interacting systems by sedimentation velocity: curve fitting algorithms for estimation of sedimentation coefficients, equilibrium and kinetic constants, BiophysChem, vol. 108, 2004, pp. 231-243.
Stefl et al., The solution structure of the ADAR2 dsRBM-RNA complex reveals a sequence-specific readout of the minor groove, Cell, vol. 143, 2010, pp. 225-237.
Sun et al., A mutated human homologue to yeast Upf1 protein has a dominant-negative effect on the decay of nonsense-containing mRNAs in mammalian cells, Proc. Natl. Acad. Sci., vol. 95, 1998, pp. 10009-10014.
Tange et al., The ever-increasing complexities of the exon junction complex, Curr. Opin. Cell Biol., vol. 16, 2004, pp, 279-284.
Terwilliger et al., Iterative model building, structure refinement and density modification with the PHENIX AutoBuild wizard. ActaCrystallogr, D. Biol.Crystallogr., vol. 64, 2008, pp. 61-69.
Terwilliger et al., Maximum-likelihood density modification. ActaCrystallogr. D. Biol.Crystallogr., vol. 56, 2000, pp. 965-972.
Thompson et al., CLUSTAL W: improving the sensitivity of progressive multiple sequence alignment through sequence weighting, position-specific gap penalties and weight matrix choice, Nucleic Acids Res., vol. 22, 1994, pp. 4673-4680.
Tian et al., The double-stranded-RNA-binding motif: interference and much more, Nat. Rev. Mol. Cell. Biol., vol. 5, 2004, pp. 1013-1023.

Valente et al., RNA binding-independent dimerization of adenosine deaminases acting on RNA and dominant negative effects of non-functional subunits on dimer functions, J BiolChem, vol. 282, 2007, pp. 16054-16061.
Van Eeden et al., Barentsz is essential for the posterior localization of oskar mRNA and colocalizes with it to the posterior pole, J. Cell. Biol., vol. 154, 2001, pp. 511-523.
Village et al., The composition of Staufen-containing RNA granules from human cells indicates their role in the regulated transport and translation of messenger RNAs, Nucleic Acids Res., vol. 32, 2004, pp. 2411-2420.
Walters et al., InvAluable junk: the cellular impact and function of Alu and B2 RNAs, IUBMB Life 61, 2009, pp. 831-837.
Wang et al., The hDcp2 protein is a mammalian mRNA decapping enzyme, Proc. Natl. Acad. Sci., vol. 99, 2002, pp. 12663-12668.
Wickham et al., Mammalian staufen is a double-stranded-RNA- and tubulin-binding protein which localizes to the rough endoplasmic reticulum, Mol. Cell. Biol., vol. 19, 1999, pp. 2220-2230.
Wilusz et al., Curbing the nonsense: the activation and regulation of mRNA surveillance, Genes Dev., vol. 15, 2001, pp. 2781-2785.
Wilusz et al., Long noncoding RNAs: functional surprises from the RNA world, Genes Dev., vol. 23, 2009, pp. 1494-1504.
Wodicka et al., Genome-wide expression monitoring in Saccharomyces cerevisiae, Nat. Biotechnol., vol. 15, 1997, pp. 1359-1367.
Xia et al., Thermodynamic parameters for an expanded nearest-neighbor model for formation of RNA duplexes with Watson-Crick base pairs, Biochemistry, vol. 37, 1998, pp. 14719-14735.
Yamashita et al., Structures of the first and second double-stranded RNA-binding domains of human TAR RNA-binding protein, Protein Sci., vol. 20, pp. 118-130.
Yang et al., Structure of Arabidopsis HYPONASTIC LEAVES1 and its molecular implications for miRNA processing, Structure, vol. 18, 2010, pp. 594-605.
Yulug et al., The frequency and position of Alu repeats in cDNAs, as determined by database searching, Genomics, vol. 27, 1995, pp. 544-548.
Zhang et al., Intron function in the nonsense-mediated decay of beta-globin mRNA: indications that pre-mRNA splicing in the nucleus can influence mRNA translation in the cytoplasm, RNA, vol. 4, 1998, pp. 801-815.
Zhang et al., RCP is a human breast cancer-promoting gene with Ras-activating function, J. Clin. Invest., vol. 119, 2009, pp. 2171-2183.
Zuker, Mfold web server for nucleic acid folding and hybridization prediction, Nucleic Acids Res., vol. 31, 2003, pp. 3406-3415.
CCP4, The CCP4 suite: programs for protein crystallography, ActaCrystallogr. D. Biol. Crystallogr., vol. 50, 1994, pp. 760-763.
Adams et al., PHENIX: a comprehensive Python-based system for macromolecular structure solution, ActaCrystallogr. D. Biol.Crystallogr., vol. 66, 2010, pp. 213-221.
Allison et al., Two distinct Staufen isoforms in Xenopus are vegetally localized during oogenesis, RNA, vol. 10, 2004, pp. 1751-1763.
Amoutzias et al., Choose your partners: dimerization in eukaryotic transcription factors, Trends BiochemSci, vol. 33, 2008, pp. 220-229.
Ashley et al., FMR1 protein: conserved RNP family domains and selective RNA binding, Science, vol. 262, 1993, pp. 563-566.
Bachand et al., Human telomerase RNA-protein interactions, Nucleic Acids Res., vol. 29, 2001, pp. 3385-3393.
Barraud et al., An extended dsRBD with a novel zinc-binding motif mediates nuclear retention of fission yeast Dicer, EMBO J., vol. 30, 2011, pp. 4223-4235.
Bartel, MicroRNAs: target recognition and regulatory functions, Cell, vol. 136, 2009, pp. 215-233.
Batzer et al., Alu repeats and human genomic diversity, Nat. Rev. Genet., vol. 3, 2002, pp. 370-379.
Belgrader et al., Nonsense but not missense mutations can decrease the abundance of nuclear mRNA for the mouse major urinary protein, while both types of mutations can facilitate exon skipping, Mol. Cell. Biol., vol. 14, 1994, pp. 6326-6336.
Binder et al., The plasminogen activator inhibitor "paradox" in cancer, Immunol. Lett., vol. 118, 2008, pp. 116-124.

(56) References Cited

OTHER PUBLICATIONS

Bond, TopDraw: a sketchpad for protein structure topology cartoons, Bioinformatics, vol. 19, 2003, pp. 311-312.
Bono et al., Molecular insights into the interaction of PYM with the Mago-Y14 core of the exon junction complex, EMBO Rep., vol. 5, 2004, pp. 304-310.
Broadus et al., Staufen-dependent localization of prospero mRNA contributes to neuroblast daughter-cell fate, Nature, vol. 391, 1998, pp. 792-795.
Campbell et al., A monomeric red fluorescent protein, PNAS, vol. 99, Jun. 11, 2002, pp. 7877-7882.
Chan et al., eIF4A3 is a novel component of the exon junction complex, RNA, vol. 10, 2004, pp. 200-209.
Chen et al., Alu element-mediated gene silencing, EMBO J., vol. 27, 2008, pp. 1694-1705.
Chen et al., AU-rich elements: characterization and importance in mRNA degradation, Trends Biochem. Sci., vol. 20, 1995, pp. 465-470.
Chiu et al., High-molecular-mass APOBEC3G complexes restrict Alu retrotransposition, Proc. Natl. Acad. Sci., vol. 103, No. 4, Oct. 17, 2006, pp. 15588-15593.
Chiu et al., The pioneer translation initiation complex is functionally distinct from but structurally overlaps with the steady-state translation initiation complex, Genes Dev., vol. 18, 2004, pp. 745-754.
Cho et al., Requirement of dimerization for RNA editing activity of adenosine deaminases acting on RNA, J. BiolChem, vol. 278, 2003, pp. 17093-17102.
Cole, Activation of PKR: an open and shut case? Trends BiochemSci, vol. 32, 2007, pp. 57-62.
Coller et al., mRNA stabilization by poly (A) binding protein is independent of poly(A) and requires translation, Genes Dev., vol. 12, 1998, pp. 3226-3235.
Cordaux et al., The impact of retrotransposons on human genome evolution, Nat. Rev. Genet., vol. 10, 2009, pp. 691-703.
Cowtan, Modified phased translation functions and their application to molecular-fragment location, ActaCrystallogr D. Biol.Crystallogr., vol. 54, 1998, pp. 750-756.
Curatola et al., Rapid degradation of Au-rich element (ARE) mRNAs is activated by ribosome transit and blocked by secondary structure at any position 5' to the Are, Mol. Cell. Biol., vol. 15, 1995, pp. 6331-6340.
Donaldson et al., Regulators and effectors of the ARF GTPases, Curr. Opin. Cell Biol., vol. 12, 2000, pp. 475-482.
Duchaine et al., A novel murine Staufen isoform modulates the RNA content of Staufen complexes, Mol. Cell. Biol., vol. 20, 2000, pp. 5592-5601.
Duchaine et al., Staufen2 isoforms localize to the somatodendritic domain of neurons and interact with different organelles, J. Cell Sci., vol. 115, 2002, pp. 3285-3295.
Emsley et al., Features and development of Coot.ActaCrystallogr, D. Biol.Crystallogr., vol. 66, 2010, pp. 486-501.
Engstrom et al., Complex Loci in human and mouse genomes, PLoS Genet., vol. 2, e47, 2006.
Ephrussi et al., Oskar organizes the germ plasm and directs localization of the posterior determinant nanos, Cell, vol. 66, 1991, pp. 37-50.
Ferraiuolo et al., A nuclear translation-like factor eIF4AIII is recruited to the mRNA during splicing and functions in nonsense-mediated decay, Proc. Natl. Acad. Sci., vol. 101, 2004, pp. 4118-4123.
Ferrandon et al., Staufen protein associates with the 3'UTR of bicoid mRNA to form particles that move in a microtubule-dependent manner, Cell, vol. 79, 1994, pp. 1221-1232.
Forch, The splicing regulator TIA-1 interacts with U1-C to promote U1 snRNP recruitment to 5' splice sites, EMBO J., vol. 21, 2002, pp. 6882-6892.
Frischmeyer et al., Nonsense-mediated mRNA decay in health and disease, Hum. Mol. Genet., vol. 8, 1999, pp. 1893-1900.
Fuerstenberg et al., Identification of Miranda protein domains regulating asymmetric cortical localization, cargo binding, and cortical release, Mol. Cell. Neurosci., vol. 12, 1998, pp. 325-339.
Furic et al., A genome-wide approach identifies distinct but overlapping subsets of cellular mRNAs associated with Staufen1- and Staufen2-containing ribonucleoprotein complexes, RNA, vol. 14, 2008, pp. 324-335.
Gan et al., A stepwise model for double-stranded RNA processing by ribonuclease III, Mol. Microbiol., vol. 67, 2008, pp. 143-154.
Gan et al., Intermediate states of ribonuclease III in complex with double-stranded RNA, Structure, vol. 13, 2005, pp. 1435-1442.
Gatfield et al., Nonsense-mediated mRNA decay in Drosophila: at the intersection of the yeast and mammalian pathways, EMBO J., vol. 22, 2003, pp. 3960-3970.
Gehring et al., Y14 and hUpf3b form an NMD-activating complex, Mol. Cell, vol. 11, 2003, pp. 939-949.
Gibson et al., Detection of dsRNA-binding domains in RNA helicase A and Drosophila maleless: implications for monomeric RNA helicases, Nucleic Acids Res., vol. 22, 1994, pp. 2552-2556.
Gong et al., lncRNAs transactivate Staufen1-mediated mRNA decay by duplexing with 3'UTRs via Alu elements, Nature, vol. 470, Feb. 10, 2011, pp. 284-288.
Gong et al., SMD and NMD are competitive pathways that contribute to myogenesis: effects on PAX3 and myogenin mRNAs, Genes Dev., vol. 23, 2009, pp. 54-66.
Goodrich et al., Hrb27C, Sqd and Otu cooperatively regulate gurken RNA localization and mediate nurse cell chromosome dispersion in Drosophila oogenesis, Development, vol. 131, 2004, pp. 1949-1958.
Gorlach et al., the mRNA poly(A)-binding protein: localization, abundance, and RNA-binding specificity, Exp. Cell Res., vol. 211, 1994, pp. 400-407.
Grentzmann et al., A dual-luciferase reporter system for studying recoding signals, RNA, vol. 4, 1998, pp. 479-486.
Guruprasad et al., Correlation between stability of a protein and its dipeptide composition: a novel approach for predicting in vivo stability of a protein from its primary sequence, Protein Eng., vol. 4, 1990, pp. 155-161.
Haase et al., TRBP, a regulator of cellular PKR and HIV-1 virus expression, interacts with Dicer and functions in RNA silencing, EMBO Rep., vol. 6, 2005, pp. 961-967.
Hachet et al., Drosophila Y14 shuttles to the posterior of the oocyte and is required for oskar mRNA transport, Curr. Biol., vol. 11, 2001, pp. 1666-1674.
Hachet et al., Splicing of oskar RNA in the nucleus is coupled to its cytoplasmic localization, Nature, vol. 428, 2004, pp. 959-963.
Hall, BioEdit: a user-friendly biological sequence alignment editor and analysis program for Windows 95/98/NT, Nucl. Acids.Symp. Ser., vol. 41, 1999, pp. 95-98.
Hammond et al., Mutations in the hrp48 gene, which encodes a Drosophila heterogeneous nuclear ribonucleoprotein particle protein, cause lethality and developmental defects and affect P-element third-intron splicing in vivo, Mol. Cell. Biol., vol. 17, 1997, pp. 7260-7267.
Hasler et al., Alu elements as regulators of gene expression, Nucleic Acids Res., vol. 34, 2006, pp. 5491-5497.
Hentze et al., A perfect message: RNA surveillance and nonsense-mediated decay, Cell, vol. 96, 1999, pp. 307-310.
Hillman et al., An unappreciated role for RNA surveillance, Genome Biol., vol. 5:R8, 2004.
Hitti et al., Oligomerization activity of a double-stranded RNA-binding domain, FEBS Lett, vol. 574, 2004, pp. 25-30.
Holm et al., Dali server: conservation mapping in 3D, Nucleic Acids Res., vol. 38, 2010, pp. W545-549.
Hung et al., Long noncoding RNA in genome regulation Prospects and mechanisms, RNA Biology, vol. 7, No. 5, Sep. Oct. 2010, pp. 582-585.
Inoue et al., Molecular mechanism for distinct neurological phenotypes conveyed by allelic truncating mutations, Nat. Genet., vol. 36, 2004, pp. 361-369.
Ishigaki et al., Evidence for a pioneer round of mRNA translation: mRNAs subject to nonsense-mediated decay in mammalian cells are bound by CBP80 and CBP20, Cell, vol. 106, 2001, pp. 607-617.
Izaurralde et al., A nuclear cap binding protein complex involved in pre-mRNA splicing, Cell, vol. 78, 1994, pp. 657-668.
Kapranov et al., Genome-wide transcription and the implications for genomic organization, Nat. Rev. Genet., vol. 8, 2007, pp. 413-423.

(56) References Cited

OTHER PUBLICATIONS

Kataoka et al., Pre-mRNA splicing imprints mRNA in the nucleus with a novel RNA-binding protein that persists in the cytoplasm, Mol. Cell, vol. 6, 2000, pp. 673-682.

Kiebler et al., The mammalian staufen protein localizes to the somatodendritic domain of cultured hippocampal neurons: implications for its involvement in mRNA transport, J. Neurosci., vol. 19, 1999, pp. 288-297.

Kim et al., HuR recruits let-7/RISC to repress c-Myc expression, Genes Dev., vol. 23, 2009, pp. 1743-1748.

Kim et al., Long-range RNA-RNA interaction between the 5' nontranslated region and the core-coding sequences of hepatitis C virus modulates the IRES-dependent translation, RNA, vol. 9, 2003, pp. 599-606.

Kim et al., Mammalian Staufenl recruits Upf1 to specific mRNA 3'UTRs so as to elicit mRNA decay, Cell, vol. 120, 2005, pp. 195-208.

Kim et al., Role of the nonsense-mediated decay factor hUpf3 in the splicing-dependent exon-exon junction complex, Science, vol. 293, 2001, pp. 1832-1836.

Kim et al., Staufen1 regulates diverse classes of mammalian transcripts, EMBO J., vol. 26, 2007, pp. 2670-2681.

Kim-Ha et al., oskar mRNA is localized to the posterior pole of the Drosophila oocyte, Cell, vol. 66, 1991, pp. 23-35.

Kim-Ha et al., Translational regulation of oskar mRNA by bruno, an ovarian RNA-binding protein, is essential, Cell, vol. 81, 1995, pp. 403-412.

Kohrmann et al., Microtubule-dependent recruitment of Staufen-green fluorescent protein into large RNA-containing granules and subsequent dendritic transport in living hippocampal neurons, Mol. Biol. Cell, vol. 10, 1999, pp. 2945-2953.

Krause et al., Immunodetection of poly(A) binding protein II in the cell nucleus, Exp. Cell Res., vol. 214, 1994, pp. 75-82.

Krichevsky et al., Neuronal RNA granules: a link between RNA localization and stimulation-dependent translation, Neuron, vol. 32, 2001, pp. 683-696.

Krissinel et al., Inference of macromolecular assemblies from crystalline state, J. Mol. Biol., vol. 372, 2007, pp. 774-797.

Kuwano et al., NF90 selectively represses the translation of target mRNAs bearing an AU-rich signature motif, Nucleic Acids Res., vol. 38, pp. 225-238.

Lau et al., Structure of the Y14-Magoh core of the exon junction complex, Curr. Biol., vol. 13, 2003, pp. 933-941.

Le et al., Identification of two RNA-binding proteins associated with human telomerase RNA, Mol. Biol. Cell, vol. 11, 2000, pp. 999-1010.

Le Hir et al., Pre-mRNA splicing alters mRNP composition: evidence for stable association of proteins at exon-exon junctions, Genes Dev., vol. 14, 2000b, pp. 1098-1108.

Le Hir et al., The exon-exon junction complex provides a binding platform for factors involved in mRNA export and nonsense-mediated mRNA decay, EMBO J., vol. 20, 2001, pp. 4987-4997.

Le Hir et al., The spliceosome deposits multiple proteins 20-24 nucleotides upstream of mRNA exon-exon junctions, EMBO J., vol. 19, 2000a, pp. 6860-6869.

Lee et al., Characterization of the human gene encoding ADP-ribosylation factor 1, a guanine nucleotide-binding activator of cholera toxin, J. Biol. Chem., vol. 267, 1992, pp. 9028-9034.

Lejeune et al., Nonsense-mediated mRNA decay in mammalian cells involves decapping, deadenylating, and exonucleolytic activities, Mol. Cell, vol. 12, 2003, pp. 675-687.

Lejeune et al., The exon junction complex is detected on CBP80-bound but not eIF4E-bound mRNA in mammalian cells: dynamics of mRNP remodeling, EMBO J., vol. 21, 2002, pp. 3536-3545.

Lesley et al., Protein production and crystallization at the joint center for structural genomics, J StructFunct Genomics, vol. 6, 2005, pp. 71-79.

Li et al., Fast is a survival protein that senses mitochondrial stress and modulates TIA-1-regulated changes in protein expression, Mol. Cell. Biol., vol. 24, 2004, pp. 10718-10732.

Li et al., Inscuteable and Staufen mediate asymmetric localization and segregation of prospero RNA during Drosophila neuroblast cell divisions, Cell, vol. 90, 1997, pp. 437-447.

Li et al., Nonsense surveillance in lymphocytes?, Immunit, vol. 8, 1998, pp. 135-141.

Liang et al., In vitro scratch assay: a convenient and inexpensive method for analysis of cell migration in vitro, Nat. Protoc., vol. 2, 2007, pp. 329-333.

Lieutaud et al., MeDor: a metaserver for predicting protein disorder, BMC Genomics, vol. 9, Suppl 2, S25, 2008.

Luo et al., Molecular mapping of the determinants involved in human Staufen-ribosome association, Biochem. J., vol. 365, 2002, pp. 817-824.

Luo et al., Pre-mRNA splicing and mRNA export linked by direct interactions between UAP56 and Aly, Nature., vol. 413, 2001, pp. 644-647.

Lykke-Andersen et al., Communication of the position of exon-exon junctions to the mRNA surveillance machinery by the protein RNPS1, Science, vol. 293, 2001, pp. 1836-1839.

Lykke-Andersen et al., Human Upf proteins target an mRNA for nonsense-mediated decay when bound downstream of a termination codon., Cell, vol. 103, 2000, pp. 1121-1131.

Macchi et al., Barentsz, a new component of the Staufen-containing ribonucleoprotein particles in mammalian cells, interacts with Staufen in an RNA-dependent manner, J. Neurosci., vol. 23, 2003, pp. 5778-5788.

Mallardo et al., Isolation and characterization of Staufen-containing ribonucleoprotein particles from rat brain, Proc. Natl. Acad. Sci., vol. 100, 2003, pp. 2100-2105.

Maquat et al., Gene expression networks: competing mRNA decay pathways in mammalian cells, BiochemSoc Trans, vol. 37, 2009, pp. 1287-1292.

Maquat, Nonsense-mediated mRNA decay: A comparative analysis of different species, Curr. Genomics, vol. 5, 2004a, pp. 175-190.

Maquat, Nonsense-mediated mRNA decay: splicing, translation and mRNP dynamics, Nat. Rev. Mol. Cell. Biol., vol. 5, 2004b, pp. 89-99.

Marchler-Bauer et al., CDD: a Conserved Domain Database for the functional annotation of proteins, NucleicAcidsRes., vol. 39, 2011, pp. D225-229.

Marion et al., A human sequence homologue of Staufen is an RNA-binding protein that is associated with polysomes and localizes to the rough endoplasmic reticulum, Mol. Cell. Biol., vol. 19, 1999, pp. 2212-2219.

Martel et al., Multimerization of Staufen1 in live cells, RNA, vol. 16, 2010, pp. 585-597.

Mathews et al., Expanded sequence dependence of thermodynamic parameters improves prediction of RNA secondary structure, J. Mol. Biol., vol. 288, 1999, pp. 911-940.

Matsuzaki et al., Miranda localizes staufen and prospero asymmetrically in mitotic neuroblasts and epithelial cells in early Drosophila embryogenesis, Development, vol. 125, 1998, pp. 4089-4098.

McCoy et al., Phaser crystallographic software, J ApplCrystallogr, vol. 40, 2007, pp. 658-674.

Mendell et al., Nonsense surveillance regulates expression of diverse classes of mammalian transcripts and mutes genomic noise, Nat. Genet, vol. 36, 2004, pp. 1073-1078.

Micklem et al., Distinct roles of two conserved Staufen domains in oskar mRNA localization and translation, EMBO J., vol. 19, 2000, pp. 1366-1377.

A

B

```
         C — G                              C — G         G — C
         U — A                              U — A         C — G
   SEQ ID NO: 36  C — G  SEQ ID NO: 37      C — G         U — A
         U — A                              C — G         G — C
         A — U                              G — C         A — U
         C — G                              U — A         G — C
         | |                                C — G         G — C
        3491202                             C — G         C — G
                                            U — A         A — U
                                            C — G         G — C
                                            U — A         A — U
                                            U — A         A — U
                                            A — U         G — C
                                            G   G         A — U
                                            U ~ G         A — U
                                            G ~ U         U — A
                                            A   G         G   G
                                            A   |         G — C
                                            A — U         U ~ G
                                            U ~ G         G   A
                                            U — A         U — A
                                            |   A         G — C
                                            |   C         A — U
                                            G — C         A — U
                                            A — U         C — G
                                            C   |         C — G
                                            U ~ G         U   G
                                            C — G         G   U
                                            C — G         G — C
                                            U — A         G — C
                                            C — G         A — U
                                            C — G         G — C
                                            G ~ U         G — C
   SEQ ID NO: 42  C — G  SEQ ID NO: 43      U — A
                  C — G                  SEQ ID NO: 44  G — C  SEQ ID NO: 45
                  U — A                                 G — C
                  C — G                                 A — U
                  | |                                   C — G
                 662518                                 | |
                                                      2522255
```

FIG. 4-3

D

```
            3368604
             |   |
             G - C
             G - C
             C - G
             C   A
             A   C
             G - C
             G - C
             C - G
             A - U
             U - A
             G - C
             G - C
             U - A
             G - C
             G - C
             C - G
             U - A
             C - G
             A - U
             U ~ G
             G - C
             C   A
             C - G
             U - A
             G - C
             U - A
             A - U
             A - U
             U - A
             C - G
             C - G
             C - G
             A - U
             G - C
             C - G
             A - U
   SEQ ID NO: 48  C - G   SEQ ID NO: 49
             U - A
             U - A
             U - A
```

FIG. 4-4

```
                                        G - C
                                        G - C
                                        G - C
                                        A - U
                                        G - C
                                        G - C
                                        C - G
                                        C - G
                                        G - C
                                        A - U
                                        G - C
                                        G - C
                                        C - G
                                        A - U
                                        G - C
                                        G - C
                                        U   G
                                        G   C
                                        G - C
                                        A - U
                                        U - A
                                        C - G
                                        A - U
                                        C - G
                                        U ~ G
                                        U - A
                                        G - C
                                        A - U
                                        G - C
                                        G - C
                                        C   A
                                        C - G
                 2303446                 A - U
                  |   |                  G - C
                  C - G                  G - C
                  C - G                  A - U
                  U - A            ⇁     G - C
                  C - G           NO:    U - A
            46    A - U           ID     U ~ G
           NO:    A - U       47  SEQ    U - A
           ID  ↽  G   U      NO:
           SEQ    U - A      ID      48    49
                             SEQ    NO:   NO:
                                    ID    ID
                                    SEQ   SEQ
```

FIG. 4-5

B

C

C

A-1

A-2

PISA Result

|  | Structure 1 | Structure 2 |
|---|---|---|
| Selection range | A | A |
| Class | Protein | Protein |
| Symmetry operation | x,y,z | y,x,-z |
| Symmetry ID | 1_555 | 7_555 |
| Number of atoms | | |
| interface | 80 (9.8%) | 82 (10.0%) |
| surface | 505 (61.7%) | 505 (61.7%) |
| total | 818 (100.0%) | 818 (100.0%) |
| Number of residues | | |
| interface | 22 (20.8%) | 22 (20.8%) |
| surface | 97 (91.5%) | 97 (91.5%) |
| total | 106 (100.0%) | 106 (100.0%) |
| Solvent-accessible area,$A^2$ | | |
| interface | 763.8 (11.3%) | 764.4 (11.3%) |
| total | 6736.3 (100.0%) | 6736.3 (61.7%) |

|  | Structure 1 | Structure 2 |
|---|---|---|
| Selection range | A | A |
| Class | Protein | Protein |
| Symmetry operation | x,y,z | -y+1,-x+1,-z+1/2 |
| Symmetry ID | 1_555 | 8_665 |
| Number of atoms | | |
| interface | 128 (15.5%) | 124 (15.0%) |
| surface | 565 (68.5%) | 565 (68.5%) |
| total | 825 (100.0%) | 825 (100.0%) |
| Number of residues | | |
| interface | 38 (35.5%) | 37 (34.6%) |
| surface | 104 (97.2%) | 104 (97.2%) |
| total | 107 (100.0%) | 107 (100.0%) |
| Solvent-accessible area,$A^2$ | | |
| interface | 1248.2 (15.4%) | 1249.7 (15.4%) |
| total | 8101.7 (100.0%) | 8101.7 (100.0%) |

FIG. 13

B

Drosophila STAUa RBD3

Human STAU1 'RBD'5

SEQUENCE LISTING

<160> NUMBER OF SEQ ID NOS: 179

<210> SEQ ID NO 1
<211> LENGTH: 3253
<212> TYPE: DNA
<213> ORGANISM: Artificial Sequence
<220> FEATURE:
<223> OTHER INFORMATION: Description of artificial sequence note =
      synthetic construct

<400> SEQUENCE: 1
aaccacttaa cctctcagaa ctgaacaaag acaacattgt tcctggaacg ccctcttttt     60
aaaaaaaggt agaactttag acttcatagc actgaattaa cctgcactga aagctgttta    120
cctgcatttg ttcactttg ttgaaagtga ccatgtctca agttcaagtg caagttcaga    180
acccatctgc tgctctctca gggagccaaa tactgaacaa gaaccagtct cttctctcac    240
agcctttgat gagtattcct tctactacta gctctctgcc ctctgaaaat gcaggtagac    300
ccattcaaaa ctctgcttta ccctctgcat ctattacatc caccagtgca gctgcagaaa    360
gcataacccc tactgtagaa ctaaatgcac tgtgcatgaa acttggaaaa aaaccaatgt    420
ataagcctgt tgacccttac tctcggatgc agtccaccta taactacaac atgagaggag    480
gtgcttatcc cccgaggtac ttttacccat ttccagttcc acctttactt tatcaagtgg    540
```

```
aactttctgt gggaggacag caatttaatg gcaaaggaaa gacaagacag gctgcgaaac      600
acgatgctgc tgccaaagcg ttgaggatcc tgcagaatga gcccctgcca gagaggctgg      660
aggtgaatgg aagagaatcc gaagaagaaa atctcaataa atctgaaata agtcaagtgt      720
ttgagattgc acttaaacgg aacttgcctg tgaatttcga ggtggcccgg agagtggcc       780 caccccacat gaagaacttt gtgaccaagg tttcggttgg ggagtttgtg ggggaaggtg      840
aagggaaaag caagaagatt tcaaagaaaa atgccgccat agctgttctt gaggagctga      900
agaagttacc gcccctgcct gcagttgaac gagtaaagcc tagaatcaaa agaaaacaa       960 aacccatagt caagccacag acaagcccag aatatggcca gggatcaat ccgattagcc      1020 gactggccca gatccagcag gcaaaaaagg agaaggagcc agagtacacg ctcctcacag      1080
agcgaggcct cccgcgccgc agggagtttg tgatgcaggt gaaggttgga aaccacactg      1140
cagaaggaac gggcaccaac aagaaggtgg ccaagcgcaa tgcagccgag aacatgctgg      1200
agatccttgg tttcaaagtc ccgcaggcgc agcccaccaa acccgcactc aagtcagagg      1260
agaagacacc cataaagaaa ccaggggatg gaagaaaagt aacctttttt gaacctggct      1320
ctggggatga aaatgggact agtaataaag aggatgagtt caggatgcct tatctaagtc      1380
atcagcagct gcctgctgga attcttccca tggtgcccga ggtcgcccag gctgtaggag      1440
ttagtcaagg acatcacacc aaagatttta ccagggcagc tccgaatcct gccaaggcca      1500
cggtaactgc catgatagcc cgagagttgt tgtatggggg cacctcgccc acagccgaga      1560
ccattttaaa gaataacatc tcttcaggcc acgtacccca tggacctctc acgagaccct      1620
ctgagcaact ggactatctt tccagagtcc agggattcca ggttgaatac aaagacttcc      1680
ccaaaaacaa caagaacgaa tttgtatctc ttatcaattg ctcctctcag ccacctctga      1740
tcagccatgg tatcggcaag gatgtggagt cctgccatga tatggctgcg ctgaacatct      1800
taaagttgct gtctgagttg gaccaacaaa gtacagagat gccaagaaca ggaaacggac      1860
caatgtctgt gtgtgggagg tgctgaacct tttctggcca tgaaccatta taaaatccca      1920
acatatatac tgaaaatact gaaactgctt tgaaaatttg gaatttctga tacctccagt      1980
gggccgagag acacggtggg taaggatgt gggcagcagc agggaagaca acagaaacac      2040
aaggaggcgg ctgtggccgg gctggactgt gcgggggttt gttgtgatgg ccactcggtg      2100
acctggcggt ccctacgcaa tagcagctgc ctgtggggaa gaggggctgc ccagccagct      2160
ggttctcccg ggacaccagc agatccacac cctgggcacc tccgtgtttg gtcttttttt      2220

tcccctgtgt gaaagaagaa acggcacgac cccttctcaa gctggctcac tcagacacat      2280
tgggacaaac cctggacagc catgccagag agaggccttt gaccggcccc agagctaaaa      2340
gcaccagaga aaatcaaatg cttcctactc agcgtgaccc aacttttcta gtgtgccacg      2400
gccccaccac ctcctgcagt acccacacca tcaccactgc тттстстттсс aacagtgatc      2460 tgtattctta gtttcattat тттcтттттga ttgatatgac actatataaa атттсcaтттт     2520 gagaatttct caattgtatc tagttaaata gcacagtttg gaaacttgtc tgagactgac      2580

tttatcaata atctaaccga caaagatcat atccatgtgt atgtggttag acatttttat      2640

tccattgact aacccaggac agtttcagtg atgcaaattg tgtgccctct ggttcagctg      2700
aaacagtcct ggactttcaa aaaccttgaa taagtctccc acagttgtat aaattggaca      2760
atttaggaat tttaaacttt agatgatcat ttggttccat ttttatttca tttttatttt       2820

tgttaatgca aacaggactt aaatgaactt tgatctctgt tttaaagatt attaaaaaac      2880
```

```
attgtgtatc tatacatatg gctcttgagg acttagcttt cactacacta caggatatga    2940
tctccatgta gtccatataa acctgcagag tgattttcca gagtgctcga tactgttaat    3000
tacatctcca ttagggctga aaagaatgac ctacgtttct gtatacagct gtgttgcttt    3060
tgatgttgtg ttactgtaca cagaagtgtg tgcactgagg ctctgcgtgt ggtccgtatg    3120
gaaagcctgg tagccctgcg agttaagtac tgcttccatt cattgtttac gctggaattt    3180
ttctccccat ggaatgtaag taaaacttaa gtgtttgtca tcaataaatg gtaatactaa    3240
aaaaaaaaaa aaa                                                       3253

<210> SEQ ID NO 2
<211> LENGTH: 577
<212> TYPE: PRT
<213> ORGANISM: Artificial Sequence
<220> FEATURE:
<223> OTHER INFORMATION: Description of artificial sequence note =
      synthetic construct

<400> SEQUENCE: 2

Met Ser Gln Val Gln Val Gln Val Gln Asn Pro Ser Ala Ala Leu Ser
1               5                   10                  15

Gly Ser Gln Ile Leu Asn Lys Asn Gln Ser Leu Leu Ser Gln Pro Leu
            20                  25                  30

Met Ser Ile Pro Ser Thr Thr Ser Ser Leu Pro Ser Glu Asn Ala Gly
        35                  40                  45

Arg Pro Ile Gln Asn Ser Ala Leu Pro Ser Ala Ser Ile Thr Ser Thr
    50                  55                  60

Ser Ala Ala Ala Glu Ser Ile Thr Pro Thr Val Glu Leu Asn Ala Leu
65                  70                  75                  80

Cys Met Lys Leu Gly Lys Lys Pro Met Tyr Lys Pro Val Asp Pro Tyr
                85                  90                  95

Ser Arg Met Gln Ser Thr Tyr Asn Tyr Asn Met Arg Gly Gly Ala Tyr
            100                 105                 110

Pro Pro Arg Tyr Phe Tyr Pro Phe Pro Val Pro Pro Leu Leu Tyr Gln
        115                 120                 125

Val Glu Leu Ser Val Gly Gly Gln Gln Phe Asn Gly Lys Gly Lys Thr
    130                 135                 140

Arg Gln Ala Ala Lys His Asp Ala Ala Lys Ala Leu Arg Ile Leu
145                 150                 155                 160

Gln Asn Glu Pro Leu Pro Glu Arg Leu Glu Val Asn Gly Arg Glu Ser
                165                 170                 175

Glu Glu Glu Asn Leu Asn Lys Ser Glu Ile Ser Gln Val Phe Glu Ile
            180                 185                 190

Ala Leu Lys Arg Asn Leu Pro Val Asn Phe Glu Val Ala Arg Glu Ser
        195                 200                 205

Gly Pro Pro His Met Lys Asn Phe Val Thr Lys Val Ser Val Gly Glu
    210                 215                 220

Phe Val Gly Glu Gly Glu Gly Lys Ser Lys Lys Ile Ser Lys Lys Asn
225                 230                 235                 240

Ala Ala Ile Ala Val Leu Glu Glu Leu Lys Lys Leu Pro Pro Leu Pro
                245                 250                 255

Ala Val Glu Arg Val Lys Pro Arg Ile Lys Lys Thr Lys Pro Ile
            260                 265                 270

Val Lys Pro Gln Thr Ser Pro Glu Tyr Gly Gln Gly Ile Asn Pro Ile
        275                 280                 285
```

```
Ser Arg Leu Ala Gln Ile Gln Gln Ala Lys Lys Glu Lys Glu Pro Glu
    290                 295                 300

Tyr Thr Leu Leu Thr Glu Arg Gly Leu Pro Arg Arg Arg Glu Phe Val
305                 310                 315                 320

Met Gln Val Lys Val Gly Asn His Thr Ala Glu Gly Thr Gly Thr Asn
                325                 330                 335

Lys Lys Val Ala Lys Arg Asn Ala Ala Glu Asn Met Leu Glu Ile Leu
            340                 345                 350

Gly Phe Lys Val Pro Gln Ala Gln Pro Thr Lys Pro Ala Leu Lys Ser
        355                 360                 365

Glu Glu Lys Thr Pro Ile Lys Lys Pro Gly Asp Gly Arg Lys Val Thr
    370                 375                 380

Phe Phe Glu Pro Gly Ser Gly Asp Glu Asn Gly Thr Ser Asn Lys Glu
385                 390                 395                 400

Asp Glu Phe Arg Met Pro Tyr Leu Ser His Gln Leu Pro Ala Gly
                405                 410                 415

Ile Leu Pro Met Val Pro Glu Val Ala Gln Ala Val Gly Val Ser Gln
            420                 425                 430

Gly His His Thr Lys Asp Phe Thr Arg Ala Ala Pro Asn Pro Ala Lys
        435                 440                 445

Ala Thr Val Thr Ala Met Ile Ala Arg Glu Leu Leu Tyr Gly Gly Thr
    450                 455                 460

Ser Pro Thr Ala Glu Thr Ile Leu Lys Asn Asn Ile Ser Ser Gly His
465                 470                 475                 480

Val Pro His Gly Pro Leu Thr Arg Pro Ser Glu Gln Leu Asp Tyr Leu
                485                 490                 495

Ser Arg Val Gln Gly Phe Gln Val Glu Tyr Lys Asp Phe Pro Lys Asn
            500                 505                 510

Asn Lys Asn Glu Phe Val Ser Leu Ile Asn Cys Ser Ser Gln Pro Pro
        515                 520                 525

Leu Ile Ser His Gly Ile Gly Lys Asp Val Glu Ser Cys His Asp Met
    530                 535                 540

Ala Ala Leu Asn Ile Leu Lys Leu Leu Ser Glu Leu Asp Gln Gln Ser
545                 550                 555                 560

Thr Glu Met Pro Arg Thr Gly Asn Gly Pro Met Ser Val Cys Gly Arg
                565                 570                 575

Cys

<210> SEQ ID NO 3
<211> LENGTH: 290
<212> TYPE: DNA
<213> ORGANISM: Artificial Sequence
<220> FEATURE:
<223> OTHER INFORMATION: Description of artificial sequence note =
      synthetic construct

<400> SEQUENCE: 3
ggccgggcgc ggtggctcac gcctgtaatc ccagcacttt gggaggccga ggcgggcgga     60
tcacctgagg tcaggagttc gagaccagcc tggccaacat ggtgaaaccc cgtctctact    120
aaaaatacaa aaattagccg ggcgtggtgg cgcgcgcctg taatcccagc tactcggag    180 gctgaggcag gagaatcgct tgaacccggg aggcggaggt tgcagtgagc cgagatcgcg    240
ccactgcact ccagcctggg cgacagagcg agactccgtc tcaaaaaaaa              290

<210> SEQ ID NO 4
```

```
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 4
cttgaaagct cagaactcgg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 5
tcagcccccg acggtctctc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 6
accgccaatc gcaaggcacc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 7
gctgatctca tccttgttcc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 8
aagtggctat gctcaaaatg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 9
ttcaggcact ttacctccac                                              20

<210> SEQ ID NO 10
<211> LENGTH: 20
```

```
<212> TYPE: DNA
<213> ORGANISM: Artificial Sequence
<220> FEATURE:
<223> OTHER INFORMATION: Description of artificial sequence note =
      synthetic construct

<400> SEQUENCE: 10
ccttgacctt gggtttcaac                                                20

<210> SEQ ID NO 11
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 11
atttgcaatg gaagcctttg                                                20

<210> SEQ ID NO 12
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 12
tgtgctgtat gagaagaacc                                                20

<210> SEQ ID NO 13
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 13
gcttcatcct tcttattagc                                                20

<210> SEQ ID NO 14
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 14
gactggccag atgctcgtgg                                                20

<210> SEQ ID NO 15
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 15
atctttggga agcggctatc                                                20

<210> SEQ ID NO 16
<211> LENGTH: 20
<212> TYPE: DNA
```

```
<213> ORGANISM: Artificial Sequence
<220> FEATURE:
<223> OTHER INFORMATION: Description of artificial sequence note =
      synthetic construct

<400> SEQUENCE: 16
ccatggccag caccatttcc                                              20

<210> SEQ ID NO 17
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 17
acctcggccg cgtgcagctc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 18
tccttcctgc gagccctgag                                              20

<210> SEQ ID NO 19
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 19
gcactgctgc catgtctttg                                              20

<210> SEQ ID NO 20
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 20
tgcaatcatt gaggattgtg                                              20

<210> SEQ ID NO 21
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 21
cactgtcaag tggatgtctc                                              20

<210> SEQ ID NO 22
<211> LENGTH: 20
<212> TYPE: DNA
<213> ORGANISM: Artificial Sequence
```

```
<220> FEATURE:
<223> OTHER INFORMATION: Description of artificial sequence note =
      synthetic construct

<400> SEQUENCE: 22
gacagagacg tgaagcactg                                           20

<210> SEQ ID NO 23
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 23
ccataaatgt tgctttatcc                                           20

<210> SEQ ID NO 24
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 24
cctggtagcc gctggccggc                                           20

<210> SEQ ID NO 25
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 25
cttctggtca gttggatttg                                           20

<210> SEQ ID NO 26
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 26
gatttatgtt gttgtagttg                                           20

<210> SEQ ID NO 27
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 27
ccaagcagcc aattttattg                                           20

<210> SEQ ID NO 28
<211> LENGTH: 20
<212> TYPE: DNA
<213> ORGANISM: Artificial Sequence
<220> FEATURE:
```

```
<223> OTHER INFORMATION: Description of artificial sequence note =
      synthetic construct

<400> SEQUENCE: 28
acagcctttc acgagtcttc                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 29
ctgctgttgg gaggcgatcc                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 30
gcgggagaag tccacaccgg                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 31
aggctgtcga gtcagcattc                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 32
agttaactgt ggactccatg                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 33
actttctcca actcatcaag                                                    20

<210> SEQ ID NO 34
<211> LENGTH: 29
<212> TYPE: DNA
<213> ORGANISM: Artificial Sequence
<220> FEATURE:
<223> OTHER INFORMATION: Description of artificial sequence note =
``` synthetic construct

<400> SEQUENCE: 34
ttgaccgctt gaagtcttta attaaatac                                    29

<210> SEQ ID NO 35
<211> LENGTH: 51
<212> TYPE: DNA
<213> ORGANISM: Artificial Sequence
<220> FEATURE:
<223> OTHER INFORMATION: Description of artificial sequence note =
      synthetic construct

<400> SEQUENCE: 35
cgaagcggcc gcaattacat tttgcaattt ggactttccg cccttcttgg c           51

<210> SEQ ID NO 36
<211> LENGTH: 124
<212> TYPE: RNA
<213> ORGANISM: Artificial Sequence
<220> FEATURE:
<223> OTHER INFORMATION: Description of artificial sequence note =
      synthetic construct

<400> SEQUENCE: 36
ugaaaggcca ggcauggugg cucaugccug uaaucccagc acuuggag gccgaggcag    60 guggaucacu ugaggccagg aguuugaaac cagccuggcc aacaugguga aaaccugucu  120
cuac                                                                124

<210> SEQ ID NO 37
<211> LENGTH: 120
<212> TYPE: RNA
<213> ORGANISM: Artificial Sequence
<220> FEATURE:
<223> OTHER INFORMATION: Description of artificial sequence note =
      synthetic construct

<400> SEQUENCE: 37
acuuccgucu ccgucaccga gugaggacau uaggauugug acccuccgac uccgcccucc   60
uagugaacuc ggguccucaa guucggucg gauccguugu aucguucugg gacagagaug   120

<210> SEQ ID NO 38
<211> LENGTH: 82
<212> TYPE: RNA
<213> ORGANISM: Artificial Sequence
<220> FEATURE:
<223> OTHER INFORMATION: Description of artificial sequence note =
      synthetic construct

<400> SEQUENCE: 38
ugugacccuc cgacuccgcc cuccuaguga acucggguuc ucaaguucug gucggauccg   60
uuguaucguu cugggacaga ga                                             82

<210> SEQ ID NO 39
<211> LENGTH: 83
<212> TYPE: RNA
<213> ORGANISM: Artificial Sequence
<220> FEATURE:
<223> OTHER INFORMATION: Description of artificial sequence note =
      synthetic construct

<400> SEQUENCE: 39
acuuggggag gccaaggcgg gaggauugcu ugagcccagg aguucaagac cagccugggc   60
aacauaccaa gacccccguc ucu                                             83

<210> SEQ ID NO 40
<211> LENGTH: 97
<212> TYPE: RNA
<213> ORGANISM: Artificial Sequence
<220> FEATURE:
<223> OTHER INFORMATION: Description of artificial sequence note =
      synthetic construct

<400> SEQUENCE: 40
acaacggauc cgaccuccga ccucacggua ccgcgcuaga accgugugac guuggaggug     60
gaagggccaa guucacuaag aggaaggagu cggaggg                             97

<210> SEQ ID NO 41
<211> LENGTH: 97
<212> TYPE: RNA
<213> ORGANISM: Artificial Sequence
<220> FEATURE:
<223> OTHER INFORMATION: Description of artificial sequence note =
      synthetic construct

<400> SEQUENCE: 41
uguugccuag gcuggaggcu ggagugcagu ggcgcaaucu cggcucacug caaccucugc     60
cuccugggcu caagcaauuc ucccaccuca gccuccc                             97

<210> SEQ ID NO 42
<211> LENGTH: 114
<212> TYPE: RNA
<213> ORGANISM: Artificial Sequence
<220> FEATURE:
<223> OTHER INFORMATION: Description of artificial sequence note =
      synthetic construct

<400> SEQUENCE: 42
cuuuggggua gagaugauuu uuauguuuua aucggcccgc accaccacgu acggacauua     60
gggucgauga acccuccgac uccguccucu uagugaaauu gaguccuccg ccuc          114

<210> SEQ ID NO 43
<211> LENGTH: 116
<212> TYPE: RNA
<213> ORGANISM: Artificial Sequence
<220> FEATURE:
<223> OTHER INFORMATION: Description of artificial sequence note =
      synthetic construct

<400> SEQUENCE: 43
gaaacuccgu cucuacuaaa aauacaaaaa auuagcuggg cguggugug ggcaccugua      60 gucccagcua cucaggaggc ugaggcagga gaauggugug aaccugggag guggag        116

<210> SEQ ID NO 44
<211> LENGTH: 152
<212> TYPE: RNA
<213> ORGANISM: Artificial Sequence
<220> FEATURE:
<223> OTHER INFORMATION: Description of artificial sequence note =
      synthetic construct

<400> SEQUENCE: 44
aggucaggag aucgagacca uccuggcuaa ugcguugaaa cuccgucucu acuaaaaaua     60
caaaaaauua gcugggcgug guggugggca ccuguagucc cagcuacuca ggaggcugag    120
gcaggagaau ggugugaacc ugggagguggag                                   152

<210> SEQ ID NO 45
<211> LENGTH: 152
<212> TYPE: RNA
<213> ORGANISM: Artificial Sequence
<220> FEATURE:
<223> OTHER INFORMATION: Description of artificial sequence note = synthetic construct

<400> SEQUENCE: 45
uccagcccuc agacucuggu gggaccgguu guaccacuuu gggguaauag augauuuuua    60
uguuguuaau cggccucac uaccacguau ggacaucggg gucgaugagu ccuccgacuc    120
cguccucuua gcgaacuugg guccuccacc uc                                 152

<210> SEQ ID NO 46
<211> LENGTH: 162
<212> TYPE: RNA
<213> ORGANISM: Artificial Sequence
<220> FEATURE:
<223> OTHER INFORMATION: Description of artificial sequence note = synthetic construct

<400> SEQUENCE: 46
ccucaaguuc uggucggacu gguuguaccu cuuuggggua gagaugauuu uuaguuuua    60 aucggcccgc accaccacgu acggacauua ggucgauga acccuccgac uccguccucu    120
uagugaaauu gagucccucg ccccaacac cacucggcuc ua                      162

<210> SEQ ID NO 47
<211> LENGTH: 164
<212> TYPE: RNA
<213> ORGANISM: Artificial Sequence
<220> FEATURE:
<223> OTHER INFORMATION: Description of artificial sequence note = synthetic construct

<400> SEQUENCE: 47
ggaguuugaa accagccugg ccaacauggu gaaaaccugu cucuacuaaa aaucaaaaaa    60
uuagccgagc guguggugc gugccuguag ucccagcuac uuaggaggcu gaggcaugag    120
aaucacuuaa accugagagg uggagguugc aguugagcca agau                    164

<210> SEQ ID NO 48
<211> LENGTH: 267
<212> TYPE: RNA
<213> ORGANISM: Artificial Sequence
<220> FEATURE:
<223> OTHER INFORMATION: Description of artificial sequence note = synthetic construct

<400> SEQUENCE: 48
ggccaggcau gguggcucau gccuguaauc ccagcacuuu gggaggccga ggcaggugga    60
ucacuugagg ccaggaguuu gaaaccagcc uggccaacau ggugaaaacc ugucucuacu    120
aaaaauacaa aaauuagccg agcgugguggg ugcgugccu aguccccagc uacuuaggag    180
gcugaggcau gagaaucacu uaaaccugag agguggaggu ugcaguugag ccaagaucac    240
gacacugcac uccagccugg gcaacgg                                       267

<210> SEQ ID NO 49
<211> LENGTH: 267
<212> TYPE: RNA
<213> ORGANISM: Artificial Sequence
<220> FEATURE:
<223> OTHER INFORMATION: Description of artificial sequence note =

-continued synthetic construct

<400> SEQUENCE: 49

| ccgacccgua ccaccgagug cagacauuag ggucgugaaa cccuccggcu ccguccgccu | 60 |
| aguggacucc aguccucaga cucugguggg accgguugua ccacuuuggg guaauagaug | 120 |
| auuuuuaugu uguuaaucgg uccucacuac cacguaugga caucgggguc gaugagaguccu | 180 |
| ccgacuccgu ccucuuagcg aacuuggguc uccaccuccc aaugucucuc gguucuaccg | 240 |
| cggugacaug agggcugacc cacuguc | 267 |

<210> SEQ ID NO 50
<211> LENGTH: 688
<212> TYPE: RNA
<213> ORGANISM: Artificial Sequence
<220> FEATURE:
<223> OTHER INFORMATION: Description of artificial sequence note =
      synthetic construct

<400> SEQUENCE: 50

| ccaagaagua gguuuuuuuu uuuuuuaaa uaaaggagag acagucucac ucuguugccc | 60 |
| aggcuggaau acaguggugu gaucauagcu cacugcagcc ucuuuuaacu ccugggcuca | 120 |
| agcaauccuu ccaaccucag cauucugagu agcugggauc acaggugcuc cccaucacac | 180 |
| ccugcuaauu uaauuuucuu guagagaca gggucuugcu auguugccua ggcuggucuu | 240 |
| gaacuccugg gcucaaguga uccucccgcc ucagccuccc aguguuagga uuacaggagu | 300 |
| gagccacugc cucugccuuc agguagcaau uuuauuagca aacuauaagc cuaaaguaau | 360 |
| aguuaaaauu cucacuguga uauucauuac uaaccccuga accuguaccc uucagcuuac | 420 |
| cacuacagua cuucuguagu agagcgagua uggguuuugg uaucagacag guccaaauuu | 480 |
| gaauucuggu ucuaccuuuc auuuaucaaa ugacuuuggg caaaguacuu aaccucucug | 540 |
| agcuuuaguu ccccuucucug uaaagaauua aaauauuuca gucuuaucgu guagaugaua | 600 |
| uacagagggc acauaacaaa uguuagaucu cucaaauguu uuucuguaac ccaaauaugc | 660 |
| uuacaacuga uuaaagaaug uucucacu | 688 |

<210> SEQ ID NO 51
<211> LENGTH: 34
<212> TYPE: DNA
<213> ORGANISM: Artificial Sequence
<220> FEATURE:
<223> OTHER INFORMATION: Description of artificial sequence note =
      synthetic construct

<400> SEQUENCE: 51

| gatgctcgag tggcattggc tttcaccacc tatg | 34 |

<210> SEQ ID NO 52
<211> LENGTH: 34
<212> TYPE: DNA
<213> ORGANISM: Artificial Sequence
<220> FEATURE:
<223> OTHER INFORMATION: Description of artificial sequence note =
      synthetic construct

<400> SEQUENCE: 52

| gtcaggatcc tgcctcaagt ccaaagcaca actg | 34 |

<210> SEQ ID NO 53
<211> LENGTH: 35
<212> TYPE: DNA

```
<213> ORGANISM: Artificial Sequence
<220> FEATURE:
<223> OTHER INFORMATION: Description of artificial sequence note =
      synthetic construct

<400> SEQUENCE: 53
gagtcaaagc ttaaaggaga gacagtctca ctctg                          35

<210> SEQ ID NO 54
<211> LENGTH: 36
<212> TYPE: DNA
<213> ORGANISM: Artificial Sequence
<220> FEATURE:
<223> OTHER INFORMATION: Description of artificial sequence note =
      synthetic construct

<400> SEQUENCE: 54
gtcagcggcc gccagttgta agcatatttg ggttac                         36

<210> SEQ ID NO 55
<211> LENGTH: 34
<212> TYPE: DNA
<213> ORGANISM: Artificial Sequence
<220> FEATURE:
<223> OTHER INFORMATION: Description of artificial sequence note =
      synthetic construct

<400> SEQUENCE: 55
gtcaggatcc cagttgtaag catatttggg ttac                           34

<210> SEQ ID NO 56
<211> LENGTH: 56
<212> TYPE: DNA
<213> ORGANISM: Artificial Sequence
<220> FEATURE:
<223> OTHER INFORMATION: Description of artificial sequence note =
      synthetic construct

<400> SEQUENCE: 56
atattcatta ctaacccctg aacccataca gttcagctta ccactacagt acttct   56

<210> SEQ ID NO 57
<211> LENGTH: 101
<212> TYPE: DNA
<213> ORGANISM: Artificial Sequence
<220> FEATURE:
<223> OTHER INFORMATION: Description of artificial sequence note =
      synthetic construct

<400> SEQUENCE: 57
gaagtactgt agtggtaagc tgaactgtat gggttcaggg gttagtaatg aatatccctg    60
aacccataca gttcagctca gaactacagt acttctgtag t                      101

<210> SEQ ID NO 58
<211> LENGTH: 45
<212> TYPE: DNA
<213> ORGANISM: Artificial Sequence
<220> FEATURE:
<223> OTHER INFORMATION: Description of artificial sequence note =
      synthetic construct

<400> SEQUENCE: 58
actacagaag tactgtagtt ctgagctgaa ctgtatgggt tcagg               45

<210> SEQ ID NO 59
<211> LENGTH: 42
```

-continued

<212> TYPE: DNA
<213> ORGANISM: Artificial Sequence
<220> FEATURE:
<223> OTHER INFORMATION: Description of artificial sequence note =
      synthetic construct

<400> SEQUENCE: 59
gagtcaaagc ttatggaaga cgccaaaaac ataaagaaag gc                          42

<210> SEQ ID NO 60
<211> LENGTH: 40
<212> TYPE: DNA
<213> ORGANISM: Artificial Sequence
<220> FEATURE:
<223> OTHER INFORMATION: Description of artificial sequence note =
      synthetic construct

<400> SEQUENCE: 60
gtcaggatcc ttacaatttg gactttccgc ccttcttggc                             40

<210> SEQ ID NO 61
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 61
gatggctagc cgccatggac tacaaagacg atgacgacaa gggatccgct tctaacttta      60
ctcagttcg                                                              69

<210> SEQ ID NO 62
<211> LENGTH: 32
<212> TYPE: DNA
<213> ORGANISM: Artificial Sequence
<220> FEATURE:
<223> OTHER INFORMATION: Description of artificial sequence note =
      synthetic construct

<400> SEQUENCE: 62
gtcagatatc gtagatgccg gagtttgctg cg                                     32

<210> SEQ ID NO 63
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 63
gatgcctagg ggcgtgatca agcccgacat g                                      31

<210> SEQ ID NO 64
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 64
gtcacctagg gccggcctgg cggggtagtc c                                      31

<210> SEQ ID NO 65

```
<211> LENGTH: 37
<212> TYPE: DNA
<213> ORGANISM: Artificial Sequence
<220> FEATURE:
<223> OTHER INFORMATION: Description of artificial sequence note =
      synthetic construct

<400> SEQUENCE: 65
gatgtctaga gtgatcaact cgccaacaa acaccag                              37

<210> SEQ ID NO 66
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 66
cagaaggcta gcccgaagag aac                                            23

<210> SEQ ID NO 67
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 67
ctcttcgggc tagccttctg g                                              21

<210> SEQ ID NO 68
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 68
gtcagggccc gagacagagt ctccgttgcc c                                   31

<210> SEQ ID NO 69
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 69
gagtcaaagc ttggcattcc ggtactgttg g                                   31

<210> SEQ ID NO 70
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 70
catccatctt tgtgccctac cc                                             22

<210> SEQ ID NO 71
<211> LENGTH: 30
```

```
<212> TYPE: DNA
<213> ORGANISM: Artificial Sequence
<220> FEATURE:
<223> OTHER INFORMATION: Description of artificial sequence note =
      synthetic construct

<400> SEQUENCE: 71
tctttaaaaa tatatatatt ttaaatatac                                       30

<210> SEQ ID NO 72
<211> LENGTH: 18
<212> TYPE: DNA
<213> ORGANISM: Artificial Sequence
<220> FEATURE:
<223> OTHER INFORMATION: Description of artificial sequence note =
      synthetic construct

<400> SEQUENCE: 72
tagaaggcac agtcgagg                                                    18

<210> SEQ ID NO 73
<211> LENGTH: 33
<212> TYPE: DNA
<213> ORGANISM: Artificial Sequence
<220> FEATURE:
<223> OTHER INFORMATION: Description of artificial sequence note =
      synthetic construct

<400> SEQUENCE: 73 gatgttttaaa taatgcactt tgggaggcca agg                                  33

<210> SEQ ID NO 74
<211> LENGTH: 32
<212> TYPE: DNA
<213> ORGANISM: Artificial Sequence
<220> FEATURE:
<223> OTHER INFORMATION: Description of artificial sequence note =
      synthetic construct

<400> SEQUENCE: 74 gatgttttaaa gacgggggtc ttggtatgtt gc                                   32

<210> SEQ ID NO 75
<211> LENGTH: 34
<212> TYPE: DNA
<213> ORGANISM: Artificial Sequence
<220> FEATURE:
<223> OTHER INFORMATION: Description of artificial sequence note =
      synthetic construct

<400> SEQUENCE: 75
gataccgcgg atggaagacg ccaaaaacat aaag                                  34

<210> SEQ ID NO 76
<211> LENGTH: 37
<212> TYPE: DNA
<213> ORGANISM: Artificial Sequence
<220> FEATURE:
<223> OTHER INFORMATION: Description of artificial sequence note =
      synthetic construct

<400> SEQUENCE: 76
gtcagaattc gcttctatta gattacattc atttcac                               37

<210> SEQ ID NO 77
<211> LENGTH: 34
<212> TYPE: DNA
```

```
<213> ORGANISM: Artificial Sequence
<220> FEATURE:
<223> OTHER INFORMATION: Description of artificial sequence note =
      synthetic construct

<400> SEQUENCE: 77
gataccgcgg atggaagacg ccaaaaacat aaag                              34

<210> SEQ ID NO 78
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 78
gtcagaattc gagacagagt ctccgttgcc c                                 31

<210> SEQ ID NO 79
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 79
ccuguacccu ucagcuuact t                                            21

<210> SEQ ID NO 80
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 80
augacuuugg gcaaaguact t                                            21

<210> SEQ ID NO 81
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 81
ggugcaaaga cagcauucct t                                            21

<210> SEQ ID NO 82
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 82
uaguagucaa gaccaauucu att                                          23

<210> SEQ ID NO 83
<211> LENGTH: 21
<212> TYPE: DNA
<213> ORGANISM: Artificial Sequence
```

```
<220> FEATURE:
<223> OTHER INFORMATION: Description of artificial sequence note =
      synthetic construct

<400> SEQUENCE: 83
uggcauucca guugaguuut t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 84
ccuauaacua caacaugagt t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 85
guuugagauu gcacuuaaat t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 86
aacguuugcc guggaugagt t                                              21

<210> SEQ ID NO 87
<211> LENGTH: 19
<212> TYPE: DNA
<213> ORGANISM: Artificial Sequence
<220> FEATURE:
<223> OTHER INFORMATION: Description of artificial sequence note =
      synthetic construct

<400> SEQUENCE: 87
caacacccca acatcttcg                                                 19

<210> SEQ ID NO 88
<211> LENGTH: 19
<212> TYPE: DNA
<213> ORGANISM: Artificial Sequence
<220> FEATURE:
<223> OTHER INFORMATION: Description of artificial sequence note =
      synthetic construct

<400> SEQUENCE: 88
ctttccgccc ttcttggcc                                                 19

<210> SEQ ID NO 89
<211> LENGTH: 20
<212> TYPE: DNA
<213> ORGANISM: Artificial Sequence
<220> FEATURE:
```

```
<223> OTHER INFORMATION: Description of artificial sequence note =
      synthetic construct

<400> SEQUENCE: 89
aatacgactc actataggga                                                  20

<210> SEQ ID NO 90
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 90
gatacttgtg ggccagggca                                                  20

<210> SEQ ID NO 91
<211> LENGTH: 19
<212> TYPE: DNA
<213> ORGANISM: Artificial Sequence
<220> FEATURE:
<223> OTHER INFORMATION: Description of artificial sequence note =
      synthetic construct

<400> SEQUENCE: 91
tctagaggat agaatggcg                                                   19

<210> SEQ ID NO 92
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 92
agcaggctgg taccggtccg                                                  20

<210> SEQ ID NO 93
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 93
accaatgttc agtacctcag                                                  20

<210> SEQ ID NO 94
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 94
cagcattctg agtagctggg atc                                              23

<210> SEQ ID NO 95
<211> LENGTH: 23
<212> TYPE: DNA
<213> ORGANISM: Artificial Sequence
<220> FEATURE:
<223> OTHER INFORMATION: Description of artificial sequence note =
``` synthetic construct

<400> SEQUENCE: 95
cagcattctg agtagctggg atc                                            23

<210> SEQ ID NO 96
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 96
ccttccaacc tcagcattct gag                                            23

<210> SEQ ID NO 97
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 97
gctcaagcaa tccttccaac ctc                                            23

<210> SEQ ID NO 98
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 98
tcttttaact cctgggctca agc                                            23

<210> SEQ ID NO 99
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 99
ggctggaata cagtggtgtg atc                                            23

<210> SEQ ID NO 100
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 100
cagtctcact ctgttgccca ggc                                            23

<210> SEQ ID NO 101
<211> LENGTH: 23
<212> TYPE: DNA
<213> ORGANISM: Artificial Sequence
<220> FEATURE:
<223> OTHER INFORMATION: Description of artificial sequence note =
      synthetic construct -continued

<400> SEQUENCE: 101
aaaggagaga cagtctcact ctg                                           23

<210> SEQ ID NO 102
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 102
aggacaatga cccaagaagt agg                                           23

<210> SEQ ID NO 103
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 103
cctttgacaa aggacaatga ccc                                           23

<210> SEQ ID NO 104
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 104
ggacttcctc tggcatgtag g                                             21

<210> SEQ ID NO 105
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 105
ccaaaggaga ccatctgacc                                               20

<210> SEQ ID NO 106
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 106
accgccaatc gcaaggcacc                                               20

<210> SEQ ID NO 107
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 107
aacgacctgt taaaggccac tc          22

<210> SEQ ID NO 108
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 108
aatacgactc actataggga          20

<210> SEQ ID NO 109
<211> LENGTH: 16
<212> TYPE: DNA
<213> ORGANISM: Artificial Sequence
<220> FEATURE:
<223> OTHER INFORMATION: Description of artificial sequence note =
      synthetic construct

<400> SEQUENCE: 109
ctgatggggc tctatg          16

<210> SEQ ID NO 110
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 110
cagcattctg agtagctggg atc          23

<210> SEQ ID NO 111
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 111
cagcattctg agtagctggg atc          23

<210> SEQ ID NO 112
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 112
aagtggctat gctcaaaatg          20

<210> SEQ ID NO 113
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 113

```
gtccaggaag aaggtgcaaa g                                              21
```

<210> SEQ ID NO 114
<211> LENGTH: 24
<212> TYPE: DNA
<213> ORGANISM: Artificial Sequence
<220> FEATURE:
<223> OTHER INFORMATION: Description of artificial sequence note =
      synthetic construct

<400> SEQUENCE: 114

```
ctaaatcttc ccatgaaata ggtg                                           24
```

<210> SEQ ID NO 115
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 115

```
ggcgtttgta gatcactcct tc                                             22
```

<210> SEQ ID NO 116
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 116

```
aaggtcggag tcaacggatt tg                                             22
```

<210> SEQ ID NO 117
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 117

```
cctgctgaag accttgtgag aag                                            23
```

<210> SEQ ID NO 118
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 118

```
gcaaggtcta cctgaggacc                                                20
```

<210> SEQ ID NO 119
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 119

```
tcttgtgcca gaggagtgtg                                              20

<210> SEQ ID NO 120
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 120
cccagtggga gtgcttgtga aa                                           22

<210> SEQ ID NO 121
<211> LENGTH: 24
<212> TYPE: DNA
<213> ORGANISM: Artificial Sequence
<220> FEATURE:
<223> OTHER INFORMATION: Description of artificial sequence note =
      synthetic construct

<400> SEQUENCE: 121
cagttgtaag catatttggg ttac                                         24

<210> SEQ ID NO 122
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 122
ttcacctcat ctcggctttc c                                            21

<210> SEQ ID NO 123
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 123
gctgatctca tccttgttcc                                              20

<210> SEQ ID NO 124
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 124
tccttacttt gcaggcatcc ag                                           22

<210> SEQ ID NO 125
<211> LENGTH: 19
<212> TYPE: DNA
<213> ORGANISM: Artificial Sequence
<220> FEATURE:
<223> OTHER INFORMATION: Description of artificial sequence note =
      synthetic construct

<400> SEQUENCE: 125
tctagaggat agaatggcg                                               19
```

<210> SEQ ID NO 126
<211> LENGTH: 18
<212> TYPE: DNA
<213> ORGANISM: Artificial Sequence
<220> FEATURE:
<223> OTHER INFORMATION: Description of artificial sequence note =
      synthetic construct

<400> SEQUENCE: 126
tcctggtgag aagtctcc                                                 18

<210> SEQ ID NO 127
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 127
gaacctgtac ccttcagctt acc                                           23

<210> SEQ ID NO 128
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 128
aacccataca gttcagctca ga                                            22

<210> SEQ ID NO 129
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 129
ttcaggcact ttacctccac                                               20

<210> SEQ ID NO 130
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 130
ggctaccata ttggacagca c                                             21

<210> SEQ ID NO 131
<211> LENGTH: 23
<212> TYPE: DNA
<213> ORGANISM: Artificial Sequence
<220> FEATURE:
<223> OTHER INFORMATION: Description of artificial sequence note =
      synthetic construct

<400> SEQUENCE: 131
ggcctttgat agaaatgtgt agg                                           23

```
<210> SEQ ID NO 132
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 132
atgcgtggtg aaactcaact gg                                                  22

<210> SEQ ID NO 133
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 133
atgacaagct tcccgttctc ag                                                  22

<210> SEQ ID NO 134
<211> LENGTH: 21
<212> TYPE: DNA
<213> ORGANISM: Artificial Sequence
<220> FEATURE:
<223> OTHER INFORMATION: Description of artificial sequence note =
      synthetic construct

<400> SEQUENCE: 134
aggatgaagt cggggcttga c                                                   21

<210> SEQ ID NO 135
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 135
cagtcaagtc cacagtcctt gg                                                  22

<210> SEQ ID NO 136
<211> LENGTH: 20
<212> TYPE: DNA
<213> ORGANISM: Artificial Sequence
<220> FEATURE:
<223> OTHER INFORMATION: Description of artificial sequence note =
      synthetic construct

<400> SEQUENCE: 136
ccaccgaaac tgcttcctcg                                                     20

<210> SEQ ID NO 137
<211> LENGTH: 22
<212> TYPE: DNA
<213> ORGANISM: Artificial Sequence
<220> FEATURE:
<223> OTHER INFORMATION: Description of artificial sequence note =
      synthetic construct

<400> SEQUENCE: 137
aagacgttct gtctcctgtg ct                                                  22
```

<210> SEQ ID NO 138
<211> LENGTH: 21
<212> TYPE: DNA
<213> ORGANISM: Artificial Sequence
<220> FEATURE:
<223> OTHER INFORMATION: Description of artificial sequence note = synthetic construct

<400> SEQUENCE: 138
gagttaaaag aggctgcagt g 21

<210> SEQ ID NO 139
<211> LENGTH: 112
<212> TYPE: PRT
<213> ORGANISM: Artificial Sequence
<220> FEATURE:
<223> OTHER INFORMATION: Description of artificial sequence note = synthetic construct

<400> SEQUENCE: 139

Lys Ala Thr Val Thr Ala Met Ile Ala Arg Glu Leu Leu Tyr Gly Gly
1               5                   10                  15

Thr Ser Pro Thr Ala Glu Thr Ile Leu Lys Asn Asn Ile Ser Ser Gly
            20                  25                  30

His Val Pro His Gly Pro Leu Thr Arg Pro Ser Glu Gln Leu Asp Tyr
        35                  40                  45

Leu Ser Arg Val Gln Gly Phe Gln Val Glu Tyr Lys Asp Phe Pro Lys
    50                  55                  60

Asn Asn Lys Asn Glu Phe Val Ser Leu Ile Asn Cys Ser Ser Gln Pro
65                  70                  75                  80

Pro Leu Ile Ser His Gly Ile Gly Lys Asp Val Glu Ser Cys His Asp
                85                  90                  95

Met Ala Ala Leu Asn Ile Leu Lys Leu Leu Ser Glu Leu Asp Gln Gln
            100                 105                 110

<210> SEQ ID NO 140
<211> LENGTH: 112
<212> TYPE: PRT
<213> ORGANISM: Artificial Sequence
<220> FEATURE:
<223> OTHER INFORMATION: Description of artificial sequence note = synthetic construct

<400> SEQUENCE: 140

Lys Ala Thr Val Thr Ala Met Ile Ala Arg Glu Leu Leu Tyr Gly Gly
1               5                   10                  15

Thr Ser Pro Thr Ala Glu Thr Ile Leu Lys Ser Asn Ile Ser Ser Gly
            20                  25                  30

His Val Pro His Gly Pro Arg Thr Arg Pro Ser Glu Gln Leu Tyr Tyr
        35                  40                  45

Leu Ser Arg Ala Gln Gly Phe Gln Val Glu Tyr Lys Asp Phe Pro Lys
    50                  55                  60

Asn Asn Lys Asn Glu Cys Val Ser Leu Ile Asn Cys Ser Ser Gln Pro
65                  70                  75                  80

Pro Leu Val Ser His Gly Ile Gly Lys Asp Val Glu Ser Cys His Asp
                85                  90                  95

Met Ala Ala Leu Asn Ile Leu Lys Leu Leu Ser Glu Leu Asp Gln Gln
            100                 105                 110

<210> SEQ ID NO 141
<211> LENGTH: 112

```
<212> TYPE: PRT
<213> ORGANISM: Artificial Sequence
<220> FEATURE:
<223> OTHER INFORMATION: Description of artificial sequence note =
      synthetic construct

<400> SEQUENCE: 141

Lys Ala Thr Val Thr Ala Met Ile Ala Arg Glu Leu Leu Tyr Gly Gly
1               5                   10                  15

Thr Ser Pro Thr Ala Glu Thr Ile Leu Lys Ser Ser Ser Ser Ser Gly
            20                  25                  30

His Phe Pro His Gly Pro Leu Thr Arg Pro Ser Glu Gln Leu Asp Tyr
        35                  40                  45

Leu Ser Asn Val Gln Gly Ile Gln Val Glu Tyr Lys Asp Phe Pro Lys
    50                  55                  60

Asn Asn Lys Asn Glu Phe Val Ser Leu Ile Asn Cys Ser Ser Gln Pro
65                  70                  75                  80

Pro Leu Ile Ser His Gly Ile Gly Lys Asp Val Glu Ser Cys His Asp
                85                  90                  95

Met Ala Ala Leu Asn Ile Leu Lys Leu Leu Ser Glu Leu Asp Gln Gln
            100                 105                 110

<210> SEQ ID NO 142
<211> LENGTH: 111
<212> TYPE: PRT
<213> ORGANISM: Artificial Sequence
<220> FEATURE:
<223> OTHER INFORMATION: Description of artificial sequence note =
      synthetic construct

<400> SEQUENCE: 142

Lys Ala Thr Val Thr Ala Met Ile Ala Arg Glu Leu Leu Tyr Gly Gly
1               5                   10                  15

Thr Ser Pro Thr Ala Glu Thr Ile Leu Lys Asn Ser Ser Ser Gly His
            20                  25                  30

Val Leu His Gly Pro Phe Thr Arg Pro Ser Glu Gln Leu Asn Tyr Leu
        35                  40                  45

Ser Gly Val Gln Gly Ile Gln Val Glu Tyr Lys Asp Phe Pro Lys Asn
    50                  55                  60

Asn Lys Asn Glu Phe Val Ser Leu Ile Asn Cys Ser Ser Gln Pro Pro
65                  70                  75                  80

Leu Ile Ser His Gly Ile Gly Lys Asp Val Glu Ser Cys His Asp Met
                85                  90                  95

Ala Ala Leu Asn Ile Leu Lys Leu Leu Ser Glu Leu Asp Gln Gln
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Description of artificial sequence note =
      synthetic construct

<400> SEQUENCE: 143

Lys Ala Thr Val Thr Ala Met Ile Ala Asn Glu Leu Leu Tyr Ala Gly
1               5                   10                  15

Thr Ser Pro Thr Ala Glu Gly Ile Leu Lys Thr Asn Asn Ser Leu Ala
            20                  25                  30

His Arg Pro Gln Gly Pro Leu Thr Arg Pro Ser Glu Gln Leu Ser Tyr
```

```
                    35                  40                  45

Leu Ala Asn Val Gln Gly Leu Gln Val Glu Tyr Lys Asp Phe Pro Lys
 50                  55                  60

Asn Asn Lys Asn Glu Phe Val Ser Leu Ile Asn Cys Ser Ser Gln Pro
65                  70                  75                  80

Pro Leu Ile Ser His Gly Ile Gly Lys Asp Val Glu Ser Cys His Asp
                85                  90                  95

Met Ala Ala Leu Asn Ile Leu Lys Leu Leu Ser Glu Leu Asp Gln Gln
                100                 105                 110

<210> SEQ ID NO 144
<211> LENGTH: 112
<212> TYPE: PRT
<213> ORGANISM: Artificial Sequence
<220> FEATURE:
<223> OTHER INFORMATION: Description of artificial sequence note =
      synthetic construct

<400> SEQUENCE: 144

Lys Ala Thr Val Thr Ala Met Ile Ala Arg Glu Leu Leu Tyr Ala Gly
 1               5                  10                  15

Ile Ser Pro Thr Ala Asp Thr Ile Leu Lys Asn Asn Asn Ala Ala Gly
                20                  25                  30

His Val Leu Arg Gly Pro Phe Thr Arg Pro Ser Glu Gln Leu Asn Tyr
                35                  40                  45

Leu Ser Arg Val Gln Gly Leu Glu Val Glu Tyr Lys Asp Phe Pro Lys
 50                  55                  60

Asn Asn Lys Asn Glu Phe Val Ser Leu Ile Asn Cys Ser Ser Gln Pro
65                  70                  75                  80

Pro Leu Ile Ser His Gly Ile Gly Lys Asp Val Glu Ser Cys His Asp
                85                  90                  95

Met Ala Ala Leu Asn Ile Leu Lys Leu Leu Ser Glu Leu Asp Gln Gln
                100                 105                 110

<210> SEQ ID NO 145
<211> LENGTH: 107
<212> TYPE: PRT
<213> ORGANISM: Artificial Sequence
<220> FEATURE:
<223> OTHER INFORMATION: Description of artificial sequence note =
      synthetic construct

<400> SEQUENCE: 145

Ser Gln Ser Cys Thr Ala Ile Ala Arg Glu Leu Leu Thr Asn Gly
 1               5                  10                  15

Thr Ser Pro Thr Ala Glu Ala Ile Gly Phe Thr Gly Lys Asn Leu Met
                20                  25                  30

Cys His Ser Ser Thr Val Gln Pro Ser Lys Gln Leu Glu Tyr Leu Ala
            35                  40                  45

Gly Ile Gln Gly Phe Gln Val Asn Tyr Ser Asp Arg Gln Asn Gly Asn
            50                  55                  60

Asp Phe Leu Thr Cys Leu Thr Leu Ser Pro Val Gln Met Thr Phe His
65                  70                  75                  80

Gly Ile Gly Ser Ser Leu Glu Ala Ser His Asp Gln Ala Ala Leu Ser
                85                  90                  95

Ala Leu Lys Gln Phe Ser Glu Gln Gly Leu Glu
                100                 105
```

```
<210> SEQ ID NO 146
<211> LENGTH: 55
<212> TYPE: PRT
<213> ORGANISM: Artificial Sequence
<220> FEATURE:
<223> OTHER INFORMATION: Description of artificial sequence note =
      synthetic construct

<400> SEQUENCE: 146

Thr Ser Asn Ser Ser Ala Thr Ile Ala Arg Glu Leu Leu Met Asn Gly
1               5                   10                  15

Thr Ser Ser Thr Ala Glu Ala Ile Gly Leu Lys Gly Ser Ser Pro Thr
                20                  25                  30

Pro Pro Cys Ser Pro Val Gln Pro Ser Lys Gln Leu Glu Tyr Leu Ala
            35                  40                  45

Arg Ile Gln Gly Phe Gln Val
        50                  55

<210> SEQ ID NO 147
<211> LENGTH: 69
<212> TYPE: PRT
<213> ORGANISM: Artificial Sequence
<220> FEATURE:
<223> OTHER INFORMATION: Description of artificial sequence note =
      synthetic construct

<400> SEQUENCE: 147

Thr Ser Asn Ser Ser Ala Thr Ile Ala Arg Glu Leu Leu Met Asn Gly
1               5                   10                  15

Thr Ser Ser Thr Ala Glu Ala Ile Gly Leu Lys Gly Ser Ser Pro Thr
                20                  25                  30

Pro Pro Cys Ser Pro Val Gln Pro Ser Lys Gln Leu Glu Tyr Leu Ala
            35                  40                  45

Arg Ile Gln Gly Phe Gln Ala Ala Leu Ser Ala Leu Lys Gln Phe Ser
        50                  55                  60

Glu Gln Gly Leu Asp
65

<210> SEQ ID NO 148
<211> LENGTH: 69
<212> TYPE: PRT
<213> ORGANISM: Artificial Sequence
<220> FEATURE:
<223> OTHER INFORMATION: Description of artificial sequence note =
      synthetic construct

<400> SEQUENCE: 148

Ser Ser Thr Ser Ser Ala Thr Val Ala Arg Glu Leu Leu Met Asn Gly
1               5                   10                  15

Thr Ser Pro Thr Ala Glu Ala Ile Gly Leu Lys Gly Ser Ser Pro Thr
                20                  25                  30

Ser Pro Cys Ser Ser Val Gln Pro Ser Lys Gln Leu Glu Tyr Leu Ala
            35                  40                  45

Arg Ile Gln Gly Phe Gln Ala Ala Leu Ser Ala Leu Lys Gln Phe Ser
        50                  55                  60

Glu Gln Gly Leu Glu
65

<210> SEQ ID NO 149
<211> LENGTH: 110
<212> TYPE: PRT
<213> ORGANISM: Artificial Sequence
```

```
-continued
```

```
<220> FEATURE:
<223> OTHER INFORMATION: Description of artificial sequence note =
      synthetic construct

<400> SEQUENCE: 149

Ser Met Ala Thr Thr Ala Thr Ile Ala Lys Glu Leu Leu Ile Asn Gly
1               5                   10                  15

Lys Ser Pro Thr Ala Asp Ala Leu Ile Lys Ser Gly Thr Gly Pro Lys
            20                  25                  30

Thr Glu Gln Lys Leu Leu Arg Pro Lys Gln Gln Leu Met Phe Leu Ala
        35                  40                  45

Glu Ile Gln Gly Leu Gln Val Glu Phe Thr Asp Phe Pro Lys Gly Asn
    50                  55                  60

Lys Pro Glu Tyr Leu Ser Leu Val Ser Ile Ala Thr Asn Pro Pro Leu
65                  70                  75                  80

Val Ala His Gly Ala Gly Pro Thr Val Asp Ser Ser Tyr Asp Ala Ala
                85                  90                  95

Ala Leu Gln Ala Leu Lys Ser Leu Thr Asp Met Asp Ile Gly
            100                 105                 110

<210> SEQ ID NO 150
<211> LENGTH: 107
<212> TYPE: PRT
<213> ORGANISM: Artificial Sequence
<220> FEATURE:
<223> OTHER INFORMATION: Description of artificial sequence note =
      synthetic construct

<400> SEQUENCE: 150

Asp Leu Gln Ala Ser Ser Ala Ile Ala Lys Glu Leu Leu Asp Gln Gly
1               5                   10                  15

Val Ser Pro Thr Ala Glu Ala Leu Arg Gln Ala Ala Pro Leu Thr Val
            20                  25                  30

Ala Pro Val Arg Pro Lys Gln Gln Leu Leu Tyr Leu Ala Glu Val Leu
        35                  40                  45

Gly Phe Gln Val His Phe Thr Asp Phe Pro Lys Gly Asn Lys Arg Asp
    50                  55                  60

Phe Leu Ser Leu Val Thr Leu Thr Thr Cys Pro Pro Gln Val Ser His
65                  70                  75                  80

Gly Ala Gly Ser Ser Leu Glu Ala Ser His Asp Glu Ala Ala Leu Ala
                85                  90                  95

Val Leu Arg Thr Leu Ala Arg Arg Gly Leu Asp
            100                 105

<210> SEQ ID NO 151
<211> LENGTH: 99
<212> TYPE: PRT
<213> ORGANISM: Artificial Sequence
<220> FEATURE:
<223> OTHER INFORMATION: Description of artificial sequence note =
      synthetic construct

<400> SEQUENCE: 151

Phe Ile Thr Asn Ser Ser Thr Ala Thr Gly Ile Lys Glu Thr Thr Gln
1               5                   10                  15

Pro Ser Arg Pro Pro Lys Thr Ser Gly Gly Leu Arg Pro Glu Ile Arg
            20                  25                  30

Leu Arg Tyr Ile Ala Gln Val Leu Glu Tyr Glu Val Glu Phe Ser Asp
        35                  40                  45
```

```
Phe Pro Lys Gly Lys Lys Gly Asp Phe Val Ser Leu Val Thr Leu Asn
        50                  55                  60

Thr Asn Pro Pro Gln Val Ser His Gly Leu Gly Ala Thr Leu Glu Glu
 65                  70                  75                  80

Ala His Asp Asn Ala Ala Ser Asn Met Met Lys Leu Leu Ser Glu Gly
                 85                  90                  95

Ser Gln Asp

<210> SEQ ID NO 152
<211> LENGTH: 148
<212> TYPE: PRT
<213> ORGANISM: Artificial Sequence
<220> FEATURE:
<223> OTHER INFORMATION: Description of artificial sequence note =
      synthetic construct

<400> SEQUENCE: 152

Ala Asn Ser Gly Asp Ser Ser Asn Ser Ser Gly Asp Ser Gln Ala
 1               5                  10                  15

Thr Glu Ala Ala Ser Glu Ser Ala Leu Asn Thr Ser Thr Gly Ser Asn
                 20                  25                  30

Thr Ser Gly Val Ser Ser Asn Ser Asn Val Gly Ala Asn Thr Asp
             35                  40                  45

Gly Asn Asn His Ala Glu Ser Lys Asn Thr Glu Ser Ser Ser Asn
 50                  55                  60

Ser Asn Ser Thr Ser Asn Thr Gln Ser Ala Gly Val His Met Lys Glu
 65                  70                  75                  80

Gln Leu Leu Tyr Leu Ser Lys Leu Leu Asp Phe Glu Val Asn Phe Ser
                 85                  90                  95

Asp Tyr Pro Lys Gly Asn His Asn Glu Phe Leu Thr Ile Val Thr Leu
                100                 105                 110

Ser Thr His Pro Pro Gln Ile Cys His Gly Val Gly Lys Ser Ser Glu
             115                 120                 125

Glu Ser Gln Asn Asp Ala Ala Ser Asn Ala Leu Lys Ile Leu Ser Lys
         130                 135                 140

Leu Gly Leu Asn
145

<210> SEQ ID NO 153
<211> LENGTH: 100
<212> TYPE: PRT
<213> ORGANISM: Artificial Sequence
<220> FEATURE:
<223> OTHER INFORMATION: Description of artificial sequence note =
      synthetic construct

<400> SEQUENCE: 153

Asp Ser Ile Ala Ser Asn Asp Ser Met Gly Thr Asn Ser Ser Gly Val
 1               5                  10                  15

Ser Ser Thr Ser Ser Val Ala Pro Lys Ala Asp Ile Gly Ala Lys Lys
                 20                  25                  30

Glu Gln Leu Leu Tyr Leu Ala Gln Leu Leu Lys Phe Glu Val Gln Phe
                 35                  40                  45

Ser Asp Phe Pro Lys Gly Asn His Gly Glu Tyr Leu Thr Leu Val Ile
             50                  55                  60

Leu Ser Thr Glu Pro Pro Gln Leu Cys His Gly Ser Gly Ala Ser Leu
 65                  70                  75                  80

Gln Glu Ser His Asp Glu Ala Ala Arg Gly Ala Leu Glu Ile Leu Ser
```

```
                    85                  90                  95

Lys Ile Gly Leu
            100

<210> SEQ ID NO 154
<211> LENGTH: 127
<212> TYPE: PRT
<213> ORGANISM: Artificial Sequence
<220> FEATURE:
<223> OTHER INFORMATION: Description of artificial sequence note =
      synthetic construct

<400> SEQUENCE: 154

Gln Ser Leu Lys Lys Asp Ala Ile Val Glu Gly Lys Ile Arg Arg Leu
1               5                   10                  15

Lys Arg Ser Lys Glu Asn Arg Arg Ala Leu Thr Ala Glu Gln Ile Val
            20                  25                  30

Glu Leu Ser Glu Arg Ala Gln Ser Tyr Leu Gln Thr Lys Asn Thr Thr
        35                  40                  45

Ile Gln Ser Ser Gln Ser Ser Ala His His His Leu Glu Gln Leu
50                  55                  60

Ser Asp Phe Phe Lys Phe Ser Leu Gln Tyr Thr Ser Phe Pro Gln Val
65                  70                  75                  80

Gly Ile Asp Gln His Phe Thr Ile Val Ser Ile Gly Leu Glu Ala Pro
                85                  90                  95

Leu Val Gly His Gly Thr Gly Cys Ser Thr Thr Glu Ala Asp Glu Asn
            100                 105                 110

Ala Ala Leu Asp Ala Ile Ala Lys Leu Lys Glu Leu Ser Ala Ser
        115                 120                 125

<210> SEQ ID NO 155
<211> LENGTH: 104
<212> TYPE: PRT
<213> ORGANISM: Artificial Sequence
<220> FEATURE:
<223> OTHER INFORMATION: Description of artificial sequence note =
      synthetic construct

<400> SEQUENCE: 155

Lys Glu Ser Val Met Asn Asn Ser Asn Ser Cys Val Asp Thr Lys
1               5                   10                  15

Lys Thr Gly Gln Thr Gln Met Lys Thr Pro Pro Gln Pro Ile Gln Gly
            20                  25                  30

Val Arg Ser Lys Asp Gln Leu Met Tyr Leu Ala Gln Leu Met Asn Ile
        35                  40                  45

Gln Val Gln Phe Ser Asp Phe Pro Lys Ala Asn His Glu Met Tyr Leu
    50                  55                  60

Thr Leu Val Ser Leu Ser Thr Asn Pro Pro Gln Val Cys His Gly Glu
65                  70                  75                  80

Gly Pro Thr Thr Glu Ala Ser His Glu Lys Ala Ala Leu Glu Ala Leu
                85                  90                  95

Lys Val Leu Ser Glu Leu Gly Leu
            100

<210> SEQ ID NO 156
<211> LENGTH: 65
<212> TYPE: PRT
<213> ORGANISM: Artificial Sequence
<220> FEATURE:
<223> OTHER INFORMATION: Description of artificial sequence note =
``` synthetic construct

<400> SEQUENCE: 156

Pro Ser Glu Gln Leu Asp Tyr Leu Ser Arg Val Gln Gly Phe Gln Val
1               5                   10                  15

Glu Tyr Lys Asp Phe Pro Lys Asn Asn Lys Asn Glu Phe Val Ser Leu
            20                  25                  30

Ile Asn Cys Ser Ser Gln Pro Pro Leu Ile Ser His Gly Ile Gly Lys
        35                  40                  45

Asp Val Glu Ser Cys His Asp Met Ala Ala Leu Asn Ile Leu Lys Leu
    50                  55                  60

Leu
65

<210> SEQ ID NO 157
<211> LENGTH: 65
<212> TYPE: PRT
<213> ORGANISM: Artificial Sequence
<220> FEATURE:
<223> OTHER INFORMATION: Description of artificial sequence note =
      synthetic construct

<400> SEQUENCE: 157

Pro Ile Ser Leu Leu Gln Glu Tyr Gly Thr Arg Ile Gly Lys Thr Pro
1               5                   10                  15

Val Tyr Asp Leu Leu Lys Ala Glu Gly Gln Ala His Gln Pro Asn Phe
            20                  25                  30

Thr Phe Arg Val Thr Val Gly Asp Thr Ser Cys Thr Gly Gln Gly Pro
        35                  40                  45

Ser Lys Lys Ala Ala Lys His Lys Ala Ala Glu Val Ala Leu Lys His
    50                  55                  60

Leu
65

<210> SEQ ID NO 158
<211> LENGTH: 68
<212> TYPE: PRT
<213> ORGANISM: Artificial Sequence
<220> FEATURE:
<223> OTHER INFORMATION: Description of artificial sequence note =
      synthetic construct

<400> SEQUENCE: 158

Lys Ser Glu Ile Ser Gln Val Phe Gly Ile Ala Leu Lys Arg Asn Leu
1               5                   10                  15

Pro Val Asn Phe Glu Val Ala Arg Glu Ser Gly Pro Pro His Met Lys
            20                  25                  30

Asn Phe Val Thr Lys Val Ser Val Gly Glu Phe Val Gly Glu Gly Glu
        35                  40                  45

Gly Lys Ser Lys Lys Ile Ser Lys Lys Asn Ala Ala Ile Ala Val Leu
    50                  55                  60

Glu Glu Leu Lys
65

<210> SEQ ID NO 159
<211> LENGTH: 68
<212> TYPE: PRT
<213> ORGANISM: Artificial Sequence
<220> FEATURE:
<223> OTHER INFORMATION: Description of artificial sequence note =
      synthetic construct -continued

<400> SEQUENCE: 159

Lys Ser Pro Ile Ser Gln Val His Glu Ile Gly Ile Lys Arg Asn Met
1               5                   10                  15

Thr Val His Phe Lys Val Leu Arg Glu Glu Gly Pro Ala His Met Lys
            20                  25                  30

Asn Phe Ile Thr Ala Cys Ile Val Gly Ser Ile Val Thr Glu Gly Glu
        35                  40                  45

Gly Asn Gly Lys Lys Val Ser Lys Arg Ala Ala Glu Lys Met Leu
    50                  55                  60

Val Glu Leu Gln
65

<210> SEQ ID NO 160
<211> LENGTH: 68
<212> TYPE: PRT
<213> ORGANISM: Artificial Sequence
<220> FEATURE:
<223> OTHER INFORMATION: Description of artificial sequence note =
      synthetic construct

<400> SEQUENCE: 160

Thr Arg Pro Ser Glu Gln Leu Asp Tyr Leu Ser Arg Val Gln Gly Phe
1               5                   10                  15

Gln Val Glu Tyr Lys Asp Phe Pro Lys Asn Asn Lys Asn Glu Phe Val
            20                  25                  30

Ser Leu Ile Asn Cys Ser Ser Gln Pro Pro Leu Ile Ser His Gly Ile
        35                  40                  45

Gly Lys Asp Val Glu Ser Cys His Asp Met Ala Ala Leu Asn Ile Leu
    50                  55                  60

Lys Leu Leu Ser
65

<210> SEQ ID NO 161
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 161
aaaaggatcc aaggccacgg taactgccat g                              31

<210> SEQ ID NO 162
<211> LENGTH: 35
<212> TYPE: DNA
<213> ORGANISM: Artificial Sequence
<220> FEATURE:
<223> OTHER INFORMATION: Description of artificial sequence note =
      synthetic construct

<400> SEQUENCE: 162
aaaagaattc ttatcagtcc aactcagaca gcaac                          35

<210> SEQ ID NO 163
<211> LENGTH: 35
<212> TYPE: DNA
<213> ORGANISM: Artificial Sequence
<220> FEATURE:
<223> OTHER INFORMATION: Description of artificial sequence note =
      synthetic construct

```
<400> SEQUENCE: 163
gattccaggt tcattacaaa gtcttcccca aaaac                              35

<210> SEQ ID NO 164
<211> LENGTH: 35
<212> TYPE: DNA
<213> ORGANISM: Artificial Sequence
<220> FEATURE:
<223> OTHER INFORMATION: Description of artificial sequence note =
      synthetic construct

<400> SEQUENCE: 164
gtttttgggg aagactttgt aatgaacctg gaatc                             35

<210> SEQ ID NO 165
<211> LENGTH: 35
<212> TYPE: DNA
<213> ORGANISM: Artificial Sequence
<220> FEATURE:
<223> OTHER INFORMATION: Description of artificial sequence note =
      synthetic construct

<400> SEQUENCE: 165
aaaagaattc ttatcagtcc aactcagaca gcaac                             35

<210> SEQ ID NO 166
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 166
aaaaaagctt aaggccacgg taactgccat g                                 31

<210> SEQ ID NO 167
<211> LENGTH: 31
<212> TYPE: DNA
<213> ORGANISM: Artificial Sequence
<220> FEATURE:
<223> OTHER INFORMATION: Description of artificial sequence note =
      synthetic construct

<400> SEQUENCE: 167
aaaaaagctt agaccctctg agcaactgga c                                 31

<210> SEQ ID NO 168
<211> LENGTH: 33
<212> TYPE: DNA
<213> ORGANISM: Artificial Sequence
<220> FEATURE:
<223> OTHER INFORMATION: Description of artificial sequence note =
      synthetic construct

<400> SEQUENCE: 168
aaaaaagctt ctaaggccac ggtaactgcc atg                               33

<210> SEQ ID NO 169
<211> LENGTH: 33
<212> TYPE: DNA
<213> ORGANISM: Artificial Sequence
<220> FEATURE:
<223> OTHER INFORMATION: Description of artificial sequence note =
      synthetic construct

<400> SEQUENCE: 169
```
aaaaaagctt ctagaccctc tgagcaactg gac                          33

<210> SEQ ID NO 170
<211> LENGTH: 30
<212> TYPE: DNA
<213> ORGANISM: Artificial Sequence
<220> FEATURE:
<223> OTHER INFORMATION: Description of artificial sequence note =
      synthetic construct

<400> SEQUENCE: 170
caccacattg gtgtgcacct ccaagcttgg                              30

<210> SEQ ID NO 171
<211> LENGTH: 42
<212> TYPE: DNA
<213> ORGANISM: Artificial Sequence
<220> FEATURE:
<223> OTHER INFORMATION: Description of artificial sequence note =
      synthetic construct

<400> SEQUENCE: 171
ccgcttcagg gcgatttcga acacttgact tatttcagat tt                42

<210> SEQ ID NO 172
<211> LENGTH: 42
<212> TYPE: DNA
<213> ORGANISM: Artificial Sequence
<220> FEATURE:
<223> OTHER INFORMATION: Description of artificial sequence note =
      synthetic construct

<400> SEQUENCE: 172
aaatctgaaa taagtcaagt gttcgaaatc gccctgaagc gg                42

<210> SEQ ID NO 173
<211> LENGTH: 28
<212> TYPE: DNA
<213> ORGANISM: Artificial Sequence
<220> FEATURE:
<223> OTHER INFORMATION: Description of artificial sequence note =
      synthetic construct

<400> SEQUENCE: 173
gaaggcacag tcgaggctga tcagcgag                                28

<210> SEQ ID NO 174
<211> LENGTH: 40
<212> TYPE: DNA
<213> ORGANISM: Artificial Sequence
<220> FEATURE:
<223> OTHER INFORMATION: Description of artificial sequence note =
      synthetic construct

<400> SEQUENCE: 174
aaaagctagc gccaccatga aacttggaaa aaaaccaatg                   40

<210> SEQ ID NO 175
<211> LENGTH: 65
<212> TYPE: DNA
<213> ORGANISM: Artificial Sequence
<220> FEATURE:
<223> OTHER INFORMATION: Description of artificial sequence note =
      synthetic construct

<400> SEQUENCE: 175

```
aaaactcgag ctattacttg tcgtcatcgt ctttgtagtc cccccgcac ctcccacaca    60 cagac                                                               65

<210> SEQ ID NO 176
<211> LENGTH: 70
<212> TYPE: DNA
<213> ORGANISM: Artificial Sequence
<220> FEATURE:
<223> OTHER INFORMATION: Description of artificial sequence note =
      synthetic construct

<400> SEQUENCE: 176
aaaactcgag ctattacttg tcgtcatcgt ctttgtagtc ccccccctgg aatccctgga   60
ctctggaaag                                                          70

<210> SEQ ID NO 177
<211> LENGTH: 72
<212> TYPE: DNA
<213> ORGANISM: Artificial Sequence
<220> FEATURE:
<223> OTHER INFORMATION: Description of artificial sequence note =
      synthetic construct

<400> SEQUENCE: 177
aaaactcgag ctattacttg tcgtcatcgt ctttgtagtc ccccccgga gctgccctgg    60 taaaatcttt gg                                                       72

<210> SEQ ID NO 178
<211> LENGTH: 29
<212> TYPE: DNA
<213> ORGANISM: Artificial Sequence
<220> FEATURE:
<223> OTHER INFORMATION: Description of artificial sequence note =
      synthetic construct

<400> SEQUENCE: 178
aaaaggatcc cctttacttt atcaagtgg                                     29

<210> SEQ ID NO 179
<211> LENGTH: 37
<212> TYPE: DNA
<213> ORGANISM: Artificial Sequence
<220> FEATURE:
<223> OTHER INFORMATION: Description of artificial sequence note =
      synthetic construct

<400> SEQUENCE: 179
aaaagaattc ttatcacggt aacttcttca gctcctc                            37
```

METHODS AND COMPOSITIONS RELATED TO STAUFEN 1 BINDING SITES FORMED BY DUPLEXING ALU ELEMENTS

This application claims the benefit of U.S. Provisional Application No. 61/440,967, filed on Feb. 9, 2011, which is incorporated by reference herein in its entirety.

This invention was made with government support under National Institutes of Health Grant GM074593, R01 GM074593, NCI T32 CA09363, 1S10 RR026501, 1S10 RR027241, NIH NIAID P30 AI078498, NIH/NCRR RR-01646, and NSF award DMR-0225180. The government has certain rights in the invention.

I. BACKGROUND OF THE INVENTION

Expression of truncated or nonsense proteins play a role or are the causative agent in many inherited disorders and cancers. These truncated or nonsense proteins result from mutations or aberrant mRNA splicing that result in early termination signals in the mRNA. Mammalian Staufen1 (Stau1) is an RNA binding protein that binds to extensive RNA secondary structures, primarily through one or more double-stranded RNA-binding domains. In mammals, the Stau1 gene is ubiquitously expressed and is involved in mRNA transport and translational control. Stau1 is associated with degradation of translationally active mRNAs that bind the double-stranded (ds)RNA binding protein STAU1, a process known as Stau1-mediated mRNA decay or SMD. What is needed or methods of identifying targets for SMD and compositions that can modulate SMD so that disorders associated with early termination signal in mRNA can be properly identified and treated.

II. SUMMARY OF THE INVENTION

In accordance with the purposes of this invention, as embodied and broadly described herein, this invention, in one aspect, relates to methods of identifying targets for Staufen 1 (Stau1) mediated decay (SMD); screening for agents that modulate SMD and treating subjects with conditions that result from or modified by affecting SMD.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows that 11 of 12 transcripts that were upregulated in human cells depleted of Stau1 using three independently performed microarray analysis are upregulated using RT-PCR and transcript-specific primers. Notably, RNAs analyzed were identical to the RNAs from Control and Stau1 siRNA-treated samples analyzed in FIG. 2. The level of each test transcript was normalized to the level of SMG7 mRNA, which is insensitive to Stau1 siRNA and served to control for variations in RNA recovery. Numbers below each lane specify the fold change in the level of each test transcript in cells treated with Stau1 siRNA relative to Control siRNA, the latter of which was defined as 1.

Figures 1, 2:
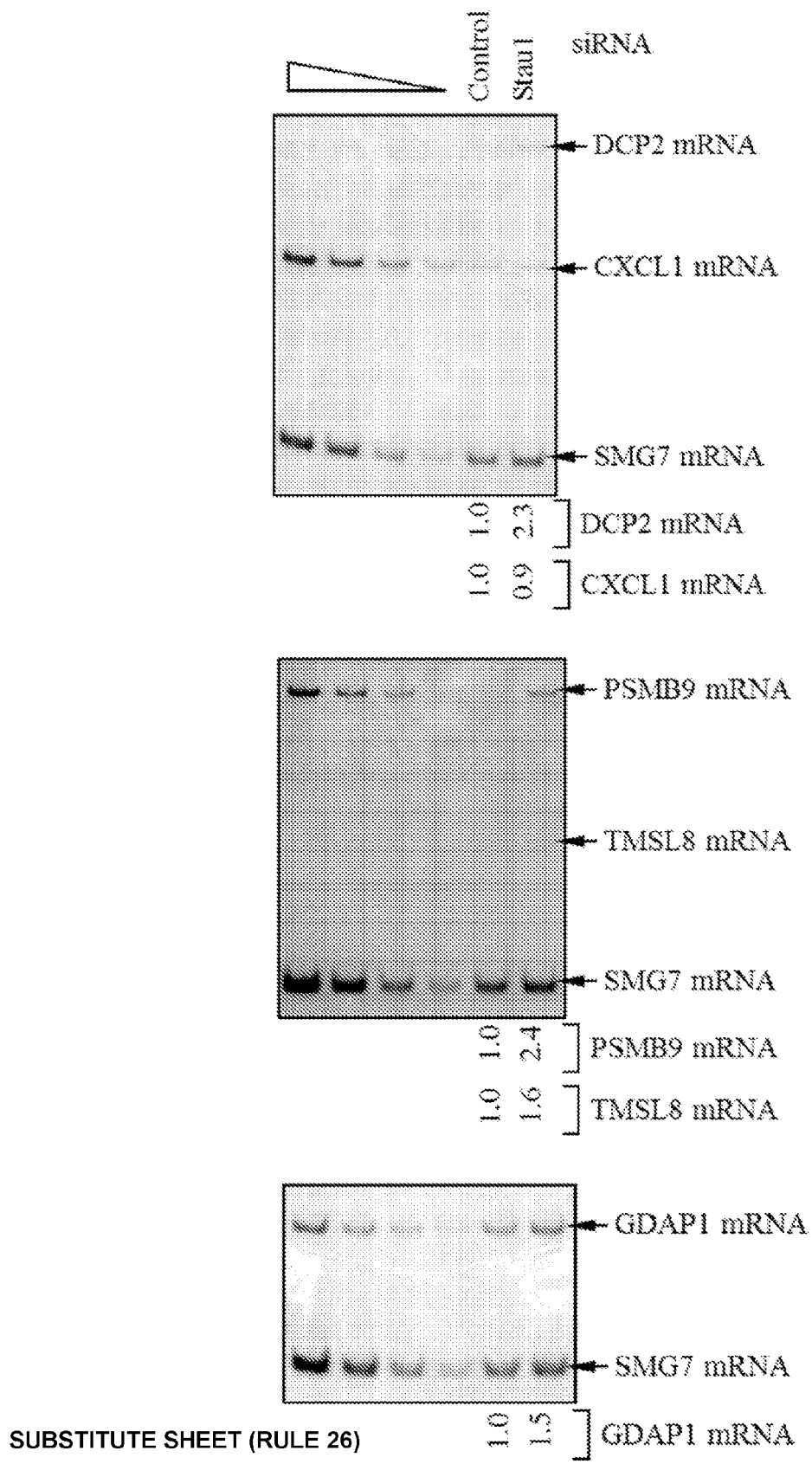
Figure 2:
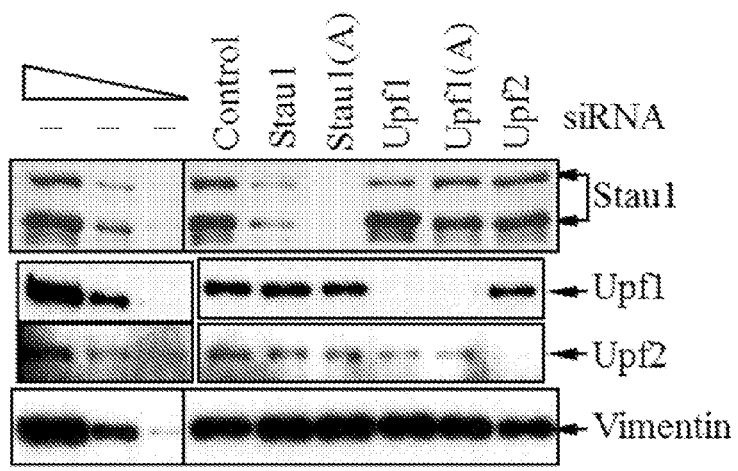
Figure 2:
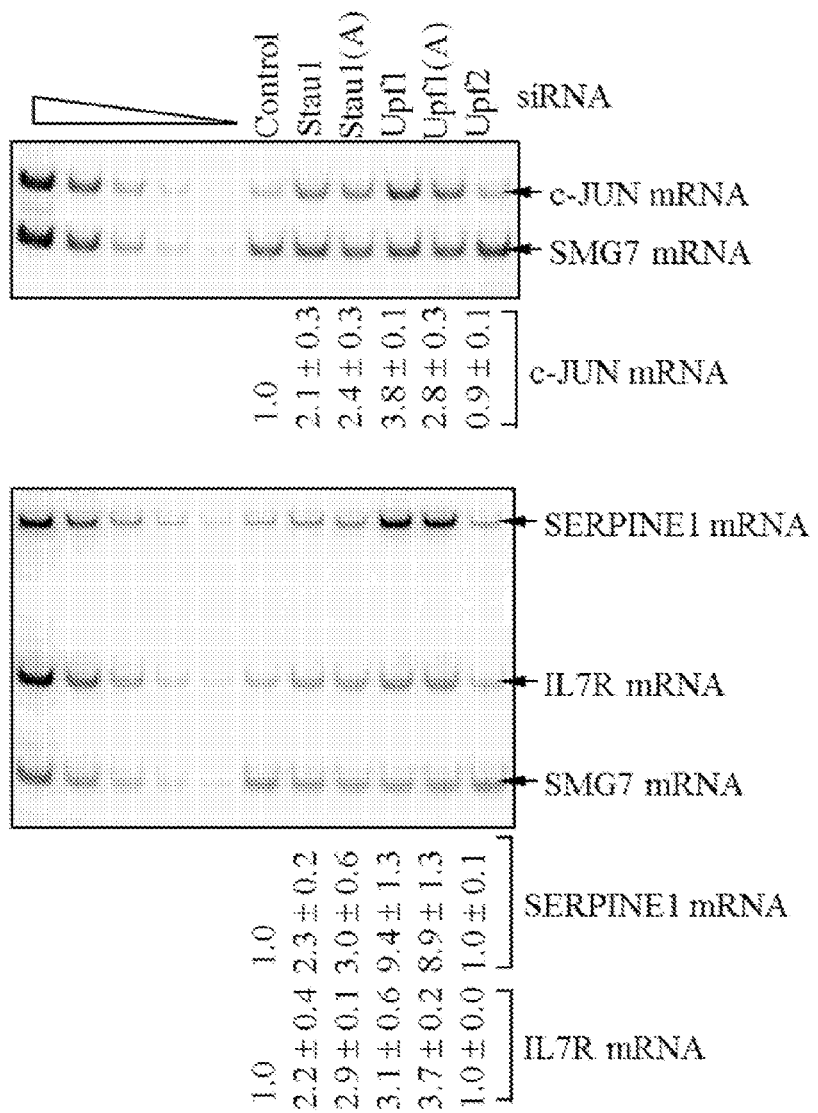

FIG. 2 shows that c-JUN, SERPINE1 and IL7R mRNAs are increased in abundance in human cells depleted of either Upf1 or Stau1 but not Upf2. HeLa cells were transiently transfected with Stau1, Stau1 (A), Upf1, Upf1(A) or Upf2 siRNA or, to control for nonspecific depletion, Control siRNA. Three days later, protein and RNA were purified. FIG. 2A shows Western blot analysis, where the level of Vimentin serves to control for variations in protein loading, and the normal level of Stau1, Upf1 or Upf2 is determined in the presence of Control siRNA. FIG. 2B shows RT-PCR analysis of the level of endogenous c-JUN mRNA (upper), SERPINE1 mRNA or IL7R mRNA (lower), each of which is normalized to the level of endogenous SMG7 mRNA. The normalized level of each mRNA in the presence of Control siRNA is defined as 1. RT-PCR results are representative of three independently performed experiments that did not differ by the amount specified.

Figure 3:
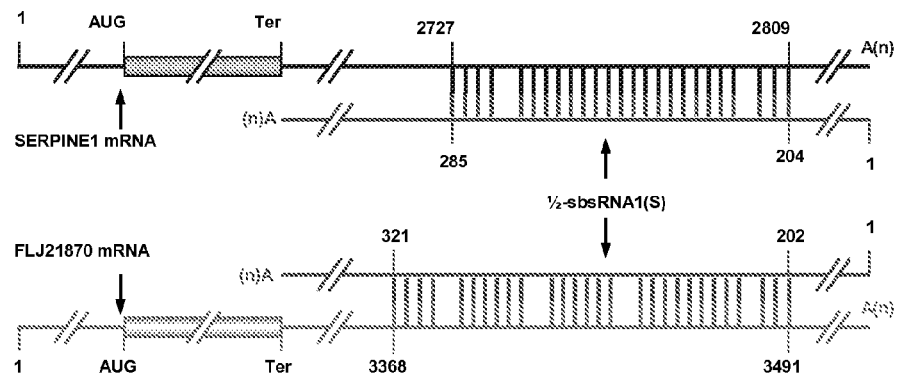
Figure 3:
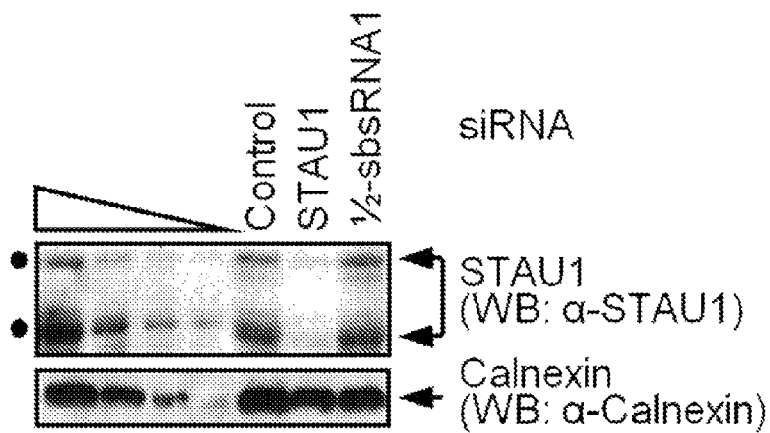
Figure 3:
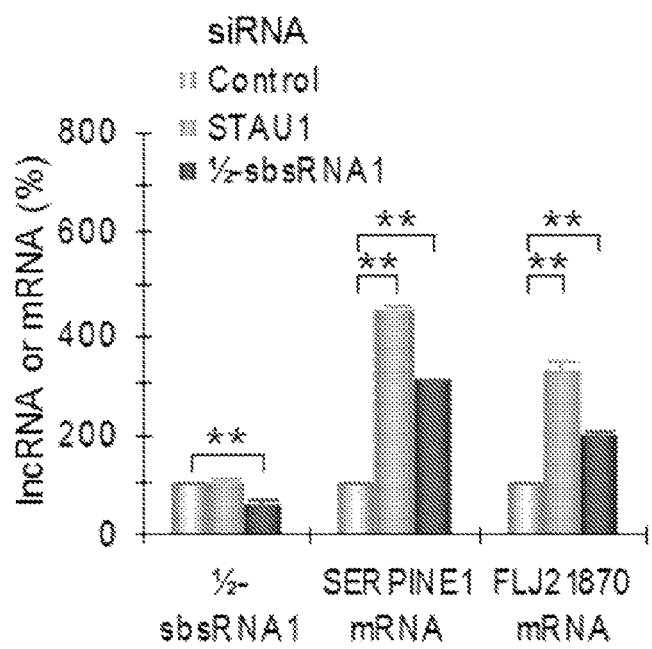
Figure 3:
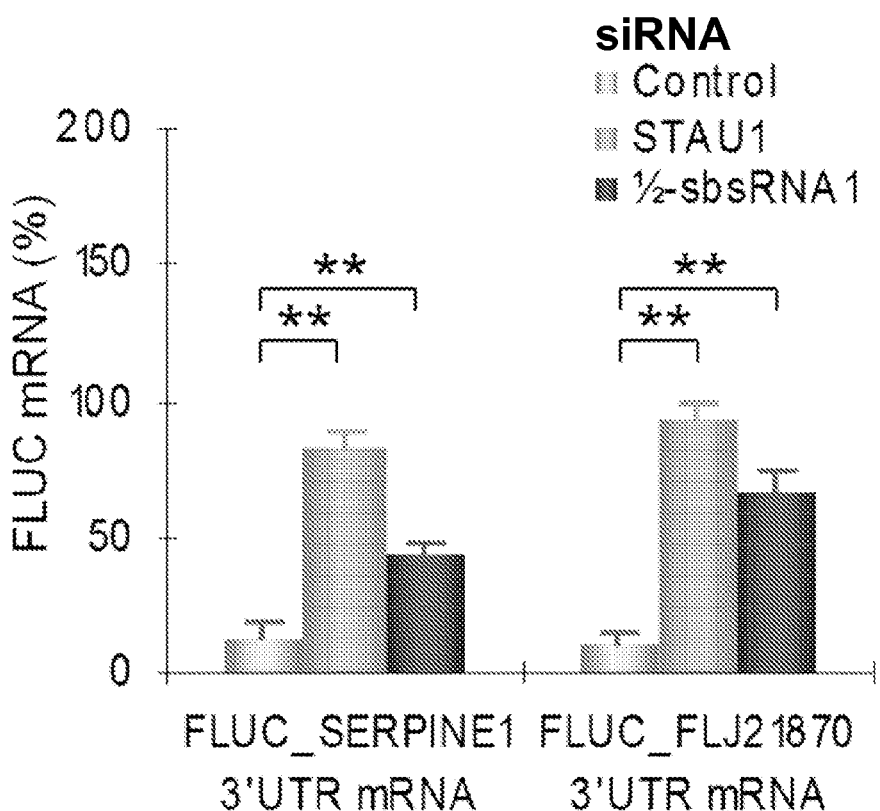
Figure 3:
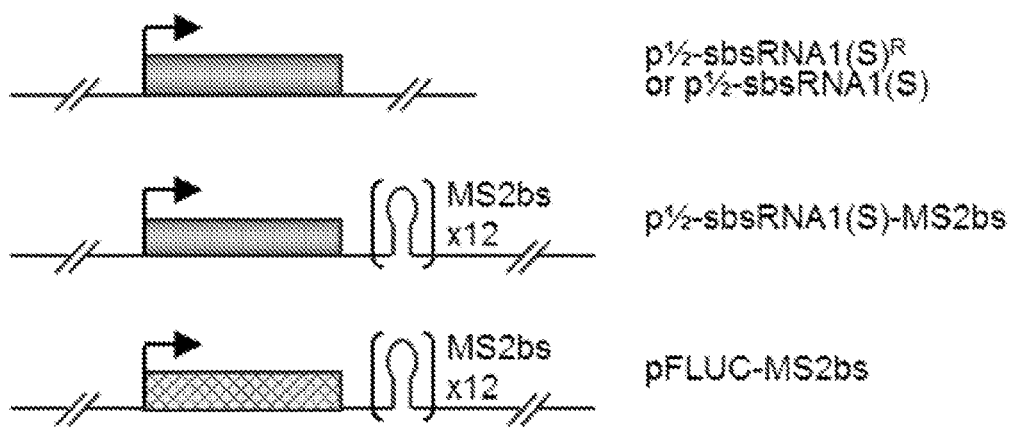
Figure 3:
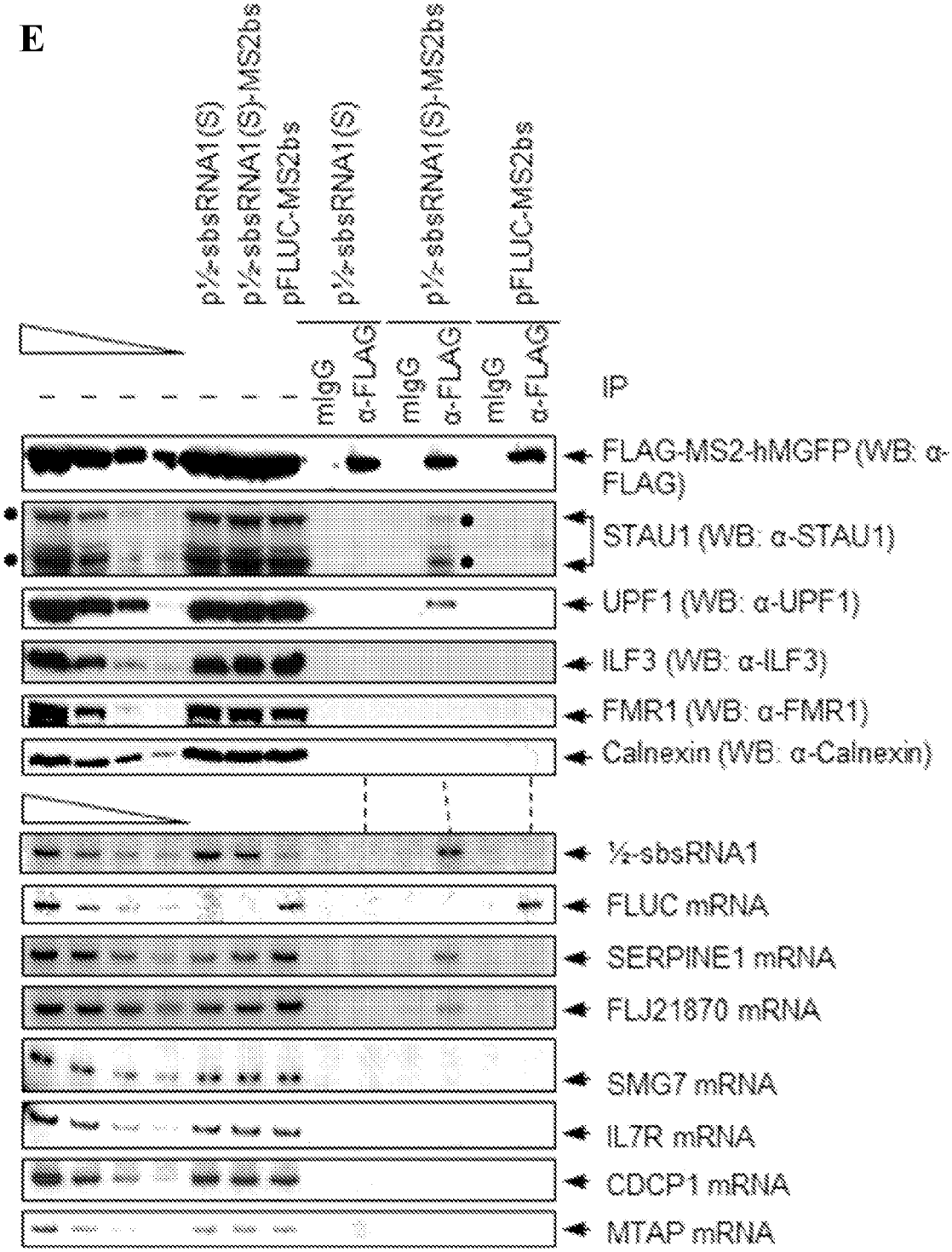
Figure 3:
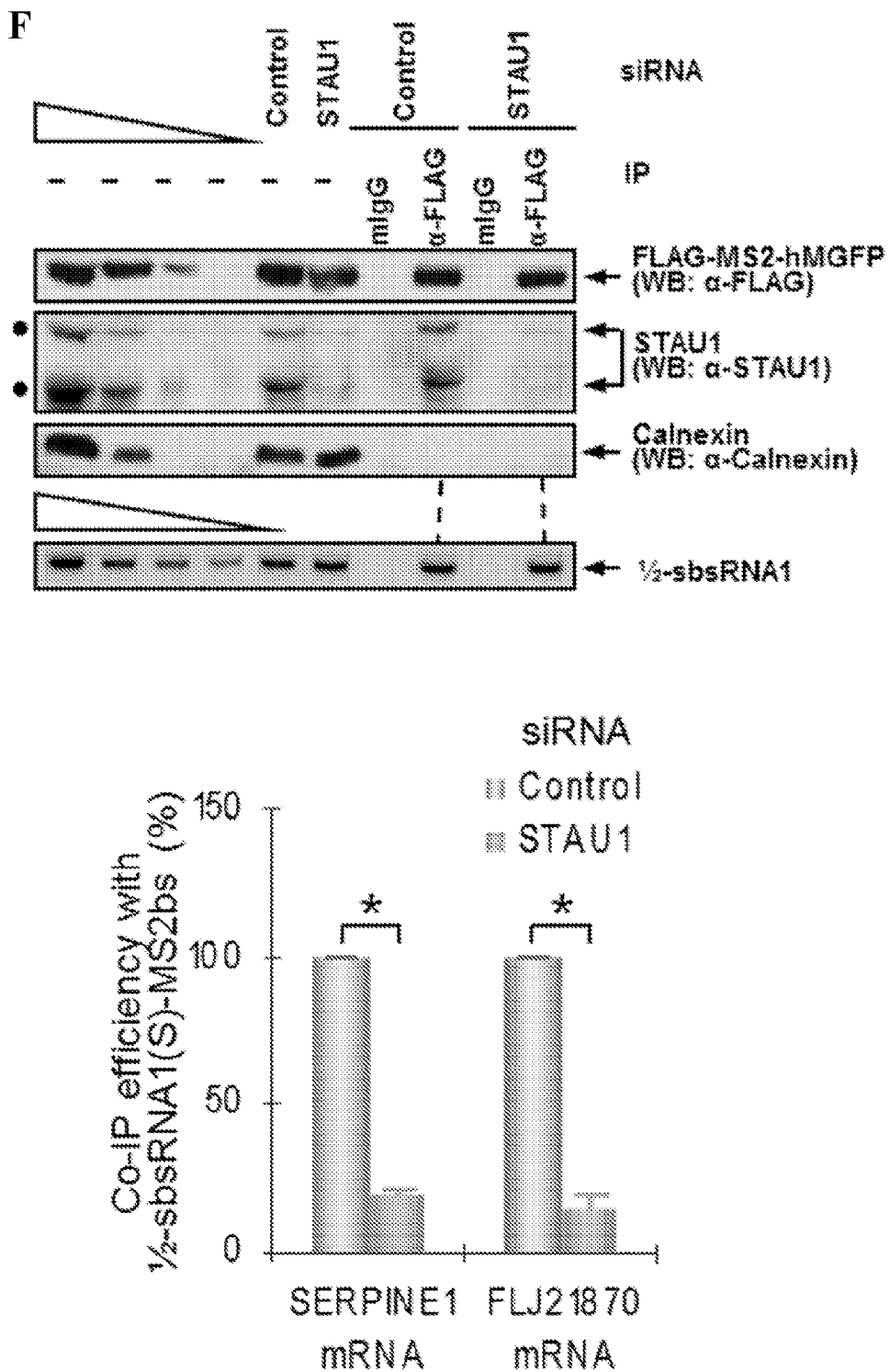

FIG. 3 shows that lncRNA_AF087999 (½-sbsRNA1) binds to and reduces the abundance of specific SMD targets. FIG. 3a shows predicted base-pairing between the Alu element within the SERPINE1 or FLJ21870 3'UTR and the Alu element within ½-sbsRNA1, where 1 was defined as the first transcribed nucleotide of each mRNA or ½-sbsRNA1(S). FIG. 3b shows at left: Western blotting (WB), using the designated antibody (α), of lysates of HeLa cells treated with the specified siRNA, where Calnexin serves as a loading control. Right: Representation of RT-sqPCR analyses of ½-sbsRNA1, SERPINE1 or FLJ21870 mRNA from the same lysates, where the normalized level of each transcript in the presence of Control siRNA was defined as 100. FIG. 3c shows representation of RT-sqPCR analyses of FLUCSERPINE1 3'UTR or FLUC-FLJ21870 3'UTR SMD reporter mRNA in cells that had been transiently transfected with the specified siRNA, where the normalized level of each transcript in the presence of Control siRNA was defined as 100. FIG. 3d shows diagrams of expression vectors encoding ½-sbsRNA1(S)R, which is siRNA-resistant, ½-sbsRNA1(S) or FLUC with or without 12 copies of the MS2 coat protein binding site (MS2bs). FIG. 3e shows western blot (upper) or RT-sqPCR (lower) before (−) or after immunoprecipitation (IP) using anti-FLAG or, as a control for nonspecific IP, mouse(m) IgG of lysates of formaldehyde-crosslinked HeLa cells that had been transiently transfected with pFLAGMS2-hMGFP and either the denoted ½-sbsRNA1(S) expression vector or pFLUC_MS2bs. FIG. 3f shows, s in 3e, except cells were treated with Control or STAU1 siRNA. Left: Western blotting. Right: RT-sqPCR, where the co-IP efficiency indicates the level of each mRNA-derived product after IP relative to before IP. Each ratio in the presence of Control siRNA was defined as 100%. Error bars indicate s.e.m. Single asterisk, n=6, P<0.01; double asterisks, n=3, P<0.05.

Figures 1, 4:
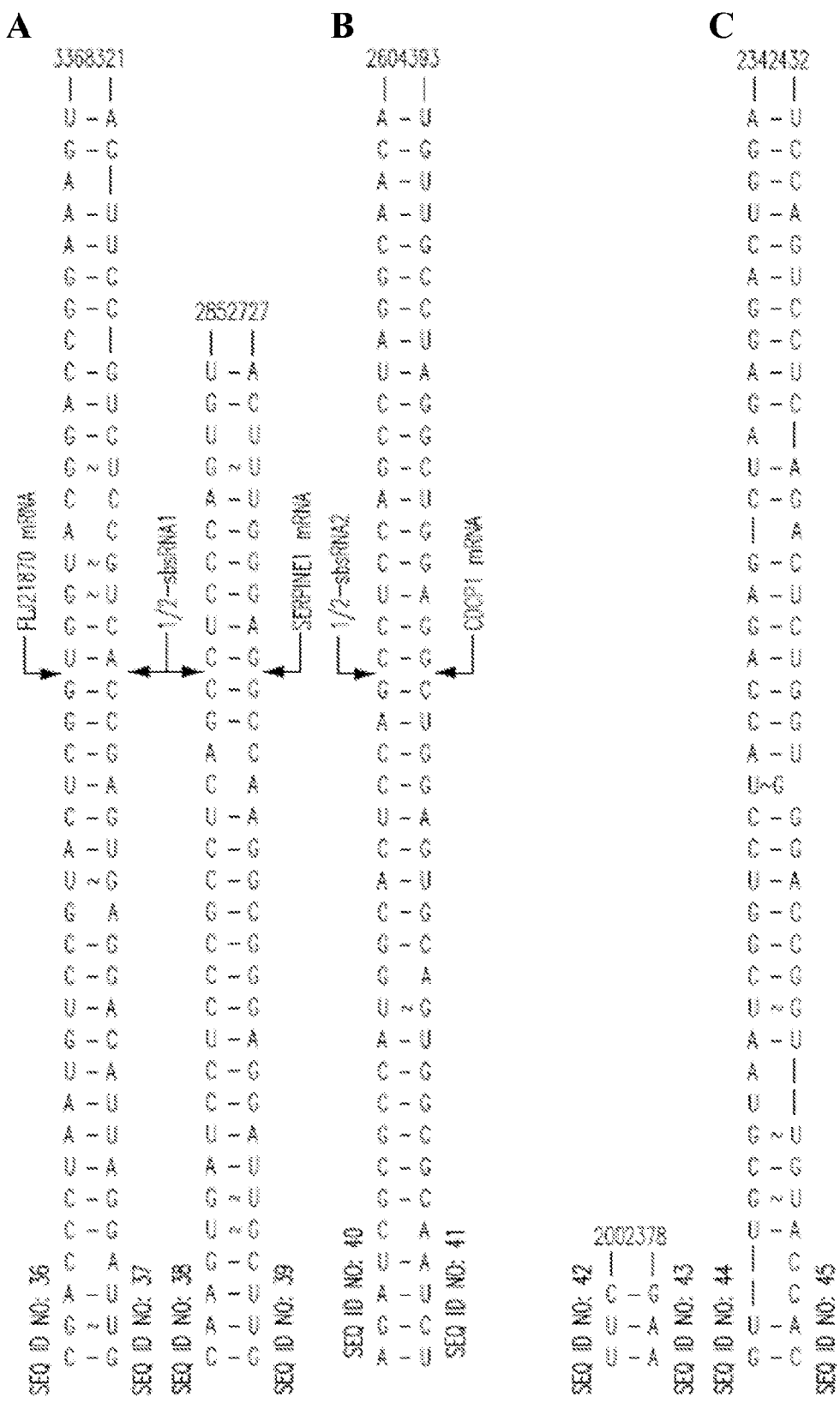
Figures 2, 4:
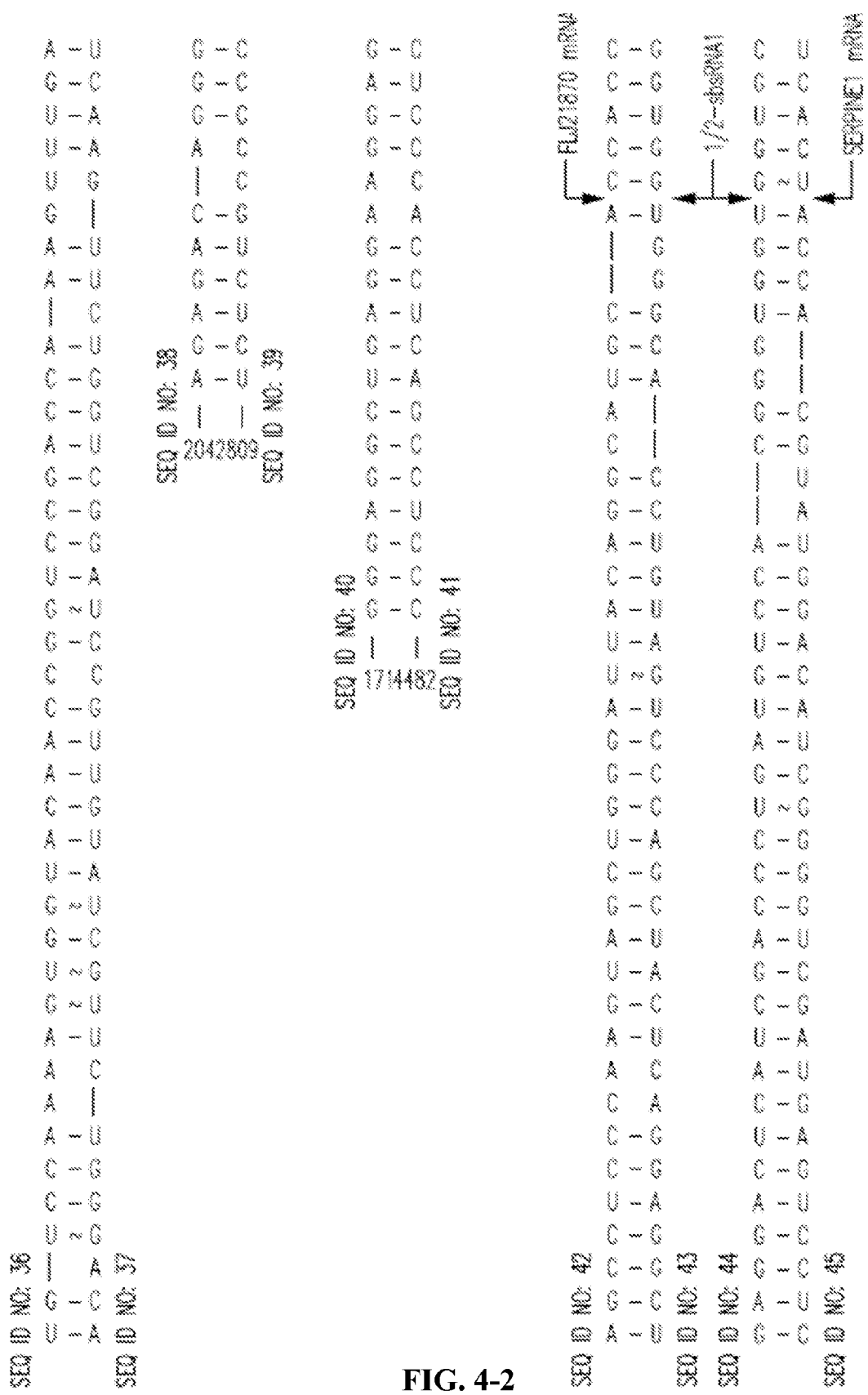

FIG. 4 shows the predicted base-pairing between the Alu element within the specified mRNA and the partially complementary Alu element within the denoted ½-sbsRNA. FIG. 4a shows predicted base-pairing between the Alu element within the SERPINE1 or FLJ21870 3'UTR and the Alu element within ½-sbsRNA1, where 1 was defined as the first transcribed nucleotide of each mRNA or ½-sbsRNA1(S). FIGS. 4b, 4c, and 4d, Essentially as in 4a.

Figures 4, 5, 6:
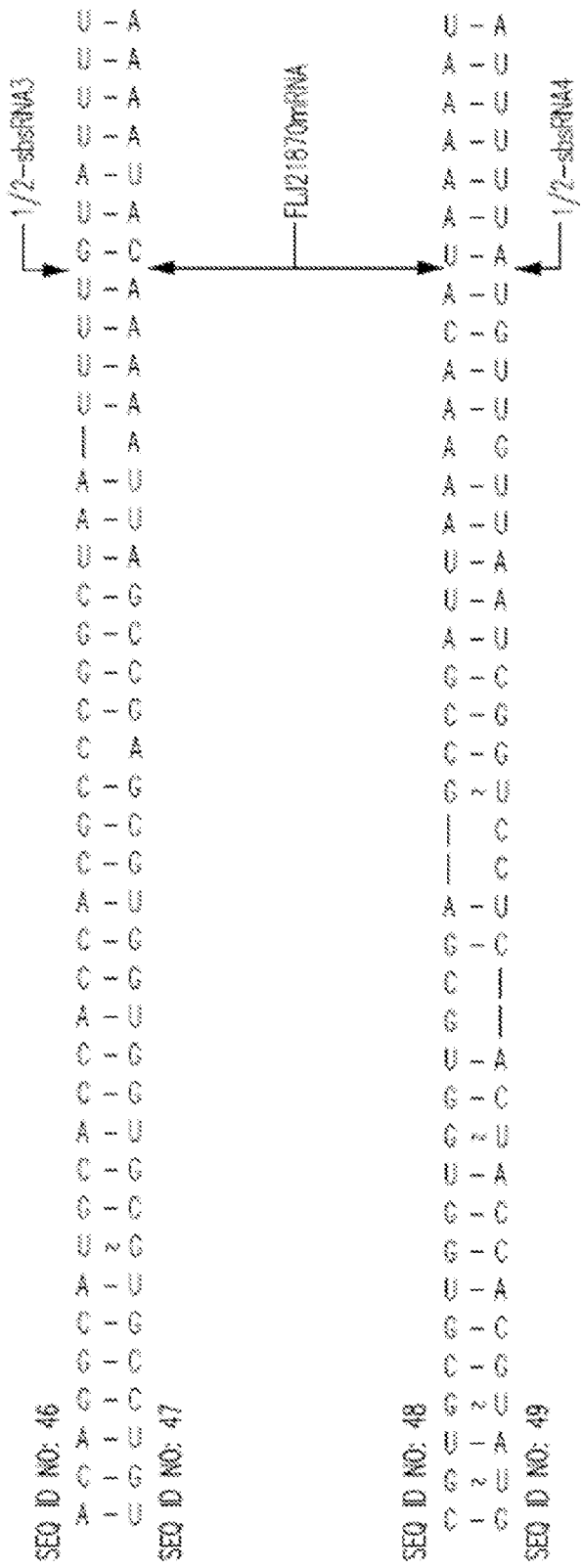

FIG. 5 shows the mapping the 5' end of ½-sbsRNA1(S), and determining that the cellular abundance of ½-sbsRNA1(S) relative to ½-sbsRNA1(L) is 3:1 in HeLa cells. FIG. 5a shows ½-sbsRNA1 mapping using an RNase Protection Assay (RPA) and three uniformly [32P]-labeled RNA probes generated in vitro by transcribing a subclone of Chr11 DNA (Chr11_66193000-66191383) to the designated restriction site. FIG. 5b shows Single stranded DNA primer extension analysis of poly(A)+HeLa-cell RNA (leftmost lane) or pcDNA3.1(+)/Zeo_Chr11_66193000-66191383 in the presence of the specified dideoxy NTP (four rightmost lanes). 1 specifies the first nucleotide of ½-sbsRNA1(S). FIG. 5c shows RTsqPCR analysis of total HeLa-cell RNA, which corroborated data shown in 5a and 5b, narrowed the 5' end of ½-sbsRNA1(S) to reside between positions −14 and +8, where +1 is the 5' end defined by primer extension in 5b. The analysis also demonstrated the presence of ½-sbsRNA1(L) at one-third the abundance of ½-sbsRNA1(S), i.e, at 0.25-fold the abundance of ½-sbsRNA1(S+L). RT was primed using random hexamers, and sqPCR was performed using one of the specified sense primers (#1-#9) and the common antisense primer. The arrow marks the transcription start site for ½-sbsRNA1(S), which maps within sense primer #8 as denoted by the dotted vertical line. FIG. 5d shows the sequence (SEQ ID NO: 50) of fulllength ½-sbsRNA1(S). Red nucleotides, Alu element; red box, putative poly(A) signal; (A)n, poly(A) tail.

FIG. 6 shows that ½-sbsRNA1 co-immunoprecipitates with STAU1 and is required for STAU1 binding to specific SMD targets. FIG. 6a shows western blotting (upper) or RT-sqPCR (lower) of lysates of formaldehyde-crosslinked HeLa cells that had been transiently transfected with the specified siRNA and either empty vector (−) or p½-sbsRNA1(S)R (+) before or after IP with anti-HA or rat IgG. After IP, each sample was spiked with in vitrosynthesized *E. coli* LACZ mRNA. The co-IP efficiency provides the level of each mRNA RT-sqPCR product after IP relative to before IP, where each ratio in the presence of Control siRNA was defined as 100%. FIG. 6b shows diagrams of pFLUC-SERPINE1 3'UTR FL, which contains the full-length (FL) SERPINE1 3'UTR, and 3'UTR deletion variants. Yellow boxes, FLUC sequences; blue bars, SERPINE1 3'UTR sequences; Δ; deletion; pale green boxes, 3'UTR of FLUC No SBS, which does not bind STAU1. The 5'-most pale green box ensures that ribosomes translating to the FLUC termination codon do not displace STAU1 that had been recruited to the ½-sbsRNA1-binding site (which is 86 nucleotides as shown in FIG. 4a). FIG. 6c shows western blotting (upper) and RTsqPCR (middle and lower) of lysates of HeLa-cells that had been transiently transfected with the noted pFLUC-SERPINE1 3'UTR test construct and the phCMV-MUP reference plasmid. Lower: The normalized level of each FLUC mRNA in the presence of Control siRNA was defined as 100%. Error bars indicate s.e.m. Single asterisk, n=6, P<0.01; double asterisks, n=3, P<0.05.

Figures 4, 5, 6, 7:
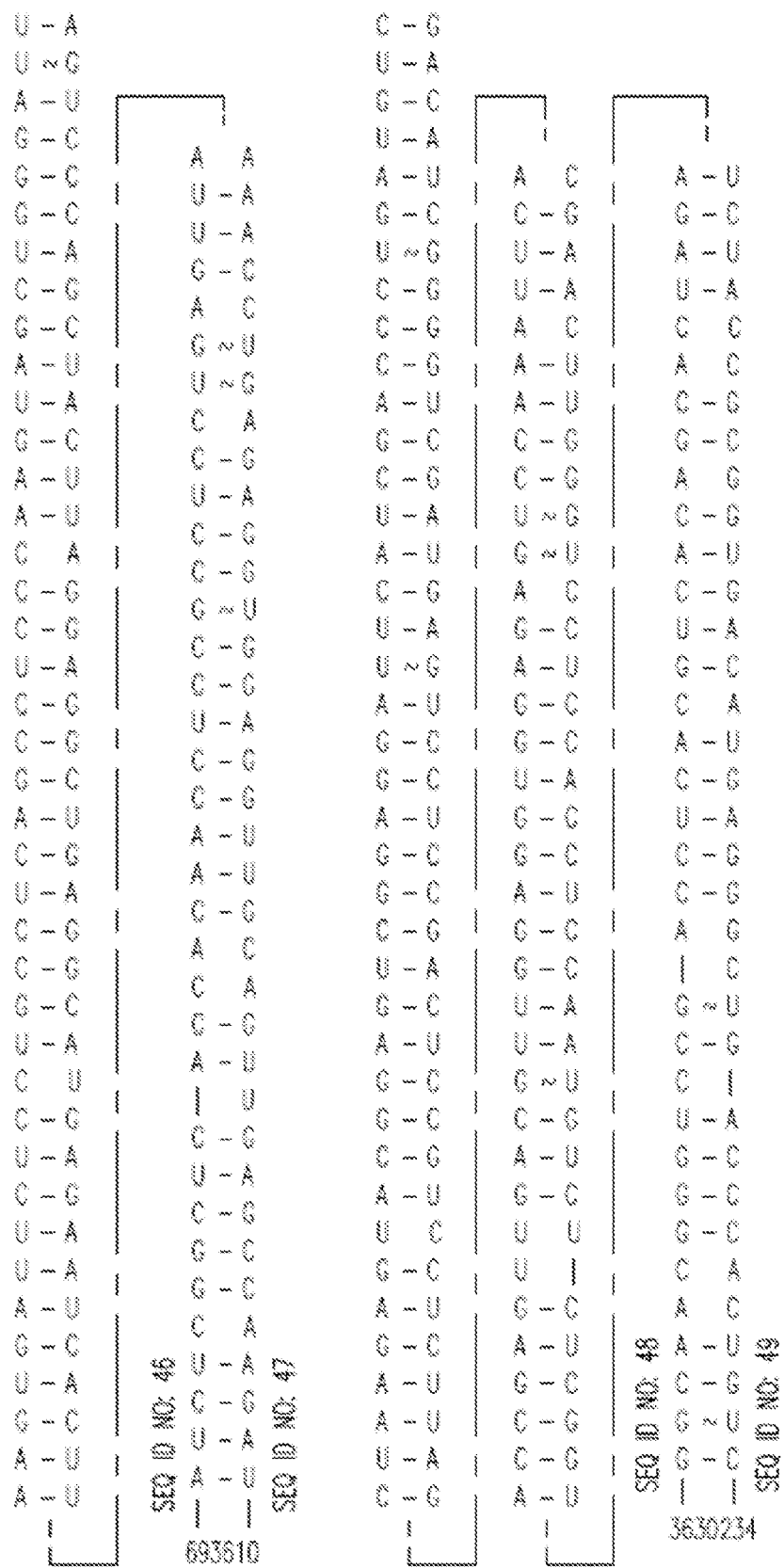
Figure 5:
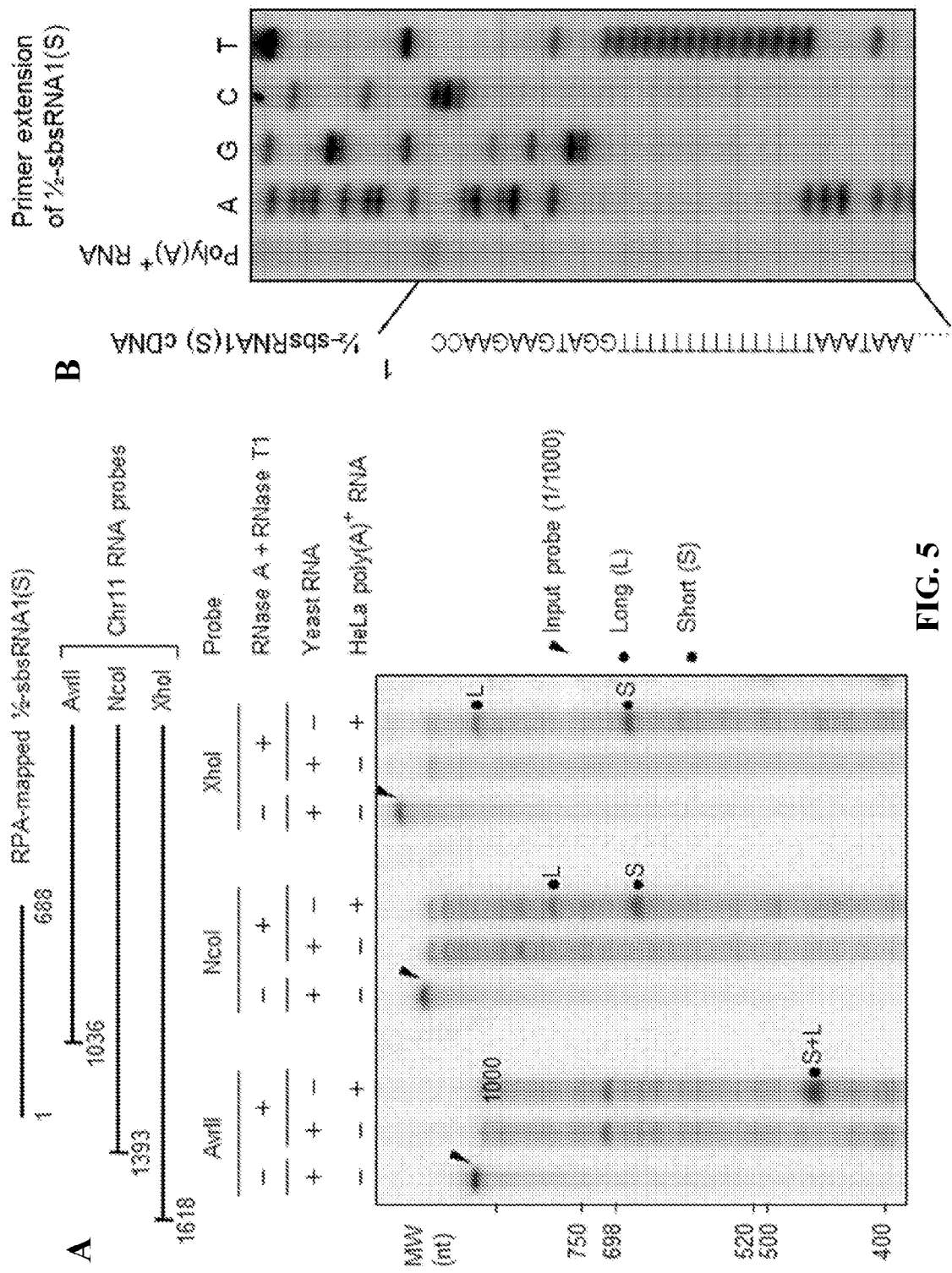
Figure 5:
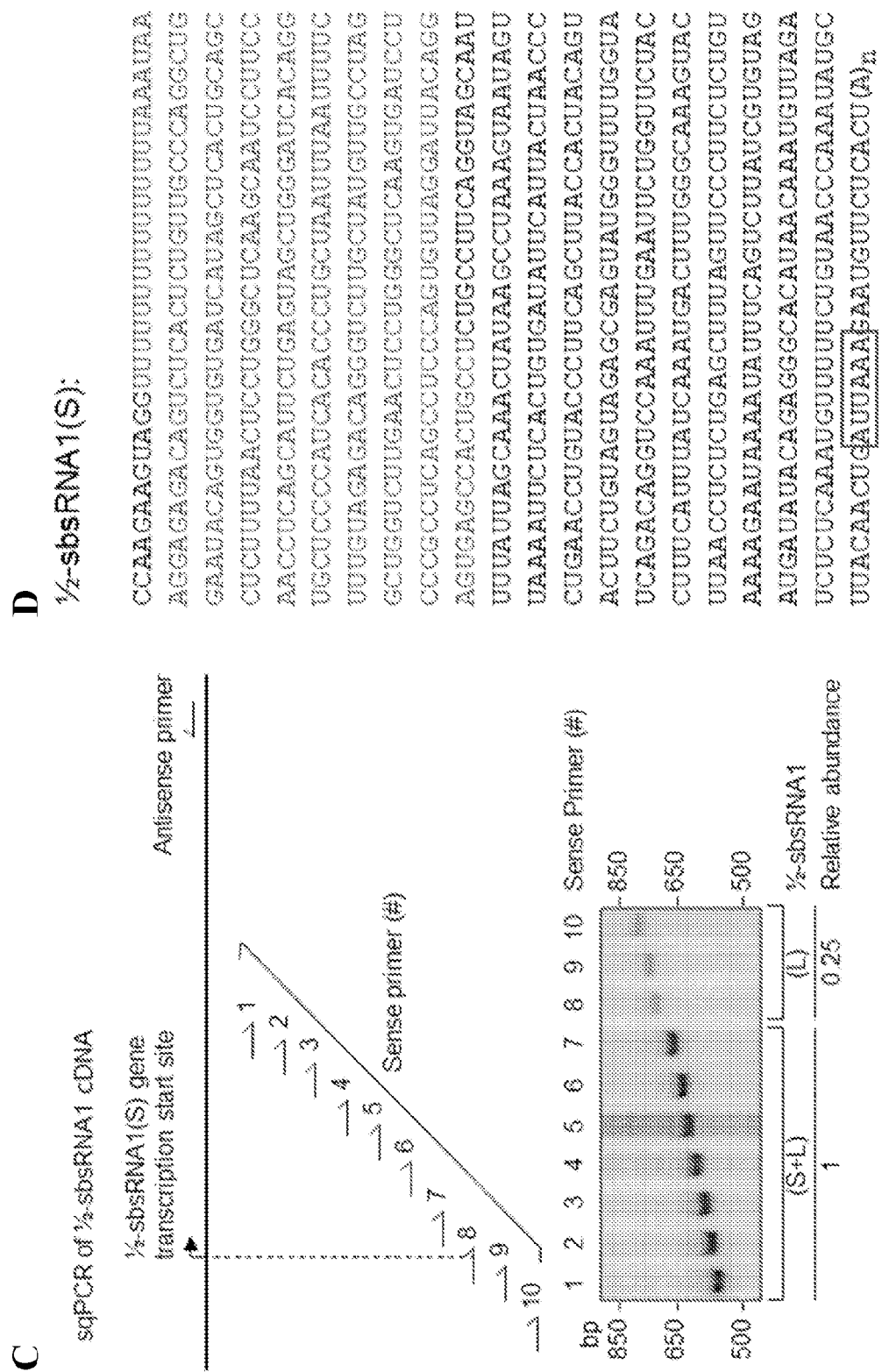
Figure 6:
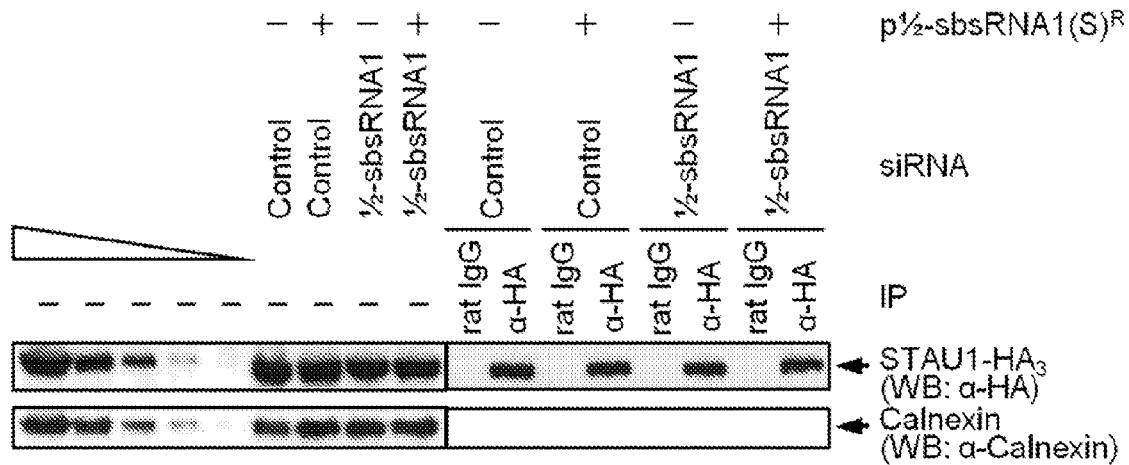
Figure 6:
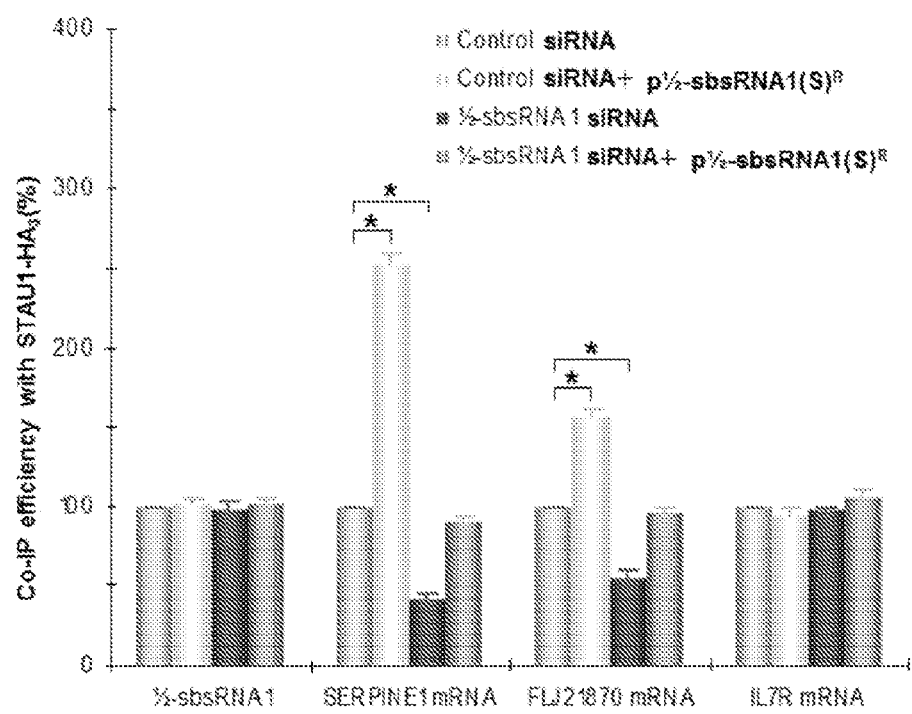
Figure 6:
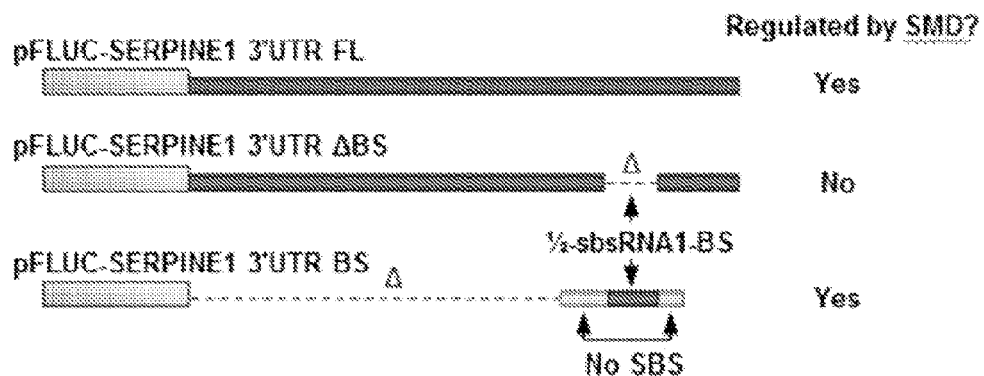
Figure 6:
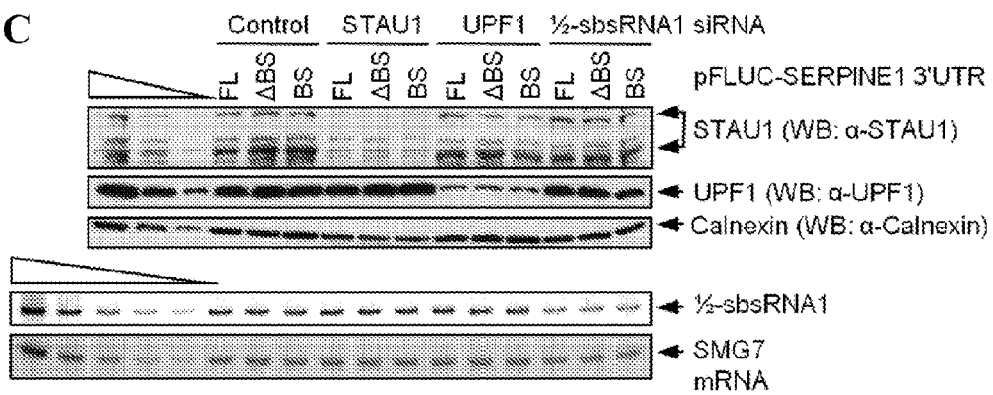
Figure 6:
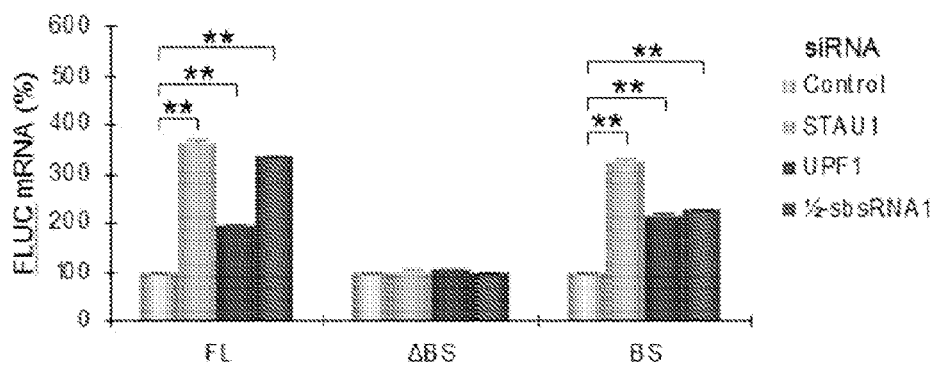
Figure 7:
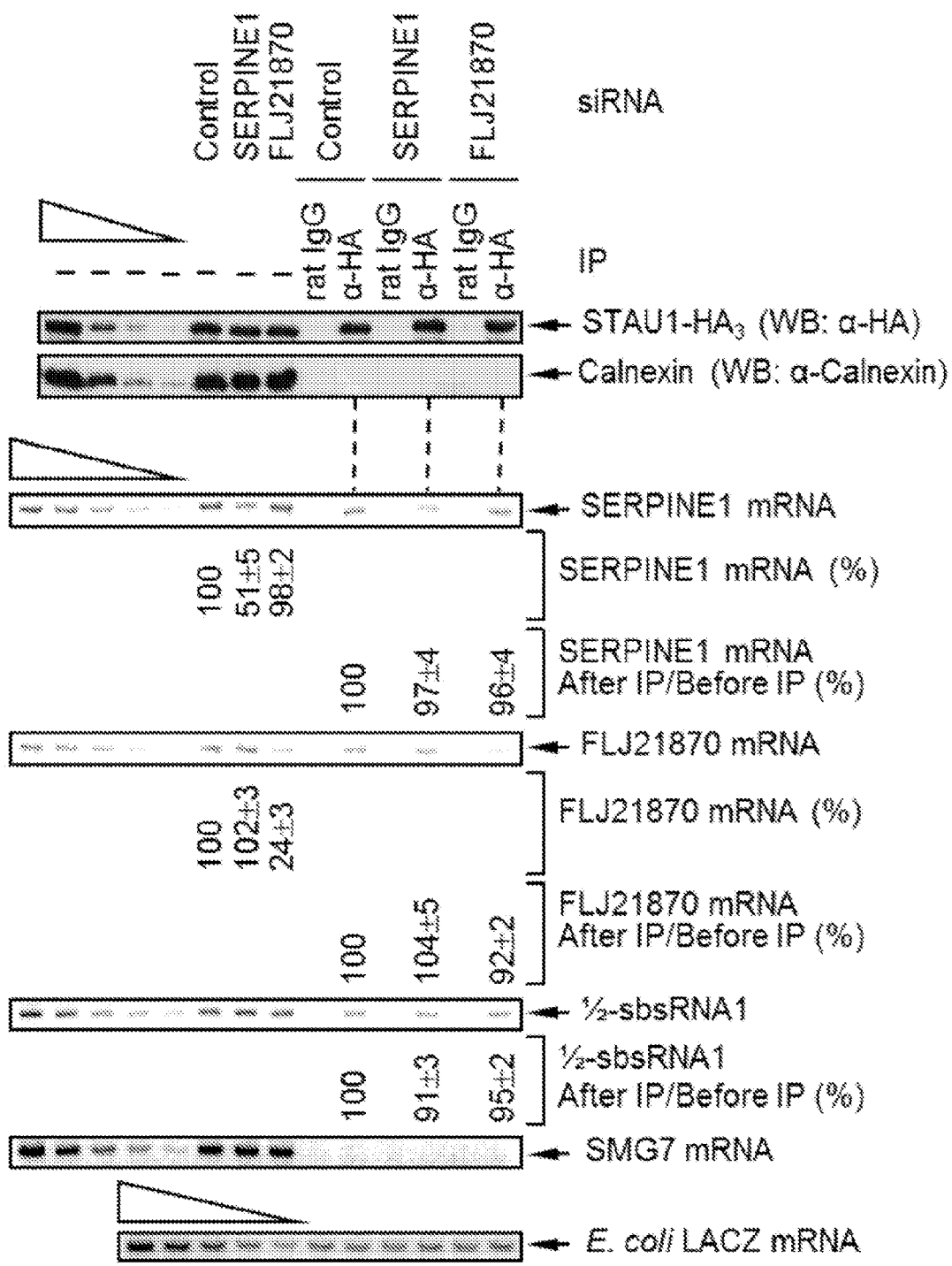

FIG. 7 shows that downregulating SERPINE1 mRNA or FLJ21870 mRNA does not decrease the efficiency with which STAU1-HA3 co-immunoprecipitates with ½-sbsRNA1. Essentially as in FIG. 6a, except that HeLa cells were transfected with the specified siRNA.

Figure 8:
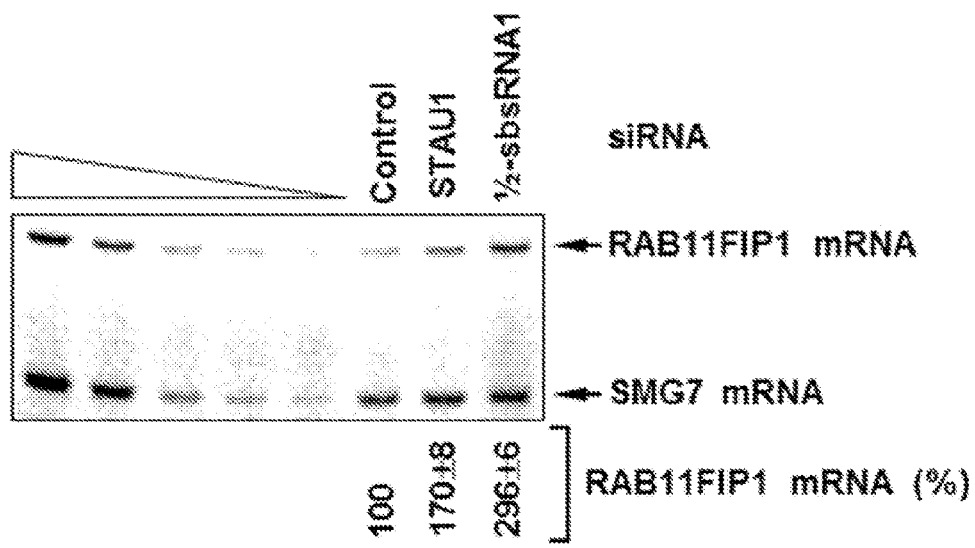
Figure 8:
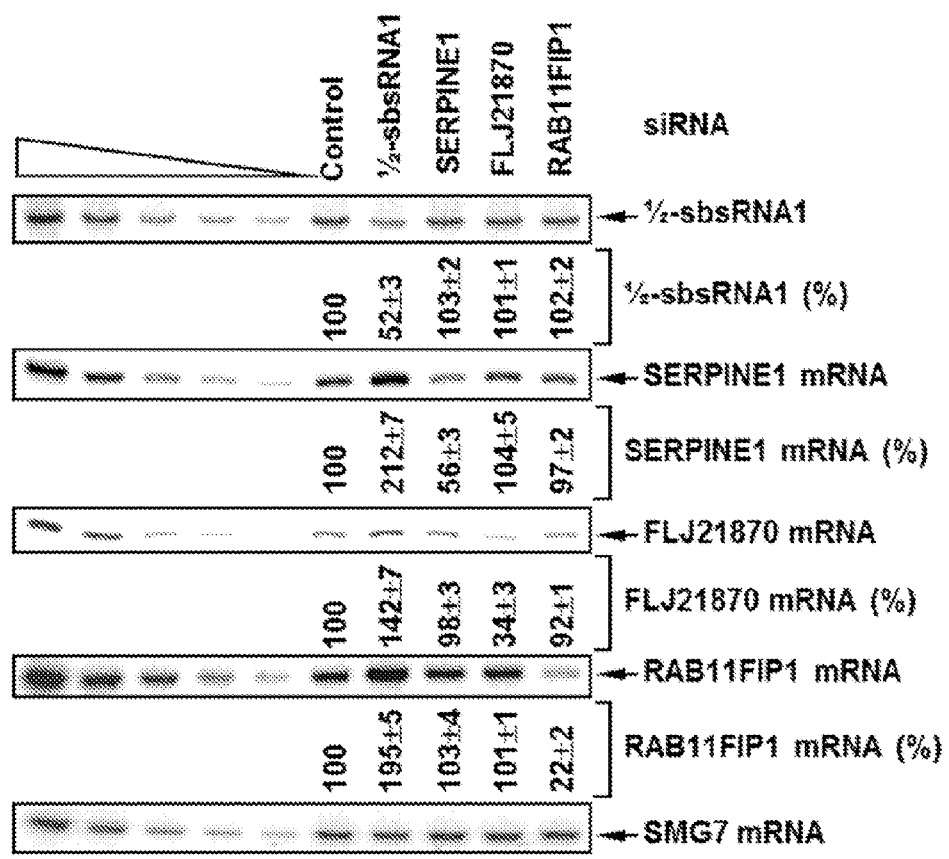
Figure 8:
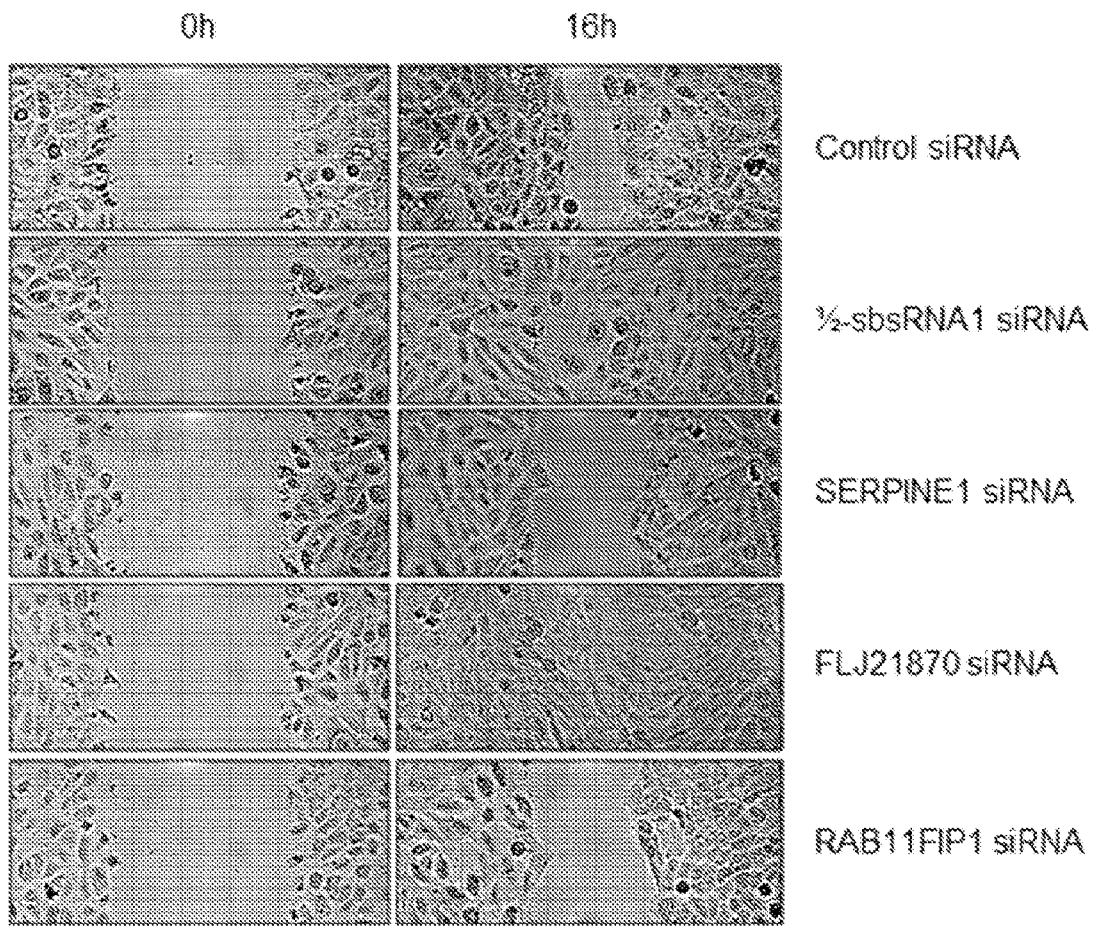

FIG. 8 shows that RAB11FIP1 mRNA is an SMD target that is down-regulated not only by STAU1 but also by ½-sbsRNA1. FIG. 8a shows RT-sqPCR was as in FIG. 3b, except that RAB11FIP1 mRNA constituted the test mRNA. FIG. 8b shows RT-sqPCR analyses of specified RNAs, where the level of SMG7 mRNA controlled for variations in RNA recovery. FIG. 8c shows phase-contrast microscopy, which measured the rate of HaCaT keratinocyte wound healing after transfection with the specified siRNA for 48 hr followed by scrape injury at 0 and 16 hr. Higher levels of SERPINE1 correlate with poorer prognoses for patients with brain tumors as well as breast, ovarian, gastric, colorectal, non-smallcell lung, renal-cell or head-and-neck cancer due to increased cancer-cell invasiveness, in at least some instances1. In fact, SERPINE 1 stimulates "wound healing" after scrape injury to keratinocyte monolayers as monitored by the migration rate of human keratinocyte HaCaT cells into a denuded wound track2. Likewise, RAB11 family interacting protein 1 (RAB11FIP1), which is also encoded by an mRNA that contains a single 3'UTR Alu element and is downregulated by STAU1 and ½-sbsRNA1 (FIG. 8a), stimulates wound-healing after scrape injury to breast epithelial MCF10A cells3. To test for ½-sbsRNA1 function in wound healing, HaCaT cells were transfected with Control siRNA, SERPINE1 siRNA, FLJ21870 siRNA, RAB11FIP1 siRNA or ½-sbsRNA1 siRNA. Each siRNA successfully downregulated its RNA target (FIG. 8b). Scrape injury repair assays that were monitored over a 16-hr period revealed that SERPINE1 siRNA or RAB11FIP1 siRNA inhibited cell movement into the wound tract, whereas ½-sbsRNA1 siRNA promoted cell movement (FIG. 8c). Thus, ½-sbsRNA1 contributes toward reducing cell migration by targeting SERPINE1 and RAB11FIP1 mRNAs for SMD. Scrape injury repair assays also indicate that FLJ21870 siRNA promoted cell movement (FIG. 8c). Since FLJ21870 function remains to be characterized, and since mechanisms that regulate FLJ21870 mRNA abundance are unknown aside from the mechanism presented here, uncovering the significance of the wound-healing result obtained using FLJ21870 siRNA requires future studies.

Figure 9:
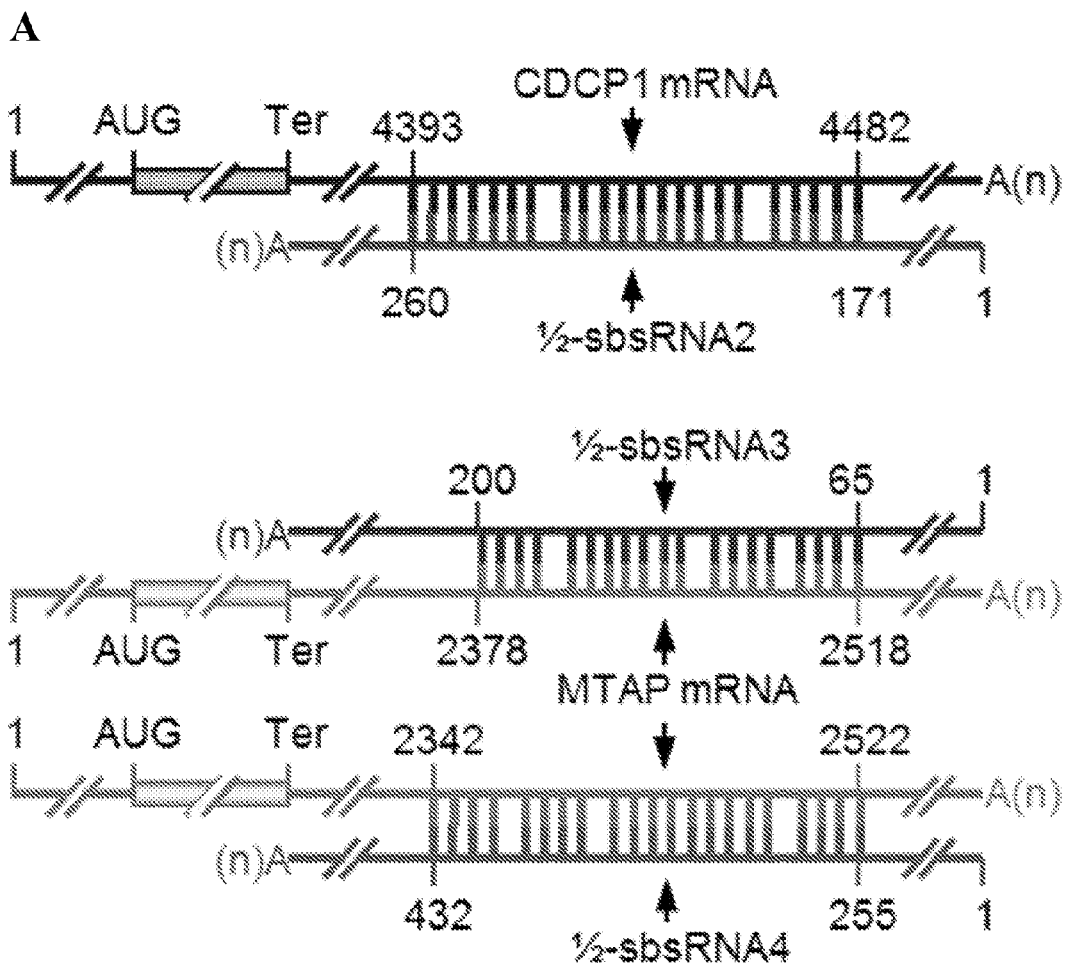
Figure 9:
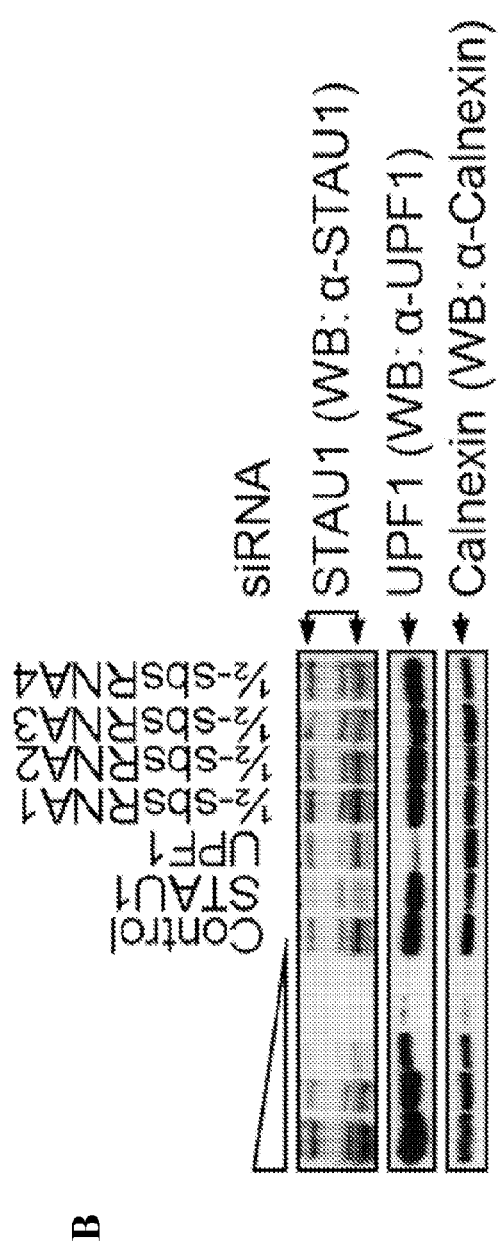
Figure 9:
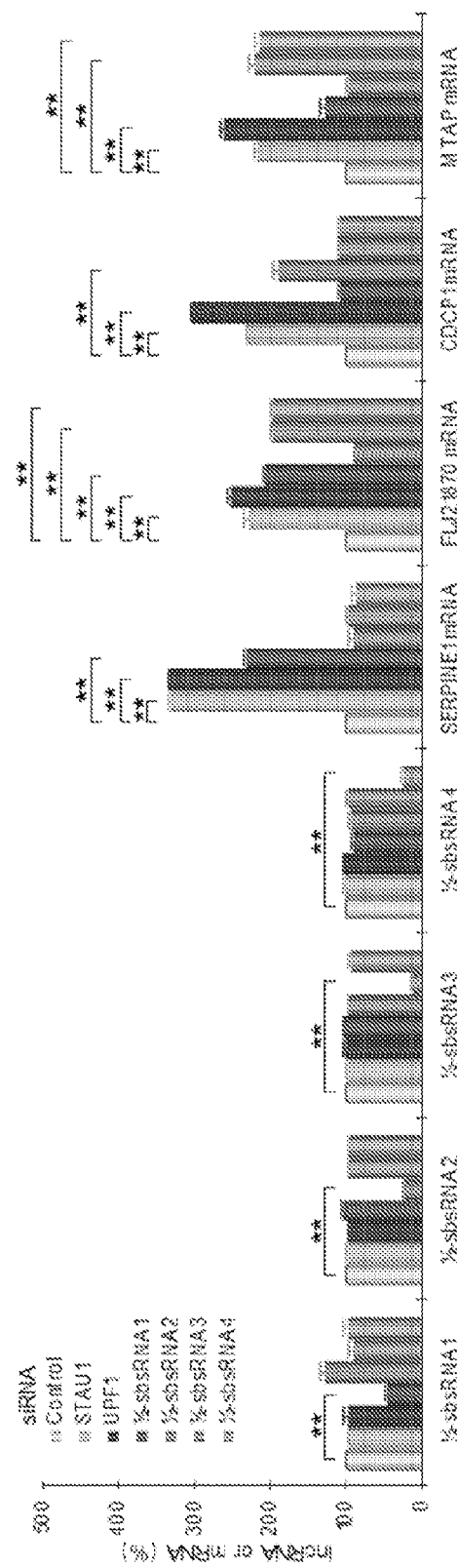
Figure 9:
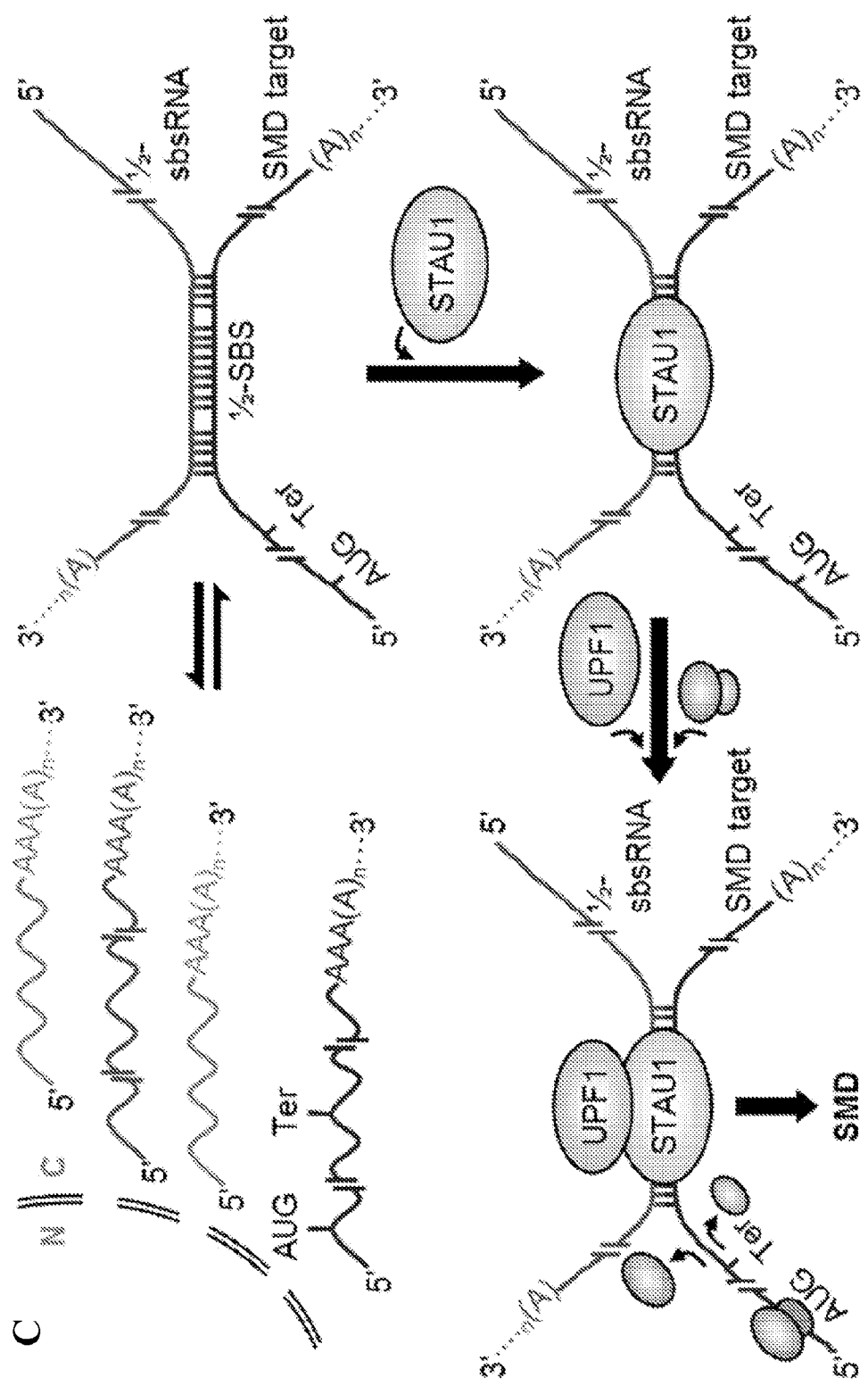

FIG. 9 shows evidence that ½-sbsRNA2, ½-sbsRNA3 and ½-sbsRNA4 base-pair with particular mRNA 3'UTRs and decrease mRNA abundance, as do STAU1 and UPF1. FIG. 9a shows the predicted base-pairing between the 3'UTR Alu element of CDCP1 mRNA (Acc#: NM_022842) and ½-sbsRNA2, or MTAP mRNA (Acc#: NM_002451) and ½-sbsRNA3 as well as ½-sbsRNA4, where 1 was defined as the first nucleotide listed in the NCBI data base for each mRNA or lncRNA. FIG. 9b is ssentially as in FIG. 3b. Error bars indicate s.e.m. Asterisk, n=6, P<0.01. FIG. 9c shows a model for how an Alu element containing ½-sbsRNA that is polyadenylated and largely cytoplasmic (red) base-pairs with a partially complementary Alu element, i.e., a half-STAU1 binding site (½-SBS), within the 3'UTR of a particular mRNA (blue) to trigger SMD. Base-pairing forms a functional SBS. The STAU1-bound SBS triggers SMD in a UPF1-dependent mechanism when translation terminates sufficiently upstream of the SBS so that translating ribosomes do not remove bound STAU1. The ½-sbsRNA is not destroyed in the process. N, nucleus; C, cytoplasm; AUG, translation initiation codon; Ter, termination codon (which is generally, but not necessarily, a normal termination codon).

Figure 10:
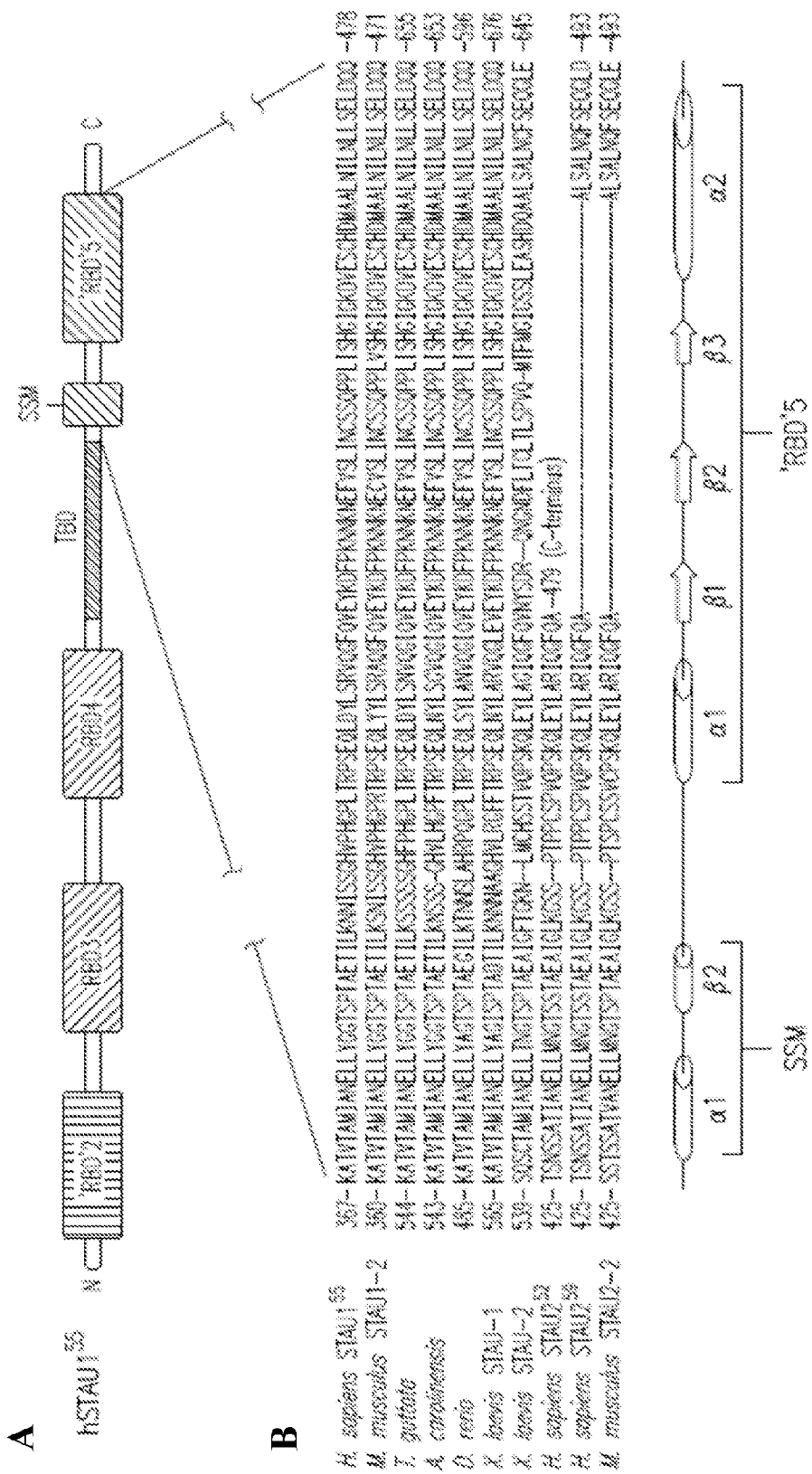
Figure 10:
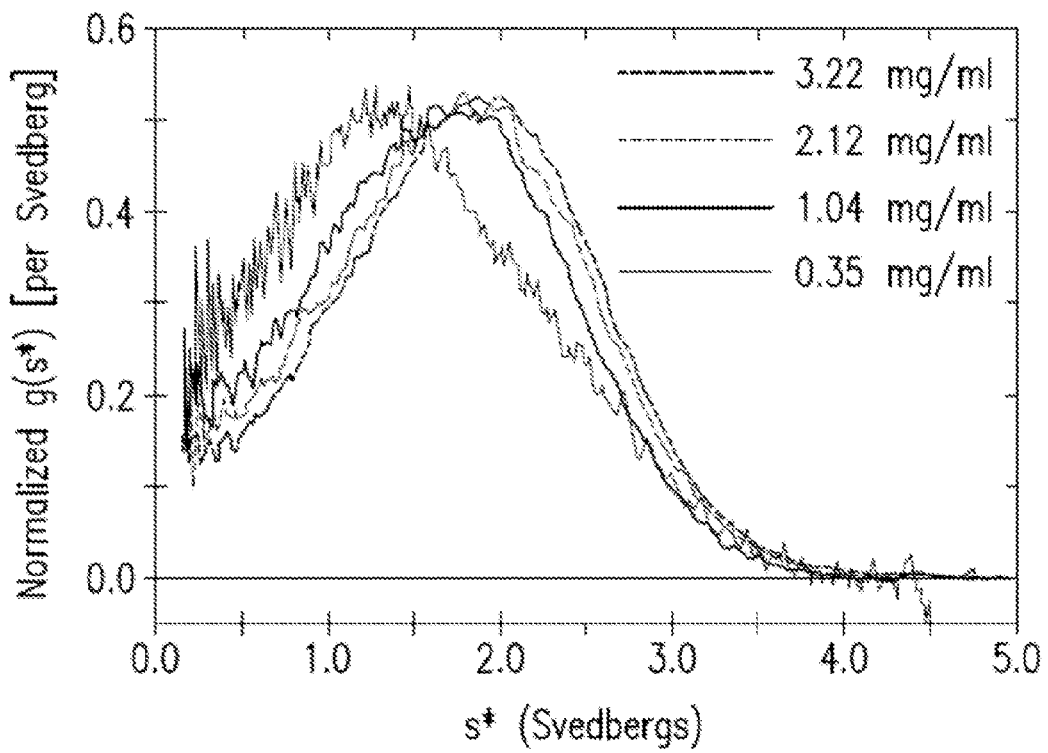
Figure 10:
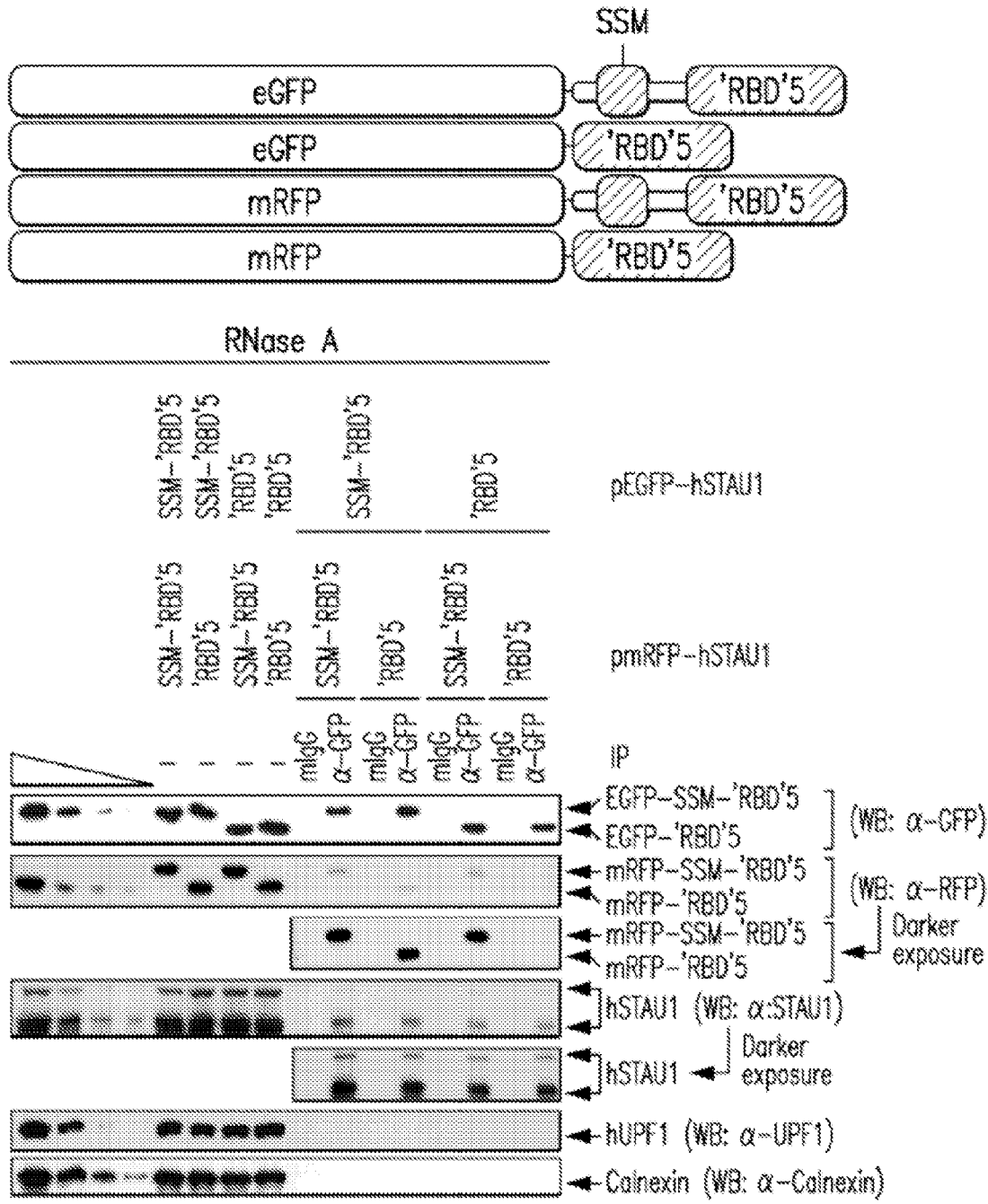

FIG. 10 shows that SSM is Critical for Dimerization of hSTAU1$^{55}$SSM-'RBD'5. FIG. 10a shows diagrams of the modular organization of domains and motifs within hSTAU1$^{55}$, its orthologs and its paralogs. Regions shown include dsRNA-binding domains (RBDs) 3 and 4 (shaded grey), which have been shown to bind dsRNA, the region that binds tubulin (TBD) in vitro (solid grey; amino acids 282-372 in STAU1$^{55}$), and the STAU-swapping motif (SSM)-'RBD'5 region (yellow; amino acids 367-476 in hSTAU1$^{55}$, which overlaps with the TBD and for which the X-ray crystal structure was reported). FIG. 10B shows SSM, which typifies hSTAU1 and hSTAU2 paralogs, is conserved in all groups of vertebrates. Multiple sequence alignment was performed using vertebrate group representatives from fish (zebrafish, *Danio rerio*, NP_991124.1 (SEQ ID NO: 143)), amphibians (African clawed frog, *Xenopus laevis*, NP_001085239.1 for STAU-1 (SEQ ID NO: 144), NP_001086918.1 for STAU-2 (SEQ ID NO: 145)), reptiles (Carolina anole; Anoliscarolinensis, XP_003220668.1 (SEQ ID NO: 142)), birds (zebra finch, *Taeniopygia guttata*; XP_002188609.1 (SEQ ID NO: 141)), and mammals, i.e., human *Homo sapiens* (NP_004593.2 for STAU1-a (SEQ ID NO: 139), NP_001157856.1 for STAU2-e (SEQ ID NO: 146), STAU2-b; NP_001157853.1 (SEQ ID NO: 147)) and mouse *Mus musculus* (STAU1-2; NP_001103375.1 (SEQ ID NO: 140), STAU2-2; NP 001104742.1 (SEQ ID NO: 148)). The secondary structure represented in yellow below the sequence alignments derives from the structure reported here. FIG. 10C shows analytical ultracentrifugation results support a model for the existence of a SSM-'RBD'5 monomer—dimer equilibrium in solution. The normalized apparent (*) sedimentation coefficient distribution (g(s*)) is plotted as a function of apparent Svedbergs (s*). FIG. 10D shows 'RBD'5 homodimerization in human cells requires SSM. HEK293T cells ($1\times10^7$/150-mm dish) were transiently transfected with a pEGFP-'RBD'5 (5 µg) and either pmRFP—SSM-'RBD'5 (5 µg) or pmRFP-'RBD'5 (5 µg). Alternatively, cells were transfected with pEGFP-SSM-'RBD'5 (5 µg) and either pmRFP—SSM-'RBD'5 (5 µg) or pmRFP-'RBD'5 (5 µg). Cell lysates were immunoprecipitated in the presence of RNase A using anti($\alpha$)-GFP or, to control for nonspecific immunoprecipitation (IP), mouse(m)IgG. Western blotting (WB) using the specified antibody, where calnexinservesto control for IP specificity. Results are representative of three independently performed experiments.

Figure 11:
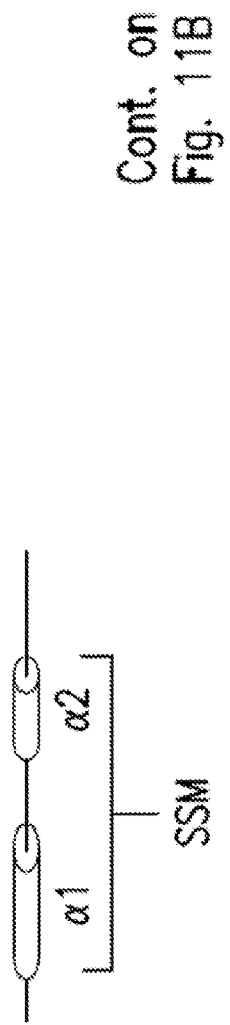
Figure 11:
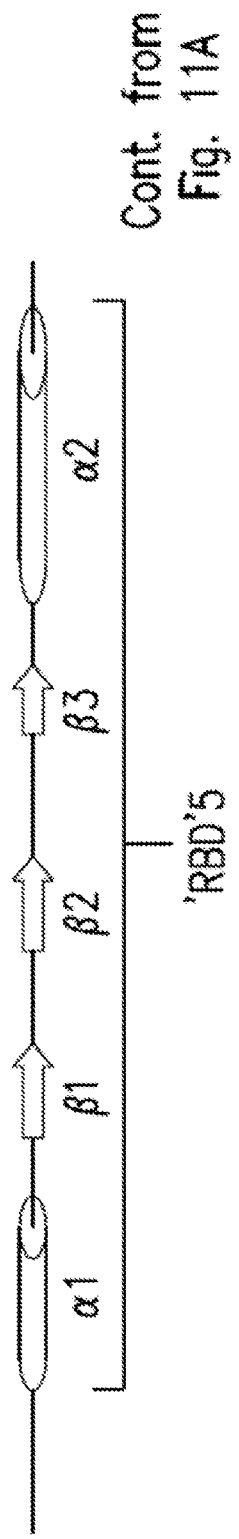

FIG. 11 shows that some but not All InvertebrateSTAU Proteins have an SSM. Multiple protein sequence alignments of the STAU proteins in FIG. 10B and STAU proteins from the following invertebrates: acorn worm, *Saccoglossus kowalevskii*, XP_002731114.1 (SEQ ID NO: 149); deer tick, *Ixodes scapularis*, XP_002433902.1 (SEQ ID NO: 150); water flea, *Daphnia pulex*, EFX74549.1 (SEQ ID NO: 151); fruit fly, *Drosophila melanogaster*, NP_476751.1 (SEQ ID NO: 152); mosquito, *Anopheles gambiae*, XP_308394.4 (SEQ ID NO: 153); roundworm, *Caenorhabditis elegans*, CCD62871.1 (SEQ ID NO: 154); red flour beetle, *Tribolium castaneum*, EFA11564.1 (SEQ ID NO: 155). The dotted lines between SSM and 'RBD'5 in this figure do not exist in FIG. 1B because weak similarities between *D. melanogaster* STAU-A, which lacks an SSM, and the SSM of other proteins shifts SSM sequences to the left.

Figure 12:
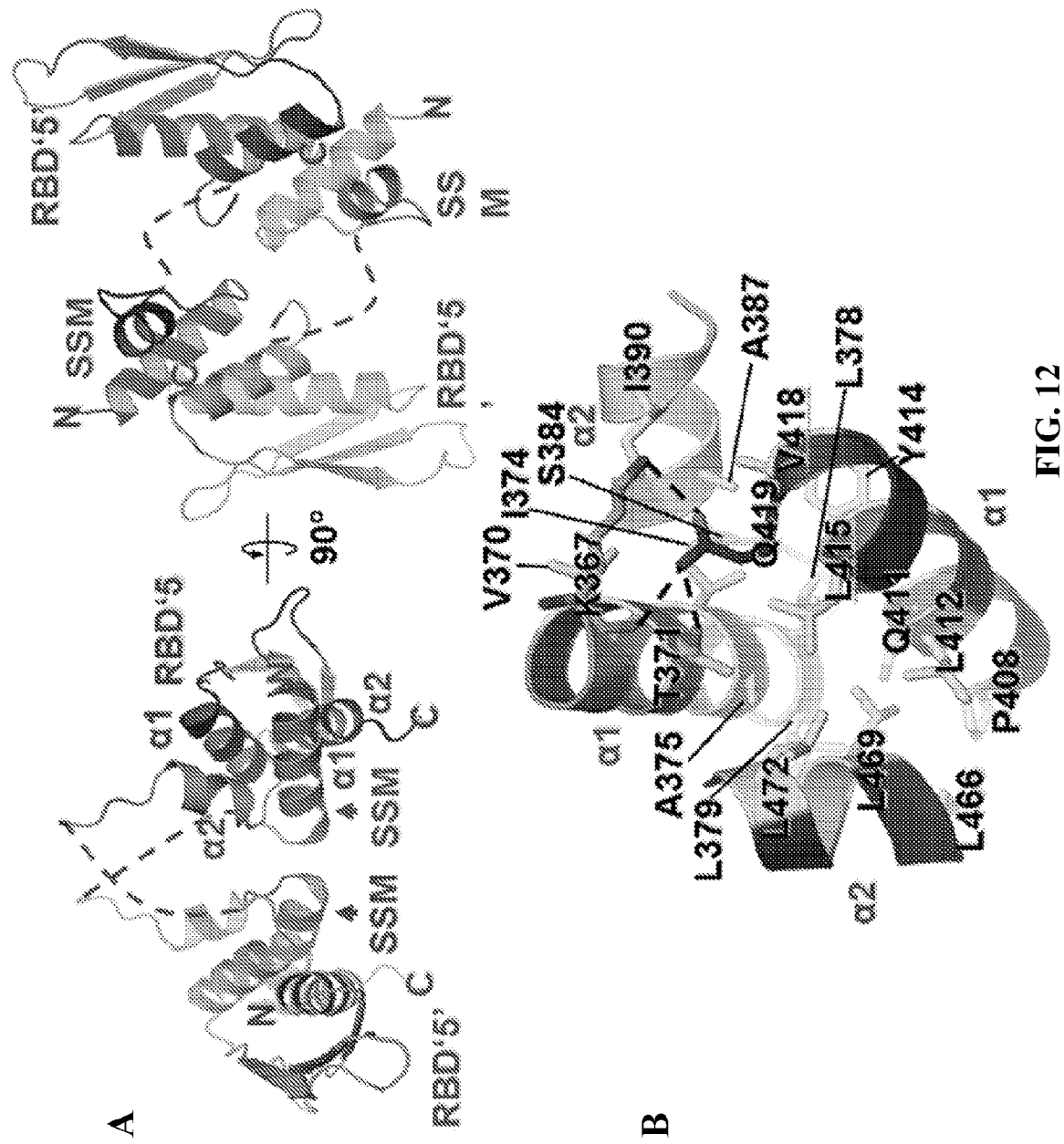

FIG. 12 shows the structure of the SSM-RBD5 Domain-Swapped Dimer. FIG. 12A shows a cartoon of the secondary structure of SSM-'RBD'5 where one molecule of SSM-'RBD'5 is green, the other molecule is blue. The two $\alpha$-helices of SSM contact the two $\alpha$-helices of 'RBD'5. Dotted lines represent the assumed linkage between SSM and 'RBD'5 since the crystal structure lacks connecting density. The rightmost dimer structure is rotated 90° around the X-axis relative to the leftmost dimer structure. FIG. 12B shows a close-up of the interaction between the SSM $\alpha$-helices (green $\alpha1$ and $\alpha2$) and the 'RBD'5 $\alpha$-helices (blue $\alpha1$ and $\alpha2$). Important residues are shown as stick representations, colored yellow, and labeled. The hydrogen-bonding interaction is shown as a dotted line.

Figure 13:
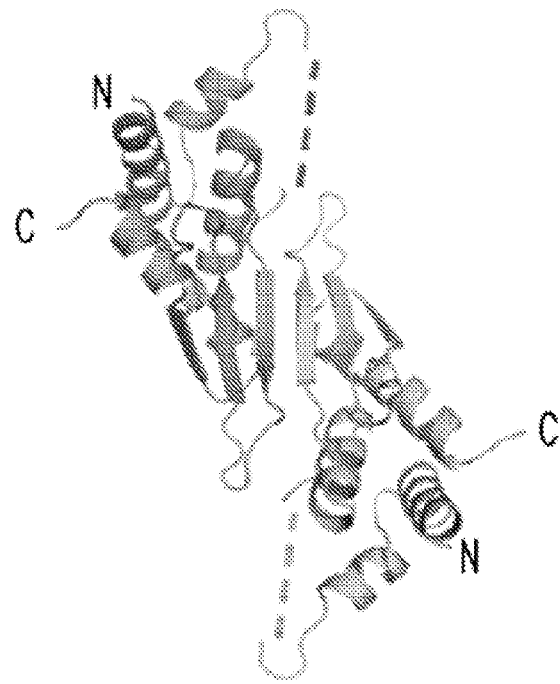
Figure 13:
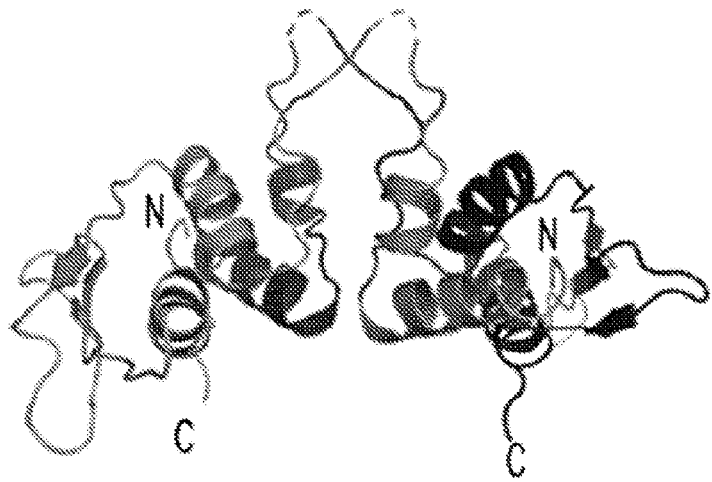
Figure 13:
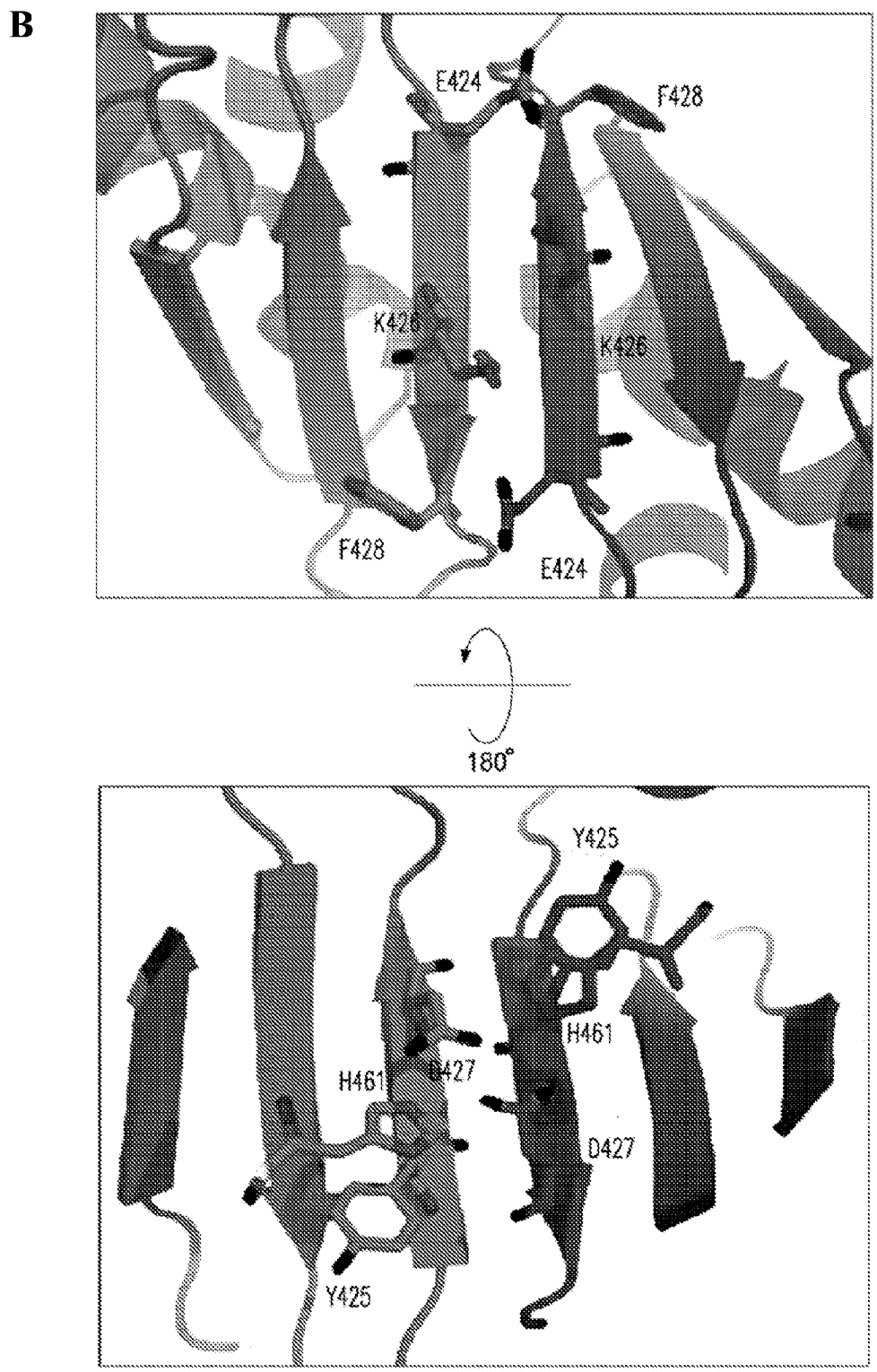

FIG. 13 shows support for SSM-'RBD'5-SSM-'RBD'5 Domain-Swapping, i.e., a transArrangement. FIG. 13A shows possible cis and trans arrangements of symmetry mates in the structure (left) and PISA results (right). FIG. 13B shows interactions of the unfavored, i.e., cis orientation. Residues of this crystal contact that were used to design SSM-'RBD'5 (E424H, D427V) are shown.

Figure 14:
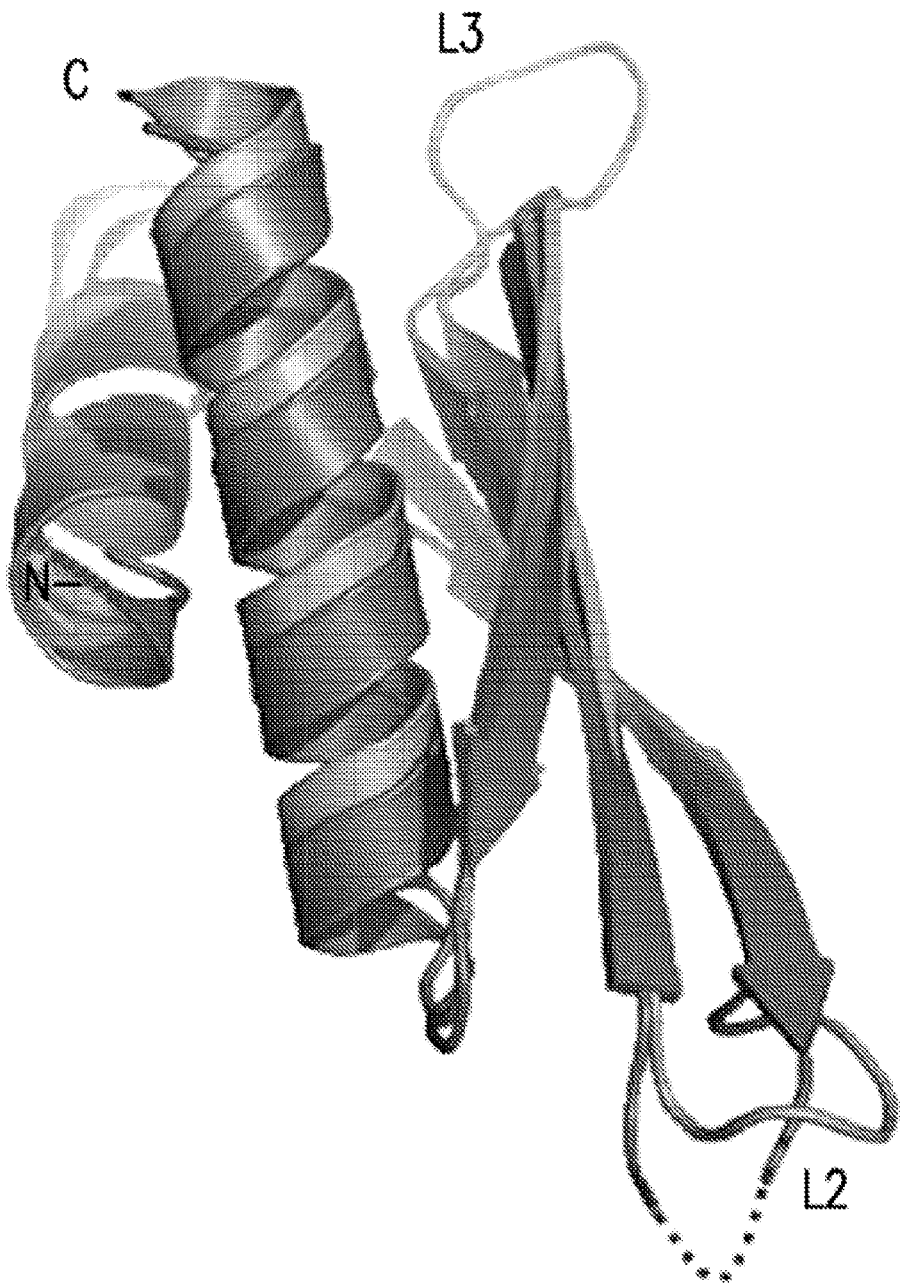
Figure 14:
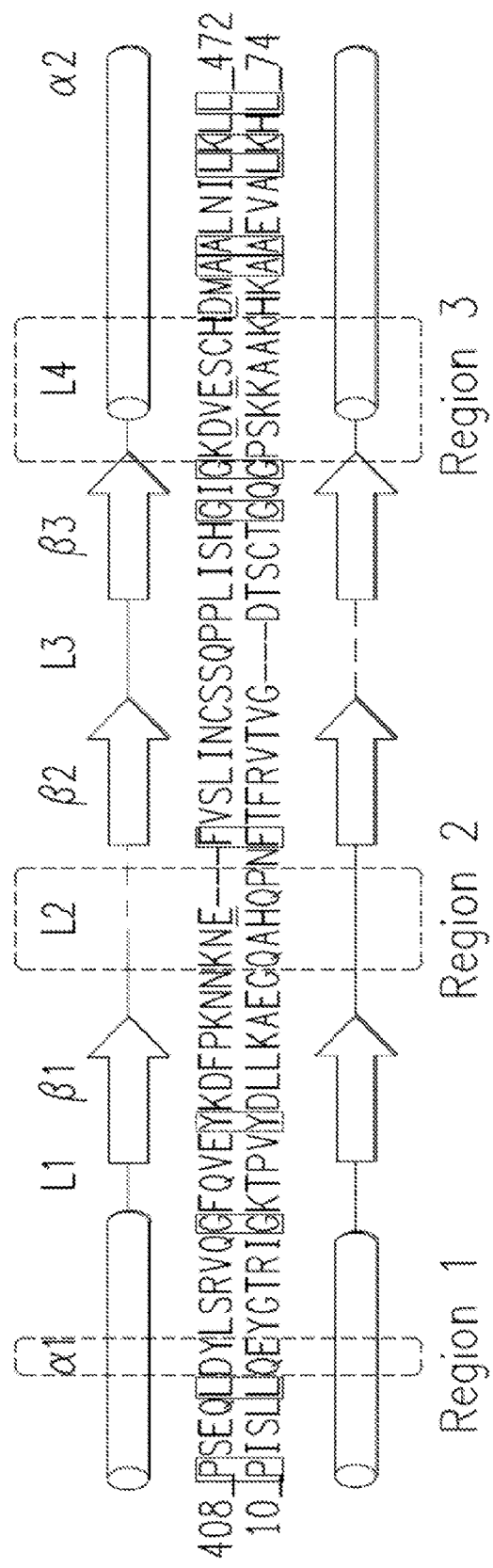
Figure 14:
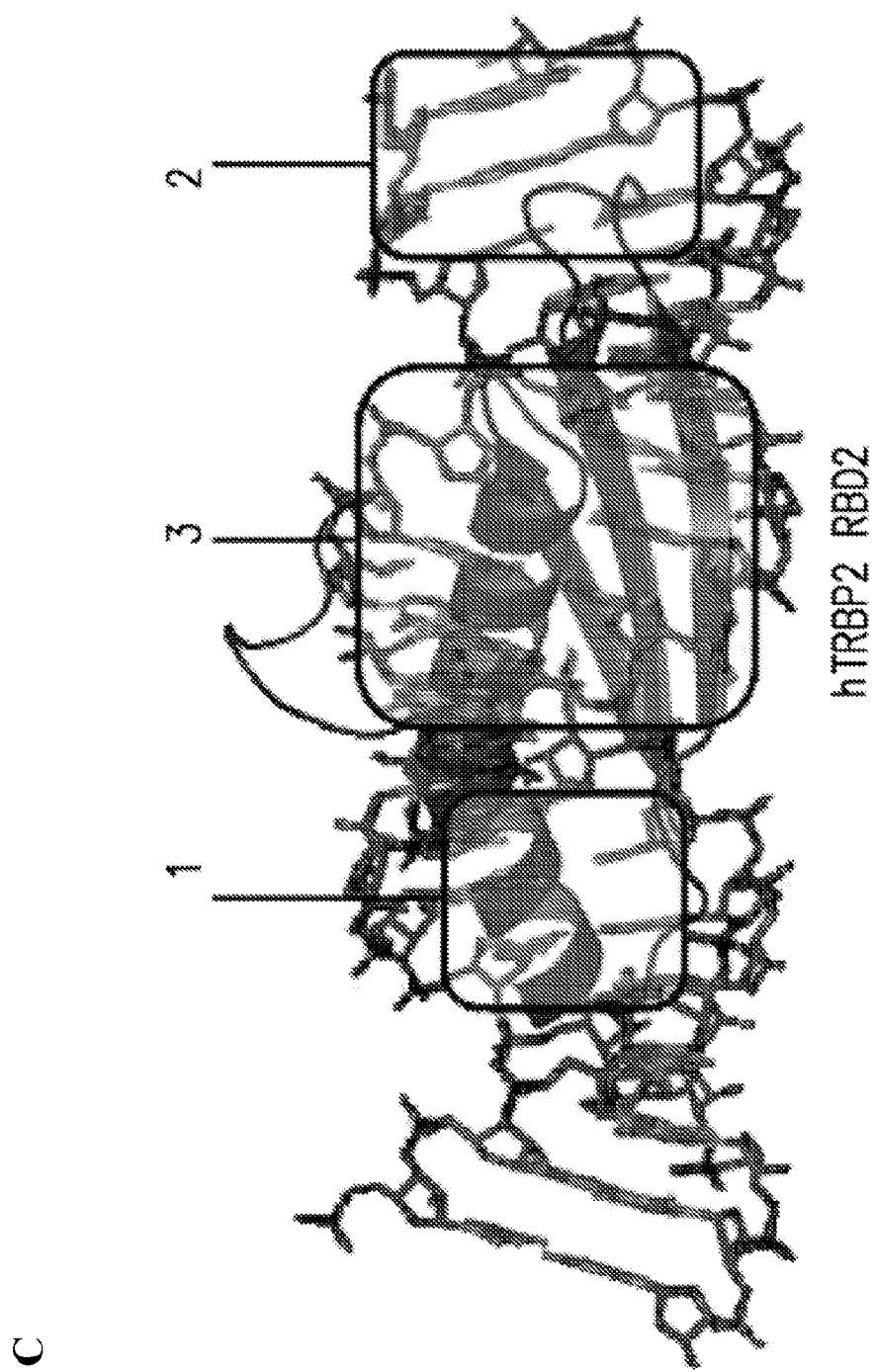
Figure 14:
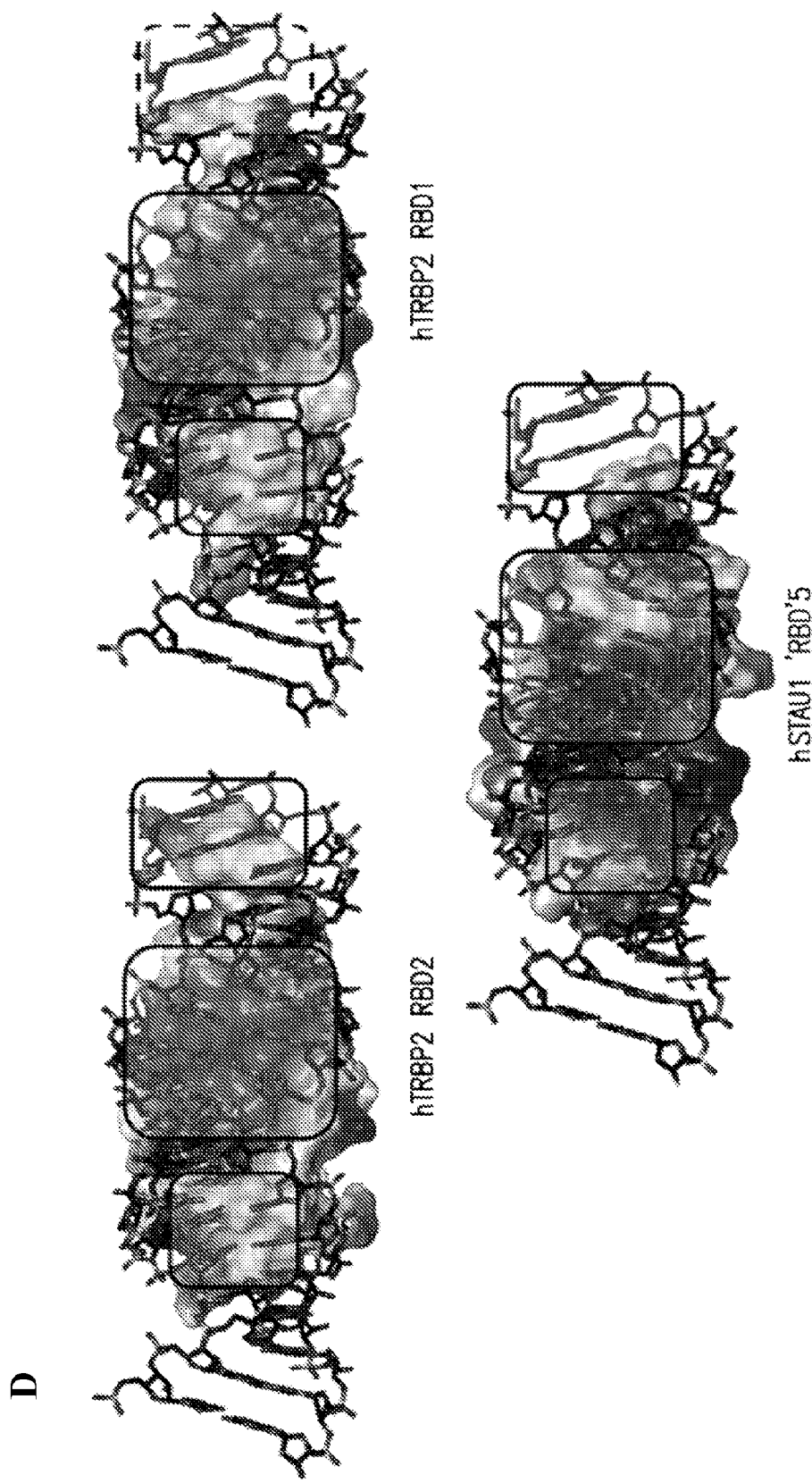

FIG. 14 shows a comparison of the Degenerate 'RBD'5 with a RBD that Binds dsRNA. FIG. 14A shows the structure-based sequence alignment of hSTAU1 'RBD'5 (top green sequence) (SEQ ID NO: 156) and hTRBP2 RBD1 (bottom grey sequence) (SEQ ID NO: 157). Conserved hydrophobic amino acids are shaded yellow, and conserved Tyr and Lys residues are shaded cyan and green, respectively. Key residues discussed in the text are blue if positively charged and red if negatively charged. Small upward-pointing arrowheads indicate the position of residues reported for hTRBD2 RBD1 and RBD2 that interact directly with dsRNA. FIG. 14B shows a cartoon of superposed hSTAU1 'RBD'5 (green) and hTRBP2 RBD1 (grey) produced by Dali. FIG. 14C shows X-ray crystal structure of hTRBP2 RBD2 in complex with dsRNA. hTRBP2 RBD2 is shown rather than hTRBP2 RBD1, which is more similar to hSTAU1 'RBD'5, since hTRBP1RBD1 lacks a complete Loop 2 (L2). Protein is blue and in cartoon-form, and dsRNA is in stick-representation. The three major interacting RBD regions of typical RBDs are approximated using round-edged enclosures to illustrate the important secondary structures. FIG. 14D shows a cartoon of either hTRBP2 RBD1 or STAU1 'RBD'5 superimposed on hTRBP2 RBD2, shown in relation to the position of dsRNA in the TRBP2 RBD2 structure. Vacuum electrostatic potentials were generated using PyMOL to illustrate charge variance, where blue is positive, red is negative, and white is neutral on the surface representation of each protein. As in C, regions necessary to interact with dsRNA are indicated.

Figure 15:
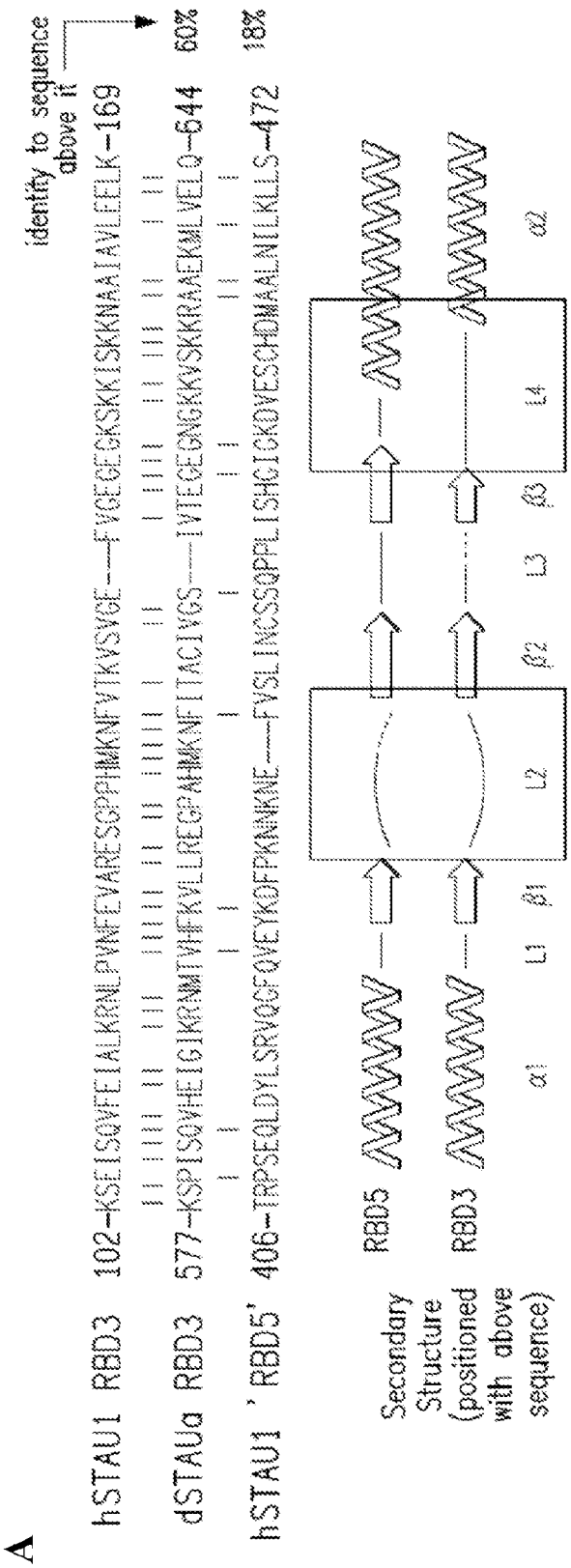
Figure 15:
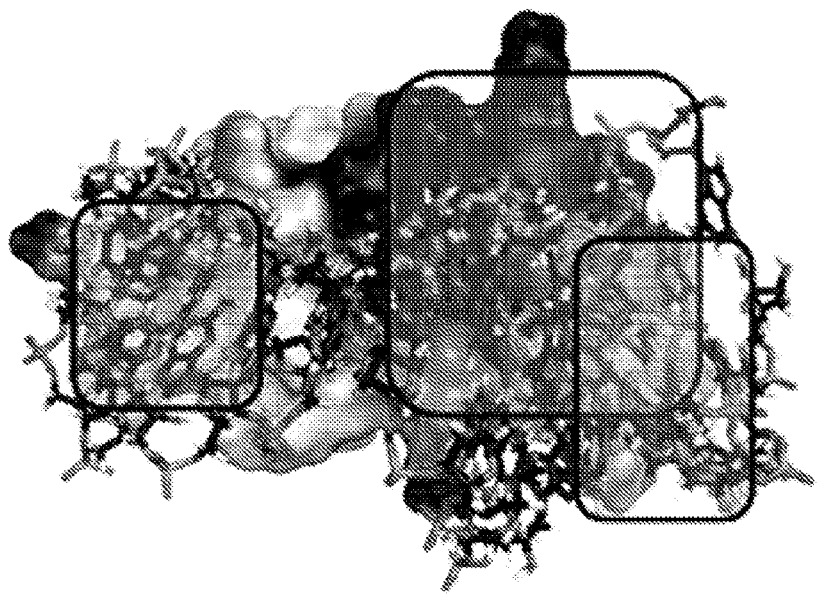
Figure 15:
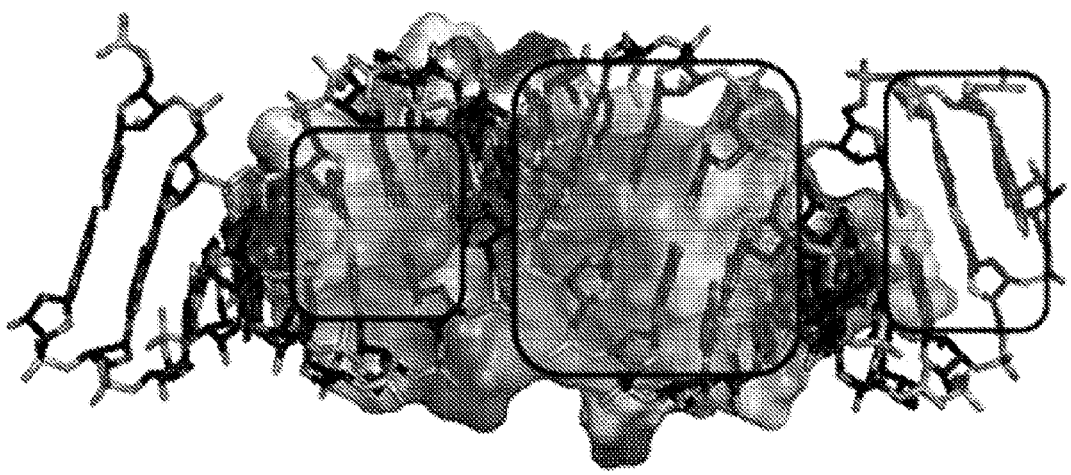

FIG. 15 shows a structural comparison of STAU1 RBD3 (hSTAU1 RBD3 SEQ ID NO: 158; dSTAUa RBD3 (SEQ ID NO: 159)) and STAU1 'RBD'5 (SEQ ID NO: 160) Through the Highly Similar NMR Structure of *D. melanogaster* STAU RBD3. FIG. 15A shows structure based sequence alignment between proteins. FIG. 15B shows vacuum electrostatic potentials were calculated using PyMOL for RBD3 (surface) and are shown in complex with the bound hairpin RNA (sticks). The hSTAU1 'RBD'5 electrostatic model from FIG. 14D is shown for comparison.

IV. DETAILED DESCRIPTION

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

As used herein, "chemical" refers to any reagent that can bind, mutate, dissolve, cleave, initiate a reaction that results in a new agent, or alter the confirmation of a target agent. An example of a chemical would be a small molecule.

As used herein, "pioneer round of translation" or "pioneering round" refers to an initial round of mRNA translation prior to steady-state translation. The round is characterized by the presence of CBP80 and CBP20 as the CAP binding proteins, PABP2 as a polyadenylation binding protein, and involves Upf2 and Upf3 or Upf3X.

In one aspect disclosed herein are methods of screening, methods of treatment, and compositions related to Staufen 1 mediated mRNA decay (SMD), targets of SMD and diseases associated with truncated or erroneous proteins.

Staufen 1

Mammalian Staufen1 (Stau1) is an RNA binding protein that binds to extensive RNA secondary structures, primarily through one or more double-stranded RNA-binding domains. In mammals, the Stau1 gene is ubiquitously expressed and generates protein isoforms having apparent molecular weights of 55 and 63 kDa. The 55-kDa isoform associates with 40S and 60S ribosomal subunits and co-localizes with the rough endoplasmic reticulum. A role for Stau1 in mRNA transport and translational control has been inferred from its presence in RNA granules that migrate within the dendrites of hippocampal neurons in a microtubule-dependent manner, as well as its encapsidation together with HIV-1 RNA in virus particles. Additionally, Stau1 interacts with telomerase RNA, suggesting that it functions during DNA replication, cell division or both, possibly by influencing telomerase RNA processing or RNP assembly or localization.

Stau1 Mediated mRNA Decay (SMD)

Staufen1 (STAU1)-mediated mRNA decay (SMD) degrades translationally active mRNAs that bind the double-stranded (ds)RNA binding protein STAU1 within their 3'-untranslated regions (3'UTRs). The STAU1 binding site (SBS) is within ADP ribosylation factor 1 (ARF1) mRNA as a 19-basepair stem with a 100-nucleotide apex. However, comparable structures within the 3'UTRs of other SMD targets were not identified. Herein is disclosed that SBSs can be formed in cis by intramolecular base-pairing within an mRNA 3'UTR, or in trans by imperfect base-pairing between an Alu element within the 3'UTR of an SMD target and another Alu element within a cytoplasmic and polyadenylated long noncoding RNA (lncRNA). When translation terminates sufficiently upstream of an SBS, association of the ATP-dependent RNA helicase UPF1 with SBS-bound STAU1 triggers mRNA decay analogously to how UPF1 association with an exon-junction complex that resides sufficiently downstream of premature termination codon triggers nonsense-mediated mRNA decay. Individual lncRNAs can downregulate a subset of SMD targets, and distinct lncRNAs can downregulate the same SMD target. These are previously unappreciated functions for ncRNAs and Alu elements.

Stau1 is involved in mRNA decay. Also, Stau1-mediated mRNA decay involves the nonsense-mediated mRNA decay (NMD) factor Upf1. In mammalian cells, the expression of protein-encoding genes requires a series of steps in which pre-mRNA is processed to mRNA in the nucleus before mRNA is translated into protein in the cytoplasm. These steps are subject to quality control to ensure that only completely processed mRNA is exported to the cytoplasm. One form of quality control, called mRNA surveillance or NMD. NMD in mammalian cells is generally a splicing-dependent mechanism that degrades newly synthesized mRNAs that prematurely terminate translation more than 50-55 nucleotides upstream of an exon-exon junction as a means to prevent the synthesis of potentially harmful truncated proteins. By so doing, NMD precludes the synthesis of the encoded truncated proteins, which can function in deleterious ways. NMD also targets naturally occurring mRNAs such as certain selenoprotein mRNAs and an estimated one-third of alternatively spliced mRNAs, some of which encode functional protein isoforms.

The dependence of NMD on splicing reflects the deposition of an exon junction complex (EJC) of proteins ~20-24 nucleotides upstream of splicing-generated exon-exon junctions. This EJC includes NMD factors Upf3 (also called Upf3a) or Upf3X (also called Upf3b), Upf2 and, presumably, Upf1. Upf3 and Upf3X appear to play a comparable role in NMD, although different isoforms of Upf3 can form distinct protein complexes. Other constituents of the EJC include Y14, RNPS1, SRm160, REF/Aly, UAP56, Mago, Pinin, and eIF4AIII. EJCs are present on mRNA that is bound at the cap by the mostly nuclear cap binding protein (CBP)80-CBP20 heterodimer, which is consistent with data indicating that NMD targets CBP80-bound mRNA during a pioneer round of translation.

Mammalian Stau1 binds the NMD factor Upf1 and the 3' untranslated region (UTR) of mRNA that encodes ADP-ribosylation factor (Arf)1. As a consequence, Stau1 mediates Arf1 mRNA decay in a mechanism that differs from NMD by occurring independently of splicing or Upf2 and Upf3X. Analogously to the Stau1-mediated mRNA decay (SMD) of Arf1 mRNA, artificially tethering Stau1 downstream of a normal termination codon also reduces mRNA abundance in a mechanism that depends on the normal termination codon and Upf1 but neither splicing nor Upf2, Upf3 or Upf3X. Notably, Stau1 plays no detectable role in the EJC-dependent NMD of either β-globin or glutathione peroxidase 1 mRNA.

ALU Elements

Disclosed herein, Stau1 can also bing to an binding site created by the imperfect base pairing on an ALU element in the 3' UTR of the mRNA of a transcript and an ALU element contained within long noncoding RNA. This is the first description of a function for long noncoding RNA (lncRNA). Whether present in the lncRNA or in the 3' UTR of the mRNA of a transcript, an ALU element is typically an approximately 300 base pair nucleic acid construct classified as short interspersed elements. ALU elements can vary in sequence, but generally correspond to the consensus sequence as set forth in SEQ ID NO: 3.

Staufen1-Mediated mRNA Decay by Swapping a Conserved Motif and a Degenerate Double-Stranded RNA-Binding Domain Human (h)STAU1 has 496- and 577-amino acid isoforms (NCBI Gene ID:6780; hSTAU1$^{55}$ and hSTAU1$^{63}$, respectively), each of which contains RBDs 2-5, and an additional isoform with six amino acids inserted into hSTAU1$^{55}$RBD3 that in the highly similar mouse ortholog diminishes dsRNA binding. Only RBD3 and RBD4 bind dsRNA in mammalian cells (thus, hereafter RBD2 and RBD5 are referred to as, respectively, 'RBD'2 and 'RBD'5), and RBD3 binds dsRNA with higher affinity than does RBD4. All three hSTAU1 isoforms also contain a tubulin-binding domain (TBD) situated between RBD4 and 'RBD'5 that probably binds tubulin based on in vitro studies of the highly similar mouse STAU1 TBD.

The hSTAU1 paralog, hSTAU2, has 479-, 504-, 538- and 570-amino acid isoforms (NCBI Gene ID: 27067; hSTAU2$^{52}$, hSTAU2$^{56}$, hSTAU2$^{59}$, and hSTAU2$^{62}$, respectively), each of which contain RBDs 2, 3 and 4, and only a partial N-terminal region of what would be hSTAU1 'RBD'5; additionally, hSTAU2$^{56}$ and hSTAU2$^{62}$ have a complete RBD1, whereas hSTAU2$^{52}$ and hSTAU2$^{59}$ contain a truncated RBD1. hSTAU2 isoforms also have a putative TBD that shares 17% identity with the hSTAU1 TBD but has yet to be shown to bind tubulin. Like hSTAU1, hSTAU2 mediates not only mRNA decay but also mRNA localization. Each paralog and even some of their isoforms function and localize differently within cells.

The X-ray crystal structure of a region of hSTAU1 includes a new motif that called the STAU-swapping motif (SSM). SSM is conserved in all examined vertebrate STAU homologs, resides N-terminal to 'RBD'5, to which it is connected by a flexible linker, and is responsible for forming hSTAU1 dimers both in vitro and in vivo. The two α-helices of SSM form a domain-swapped interaction with the N-terminal α-helix of 'RBD'5 so as to result in full-length hSTAU1 dimerization. This is a previously unappreciated role for an RBD that no longer binds dsRNA. In cells, disrupting hSTAU1 dimerization either by deleting SSM-'RBD5' from one of the two interacting proteins, or by expressing exogenous 'RBD'5 in the presence of two full-length proteins, reduces the ability of full-length hSTAU1 to co-immunoprecipitate with hUPF1, and thus, reduces the efficiency of SMD.

Herein is shown new motif that typifies STAU homologs from all vertebrate classes and is responsible for human (h)STAU1homodimerization. The crystal structure reveals that this motif, now named SSM for 'Staufen-swapping motif', and dsRNA-binding domain (RBD)$_5$, which has diverged from a prototypic RBD and no longer binds dsRNA, mediate domain swapping: the two SSM α-helices of one molecule interact mainly through a hydrophobic patch with the two 'RBD'5α-helices of a second molecule, and vice versa. 'RBD'5 adopts the canonical α-β-β-β-α fold of a functional RBD, but lacks residues and key features needed to bind duplexed RNA. In cultured cells, the SSM and N-terminal α-helix of 'RBD'5 are sufficient for hSTAU1-hSTAU1 dimerization, and dimerization is critical for efficient SMD.

Methods of Identifying SMD Targets

Expression of truncated or erroneous proteins can have severe effects on a person expressing said proteins. The truncated or erroneous proteins can have dominant negative effects or result in gain-of function mutations that can have severe consequences and result in cancers and other disorders. It is the role of SMD to reduce the occurrence of the truncated or erroneous proteins before they are expressed. Significantly, knowing the targets of SMD would provide new targets for treatments of disease, assessment of risks groups for disease, and diagnosis of a disease. Accordingly, disclosed herein are methods of identifying a Staufen 1 (Stau1)-binding site (SBS) that mediates Stau1-mediated mRNA decay (SMD) comprising the steps of a) down-regulating Stau1 or an ALU element-containing long noncoding RNA (lncRNA); b) identifying transcripts that are up-regulated at least 1.8-fold upon downregulation of Stau1 or the ALU element-containing lncRNA, wherein transcripts that are up-regulated at least 1.8-fold are SMD targets; and c) identifying an ALU element within the 3' UTR of the transcript of the SMD target, wherein the ALU element comprises a first strand of the SBS.

The methods disclosed herein utilize the down-regulation of Stau1 or lncRNA to identify SMD targets as such targets will increase in amount or expression by virtue of not being degraded by SMD. It is also understood that one method of down regulating Stau1 or lncRNA is through the use of siRNA. Further it is understood and discussed herein that there are many methods that can be used to detect the up-regulation of genes, mRNA, or proteins that are known in the art and include but are not limited to microarray, northern blot, southern blot, and western blot.

There are many SMD binding sites (SBS) and the sequence and identity of said sites is associated with SMD targets identified in the Examples below. Thus, disclosed herein are methods of identifying SBS, wherein the SMD target is selected from the group consisting of IFI44, FBLIM1, CLDN11, PDLIM3, OASL, TAF7L, NOX4, AIM1, SERPINE1, DCP2, EIF5A2, CEP135, LRRFIP1, ZFP90, TP53, PHLPP2, EHHADH, CCDC125, NUAK2, AKT2, APPL1, COL16A1, RIPK1, MGC14799, GNAS, DFFA, CSDA, SEC61A1, PSMD12, C4orf9, FLJ10613, GNE, FLJ30656, LOC149603, TEGT, MCM4, LOC63929, KIAA0186, PRKAR2A, NUTF2, GDF1, PAICS, TMPO, AAMP, IF, FN1, IFIT2, SCG2, STMN3, GAP43, CKMT1, OSF-2, FLJ25348, GNG4, FLJ33505, FBLP-1, IGFBP5, ITGB3, IFIT4, ALP, TAGLN, TFPI2, CTNNAL1, THBS1, PTPRO, CEB1, MGC29643, FLJ20035, AIM1, C14orf141, DUSP6, G1P2, FLJ20637, SLAMF1, SCLY, IL7R, ARHGDIB, ACTA2, CXCL1, RIG-1, IFIT1, FLY34064, MGC19764, TLE4, DACT1, C9orf39, JUN, IGA4, TNC, FLJ13621, MICAL2, TMSNB, PTGER4, C14orf128, GDAP1, ZFP36L1, UNG, CDKAL1, ALDH1A3, PSMB9, PHF11, BANK1, KIAA0143, GBP1, EPPK1, ACTN1, RNF20, LRRFIP1, LOC150759, DPYSL3, PSK-1, ZFP90, TP53, LOC148418, TGFB1I1, ETV1, ARHGAP19, SOCS2, CDK5R1, SDS3, SCDGF-B, HDAC8, HMGB3, KIAA0931, DFKZp761K1423, PTPRF, TXNRD3, CGI-72, MGC15634, HES1, C11orf9, and TOIA1.

It is further understood that because the SBS can be the result of imperfect base pairing between an ALU element contained within lncRNA and ALU element on an SMD target; where the screening method comprises the down regulation of Stau1, the method further comprises step d. identifying an ALU element in a cytoplasmic polyadenaleted lncRNA that contains an ALU element that base pairs with the ALU element in the SMD target, wherein the ALU element of the lncRNA comprises a second strand of the SBS. It is understood and disclosed herein that there are many methods that may be used to uncover the identity of an lncRNA including, but not limited to, co-immunoprecipitation and the computation alalyses employed herein. Thus, for example disclosed herein are methods of identifying a SBS of SMD comprising a) transiently expressing an ALU element-containing lncRNA linked to a reporter gene; and b) immunoprecipitating the ALU element-containing lncRNA using an anti-reporter protein antibody; wherein ALU elements within RNA that encode proteins other than Stau1 that are co-immunoprecipitated with the ALU element of the lncRNA is a target SMD binding site (see, for example, Example 6).

Methods of Screening

An agent that is able to modulate SMD is useful for the treatment and study of SMD related disorders. Thus, specifically disclosed are methods of screening for an agent that modulates Stau1-mediated mRNA decay (SMD) comprising incubating the agent with a stably transfected cell comprising a reporter gene with a 3' UTR ALU element; a lncRNA containing a corresponding ALU element; and Stau1, and assaying the amount of mRNA of the reporter gene in the cell. An increase or decrease in the amount of mRNA of the reporter gene relative to the amount of mRNA of the reporter gene in the absence of the agent indicates an agent or substance that modulates SMD activity. Also disclosed are methods of identifying an agent that binds a SBS comprising contacting the SBS with the agent to be screened, wherein the SBS comprises an ALU element from a SMD target and an ALU element from a lncRNA that base pairs with the ALU element from the SMD target.

It is understood that another means by which one of skill in the art may use to screen for agents that modulated SMD is through the detection or measurement of complexes such as an SMD-target-Stau1 complex. It is understood that by "SMD complex" is any combination of one or more of the essential components of SMD. Thus, for example, specifically disclosed are screening methods wherein the complex comprises Upf1 and Stau1. Also disclosed are screening methods wherein the complex comprises one of Upf1 and Stau1. Thus, for example disclosed are methods of screening for an agent that modulates SMD comprising a) incubating the agent with an SMD target and Stau1 forming an agent-SMD target-Stau1 mixture, and b) assaying the amount of SMD target-Stau1 complex present in the mixture, wherein a increase or decrease in the amount of SMD target-Stau1 complex relative to the amount of SMD target-Stau1 complex in the absence of the agent indicates that the agent promotes or inhibits SMD, respectively. Also disclosed are methods of screening for an agent that modulates SMD comprising a) incubating the agent with an SMD target and Stau1 forming an agent-SMD target-Stau1 mixture, and b) assaying the amount of SMD target present in the mixture, wherein a increase or decrease in the amount of SMD target relative to the amount of SMD target in the absence of the agent indicates that the agent inhibits or promotes SMD, respectively.

Also disclosed is a method of screening for an agent that modulates Stau1-mediated mRNA decay (SMD) comprising incubating the agent to be screened with a stably transfected cell comprising a reporter gene with a nonsense-mutation and Stau1, and assaying the amount of SMD in the cell, wherein a increase or decrease in the amount of mRNA relative to the amount of mRNA in the absence of the agent indicates a agent that modulates SMD activity.

It is understood that many fragments or minor variants of the disclosed protein can be used in the disclosed methods. Thus, specifically disclosed are screening methods wherein the Stau1 has at least 80%, 85%, 90%, or 95% identity to the sequence set forth in SEQ ID NO: 2, or an SMD-active fragment thereof. It is also understood that the disclosed methods contemplate that the SBS within the SMD target comprises an ALU element in the 3' UTR of the SMD target. It is understood that ALU sequences can vary from SMD target to target but typically reflect the ALU element consensus sequence set forth in SEQ ID NO: 3. Therefore disclosed herein are methods wherein the ALU element has at least 50%, 55%, 60%, 65%, 70%, 75%, 80%, 85%, 90%, 95% identity to the consensus ALU element set forth in SEQ ID NO: 3.

Disclosed herein are methods of screening for an agent that modulates Stau1-mediated mRNA decay (SMD) comprising, administering an agent to a system, wherein the system comprises the components for SMD activity, and assaying the effect of the agent on the amount of SMD activity in the system, a change in the amount of SMD activity present in the system compared to the amount of SMD activity in the system in the absence of the agent indicates the agent is a modulator. Thus, specifically contemplated and herein disclosed are methods of modulating Stau1-mediated mRNA decay (SMD) activity comprising administering an agent, wherein the agent is identified by the disclosed screening methods.

The agents that can be used to modulate SMD can function by inhibiting the binding of Stau1 to its binding site. For example, an agent that competitively binds a Stau1 binding site can inhibit SMD. Therefore, specifically disclosed are methods of identifying an agent that binds a Stau1 binding site comprising contacting the agent to be screened with the Stau1 binding site. Also disclosed are methods of identifying an agent that binds a Stau1 binding site wherein one strand of the Stau1 binding has at least 80%, 85%, 90%, or 95% identity to the sequence set forth in SEQ ID NO: 3.

Also disclosed are screening and treatment methods, wherein the agent binds Upf1, an ALU element containing lncRNA, an SMD target, the SBS of an SMD target (such as for example an ALU element in the 3' UTR of the SMD target), or Stau1. As used herein, "binds" or "interacts" means to affect an agent either directly or indirectly through cooperative function, competitive inhibition, non-competitive inhibition, binding, or contacting the agent, a target molecule, an accessory molecule, or alternative portion of a system so as to effect at least one function. The interaction can be stimulatory or cooperative in nature having an additive or synergistic effect. The interaction can also result in the inhibition of a process or target molecule.

The disclosed methods function by modulating SMD. Herein, it is understood that by "modulation" or "modulating" is meant either an increase or a decrease in SMD activity. Alternatively, Staufen 1 can modulate mRNA transcripts through the stabilization or destabilization of an mRNA. Whether SMD levels are increased or decreased in a subject with a condition resulting from a mutation that generates a nonsense codon (including but not limited to a nonsense mutation) depends on the particular mRNA that is affected, the binding of Staufen1 and, where binding of Stau1 occurs. A decrease in SMD activity could increase the amount of mRNA that is available for translation. Thus, for example, modulation can be measured by, e.g., comparing the level of the mRNA harboring a premature or alternative termination codon relative to an unaffected cellular RNA to the level of that mRNA lacking a premature or alternative termination codon to the same unaffected cellular RNA. Subsequent nonsense suppression could be used to increase the amount of the encoded full-length protein. Conversely, an increase in SMD activity would decrease the amount of mRNA that is available for translation so as to reduce production of the encoded truncated protein. Thus, it is understood and herein contemplated that the disclosed methods can be used to modulate the expression of genes by modulating SMD (e.g., to decrease mRNA from a truncated protein, one would increase SMD activity. A decrease in SMD activity would be used to increase the amount of mRNA of a truncated protein available). Notably, SMD can also target mRNAs that do not have a premature or alternative termination codon, providing another means by which gene expression could be regulated.

Thus, for example, specifically disclosed are methods wherein the modulation is a decrease in Stau1-mediated mRNA decay. A "decrease" can refer to any change that results in a smaller amount of Stau1 mRNA mediated decay. Thus, a "decrease" can refer to a reduction in an activity. An agent is also understood to decrease the genetic output of a gene when the genetic output of the gene product with the agent is less relative to the output of the gene product without the agent. Also for example, a decrease can be a change in the symptoms of a disorder such that the symptoms are less than previously observed. In the case of a decrease in Stau1 mRNA mediated decay, it is understood and herein contemplated that a decrease can include, but is not limited to, a 10%, 20%, 30%, 40%, 50%, 60%, 70%, 80%, 90%, or 100% reduction. A decrease can but does not have to result in the complete ablation of a substance or activity. Therefore, for example, a decrease in SMD would result in the presence of more gene products with early or alternative termination sites (i.e., a decrease in SMD activity). It is understood that the term "inhibits" or "inhibition" refers to any degree of decrease as compared to a control. Thus, for example, "inhibition" can refer to a 10%, 20%, 30%, 40%, 50%, 60%, 70%, 80%, 90%, or 100% reduction as compared to a control.

Also disclosed are methods wherein the modulation is an increase in Stau1-mediated mRNA decay. An "increase" can refer to any change that results in a larger amount of a Stau1 mediated mRNA decay activity. Thus, for example, an increase in the amount in SMD of a particular mRNA can include but is not limited to a 10%, 20%, 30%, 40%, 50%, 60%, 70%, 80%, 90%, or 100% increase. It is understood and herein contemplated that an increase in SMD would result in a subsequent decrease in the amount of gene products with early or alternative termination sites.

It is understood and herein contemplated that the disclosed screening and treatment methods can utilize the modulation of the level of mRNA or protein expression. It is also understood and herein contemplated that Stau1 can increase or decrease the abundance of an mRNA independently of SMD. Likewise, it is understood and herein contemplated that not all SMD activity occurs through the involvement of Stau1 and Upf1, but can be Upf1 independent. By "modulating the level of mRNA" is meant that the abundance of a target transcript can be increased or decreased by the expression of Stau1. The ability to modulate the abundance of target genes can be achieved in conjunction with or independently of Upf1. It is understood that such effect can be either direct or indirect. By "direct effect" is meant that Stau1 acts on the targeted mRNA itself and by "indirect effect" is meant that Stau1 acts by an intermediary, including for example, a nucleic acid. Thus, Stau1 down-regulation can result either directly or indirectly in the down reulation of target mRNA levels. It is understood that whether the effect is direct or indirect will depend on the target gene. One of skill in the art will be able to determine whether the effect is direct or indirect given the target gene. Thus specifically disclosed and herein contemplated are methods of identifying genes modulated by the down-regulation of Stau1 or an ALU containing lncRNA comprising incubating a agent that down-regulates SMD with a stably transfected cell comprising Stau1 and one or more selected genes comprising one or more nonsense-mutations, and assaying the amount of protein expressed of the gene being screened or mRNA present for the gene being screened, wherein a increase or decrease in the amount of protein or mRNA relative to the amount of protein or mRNA in the absence of the siRNA indicates a gene that is modulated by Stau1 activity.

It is understood that these methods can be used to identify genes that are up-regulated or down regulated by the down-regulation of Stau1 as well as identify those genes whose abundance increases or decreases with the down-regulation of Stau1. It is understood and herein contemplated that one example of an agent that can down regulate SMD is small interfering RNA (siRNA) to a component of SMD such as Stau1 or lncRNA.

Although Stau1 can modulate mRNA levels independently of Upf1 and SMD, dependent modulation can also occur. Thus, disclosed herein are methods of identifying genes modulated by the down-regulation of Upf1 comprising a) transfecting a small interfering RNA (siRNA) that down-regulates SMD into a cell comprising Upf1 and one or more selected genes comprising one or more nonsense-mutations, and b) assaying the amount of protein expressed of the gene being screened or mRNA present for the gene being screened, wherein a increase or decrease in the amount of protein or mRNA relative to the amount of protein or mRNA in the absence of the siRNA indicates a gene that is modulated by Upf1 activity. Also disclosed are method of identifying genes modulated by the down-regulation of SMD comprising a) transfecting a small interfering RNA (siRNA) that down-regulates SMD into a cell comprising UPf1, Stau1, and one or more selected genes comprising one or more nonsense-mutations, and b) assaying the amount of protein expressed of the gene being screened or mRNA present for the gene being screened, wherein a increase or decrease in the amount of protein or mRNA relative to the amount of protein or mRNA in the absence of the siRNA indicates a gene that is modulated by SMD activity. It is understood that the siRNA can be, for example, Upf1 siRNA or Stau1 siRNA.

Various assays are known in the art that can be used to measure mRNA levels or protein expression. For example, mRNA levels can be measured by microarray or RT-PCR. Protein expression can be measured by Western blot. It is understood and herein contemplated that the disclosed methods of identifying genes can be used with any method of measuring protein expression or mRNA levels known to those of skill in the art.

Also disclosed are methods of modulating the level of an mRNA comprising administering to a subject an effective amount of an agent that modulates Stau1, wherein the modulation Stau1 directly or indirectly modulates the mRNA. Also disclosed are methods of treating a disorder in a subject comprising administering to the subject an agent, wherein the agent modulates Stau1 wherein the modulation of Stau1 modulates that level of mRNA abundance of another gene.

The disclosed compositions and methods can be used to evaluate the expression of genes involved in SMD and in particular in or as a result of the pioneer round of translation. Specifically contemplated are methods wherein mRNA from a system comprising a nonsense-mutation is assayed using a micro array. Genes identified as having significantly (as determined by the manufacturers specifications of the array) increased or decreased expression are comodulators of SMD.

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

Methods of Treating

The invention described herein in one aspect relates to methods of treating a disorder in a subject comprising administering to the subject an agent, wherein the agent modulates Stau1-mediated mRNA decay (SMD). For example disclosed herein are methods of treating a disorder associated with expression of a truncated or erroneous protein in a subject comprising administering to the subject an agent, wherein the agent increases SMD of the gene encoding the target protein in the subject.

It is understood and herein contemplated that the term "treating" can refer to any method that improves a disorder in a subject. The improvement can include but is not limited to a decrease in one or more symptoms of the disorder such that the disorder is reduced. Treating is understood to include small improvements in the disorder up to and including the complete ablation of the disorder. For example, the treatment can result in a 10%, 20%, 30%, 40%, 50%, 60%, 70%, 80%, 90%, or 100% reduction in the disorder.

It is understood and herein contemplated that the disorders to be treated can be the result of or related to the expression truncated or erroneous proteins. Such proteins can be the result of aberrant mRNA splicing that leads to premature termination of the mRNA. It is understood that the mRNA that encodes the truncated or erroneous protein can comprise at least one ALU element in its 3' UTR. There are many disorders that can be treated with the disclosed methods. It is understood and herein contemplated that a "disorder" means any inherited or acquired disease or condition associated with Stau1 mediated mRNA decay that has a negative effect relative to the wild-type state. For example, the disorder can be inherited genetic disorder. Inherited genetic disorders are disorders that result from the presence of an abherent gene or genes that alter the way an interaction, system or pathway works. As used herein, "system" refers to any cell, organism, or in vitro assay or culture. Such a system includes components necessary for SMD activity. Such components can include, for example, but are not limited to Stau1 and Upf1. Thus for example, specifically contemplated are methods disclosed herein wherein the disorder is a genetic disorder, and wherein the genetic disorder can be selected from the group consisting of cystic fibrosis, hemophilia, mucopolysaccharidoses, muscular dystrophy, anemia, glycolytic enzyme deficiency, connective tissue disorder, DNA repair disorder, dementia, Diabetes mellitus type II, Alzheimer's disease, Marfan's syndrome, β-Thalasimia, Neurofibromatosis, Hypercholesterolemia, Sandhoff disease, epidermolysis bullosa simplex, insulin resistance, maple syrup urine disease, hereditary fructose intolerance, inherited immunodeficiency, inherited cancer, carbohydrate metabolism disorder, amino acid metabolism disorder, lipoprotein metabolism disorder, lipid metabolism disorder, lysomal enzymes disorder, steroid metabolism disorder, purine metabolism disorder, pyrimidine metabolism disorder, metal metabolism disorder, porphyrin metabolism disorder, and heme metabolism disorder.

Also for example, a disorder can be dementia. Dementias can include but are not limited to Alzheimer's, Lewy Body dementia, Binswanger's dementia, or dementias associated with Parkinson's Disease, progressive supranuclear palsy, Huntington's disease, Pick's disease, Creutzfeldt-Jakob disease, Gerstmann-Straussler-Scheinker disease, AIDS, or trauma.

Disorders can also include acquired disorders. Acquired disorders are disorders that result from some external insult or injury, or from an unknown mechanism that is not derived from a genetic characteristic. Thus by "acquired disorder" is meant any disorder that lacks a clear genetically inherited link. For example, an infection or malignancy without a clear genetically inherited link. For example, acquired disorders can result from chemical exposure, radiation exposure, or random mutation in a gene that was not present in the subject earlier. Thus for example, an acquired disorder can comprise a cancer.

Also disclosed are methods of the invention, wherein the disorder is an acquired disorder. The acquired disorder is, by way of example but not by way of a limitation, a cancer. Such a cancer may be related to mutations such as mutations in p53 or BRCA-1.

The disclosed compositions can be used to treat any disease where uncontrolled cellular proliferation occurs such as cancers. A representative but non-limiting list of cancers that the disclosed compositions can be used to treat is the following: lymphoma, B cell lymphoma, T cell lymphoma, leukemia, carcinoma, sarcoma, glioma, blastoma, neuroblastoma, Ewing's sarcoma, gastric cancer, lung cancer, plasmacytoma, histiocytoma, melanoma, mycosis fungoide, hypoxic tumor, myeloma, metastatic cancer, bladder cancer, brain cancer, nervous system cancer, head and neck cancer, ovarian cancer, pancreatic cancer, prostate cancer, skin cancer, liver cancer, colon cancer, cervical cancer, breast cancer, epithelial cancer, renal cancer, genitourinary cancer, pulmonary cancer, esophageal carcinoma, hematopoietic cancers, testicular cancer, and colorectal cancer.

Disclosed and herein contemplated are methods wherein the SMD occurs in or as a result of the pioneering round of translation. Notably, SMD can also occur during steady-state translation. During steady-state translation, can target eIF4E-bound mRNA.

As used herein, "subject" refers to any cell, tissue, system, or organism used to study or treat a disorder relating to SMD, including, for example, human patients with conditions that result from SMD or cell lines used to study aspects of SMD. Thus, in one embodiment the subject is a mammal. It is specifically contemplated that mammal can include but is not limited to human or non-human primate.

Also disclosed are methods of treating a disorder in a subject comprising administering to the subject a substance, wherein the substance modulates Stau1-mediated mRNA decay. Modulation of Stau1-mediated mRNA decay can result in a decrease in SMD. The decrease in SMD would increase the abundance of the nRNA containing a premature or alternative termination codon.

Specifically disclosed herein are methods of facilitating Stau1-mediated mRNA decay comprising contacting a system comprising the components for SMD with Stau1. Also disclosed are methods of facilitating Stau1-mediated mRNA decay comprising contacting with a system, wherein the system comprises the components for SMD such as, for example, an ALU element containing lncRNA, Upf1, Upf2, or Upf3. Also disclosed are methods of facilitating Stau1-mediated mRNA decay comprising contacting the SMD target with Stau1 and/an ALU element containing lncRNA. The combination of Stau1 and lncRNA can be simultaneous or sequential.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies or other agents can be administered intravenously, intraperitoneally, intramuscularly, subcutaneously, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

The disclosed methods and compositions can also be used for example as tools to isolate and test new drug candidates for a variety of diseases. They can also be used for the continued isolation and study, for example, SMD. There use as exogenous DNA delivery devices can be expanded for nearly any reason desired by those of skill in the art.

The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed in SEQ ID NOS:1, 2, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, Stau1, are also disclosed. Thus, the products produced using the combinatorial or screening approaches that involve the disclosed compositions, such as, Stau1, are also considered herein disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo SMD activity or a modified activity. For example, phage display libraries have been used to isolate numerous peptides that interact with a specific target.

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art.

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest. Cohen et al. modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

As used herein combinatorial methods and libraries included traditional screening methods and libraries as well as methods and libraries used in interactive processes.

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, Stau1 and Upf1, are also disclosed. Thus, the products produced using the molecular modeling approaches that involve the disclosed compositions, such as, Stau1 and Upf1, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

Although described above with reference to design and generation of compounds which could alter binding, one could also screen libraries of known compounds, including natural products or synthetic chemicals, and biologically active materials, including proteins, for compounds which alter substrate binding or enzymatic activity.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as described herein. The antibodies are tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies of the invention can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the Stau1 or Upf1 described herein.

The monoclonal antibodies may also be made by recombinant DNA methods. DNA encoding the monoclonal antibodies of the invention can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

The human antibodies of the invention can be prepared using any technique. Human antibodies of the invention (and fragments thereof) can also be produced using phage display libraries.

The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,*

90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody.

Methods for humanizing non-human antibodies are well known in the art. For example, humanized antibodies can be generated according to the methods of Winter and co-workers, by substituting rodent CDRs or CDR sequences for the corresponding sequences of a human antibody.

Antibodies of the invention are preferably administered to a subject in a pharmaceutically acceptable carrier as described above. Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 µg/kg to up to 100 mg/kg of body weight or more per day, depending on the factors mentioned above.

Following administration of an antibody for treating, inhibiting, or preventing a condition, the efficacy of the therapeutic antibody can be assessed in various ways well known to the skilled practitioner. Specifically, SMD can be assessed directly or indirectly as taught herein.

In the methods described above which include the administration and uptake of exogenous DNA into the cells of a subject (i.e., gene transduction or transfection), the nucleic acids of the present invention can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome. The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

As one example, if the antibody-encoding nucleic acid of the invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection. A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds.

Compositions

The disclosed screening and treatment methods make use of agents administered to a subject to achieve a desired effect. It is understood and herein contemplated that "agent" can refer to any compound, functional nucleic acid, siRNA, peptide, protein, antibody, or small molecule. Thus, for example, one embodiment of the disclosed methods is a method of treating a subject with an agent wherein the substance is Stau1, an ALU element-containing lncRNA that base pairs with the ALU element in the mRNA of the 3' UTR of the truncated or erroneous protein, or a complex comprising one or more of an ALU element-containing lncRNA, Stau1 Upf1, Upf2, and Upf3. Thus, for example, disclosed It is understood that by "SMD complex" is any combination of one or more of the essential components of SMD. Such administration can be direct or indirect. For example, the Stau1 can be administered directly or by transfer with a subject with a Stau1 encoding nucleic acid or by administering to the subject a compound that modulates SMD.

An agent that modulates SMD can be a nucleic acid. Therefore specifically disclosed and herein contemplated is an agent, wherein the agent is a vector comprising a nucleic acid that encodes an SMD modulator. Also disclosed is a vector comprising a nucleic acid that encodes an SMD modulator. Also disclosed is a cell comprising the disclosed vectors.

Thus specifically contemplated and disclosed herein is an agent that modulates SMD, wherein the substance is an siRNA that modulates SMD. It is understood that the siRNA can bind any factor that modulates SMD. For example, specifically disclosed is an siRNA, wherein the siRNA binds Upf1. Also disclosed is a substance comprising siRNA, wherein the siRNA binds Stau1. It is further understood that providing additional components of SMD can facilitate increased SMD activity. For example, wherein the agent is Stau1, additional Stau1 will be available to bind to the SBS. Additionally, wherein the agent is an ALU element-containing lncRNA, an additional component of the SBS is provided to bind with the ALU element in the 3' UTR of the SMD target. Thus disclosed herein are agents, wherein the agent is Stau1, an lncRNA, or an siRNA that binds to an ALU element.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular Stau1 or ALU element is disclosed and discussed and a number of modifications that can be made to a number of molecules including the Stau1 or the ALU element are discussed, specifically contemplated is each and every combination and permutation of Stau1 and the ALU element and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

As used throughout, when reference is made to a particular protein or nucleic acid, some variation in amino acid or nucleotide sequence is expected without a substantial decline in function. Thus, Stau1 can include proteins or nucleic acid sequences having at least 80%, 85%, 90%, or 95% identity to the sequence set forth in SEQ ID NO: 1 or 2, or fragment thereof. Also disclosed are methods of the invention, wherein the ALU element of the lncRNA has at least 50%, 55%, 60%, 65%, 70%, 75%, 80%, 85%, 90%, or 95% identity to the sequence set forth in SEQ ID NO: 3, or fragment thereof.

It is understood that one way to define any known variants and derivatives or those that might arise, of the disclosed genes and proteins herein is through defining the variants and derivatives in terms of homology to specific known sequences. For example SEQ ID NO: 1 sets forth a particular sequence of a Stau1 encoding nucleic acid, and SEQ ID NO: 2 sets forth a particular sequence of the protein encoded by SEQ ID NO: 1, an Stau1 protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

There are a variety of molecules disclosed herein that are nucleic acid based, including for example the nucleic acids that encode, for example Stau1 and Upf1, as well as various functional nucleic acids. The disclosed nucleic acids are made up of, for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modifcation, such as 2'-β-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O—, S—, or N-alkyl; O—, S—, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$O]$_m$ $CH_3$, —O$(CH_2)_n$OCH$_3$, —O$(CH_2)_n$ NH$_2$, —O$(CH_2)_n$ CH$_3$, —O$(CH_2)_n$—ONH$_2$, and —O$(CH_2)_n$ON [$(CH_2)_n$ CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S, Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

There are a variety of sequences related to the Stau1 and Upf1 gene having the following Genbank Accession Numbers: BC050432 and NM_002911, respectively. These sequences and others are herein incorporated by reference in their entireties as well as for individual subsequences contained therein.

One particular sequence set forth in SEQ ID NO: 1 and having Genbank accession number BC050432 is used herein, as an example, to exemplify the disclosed compositions and methods. It is understood that the description related to this sequence is applicable to any sequence related to Stau1 unless specifically indicated otherwise. Those of skill in the art understand how to resolve sequence discrepancies and differences and to adjust the compositions and methods relating to a particular sequence to other related sequences (i.e. sequences of Upf1, SMD targets, ALU elements, ALU element containing lncRNA). Primers and/or probes can be designed for any Stau1 or Upf1 sequence given the information disclosed herein and known in the art.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than $10^{-6}$. It is more preferred that antisense molecules bind with a $k_d$ less than $10^{-8}$. It is also more preferred that the antisense molecules bind the target molecule with a $k_d$ less than $10^{-10}$. It is also preferred that the antisense molecules bind the target molecule with a $k_d$ less than $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $k_d$s from the target molecule of less than $10^{-12}$ M. It is preferred that the aptamers bind the target molecule with a $k_d$ less than $10^{-6}$. It is more preferred that the aptamers bind the target molecule with a $k_d$ less than $10^{-8}$. It is also more preferred that the aptamers bind the target molecule with a $k_d$ less than $10^{-10}$. It is also preferred that the aptamers bind the target molecule with a $k_d$ less than $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10 fold lower than the $k_d$ with a background binding molecule. It is more preferred that the aptamer have a $k_d$ with the target molecule at least 100 fold lower than the $k_d$ with a background binding molecule. It is more preferred that the aptamer have a $k_d$ with the target molecule at least 1000 fold lower than the $k_d$ with a background binding molecule. It is preferred that the aptamer have a $k_d$ with the target molecule at least 10000 fold lower than the $k_d$ with a background binding molecule. It is preferred when doing the comparison for a polypeptide for example, that the background molecule be a different polypeptide.

It is understood herein that "siRNA" referes to double-stranded RNAs that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends. The direction of dsRNA processing determines whether a sense or an antisense target RNA can be cleaved by the produced siRNA endonuclease complex. Thus, siRNAs can be used to modulate transcription, for example, by silencing genes such as Stau1 and Upf1. The effects of siRNAs have been demonstrated in cells from a variety of organisms, including *Drosophila, C. elegans*, insects, frogs, plants, fungi, mice and humans. In certain examples, siRNAs are directed against certain target genes to down regulate gene expression. For example, Stau1, ALU element containing lncRNA, SMD targets, or Upf1 expression can be down regulated by specifically targeting the siRNA to Stau1 or Upf1.

As discussed herein there are numerous variants of the Stau1 protein and Upf1 protein that are known and herein contemplated. In addition, to the known functional Stau1 and Upf1 strain variants, there are derivatives of the Stau1 and Upf1 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by crosslinking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala; A |
| arginine | Arg; R |
| asparagine | Asn; N |
| aspartic acid | Asp; D |
| cysteine | Cys; C |
| glutamic acid | Glu; E |
| glutamine | Gln; Q |
| glycine | Gly; G |
| histidine | His; H |
| isolelucine | Ile; I |
| leucine | Leu; L |
| lysine | Lys; K |
| methionine | Met; M |
| phenylalanine | Phe; F |
| proline | Pro; P |
| serine | Ser; S |
| threonine | Thr; T |
| tyrosine | Tyr; Y |
| tryptophan | Trp; W |
| valine | Val; V |

TABLE 2

Amino Acid Substitutions
Original Residue Exemplary Conservative
Substitutions, others are known in the art.

Ala; Ser
Arg; Lys, Gln
Asn; Gln; His
Asp; Glu
Cys; Ser
Gln; Asn; Lys
Glu; Asp
Gly; Pro
His; Asn; Gln
Ile; Leu; Val
Leu; Ile; Val
Lys; Arg; Gln;
Met; Leu; Ile
Phe; Met; Leu; Tyr
Ser; Thr
Thr; Ser
Trp; Tyr
Tyr; Trp; Phe
Val; Ile; Leu

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 2 sets forth a particular sequence of Stau1. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:2 is set forth in SEQ ID NO:1. It is understood that all of the nucleic acid sequences that encode this particular derivative of the Stau1 are also disclosed including for example SEQ ID NO:1 which set forth two of the degenerate nucleic acid sequences that encode the particular polypeptide set forth in SEQ ID NO:2. It is also understood that while no amino acid sequence indicates what particular DNA sequence encodes that protein within an organism, where particular variants of a disclosed protein are disclosed herein, the known nucleic acid sequence that encodes that protein in the particular Stau1 from which that protein arises is also known and herein disclosed and described.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science*, 247, 1465-1468, (1990); and Wolff, J. A. *Nature*, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus.

As used herein, plasmid or viral vectors are agents that transport the disclosed nucleic acids, such as Stau1 and Upf1 into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors.

Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms. A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites Recombinant adenoviruses achieve gene transduction by binding to specific cell surface receptors, after which the virus is internalized by receptor-mediated endocytosis, in the same manner as wild type or replication-defective adenovirus.

A viral vector can be one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Preferred promoters controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

Enhancer generally refers to a sequence of DNA that functions at no fixed distance from the transcription start site and can be either 5' to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription that may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The viral vectors can include a nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells that were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells that have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Disclosed herein are kits that are drawn to reagents that can be used in practicing the methods disclosed herein. The kits can include any reagent or combination of reagents discussed herein or that would be understood to be required or beneficial in the practice of the disclosed methods. For example, the kits could include primers to perform the amplification reactions discussed in certain embodiments of the methods, as well as the buffers and enzymes required to use the primers as intended. The kits could include systems comprising the essential elements of SMD activity.

The compositions disclosed herein and the compositions necessary to perform the disclosed methods can be made using any method known to those of skill in the art for that particular reagent or compound unless otherwise specifically noted.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Identification of mRNAs Bound by Staufen-1

TABLE 3

Genes that Encode Putative Stau1-binding mRNAs as Determined by Microarray Analysis

| Gene Symbol | Accession Number | Unigene Name |
| --- | --- | --- |
| ARF1 | AA580004 | ADP-ribosylation factor 1 |
| MGC14799 | BC005995 | hypothetical protein MGC14799 |
| GNAS | AF064092 | GNAS complex locus |
| DFFA | NM_004401 | DNA fragmentation factor 45kDa alpha polypeptide |
| CSDA | NM_003651 | cold shock domain protein A |
| SEC61A1 | NM_013336 | Sec61 alpha 1 subunit (*S. cerevisiae*) |
| PSMD12 | NM_002816 | proteasome (prosome macropain) 26S subunit non-ATPase 12 |
| EIF5A | NM_001970 | eukaryotic translation initiation factor 5A |
| C4orf9 | R06783 | chromosome 4 open reading frame 9 |
| FLJ10613 | NM_019067 | hypothetical protein FLJ10613 |
| GNE | NM_005476 | glucosamine (UDP-N-acetyl)-2-epimerase/N-acetylmannosamine kinase |
| FLJ30656 | AW873564 | *H. sapiens* transcribed sequences |
| LOC149603 | AA085748 | hypothetical protein LOC149603 |
| TEGT | NM_003217 | testis enhanced gene transcript (BAX inhibitor 1) |
| MCM4 | AI859865 | MCM4 minichromosome maintenance deficient 4 (*S. cerevisiae*) |
| LOC63929 | NM_022098 | hypothetical protein LOC63929 |
| KIAA0186 | NM_021067 | KIAA0186 gene product |
| PRKAR2A | BF246917 | protein kinase cAMP-dependent regulatory type II alpha |
| NUTF2 | NM_005796 | nuclear transport factor 2 |
| GDF1 | NM_001492 | growth differentiation factor 1 |
| PAICS | AA902652 | phosphoribosylaminoimidazole carboxylase phosphoribosylaminoimidazole succinocarboxamide synthetase |
| TMPO | AF113682 | thymopoietin |
| AAMP | NM_001087 | angio-associated migratory cell protein |

293 cells were transiently transfected with a plasmid that expressed Stau1-HA$_3$ or, to control for nonspecific IP, Stau1-6xHis. Biotin-labeled cRNA was synthesized from RNA that had been immunopurified using anti-HA antibody and hybridized to Affymetrix U133A microarrays. Changes of at least 2.5-fold were scored as Stau1-interacting transcripts.

TABLE 4

Transcripts up-regulated after down-regulating Stau1 in two independently performed analyses
(Note: Redundancies reflect different wells in each microarray)

| | |
|---|---|
| AFFX-M27830_5_at | Unknown transcript |
| 211506_s_at | Unknown transcript (don't know if same as above) |
| 205660_at | 2'-5'-oligoadenylate synthetase-like |
| 210797_s_at | 2'-5'-oligoadenylate synthetase-like /// 2'-5'-oligoadenylate synthetase-like |
| 212543_at | absent in melanoma 1 |
| 200974_at | actin alpha 2 smooth muscle aorta |
| 204470_at | chemokine (C-X-C motif) ligand 1 (melanoma growth stimulating activity alpha) |
| 228335_at | claudin 11 (oligodendrocyte transmembrane protein) |
| 202712_s_at | creatine kinase mitochondrial 1 (ubiquitous) |
| 219863_at | cyclin-E binding protein 1 |
| 210764_s_at | cysteine-rich angiogenic inducer 61 |
| 232165_at | epiplakin 1 |
| 232164_s_at | epiplakin 1 |
| 216442_x_at | fibronectin 1 |
| 210495_x_at | fibronectin 1 |
| 212464_s_at | fibronectin 1 |
| 211719_x_at | fibronectin 1 /// fibronectin 1 |
| 212473_s_at | flavoprotein oxidoreductase MICAL2 |
| 226269_at | ganglioside-induced differentiation-associated protein 1 |
| 204471_at | growth associated protein 43 |
| 205184_at | guanine nucleotide binding protein (G protein) gamma 4 |
| 209657_s_at | heat shock transcription factor 2 |
| 227547_at | *Homo sapiens* transcribed sequence with moderate similarity to protein ref:NP_071431.1 (*H. sapiens*) cytokine receptor-like factor 2; cytokine receptor CRL2 precursor [*Homo sapiens*] |
| 230831_at | *Homo sapiens* transcribed sequences |
| 218986_s_at | hypothetical protein FLJ20035 |
| 235417_at | hypothetical protein FLJ25348 |
| 1562415_a_at | hypothetical protein FLJ25348 |
| 212909_at | hypothetical protein MGC29643 |
| 211959_at | insulin-like growth factor binding protein 5 |
| 214453_s_at | interferon-induced protein 44 |
| 226757_at | interferon-induced protein with tetratricopeptide repeats 2 |
| 229450_at | interferon-induced protein with tetratricopeptide repeats 4 |
| 205798_at | interleukin 7 receptor |
| 202859_x_at | interleukin 8 |
| 201650_at | keratin 19 /// keratin 19 |
| 224657_at | mitogen-inducible gene 6 |
| 242456_at | MRE11 meiotic recombination 11 homolog A (*S. cerevisiae*) |
| 210809_s_at | osteoblast specific factor 2 (fasciclin I-like) |
| 201288_at | Rho GDP dissociation inhibitor (GDI) beta |
| 204035_at | secretogranin II (chromogranin C) |
| 59705_at | selenocysteine lyase |
| 222557_at | stathmin-like 3 |
| 221477_s_at | superoxide dismutase 2 mitochondrial |
| 220325_at | TAF7-like RNA polymerase II TATA box binding protein (TBP)-associated factor 50kDa |
| 235086_at | thrombospondin 1 |
| 201108_s_at | thrombospondin 1 |
| 201109_s_at | thrombospondin 1 |
| 209277_at | tissue factor pathway inhibitor 2 |
| 205547_s_at | transgelin |
| 1555724_s_at | transgelin |
| 206508_at | tumor necrosis factor (ligand) superfamily member 7 |
| 202330_s_at | uracil-DNA glycosylase |

The microarray results indicate that SMD can be utilized by mammalian cells to regulate the abundance of hundreds of cellular transcripts and, hence, expression of the encoded proteins. Transcripts identified to be regulated by SMD have a broad range of cellular functions that include signal transduction, cell proliferation, cell metabolism, immune response, DNA repair, and transcriptional regulation. Therefore, SMD can play a key role in establishing and maintaining cellular homeostasis. For example, SMD naturally targets transcripts encoding the IL-7 receptor (IL-7R), c-JUN, and SERPINE1 (also called PAI1). Down regulating cellular Staufen1 or Upf1 but not Upf2 increased the abundance of each cellular mRNA.

Example 2

A Minimized Stau1 Binding Site Resides 67 Nucleotides Downstream of the Normal Termination Codon of Arf1 mRNA and Mediates mRNA Decay The finding in two independently performed microarray analyses that there are at least 23 293-cell mRNAs that bind Stau1 (Table 3) indicates that SMD is used by cells to coordinately regulate a battery of genes—a number of which are involved in cell growth, division or both—in response to changes in the cellular abundance or specific activity of Stau1, Upf1 or both (see below). If binding is sufficiently downstream of the normal termination codon, then these mRNAs should, like Arf1 mRNA, be natural targets of SMD in a mechanism that is EJC-independent.

To construct pcFLuc(UAA→CAA)-MS2bs, which lacks a termination codon upstream of the MS2 binding sites, pcFLuc-8bs that had been digested with NotI and EcoRV was ligated to a PCR-amplified fragment that contains C-terminus of FLuc in which the UAA codon was converted to a CAA codon and had been digested with NotI and EcoRV. The PCR reactions were performed using pR/HCV/F and two primers: 5'-TTGACCGCTTGAAGTCTTTAATTAAATAC-3' (sense) (SEQ ID NO: 34) and 5'-CGAAGCGGCCGCAATTA-CATTTTGCAATTTGGACTTTCCGCCCTTCTTGGC-3' (antisense) (SEQ ID NO: 35). Underlined nucleotides specify a NotI site.

Example 3

Identification of HeLa-Cell Transcripts are Regulated Upon Stau1 Depletion

To identify physiologic SMD targets, HeLa-cell RNA from three independently performed transfections, in which the level of cellular Stau1 was depleted to as little as 4% of normal (where normal is defined as the level in the presence of Control siRNA), was separately hybridized to microarrays. Sequences from 18,279 HeLa-cell transcripts were analyzed, representing 34% of the array probe sets, in all three hybridization experiments. It was observed that 124 transcripts, or 1.1% of the HeLa-cell transcriptome that was analyzed, were upregulated at least 2-fold in all three transfections (Table 5).

TABLE 5

Transcripts upregulated in human cells depleted of Stau1 in three independently performed microarray analyses

| Transcript | Fold change | Abbreviation | Probe set |
|---|---|---|---|
| *Homo sapiens* hypothetical protein LOC339468 mRNA (cDNA clone IMAGE: 5166507) partial cds | 9.79 | | 1562908_at |
| I factor (complement) | 8.78 | IF | 1555564_a_at |
| fibronectin 1 | 7.98 | FN1 | 216442_x_at |
| interferon-induced protein with tetratricopeptide repeats 2 | 7.51 | IFIT2 | 226757_at |
| | 5.91 | | 211506_s_at |
| interferon-induced protein 44 | 5.88 | IFI44 | 214059_at |
| secretogranin II (chromogranin C) | 5.62 | SCG2 | 204035_at |
| stathmin-like 3 | 5.53 | STMN3 | 222557_at |
| growth associated protein 43 | 5.48 | GAP43 | 204471_at |
| creatine kinase mitochondrial 1 (ubiquitous) | 5.35 | CKMT1 | 202712_s_at |
| osteoblast specific factor 2 (fasciclin I-like) | 5.30 | OSF-2 | 210809_s_at |
| hypothetical protein FLJ25348 | 4.77 | FLJ25348 | 1562415_a_at |
| guanine nucleotide binding protein (G protein) gamma 4 | 4.75 | GNG4 | 205184_at |
| hypothetical protein FLJ33505 | 4.73 | FLJ33505 | 1561114_a_at |
| filamin-binding LIM protein-1 | 4.71 | FBLP-1 | 1555480_a_at |
| claudin 11 (oligodendrocyte transmembrane protein) | 4.50 | CLDN11 | 228335_at |
| *Homo sapiens* transcribed sequence with weak similarity to protein ref: NP_060265.1 (*H. sapiens*) hypothetical protein FLJ20378 [*Homo sapiens*] | 4.46 | | 235629_at |
| insulin-like growth factor binding protein 5 | 4.30 | IGFBP5 | 211959_at |
| integrin beta 3 (platelet glycoprotein IIIa antigen CD61) | 4.18 | ITGB3 | 204627_s_at |
| interferon-induced protein with tetratricopeptide repeats 4 | 4.13 | IFIT4 | 229450_at |
| alpha-actinin-2-associated LIM protein | 3.97 | ALP | 210170_at |
| transgelin | 3.94 | TAGLN | 205547_s_at |
| 2'-5'-oligoadenylate synthetase-like /// 2'-5'-oligoadenylate synthetase-like | 3.86 | OASL | 210797_s_at |
| tissue factor pathway inhibitor 2 | 3.82 | TFPI2 | 209277_at |
| catenin (cadherin-associated protein) alpha-like 1 | 3.80 | CTNNAL1 | 213712_at |
| *Homo sapiens* cDNA: FLJ20914 fis clone ADSE00646 | 3.76 | | 234597_at |
| thrombospondin 1 | 3.73 | THBS1 | 201108_s_at |
| protein tyrosine phosphatase receptor type O | 3.62 | PTPRO | 1554199_at |
| cyclin-E binding protein 1 | 3.60 | CEB1 | 219863_at |
| NADPH oxidase 4 | 3.59 | NOX4 | 219773_at |
| hypothetical protein MGC29643 | 3.58 | MGC29643 | 212909_at |
| *Homo sapiens* uncharacterized gastric protein ZA43P mRNA partial cds | 3.43 | | 232696_at |
| *Homo sapiens* similar to KIAA0563-related gene (LOC376854) mRNA | 3.42 | | 1562921_at |
| hypothetical protein FLJ20035 | 3.40 | FLJ20035 | 218986_s_at |
| *Homo sapiens* cDNA FLJ41180 fis clone BRACE2043142 | 3.40 | | 227890_at |
| tissue factor pathway inhibitor 2 | 3.35 | TFPI2 | 209278_s_at |
| absent in melanoma 1 | 3.34 | AIM1 | 212543_at |
| chromosome 14 open reading frame 141 | 3.29 | C14orf141 | 223690_at |
| dual specificity phosphatase 6 | 3.29 | DUSP6 | 208891_at |
| interferon alpha-inducible protein (clone IFI-15K) | 3.19 | G1P2 | 205483_s_at |
| serine (or cysteine) proteinase inhibitor clade E (nexin plasminogen activator inhibitor type 1) member 1 | 3.16 | SERPINE1 | 202628_s_at |
| *Homo sapiens* cDNA FLJ23692 fis clone HEP10227 | 3.13 | | 235846_at |
| hypothetical protein FLJ20637 | 3.04 | FLJ20637 | 219352_at |
| signaling lymphocytic activation molecule family member 1 | 3.00 | SLAMF1 | 206181_at |
| selenocysteine lyase | 2.98 | SCLY | 59705_at |

TABLE 5-continued

Transcripts upregulated in human cells depleted of Stau1 in three independently performed microarray analyses

| Transcript | Fold change | Abbreviation | Probe set |
|---|---|---|---|
| interleukin 7 receptor | 2.97 | IL7R | 205798_at |
| Rho GDP dissociation inhibitor (GDI) beta | 2.94 | ARHGDIB | 201288_at |
| actin alpha 2 smooth muscle aorta | 2.94 | ACTA2 | 200974_at |
| chemokine (C-X-C motif) ligand 1 (melanoma growth stimulating activity alpha) | 2.84 | CXCL1 | 204470_at |
| DEAD/H (Asp-Glu-Ala-Asp/His) box polypeptide | 2.83 | RIG-I | 218943_s_at |
| insulin-like growth factor binding protein 5 | 2.78 | IGFBP5 | 211958_at |
| interferon-induced protein with tetratricopeptide repeats 1 | 2.78 | IFIT1 | 203153_at |
| *Homo sapiens* hypothetical protein LOC285103 mRNA (cDNA clone IMAGE: 5273139) partial cds | 2.76 | | 227966_s_at |
| decapping enzyme hDcp2 | 2.74 | DCP2 | 212919_at |
| hypothetical protein FLJ34064 | 2.73 | FLJ34064 | 1553244_at |
| eukaryotic translation initiation factor 5A2 | 2.73 | EIF5A2 | 235289_at |
| hypothetical protein MGC19764 | 2.71 | MGC19764 | 1557078_at |
| *Homo sapiens* BIC noncoding mRNA complete sequence | 2.69 | | 229437_at |
| transducin-like enhancer of split 4 (E(sp1) homolog *Drosophila*) | 2.68 | TLE4 | 235765_at |
| dapper homolog 1 antagonist of beta-catenin (*xenopus*) | 2.67 | DACT1 | 219179_at |
| chromosome 9 open reading frame 39 | 2.64 | C9orf39 | 220095_at |
| *Homo sapiens* transcribed sequences | 2.61 | | 229242_at |
| v-jun sarcoma virus 17 oncogene homolog (avian) | 2.58 | JUN | 201466_s_at |
| integrin alpha 4 (antigen CD49D alpha 4 subunit of VLA-4 receptor) | 2.56 | ITGA4 | 205885_s_at |
| *Homo sapiens* cDNA FLJ40697 fis clone THYMU2025406 | 2.53 | | 235203_at |
| *Homo sapiens* transcribed sequences | 2.53 | | 236817_at |
| tenascin C (hexabrachion) | 2.52 | TNC | 201645_at |
| hypothetical protein FLJ13621 | 2.50 | FLJ13621 | 207286_at |
| flavoprotein oxidoreductase MICAL2 | 2.47 | MICAL2 | 212473_s_at |
| *Homo sapiens* cDNA FLJ46457 fis clone THYMU3020856 | 2.44 | | 225007_at |
| thymosin beta identified in neuroblastoma cells | 2.44 | TMSNB | 205347_s_at |
| prostaglandin E receptor 4 (subtype EP4) | 2.42 | PTGER4 | 204897_at |
| chromosome 14 open reading frame 128 | 2.41 | C14orf128 | 228889_at |
| ganglioside-induced differentiation-associated protein 1 | 2.41 | GDAP1 | 226269_at |
| zinc finger protein 36 C3H type-like 1 | 2.38 | ZFP36L1 | 211965_at |
| uracil-DNA glycosylase | 2.37 | UNG | 202330_s_at |
| hypothetical protein MGC27277 | 2.37 | MGC27277 | 242283_at |
| *Homo sapiens* cDNA FLJ10158 fis clone HEMBA1003463. | 2.35 | | 232125_at |
| CDK5 regulatory subunit associated protein 1-like 1 | 2.34 | CDKAL1 | 214877_at |
| *Homo sapiens* transcribed sequence with moderate similarity to protein ref: NP_071431.1 (*H. sapiens*) cytokine receptor-like factor 2 | 2.32 | | 227547_at |
| aldehyde dehydrogenase 1 family member A3 | 2.32 | ALDH1A3 | 203180_at |
| proteasome (prosome macropain) subunit beta type 9 (large multifunctional protease 2) | 2.29 | PSMB9 | 204279_at |
| PHD finger protein 11 | 2.27 | PHF11 | 221816_s_at |
| B-cell scaffold protein with ankyrin repeats 1 | 2.27 | BANK1 | 219667_s_at |
| KIAA0143 protein | 2.26 | KIAA0143 | 212150_at |
| guanylate binding protein 1 interferon-inducible 67kDa | 2.26 | GBP1 | 202270_at |
| epiplakin 1 | 2.25 | EPPK1 | 232164_s_at |
| actinin alpha 1 | 2.24 | ACTN1 | 211160_x_at |
| ring finger protein 20 | 2.22 | RNF20 | 222683_at |
| leucine rich repeat (in FLII) interacting protein 1 | 2.22 | LRRFIP1 | 223492_s_at |
| *Homo sapiens* cDNA FLJ39819 fis clone SPLEN2010534. | 2.21 | | 1556111_s_at |
| hypothetical protein LOC150759 | 2.21 | LOC150759 | 213703_at |
| dihydropyrimidinase-like 3 | 2.20 | DPYSL3 | 201431_s_at |
| type I transmembrane receptor (seizure-related protein) | 2.20 | PSK-1 | 233337_s_at |
| zinc finger protein 90 homolog (mouse) | 2.20 | ZFP90 | 235698_at |
| tumor protein p53 (Li-Fraumeni syndrome) | 2.20 | TP53 | 211300_s_at |
| *Homo sapiens* cDNA FLJ11465 fis clone HEMBA1001636. | 2.19 | | 228632_at |
| dnaj-like protein | 2.17 | LOC148418 | 229402_at |
| transforming growth factor beta 1 induced transcript 1 | 2.15 | TGFB1I1 | 209651_at |
| ets variant gene 1 | 2.15 | ETV1 | 221911_at |
| Rho GTPase activating protein 19 | 2.14 | ARHGAP19 | 212738_at |
| *Homo sapiens* hypothetical LOC284120 (LOC284120) mRNA | 2.13 | | 241394_at |
| suppressor of cytokine signaling 2 | 2.13 | SOCS2 | 203373_at |
| cyclin-dependent kinase 5 regulatory subunit 1 (p35) | 2.11 | CDK5R1 | 204995_at |
| likely ortholog of mouse Sds3 | 2.11 | SDS3 | 233841_s_at |
| *Homo sapiens* transcribed sequences | 2.09 | | 244091_at |
| spinal cord-derived growth factor-B | 2.09 | SCDGF-B | 219304_s_at |
| *Homo sapiens* cDNA FLJ37290 fis clone BRAMY2014469. | 2.09 | | 231026_at |
| histone deacetylase 8 | 2.07 | HDAC8 | 223908_at |
| | 2.06 | | 1567079_at |
| *Homo sapiens* transcribed sequence with weak similarity to protein pir: I38588 (*H. sapiens*) I38588 reverse transcriptase homolog-human retrotransposon L1 | 2.06 | | 235302_at |

TABLE 5-continued

Transcripts upregulated in human cells depleted of Stau1 in three independently performed microarray analyses

| Transcript | Fold change | Abbreviation | Probe set |
|---|---|---|---|
| *Homo sapiens* full length insert cDNA clone YP61C10 | 2.06 | | 1561631_at |
| high-mobility group box 3 | 2.05 | HMGB3 | 225601_at |
| KIAA0931 protein | 2.05 | KIAA0931 | 213407_at |
| *Homo sapiens* cDNA FLJ33441 fis clone BRACE2021932. | 2.04 | | 1556081_at |
| hypothetical protein DKFZp761K1423 | 2.04 | DKFZp761K1423 | 218613_at |
| protein tyrosine phosphatase receptor type F | 2.04 | PTPRF | 200635_s_at |
| thioredoxin reductase 3 | 2.03 | TXNRD3 | 59631_at |
| CGI-72 protein | 2.03 | CGI-72 | 231967_at |
| hypothetical protein MGC15634 | 2.03 | MGC15634 | 242923_at |
| enoyl-Coenzyme A hydratase/3-hydroxyacyl Coenzyme A dehydrogenase | 2.03 | EHHADH | 205222_at |
| hairy and enhancer of split 1 (*Drosophila*) | 2.02 | HES1 | 203394_s_at |
| chromosome 11 open reading frame 9 | 2.00 | C11orf9 | 204073_s_at |
| TIA1 cytotoxic granule-associated RNA binding protein | 2.00 | TIA1 | 1554890_a_at |

The validity of the microarray results was tested for 12 of the upregulated transcripts and 6 of the downregulated transcripts using RT-PCR and a primer pair that is specific for each transcript (Table 6).

TABLE 6

Primer pairs used to amplify transcripts found in microarray analyses to be upregulated or downregulated in human cells

| Gene | Primer (Sense) | | Primer (Antisense) | |
|---|---|---|---|---|
| c-JUN | 5'-CTT GAA AGC TCA GAA CTC GG-3' | SEQ ID NO: 4 | 5'-TCA GCC CCC GAC GGT CTC TC-3' | SEQ ID NO: 5 |
| SERPINE1 | 5'-ACC GCC AAT CGC AAG GCA CC-3' | SEQ ID NO: 6 | 5'-GCT GAT CTC ATC CTT GTT CC-3' | SEQ ID NO: 7 |
| IL7R | 5'-AAG TGG CTA TGC TCA AAA TG-3' | SEQ ID NO: 8 | 5'-TTC AGG CAC TTT ACC TCC AC-3' | SEQ ID NO: 9 |
| IF | 5'-CCT TGA CCT TGG GTT TCA AC-3' | SEQ ID NO: 10 | 5'-ATT GCA ATG GAA GC CTT TG-3' | SEQ ID NO: 11 |
| GAP43 | 5'-TGT GCT GTA TGA GAA GAA CC-3' | SEQ ID NO: 12 | 5'-GCT TCA TCC TTC TTA TTA GC-3' | SEQ ID NO: 13 |
| CKMT1 | 5'-GAC TGG CCA GAT GCT CGT GG-3' | SEQ ID NO: 14 | 5'-ATC TTT GGG AAG CGG CTA TC-3' | SEQ ID NO: 15 |
| STMN3 | 5'-CCA TGG CCA GCA CCA TTT CC-3' | SEQ ID NO: 16 | 5'-ACC TCG GCC GCG TGC AGC TC-3' | SEQ ID NO: 17 |
| TAGLN | 5'-TCC TTC CTG CGA GCC CTG AG-3' | SEQ ID NO: 18 | 5'-GCA CTG CTG CCA TGT CTT TG-3' | SEQ ID NO: 19 |
| OASL | 5'-TGC AAT CAT TGA GGA TTG TG-3' | SEQ ID NO: 20 | 5'-CAC TGT CAA GTG GAT GTC TC-3' | SEQ ID NO: 21 |
| GDI1 | 5'-GAC AGA GAC GTG AAG CAC TG-3' | SEQ ID NO: 22 | 5'-CCA TAA ATG TTG CTT TAT CC-3' | SEQ ID NO: 23 |
| CXCL1 | 5'-CCT GGT AGC CGC TGG CCG GC-3' | SEQ ID NO: 24 | 5'-CTT CTG GTC AGT TGG ATT TG-3' | SEQ ID NO: 25 |
| DCP2 | 5'-GAT TTA TGT TGT TGT AGT TG-3' | SEQ ID NO: 26 | T 5'-CCA AGC AGC CAA TT TAT TG-3' | SEQ ID NO: 27 |
| TMSL8 | 5'-ACA GCC TTT CAC GAG TCT TC-3' | SEQ ID NO: 28 | 5'-CTG CTG TTG GGA GGC GAT CC-3' | SEQ ID NO: 29 |
| PSMB9 | 5'-GCG GGA GAA GTC CAC ACC GG-3' | SEQ ID NO: 30 | 5'-AGG CTG TCG AGT CAG CAT TC-3' | SEQ ID NO: 31 |
| GDAP1 | 5'-AGT TAA CTG TGG ACT CCA TG-3' | SEQ ID NO: 32 | 5'-ACT TTC TCC AAC TCA TCA AG-3' | SEQ ID NO: 33 |

Results demonstrated that 11 of the 12 were increased in abundance by 1.5-fold to 8.5-fold (FIG. 1) upon Stau1 depletion. Therefore, the microarray results can generally be viewed as a reliable assessment of changes in transcript abundance upon Stau1 depletion.

Example 4

Stau1 or Upf1 Depletion Increases the Abundance of c-JUN, SERPINE and IL7R 3' mRNAs Four of the transcripts that were found to be upregulated when Stau1 is depleted were also found in microarray analyses to be upregulated when Upf1 is depleted (Table 7).

TABLE 7

Transcripts upregulated in human cells depleted of either Stau1 (three independently performed microarray analyses in this study) or Upf1 (Mendell et al., 2004)

| Transcript | Product function | Relative increase (microarray value) | |
|---|---|---|---|
| | | Stau1 depletion | Upf1 depletion |
| Serine (or cysteine) proteinase inhibitor clade E (nexin plasminogen activator inhibitor type 1) member 1 (SERPINE1) | Bait for tissue plasminogen activator, urokinase, and protein C | 3.2 | 3.8 |
| Interleukin 7 receptor (IL7R) | Receptor for interleukin 7 | 3.0 | 2.1 |
| v-jun sarcoma virus 17 oncogene homolog (avian) (c-JUN) | Proto oncogene | 2.6 | 5.3 |
| Protein tyrosine phosphatase receptor type F (PTPRF) | Cell adhesion receptor | 2.0 | 2.8 |

Interestingly, the upregulation of three of these transcripts could not be explained by the EJC-dependent rule that applies to NMD. The three transcripts encode serine (or cysteine) proteinase inhibitor Glade E (nexin plasminogen activator inhibitor type 1) member 1 (Serpine1), interleukin 7 receptor (IL7R), and v-jun sarcoma virus 17 oncogene homolog (avian) (c-jun).

To assess the possibility that each transcript is an SMD target, HeLa cells were transiently transfected with one of six small interfering (si) RNAs (Kim et al., 2005): Stau1 or Stau1(A) siRNA, which targeted a different Stau1 mRNA sequence; Upf1 or Upf1(A) siRNA, which targeted a different UPF1 mRNA sequence; Upf2 siRNA, which has no effect on SMD; or a nonspecific Control siRNA. Two days later, protein and RNA were isolated for analysis using Western blotting and RT-PCR, respectively.

Western blotting revealed that Stau1 or Stau1 (A) siRNA depleted the cellular level of Stau1 to 21% or 3% of normal, respectively, Upf1 or Upf1(A) siRNA depleted the cellular the level of Upf1 to 1% or 2% of normal, respectively, and Upf2 siRNA depleted the cellular level of Upf2 to 1% of normal (FIG. 2A, where normal in each case is defined as the level in the presence of Control siRNA after normalization to the level of Vimentin). It was found that c-JUN, SERPINE and IL7R transcripts were upregulated 2.1-fold to 3.8-fold when Stau1 or Upf1 was depleted, but unaffected when Upf2 was depleted (FIG. 2B, where each transcript is normalized to the level of SMG7 mRNA). These results indicate that each transcript is targeted for SMD.

Example 5

Stau1 binds the 3' UTR of c-JUN, SERPINE and IL7R 3' mRNAs

To further investigate whether each of the three transcripts is an SMD target, (i) nucleotides 481-671 of the c-JUN 3' UTR, which include the 151-nucleotide class III (i.e., non-AUUUA) AU-rich element (ARE)(Peng et al., 1996) plus 45 flanking nucleotides; (ii) nucleotides 1-1575 of the SERPINE1 3' UTR or (iii) nucleotides 1-339 of IL7R mRNA were inserted immediately downstream of the Firefly (F) Luciferase (Luc) translation termination codon within pcFLuc. For each 3' UTR, nucleotide 1 is defined as the nucleotide immediately 3' to the normal termination codon. The encoded hybrid transcripts were tested for Stau1-HA$_3$ binding.

Example 6 lncRNAs Transactivate SMD by Duplexing with 3' UTRs Via Alu Elements

The failure using Mfold to identify dsRNA structures similar to the SBS of ARF1 mRNA within the 3'UTRs of other SMD targets led to the observation that two well characterized SMD targets—plasminogen activator inhibitor type 1 (SERPINE1) mRNA and hypothetical protein FLJ21870 mRNA—contain a single 3'UTR Alu element. Approximately 13% of the ~1.6% of protein-encoding transcripts in human epithelial HeLa cells that are upregulated at least 1.8-fold upon STAU1 downregulation in three independently performed microarray analyses contain a single 3'UTR Alu element (Table 8). This percentage is higher than the ~4% of HeLa-cell protein encoding transcripts that contain one or more 3'UTR Alu elements, indicating that 3'UTR Alu elements are enriched in SMD targets relative to the bulk of cellular mRNAs.

TABLE 8

Human genes encoding transcripts that are upregulated at least 1.8-fold upon STAU1 downregulation and contain a single 3'UTR Alu element

| Gene symbol | NCBI accession # | Fold upregulation* | Alu motif in 3'UTR | Full name of gene |
|---|---|---|---|---|
| IFI44 | NM_006417 | 5.88 | AluSq | interferon-induced protein 44 |
| FBLIM1 | NM_017556 | 4.71 | AluSz | filamin-binding LIM protein 1 |
| CLDN11 | NM_005602 | 4.50 | AluJb | claudin 11 |
| PDLIM3 | NM_014476 | 3.97 | AluSx | PDZ and LIM domain 3 |

TABLE 8-continued

Human genes encoding transcripts that are upregulated at least 1.8-fold upon STAU1 downregulation and contain a single 3'UTR Alu element

| Gene symbol | NCBI accession # | Fold upregulation* | Alu motif in 3'UTR | Full name of gene |
|---|---|---|---|---|
| OASL | NM_003733 | 3.86 | AluJo | 2'-5'-oligoadenylate synthetase-like |
| TAF7L | NM_024885 | 3.72 | FLAM_A | TAF7-like RNA polymerase II, TATA box-binding protein (TBP)-associated factor, 50kDa |
| NOX4 | NM_016931 | 3.59 | AluSg7 | NADPH oxidase 4 |
| AIM1 | NM_001624 | 3.34 | AluJb | absent in melanoma 1 |
| SERPINE1 | NM_000602 | 3.16 | AluJo | serpin peptidase inhibitor, clade E (nexin, plasminogen activator inhibitor type 1), member 1 |
| DCP2 | NM_152624 | 2.74 | AluSp | DCP2 decapping enzyme homolog (S. cerevisiae) |
| EIF5A2 | NM_020390 | 2.73 | AluSx3 | eukaryotic translation initiation factor 5A2 |
| CEP135 | NM_025009 | 2.50 | AluSx1 | centrosomal protein 135kDa |
| LRRFIP1 | NM_004735 | 2.22 | AluSq2 | leucine-rich repeat (in FLII) interacting protein 1 |
| ZFP90 | NM_133458 | 2.20 | AluJb | zinc-finger protein 90 homolog (mouse) |
| TP53 | NM_000546 | 2.20 | AluJb | tumor protein p53 |
| PHLPP2 | NM_015020 | 2.05 | AluSx | PH domain and leucine-rich repeat protein phosphatase 2 |
| EHHADH | NM_001966 | 2.03 | AluJr | enoyl-CoA, hydratase/3-hydroxyacyl CoA dehydrogenase |
| CCDC125 | NM_176816 | 1.99 | AluY | coiled-coil domain-containing 125 |
| CDCP1 | NM_022842 | 1.98 | AluJb | CUB domain-containing protein 1 |
| NUAK2 | NM_030952 | 1.96 | AluSp | NUAK family, SNF1-like kinase, 2 |
| AKT2 | NM_001626 | 1.84 | AluJr | v-akt murine thymoma viral oncogene homolog 2 |
| APPL1 | NM_012096 | 1.83 | AluY | adaptor protein, phosphotyrosine interaction, PH domain and leucine zipper-containing 1 |
| COL16A1 | NM_001856 | 1.81 | FLAM_A | collagen, type XVI, alpha 1 |
| RIPK1 | NM_003804 | 1.81 | AluJo | receptor (TNFRSF)-interacting serine-threonine kinase 1 |

*Minimum fold upregulation in each of three independently performed microarray analyses Alu elements are the most prominent repeats in the human genome: they constitute more than 10% of DNA sequences, are present at up to 1.4 million copies per cell, and share a 300-nucleotide consensus sequence of appreciable similarity among subfamilies. To date, Alu elements have been documented to be cis-effectors of protein encoding gene expression by influencing transcription initiation or elongation, alternative splicing, A-to-I editing or translation initiation. Since ncRNAs that perfectly basepair with mRNA can function in trans to generate endogenous siRNAs, imperfect base-pairing between the Alu element of a ncRNA and the Alu element of an mRNA 3'UTR can create an SBS so as to regulate mRNA decay. The focus of the experiments disclosed herein were on mRNAs that contain a single 3'UTR Alu-element to avoid the possibility of intramolecular base-pairing between inverted Alu elements, which can result in A-to-I editing and nuclear retention.

Analysis of Antisense ncRNA Pipeline identified 378 lncRNAs that contain a single Alu element (Table 9).

TABLE 9

Features of lncRNAs that contain a single Alu elemen

| lncRNA accession #* | lncRNA Alu motif** | ΔG (kcal/mol) of predicted duplexes formed between the Alu element of each specified lncRNA and the 3'UTR Alu element of four proven SMD targets *** | | | |
|---|---|---|---|---|---|
| | | SERPINE1 mRNA | FLJ21870 mRNA | CDCP1 mRNA | MTAP mRNA |
| ASO1026 | FLAM_C | -48.5 | -100.5 | 0.0 | -100.5 |
| ASO1113 | AluSx | 0.0 | 0.0 | -44.2 | -21.8 |
| ASO1151 | FLAM_C | 0.0 | -60.9 | 0.0 | -38.7 |
| ASO1162 | AluSx | -37.8 | -43.7 | -12.8 | -31.8 |
| ASO1170 | FRAM | 0.0 | -19.2 | -91.3 | 0.0 |
| ASO1178 | FLAM_C | 0.0 | -60.7 | 0.0 | -70.6 |
| ASO1183 | SVA_A | 0.0 | -83.2 | -25.1 | -24.7 |
| ASO1195 | FLAM_C | 0.0 | -81.4 | -21.1 | -65.1 |
| ASO1208 | SVA_F | -28.8 | 0.0 | 0.0 | -45.6 |
| ASO1213 | SVA_F | -28.8 | 0.0 | 0.0 | -45.6 |
| ASO1220 | AluY | -22.7 | -90.5 | -18.5 | -83.9 |
| ASO1259 | AluJb | 0.0 | -25.7 | -71.6 | 0.0 |
| ASO1267 | AluJb | -28.7 | -21.2 | -107.9 | 0.0 |
| ASO1282 | AluJb | 0.0 | 0.0 | -90.6 | -19.9 |
| ASO1285 | AluSx | 0.0 | -61.4 | 0.0 | -38.9 |
| ASO1289 | FLAM_C | 0.0 | .00.0 | -55.8 | -23.4 |
| ASO1296 | AluJb | -12.5 | -48.3 | -9.7 | -26.8 |
| ASO1320 | FLAM_C | -43.0 | -28.4 | 0.0 | -28.4 |
| ASO1321 | AluJb | -24.6 | -54.0 | 0.0 | -17.4 |
| ASO1323 | AluSx | 0.0 | -86.8 | 0.0 | -42.1 |
| ASO1326 | AluJb | 0.0 | -29.5 | -114.2 | 0.0 |

TABLE 9-continued

Features of lncRNAs that contain a single Alu elemen

| | | | | | |
|---|---|---|---|---|---|
| ASO1362 | FLAM_C | 0.0 | -21.9 | 0.0 | -23.9 |
| ASO1379 | FLAM_C | 0.0 | 0.0 | -40.1 | 0.0 |
| ASO1392 | AluJb | 0.0 | 0.0 | -107.9 | 0.0 |
| ASO1409 | AluJb | -41.8 | -90.2 | 0.0 | -46.9 |
| ASO1410 | AluJb | -41.8 | -90.2 | 0.0 | -46.9 |
| ASO1433 | FLAM_C | 0.0 | 0.0 | -26.4 | 0.0 |
| * | tRNA-Ala- | * | .0 | .0 | .0 |
| ASO1445 | GCY_ | 0.0 | -23.0 | 0.0 | -27.9 |
| ASO1446 | AluSx | 0.0 | -85.2 | 0.0 | -80.6 |
| * | tRNA-Ala- | * | .0 | .0 | .0 |
| ASO1450 | GCY_ | 0.0 | 0.0 | -32.9 | 0.0 |
| ASO1456 | FLAM_C | 0.0 | 0.0 | -34.8 | 0.0 |
| ASO1470 | AluSx | -18.8 | 0.0 | 0.0 | -21.4 |
| ASO1476 | AluJb | -50.0 | -106.8 | -18.5 | -107.4 |
| ASO1480 | FLAM_C | -13.5 | -17.4 | -96.7 | 0.0 |
| ASO1483 | AluSx | 0.0 | -68.0 | -31.6 | -66.4 |
| ASO1487 | AluJb | -37.1 | -83.3 | 0.0 | -83.2 |
| ASO1488 | FLAM_C | 0.0 | -25.5 | -42.7 | 0.0 |
| ASO1496 | FLAM_C | 0.0 | 0.0 | -66.8 | 0.0 |
| ASO1497 | AluJb | 0.0 | -19.1 | -69.8 | -17.9 |
| ASO1498 | AluSx | 0.0 | -18.4 | -103.8 | -24.4 |
| ASO1500 | FLAM_C | 0.0 | -21.8 | -66.3 | -18.1 |
| ASO1503 | FLAM_C | 0.0 | -24.1 | 0.0 | 0.0 |
| * | tRNA-Thr- | * | .0 | .0 | .0 |
| ASO1511 | ACA | 0.0 | 0.0 | 0.0 | 0.0 |
| ASO1514 | AluJb | -49.6 | -99.2 | 0.0 | -94.3 |
| * | tRNA-Ala- | * | .0 | .0 | .0 |
| ASO1521 | GCY_ | 0.0 | 0.0 | 0.0 | -19.5 |
| ASO1523 | AluSx | 0.0 | -88.5 | 0.0 | -43.8 |
| ASO1535 | AluJb | -48.5 | -66.8 | 0.0 | -66.3 |
| ASO1545 | AluJb | -48.1 | -99.7 | 0.0 | -96.4 |
| ASO1546 | AluJb | -48.3 | -65.4 | -24.9 | -13.2 |
| ASO1566 | FLAM_C | 0.0 | -17.0 | -47.4 | -15.2 |
| ASO1569 | AluSx | 0.0 | -22.8 | -71.5 | -27.2 |
| ASO1601 | AluSx | 0.0 | -71.0 | -21.1 | -74.4 |
| ASO1632 | AluJb | -99.5 | -222.1 | -24.7 | -84.2 |
| ASO1636 | AluJb | -84.8 | -85.5 | -9.7 | -103.2 |
| ASO1668 | AluY | 0.0 | 0.0 | -112.8 | 0.0 |
| ASO1674 | AluSx | -35.7 | -53.6 | 0.0 | -116.7 |
| ASO1700 | AluY | -46.0 | -122.6 | -35.1 | -128.7 |
| ASO1705 | FRAM | 0.0 | 0.0 | -81.2 | -26.5 |
| ASO1714 | AluJb | 0.0 | 0.0 | -135.9 | 0.0 |
| ASO1719 | AluSx | 0.0 | -17.2 | -148.9 | -25.4 |
| ASO1721 | AluJb | -119.7 | -99.2 | -22.9 | -77.0 |
| ASO1726 | AluSx | 0.0 | 0.0 | -118.6 | 0.0 |
| ASO1729 | AluSx | 0.0 | .00.0 | -107.3 | -25.2 |
| ASO1730 | AluJb | 0.0 | 0.0 | -141.1 | 0.0 |
| ASO1736 | AluSx | -70.3 | -258.5 | -31.4 | -230.1 |
| ASO1737 | AluY | -68.2 | -339.0 | -22.6 | -235.5 |
| ASO1751 | AluSx | 0.0 | -39.2 | -138.7 | 0.0 |
| ASO1754 | FRAM | -10.9 | -29.3 | -103.9 | -14.9 |
| ASO1757 | FLAM_C | -110.8 | -163.4 | -18.1 | -88.9 |
| ASO1763 | FLAM_C | 0.0 | 0.0 | -167.3 | -23.4 |
| ASO1766 | AluJb | -134.1 | -177.1 | -16.3 | -78.2 |
| ASO1768 | AluJb | 0.0 | 0.0 | -128.2 | 0.0 |
| ASO1770 | AluY | 0.0 | -26.7 | -175.9 | -32.5 |
| ASO1781 | AluSx | -61.9 | -255.5 | -36.7 | -166.0 |
| ASO1787 | AluJb | -57.9 | -236.0 | -49.9 | -104.8 |
| ASO1794 | FRAM | 0.0 | -52.8 | -16.3 | -71.9 |
| ASO1803 | AluSx | -16.5 | 0.0 | -214.9 | 0.0 |
| ASO1808 | AluJb | 0.0 | -27.9 | -133.9 | -39.9 |
| ASO1810 | AluJb | 0.0 | -28.4 | -189.3 | -32.6 |
| ASO1812 | AluSx | -76.6 | -226.2 | 0.0 | -348.3 |
| ASO1818 | AluY | -62.2 | -407.9 | -23.6 | -229.1 |
| ASO1821 | AluSx | -45.5 | -108.9 | -19.5 | -126.2 |
| ASO1823 | AluJb | -63.7 | -146.4 | -26.6 | -280.7 |
| ASO1825 | AluSx | -54.1 | -118.7 | -23.7 | -120.8 |
| ASO1827 | AluSx | -123.4 | -262.6 | 0.0 | -260.0 |
| ASO1829 | FLAM_C | -95.9 | -137.3 | -22.3 | -92.1 |
| ASO1841 | AluJb | 0.0 | -22.9 | -99.6 | -20.8 |
| ASO1862 | AluSx | 0.0 | 0.0 | -176.7 | -33.0 |
| ASO1871 | FLAM_C | -115.9 | -159.7 | -12.2 | -79.7 |
| ASO1876 | AluSx | -114.0 | -203.4 | -11.3 | -197.5 |
| ASO1880 | AluJb | -55.4 | -110.3 | -16.6 | -95.4 |
| ASO1885 | AluJb | -13.5 | -16.3 | -358.2 | 0.0 |
| ASO1895 | AluJb | -73.1 | -157.0 | -27.0 | -113.5 |
| ASO1897 | AluSx | -70.1 | -101.1 | -18.5 | -121.4 |
| ASO1901 | AluSx | -72.7 | -204.9 | -20.9 | -341.3 |
| ASO1906 | AluSx | 0.0 | 0.0 | -193.9 | -30.6 |
| ASO1912 | AluSx | -106.7 | -445.6 | -21.1 | -255.7 |
| ASO1928 | AluJb | -88.5 | -208.0 | -8.3 | -105.5 |
| ASO1934 | AluJb | 0.0 | 0.0 | -135.9 | 0.0 |
| ASO1957 | AluSx | -65.9 | -232.4 | 0.0 | -300.0 |
| ASO1959 | AluSx | 0.0 | -35.5 | -181.4 | -34.0 |
| ASO1966 | AluSx | -16.5 | 0.0 | -214.9 | 0.0 |
| ASO1980 | AluSx | 0.0 | -27.5 | -192.2 | -30.6 |
| ASO1993 | AluSx | -26.6 | -136.8 | -38.8 | -77.6 |
| ASO1994 | AluSx | -88.2 | -207.7 | -19.7 | -105.5 |
| ASO1995 | AluSx | 0.0 | 0.0 | -118.6 | 0.0 |
| ASO1998 | AluSx | -108.2 | -444.2 | -27.6 | -264.2 |
| ASO2002 | AluJb | -84.6 | -302.6 | 0.0 | -135.6 |
| ASO2003 | AluSx | 0.0 | 0.0 | -118.6 | 0.0 |
| ASO2015 | AluSx | 0.0 | 0.0 | -118.6 | 0.0 |
| ASO2016 | AluSx | -31.5 | -49.3 | 0.0 | -125.8 |
| ASO2020 | AluSx | 0.0 | 0.0 | -118.6 | 0.0 |
| ASO2026 | AluJb | -77.8 | -113.2 | -23.1 | -99.1 |
| ASO2028 | AluSx | -125.2 | -223.9 | -34.2 | -128.7 |
| ASO2029 | AluJb | -77.8 | -113.2 | -23.1 | -99.1 |
| ASO2031 | AluSx | -13.9 | .00.0 | -157.2 | -13.1 |
| ASO2037 | AluSx | -76.9 | -116.5 | -22.4 | -103.5 |
| ASO2042 | FLAM_C | 0.0 | 0.0 | -68.8 | 0.0 |
| ASO2046 | AluSx | 0.0 | 0.0 | -118.6 | 0.0 |
| ASO2059 | FRAM | -78.0 | -73.0 | -31.5 | -65.2 |
| ASO2066 | AluJb | 0.0 | -21.7 | -121.2 | -25.9 |
| ASO2070 | AluSx | -114.2 | -447.6 | -19.7 | -190.2 |
| ASO2087 | FLAM_C | -116.1 | -163.8 | -36.5 | -87.0 |
| ASO2100 | FLAM_C | 0.0 | 0.0 | -153.3 | 0.0 |
| ASO2101 | AluSx | 0.0 | 0.0 | -179.1 | -29.8 |
| ASO2120 | AluJb | 0.0 | 0.0 | -240.5 | -21.7 |
| ASO2124 | FLAM_C | -89.4 | -102.7 | -37.4 | -30.7 |
| ASO2126 | AluJb | -13.2 | -36.1 | -136.0 | -39.8 |
| ASO2127 | AluSx | 0.0 | 0.0 | -210.2 | -26.2 |
| ASO2128 | FLAM_C | -115.2 | -155.5 | 0.0 | -71.8 |
| ASO2131 | AluSx | 0.0 | 0.0 | -159.1 | -16.3 |
| * | tRNA-Arg- | * | .0 | .0 | .0 |

TABLE 9-continued

Features of lncRNAs that contain a single Alu elemen

| | | | | | |
|---|---|---|---|---|---|
| ASO2147 | AGA | -23.7 | 0.0 | -19.3 | -19.8 |
| ASO2153 | AluJb | 0.0 | -21.7 | -121.2 | -25.9 |
| ASO2160 | AluY | -62.1 | -208.4 | -18.8 | -218.5 |
| ASO2168 | AluJb | 0.0 | -25.1 | -144.0 | -30.9 |
| ASO2179 | AluJb | 0.0 | -26.5 | -202.3 | 0.0 |
| ASO2181 | AluY | -66.2 | -210.7 | -26.4 | -286.2 |
| ASO2185 | AluSx | -70.8 | -233.4 | 0.0 | -360.9 |
| ASO2186 | AluSx | -69.1 | -116.0 | -15.4 | -103.5 |
| ASO2188 | AluY | 0.0 | -23.6 | -196.1 | -29.5 |
| ASO2192 | AluSx | 0.0 | 0.0 | -118.6 | 0.0 |
| ASO2209 | AluSx | -96.3 | -147.9 | -39.9 | -150.6 |
| ASO2218 | FRAM | -60.9 | -79.6 | -20.1 | -114.9 |
| ASO2236 | AluSx | 0.0 | -20.0 | -96.5 | -33.9 |
| ASO2239 | FLAM_C | 0.0 | 0.0 | -114.3 | -40.9 |
| ASO2241 | AluSx | 0.0 | -33.3 | -193.9 | -15.6 |
| ASO2242 | AluY | -27.9 | -54.5 | 0.0 | -90.9 |
| ASO2262 | AluJb | -116.5 | -279.2 | 0.0 | -105.5 |
| ASO2282 | AluY | 0.0 | -12.7 | -165.3 | -29.5 |
| ASO2287 | AluSx | 0.0 | 0.0 | -189.6 | -12.6 |
| ASO2299 | AluJb | 0.0 | 0.0 | -78.4 | 0.0 |
| ASO2301 | AluJb | -42.8 | -25.6 | -20.4 | -41.0 |
| ASO2319 | AluJb | -50.9 | -60.1 | 0.0 | -17.9 |
| ASO2320 | AluSx | 0.0 | -21.2 | -79.8 | -19.9 |
| ASO2321 | FLAM_C | -41.3 | -53.5 | 0.0 | -16.2 |
| ASO2347 | FLAM_C | -42.2 | -79.9 | 0.0 | -53.7 |
| ASO2356 | AluJb | 0.0 | 0.0 | -40.7 | 0.0 |
| ASO2360 | AluSx | 0.0 | -77.7 | 0.0 | -29.3 |
| ASO2362 | AluJb | -27.9 | -21.2 | -98.8 | -24.4 |
| ASO2368 | AluJb | -49.6 | -57.5 | 0.0 | -30.2 |
| ASO2370 | AluJb | -24.2 | -12.3 | -23.4 | -31.8 |
| ASO2373 | AluJb | 0.0 | -14.4 | 0.0 | 0.0 |
| ASO2378 | AluSx | 0.0 | 0.0 | -28.0 | 0.0 |
| ASO2385 | AluSx | 0.0 | 0.0 | -46.7 | 0.0 |
| ASO2395 | FLAM_C | 0.0 | -60.5 | -33.1 | -23.2 |
| ASO2414 | FLAM_C | 0.0 | -68.3 | 0.0 | -53.0 |
| ASO2418 | AluSx | 0.0 | -25.4 | -85.4 | -40.4 |
| ASO2443 | AluJb | -25.9 | -41.8 | -12.2 | -36.7 |
| ASO2469 | AluJb | -61.3 | -106.3 | -39.2 | -102.4 |
| ASO2474 | AluJb | 0.0 | 0.0 | -28.3 | 0.0 |
| ASO2479 | AluJb | -48.6 | -111.1 | -20.1 | -94.5 |
| ASO2488 | AluJb | 0.0 | 0.0 | -39.3 | 0.0 |
| * ASO2490 | tRNA-Ala-GCY_ | * 0.0 | .0 0.0 | .0 0.0 | .0 -21.7 |
| ASO2495 | AluJb | -53.4 | -63.3 | -22.2 | -55.4 |
| ASO2510 | AluJb | -39.0 | -72.6 | -7.2 | -48.6 |
| ASO2515 | AluJb | -49.6 | -57.5 | 0.0 | -30.2 |
| ASO2518 | AluJb | -57.0 | -120.5 | -11.7 | -99.6 |
| ASO2520 | AluJb | 0.0 | 0.0 | -56.6 | 0.0 |
| ASO2532 | AluSx | 0.0 | -41.8 | 0.0 | -24.8 |
| ASO2565 | AluSx | -29.2 | -21.2 | -98.1 | 0.0 |
| ASO2570 | AluJb | -21.4 | -63.4 | -19.8 | -68.6 |
| ASO2576 | FLAM_C | 0.0 | 0.0 | -28.1 | 0.0 |
| * ASO2580 | tRNA-Ala-GCY_ | * -25.5 | .0 0.0 | .0 -40.1 | .0 0.0 |
| ASO2593 | FRAM | -22.9 | -52.3 | 0.0 | -38.1 |
| ASO2601 | AluSx | 0.0 | -21.2 | -47.3 | -23.0 |
| ASO2603 | AluJb | -49.5 | -90.4 | 0.0 | -105.2 |
| ASO2605 | FRAM | -50.5 | -88.5 | -13.2 | -69.0 |
| ASO2608 | AluJb | -34.2 | -40.3 | -20.3 | -50.1 |
| ASO2610 | AluSx | -29.2 | -21.2 | -98.1 | 0.0 |
| ASO2616 | AluSx | 0.0 | -77.7 | 0.0 | -29.3 |
| ASO2617 | AluJb | 0.0 | -73.5 | 0.0 | -30.2 |
| ASO2620 | AluJb | -35.9 | -56.8 | 0.0 | -64.5 |
| ASO2633 | AluSx | 0.0 | -78.8 | -18.5 | -64.0 |
| ASO2634 | AluSx | -51.4 | -87.7 | -22.2 | -65.3 |
| ASO2640 | AluSx | -33.4 | -34.2 | -14.9 | -36.7 |
| ASO2643 | FLAM_C | -58.7 | -66.3 | 0.0 | -64.9 |
| ASO2659 | FLAM_C | -16.1 | -69.5 | 0.0 | -50.0 |
| ASO2665 | AluJb | 0.0 | 0.0 | -41.9 | 0.0 |
| ASO2672 | AluSx | 0.0 | 0.0 | -85.3 | -19.9 |
| ASO2673 | AluJb | 0.0 | -22.1 | -27.7 | -26.3 |
| ASO2674 | FLAM_C | 0.0 | 0.0 | -45.5 | 0.0 |
| ASO2684 | FLAM_C | 0.0 | -61.4 | -15.7 | -61.1 |
| ASO2689 | AluJb | -38.0 | -76.7 | -25.8 | -72.3 |
| ASO2704 | AluSx | -31.4 | -96.2 | 0.0 | -84.5 |
| ASO2713 | AluJb | -48.6 | -100.7 | -10.7 | -93.4 |
| ASO2719 | FLAM_C | -49.7 | -97.9 | 0.0 | -50.6 |
| ASO2725 | AluSx | -58.1 | -114.4 | -22.2 | -90.4 |
| ASO2741 | AluJb | -12.1 | -68.5 | 0.0 | -75.8 |
| ASO2753 | FLAM_C | -60.3 | -113.9 | 0.0 | -72.3 |
| ASO2759 | SVA_A | -22.9 | 0.0 | 0.0 | -73.7 |
| ASO2768 | AluSx | 0.0 | -13.0 | -70.9 | -20.5 |
| ASO2769 | AluSx | 0.0 | 0.0 | -81.5 | 0.0 |
| ASO2774 | AluJb | -13.9 | -73.1 | -18.6 | -66.6 |
| ASO2776 | FRAM | 0.0 | -99.6 | 0.0 | -86.6 |
| ASO2785 | FLAM_C | -17.7 | 0.0 | -54.6 | 0.0 |
| ASO2806 | AluSx | -48.6 | -106.5 | -13.6 | -57.6 |
| ASO2815 | FRAM | -20.3 | -20.0 | -48.5 | -21.9 |
| ASO2834 | AluY | 0.0 | 0.0 | -39.2 | -18.7 |
| ASO2846 | AluJb | -24.6 | 0.0 | -74.0 | 0.0 |
| * ASO2867 | tRNA-Ala-GCY_ | * 0.0 | .0 0.0 | .0 0.0 | .0 -22.9 |
| ASO2883 | AluSx | 0.0 | -25.4 | -85.4 | -40.4 |
| ASO2894 | AluSx | 0.0 | -21.7 | 0.0 | -33.4 |
| ASO2897 | AluJb | -47.2 | -100.5 | -25.9 | -86.3 |
| ASO2907 | AluSx | 0.0 | 0.0 | -20.1 | 0.0 |
| ASO2911 | AluJb | -48.6 | -64.3 | -11.3 | -53.9 |
| ASO2913 | FRAM | -28.4 | -30.6 | -50.6 | 0.0 |
| ASO2930 | AluJb | -38.0 | -74.7 | -31.9 | -39.0 |
| ASO2931 | AluJb | -20.8 | -109.6 | -23.7 | -104.3 |
| * ASO2936 | tRNA-Ala-GCY_ | * 0.0 | .0 0.0 | .0 0.0 | .0 0.0 |
| * ASO2941 | tRNA-Ala-GCY_ | * 0.0 | .0 0.0 | .0 0.0 | .0 0.0 |
| * ASO2951 | tRNA-Ala-GCA | * 0.0 | .0 0.0 | .0 0.0 | .0 0.0 |
| ASO2966 | AluJb | -46.8 | -110.7 | -13.2 | -95.9 |
| ASO2981 | AluSx | -50.9 | -103.1 | 0.0 | -96.8 |
| ASO3003 | AluJb | -24.0 | -20.8 | -110.2 | 0.0 |
| ASO3015 | AluSx | -25.6 | -21.2 | -37.7 | 0.0 |
| ASO3025 | AluJb | 0.0 | 0.0 | -56.1 | -18.9 |
| ASO3037 | AluJb | -18.4 | -42.5 | -26.6 | -52.0 |

TABLE 9-continued

Features of lncRNAs that contain a single Alu elemen

| | | | | | |
|---|---|---|---|---|---|
| ASO3061 | AluJb | 0.0 | -21.2 | -111.0 | 0.0 |
| ASO3064 | FLAM_C | 0.0 | 0.0 | -60.3 | 0.0 |
| * | tRNA-Ala- | * | .0 | .0 | .0 |
| ASO3070 | GCY_ | 0.0 | 0.0 | -9.9 | 0.0 |
| ASO3086 | AluSx | 0.0 | 0.0 | -30.1 | 0.0 |
| ASO3093 | FLAM_C | -49.7 | -70.8 | 0.0 | -59.4 |
| ASO3103 | FLAM_C | -30.9 | -52.0 | -20.1 | -46.7 |
| ASO3111 | FRAM | -43.0 | -89.5 | 0.0 | -69.7 |
| ASO3112 | AluJb | 0.0 | 0.0 | -57.2 | -24.3 |
| ASO3116 | AluJb | 0.0 | 0.0 | -46.9 | 0.0 |
| ASO3137 | FLAM_C | -52.7 | -112.4 | 0.0 | -82.2 |
| ASO3154 | AluJb | -48.3 | -99.4 | 0.0 | -86.6 |
| ASO3167 | AluJb | -32.2 | -51.7 | 0.0 | -59.9 |
| * | tRNA-Ala- | * | .0 | .0 | .0 |
| ASO3179 | GCY_ | 0.0 | -18.9 | -18.7 | 0.0 |
| * | tRNA-Ala- | * | .0 | .0 | .0 |
| ASO3181 | GCY_ | 0.0 | 0.0 | -12.7 | 0.0 |
| ASO3183 | FLAM_C | 0.0 | -22.4 | -47.8 | -15.8 |
| ASO3200 | AluSx | -25.0 | -76.1 | -18.6 | -71.2 |
| ASO3209 | FRAM | -13.5 | 0.0 | -77.3 | 0.0 |
| ASO3222 | FLAM_C | 0.0 | 0.0 | -52.2 | -26.8 |
| ASO3245 | AluJb | -45.0 | -71.8 | 0.0 | -67.1 |
| ASO3260 | FLAM_C | 0.0 | 0.0 | -33.6 | 0.0 |
| ASO3267 | AluJb | 0.0 | -46.1 | 0.0 | -24.6 |
| ASO3268 | AluJb | -23.0 | -34.2 | 0.0 | -43.0 |
| * | tRNA-Thr- | * | .0 | .0 | .0 |
| ASO3280 | ACA | -16.7 | -16.8 | -18.5 | 0.0 |
| ASO3281 | AluJb | 0.0 | -21.8 | -85.3 | 0.0 |
| ASO3286 | FLAM_C | -20.1 | -29.3 | -26.3 | -50.1 |
| ASO3290 | AluJb | -17.2 | -107.2 | -11.3 | -95.9 |
| ASO3300 | AluSx | -51.3 | -114.4 | 0.0 | -99.9 |
| ASO3303 | FLAM_C | -53.7 | -20.6 | 0.0 | -43.6 |
| ASO3304 | FLAM_C | -11.2 | -76.3 | -11.2 | -61.2 |
| ASO3307 | AluJb | -24.0 | -27.9 | -102.1 | -24.1 |
| ASO3310 | FLAM_C | 0.0 | -19.9 | -69.8 | -21.0 |
| ASO3329 | FRAM | -23.0 | -50.1 | -30.4 | -42.3 |
| ASO3334 | FRAM | -49.0 | -83.0 | 0.0 | -8.7 |
| ASO3347 | AluJb | 0.0 | -18.7 | -24.8 | 0.0 |
| ASO3351 | AluSx | 0.0 | -59.7 | -30.3 | -23.2 |
| ASO3355 | AluSx | 0.0 | 0.0 | -61.6 | -17.8 |
| ASO3357 | AluSx | 0.0 | -39.0 | -25.5 | -40.3 |
| ASO3360 | BC200 | -63.7 | -35.2 | -20.1 | -35.8 |
| ASO3363 | tRNA-Ala- | 0.0 | 0.0 | 0.0 | -29.6 |
| * | GCY_ | * | .0 | .0 | .0 |
| * | tRNA-Ala- | * | .0 | .0 | .0 |
| ASO3365 | GCA | 0.0 | 0.0 | 0.0 | 0.0 |
| * | tRNA-Ala- | * | .0 | .0 | .0 |
| ASO3369 | GCY_ | -25.6 | 0.0 | 0.0 | 0.0 |
| ASO3378 | AluSx | 0.0 | -22.4 | -59.1 | 0.0 |
| * | tRNA-Ala- | * | .0 | .0 | .0 |
| ASO3383 | GCY_ | 0.0 | -31.3 | 0.0 | -25.7 |
| ASO3389 | AluJb | 0.0 | -21.8 | -53.6 | -19.2 |
| ASO3390 | FLAM_C | -32.9 | -62.4 | 0.0 | -25.1 |
| ASO3397 | FLAM_C | 0.0 | 0.0 | -41.5 | 0.0 |
| ASO3406 | AluY | -42.6 | -73.1 | 0.0 | -85.2 |
| ASO3413 | AluJb | -40.7 | -104.3 | -21.0 | -94.6 |
| ASO3428 | AluSx | 0.0 | 0.0 | -321.7 | -25.6 |
| ASO3436 | AluJb | -85.0 | -97.7 | -34.7 | -126.7 |
| ASO3442 | AluJb | -118.6 | -189.7 | 0.0 | -106.4 |
| ASO3455 | FLAM_C | -100.3 | -46.3 | 0.0 | -49.5 |
| ASO3457 | AluSx | -118.5 | -382.1 | -25.2 | -253.0 |
| ASO3459 | AluJb | -75.1 | -94.2 | -20.3 | -74.7 |
| ASO3462 | AluY | 0.0 | 0.0 | -205.2 | -29.2 |
| ASO3466 | AluJb | -138.4 | -155.0 | -24.1 | -183.9 |
| ASO3467 | FLAM_C | -99.8 | -74.3 | 0.0 | -71.5 |
| ASO3470 | AluSx | 0.0 | 0.0 | -89.0 | -19.6 |
| ASO3476 | AluY | 0.0 | -31.1 | -117.9 | -25.7 |
| ASO3478 | AluSx | 0.0 | 0.0 | -135.9 | 0.0 |
| ASO3481 | AluJb | 0.0 | -27.7 | -150.2 | -18.7 |
| ASO3488 | AluSx | -66.4 | -261.9 | -19.1 | -203.1 |
| ASO3491 | AluJb | -101.9 | -156.1 | -22.2 | -142.2 |
| ASO3493 | AluSx | -122.0 | -263.5 | 0.0 | -252.5 |
| ASO3498 | AluJb | 0.0 | -26.9 | -198.5 | -34.7 |
| ASO3502 | AluJb | -29.9 | -29.8 | -96.7 | -31.2 |
| ASO3505 | AluSx | -61.3 | -116.0 | -21.1 | -142.5 |
| ASO3506 | AluY | -49.9 | -150.9 | 0.0 | -153.9 |
| ASO3517 | AluSx | 0.0 | -17.2 | -216.8 | -36.6 |
| ASO3520 | AluSx | 0.0 | 0.0 | -118.6 | 0.0 |
| ASO3521 | AluSx | 0.0 | 0.0 | -118.6 | 0.0 |
| ASO3528 | AluY | -62.7 | -326.8 | -18.1 | -403.8 |
| ASO3534 | AluSx | 0.0 | -30.6 | -166.4 | -15.5 |
| ASO3535 | AluJb | -118.2 | -88.2 | -20.6 | -107.8 |
| ASO3539 | AluSx | 0.0 | 0.0 | -93.0 | 0.0 |
| ASO3545 | FRAM | -59.2 | -66.7 | -39.4 | -85.4 |
| ASO3546 | AluSx | -98.4 | -352.8 | -26.7 | -144.0 |
| ASO3548 | AluSx | -101.8 | -214.3 | 0.0 | -163.2 |
| ASO3556 | AluSx | -125.2 | -223.9 | -34.2 | -128.7 |
| ASO3557 | AluY | 0.0 | 0.0 | -100.8 | 0.0 |
| ASO3563 | AluSx | -80.9 | -124.3 | -18.8 | -145.5 |
| ASO3566 | FRAM | -41.7 | -44.4 | 0.0 | -82.3 |
| ASO3573 | FRAM | -42.8 | -56.2 | -33.0 | -55.0 |
| ASO3583 | AluSx | 0.0 | 0.0 | -139.0 | -29.2 |
| ASO3584 | AluSx | 0.0 | 0.0 | -149.3 | -31.3 |
| ASO3586 | FLAM_C | -99.6 | -83.9 | 0.0 | -59.4 |
| ASO3593 | AluSx | -109.1 | -245.4 | -18.8 | -245.8 |
| ASO3595 | AluSx | -65.5 | -111.8 | 0.0 | -125.0 |
| ASO3601 | AluSx | 0.0 | 0.0 | -82.9 | 0.0 |
| ASO3604 | FRAM | -87.8 | -65.0 | 0.0 | -78.3 |
| ASO3606 | AluSx | -117.8 | -362.6 | -14.5 | -248.3 |
| ASO3609 | AluY | 0.0 | -31.9 | -192.0 | -19.3 |
| ASO3629 | AluSx | 0.0 | 0.0 | -211.8 | 0.0 |
| ASO3630 | AluSx | -95.6 | -420.4 | -17.1 | -210.7 |
| ASO3633 | FLAM_C | -54.9 | -96.3 | 0.0 | -110.2 |
| ASO3635 | AluSx | -74.1 | -220.9 | -43.4 | -163.2 |
| ASO3645 | AluSx | 0.0 | 0.0 | -214.0 | -39.8 |
| ASO3661 | AluSx | 0.0 | -89.9 | -10.6 | -72.5 |
| ASO3667 | AluSx | 0.0 | -19.6 | -153.7 | -26.3 |
| ASO3668 | AluSx | -45.7 | -110.5 | -42.2 | -100.3 |
| ASO3673 | AluY | 0.0 | 0.0 | -71.1 | 0.0 |
| ASO3674 | FLAM_C | 0.0 | -22.8 | -60.8 | 0.0 |
| ASO3680 | FLAM_C | -118.4 | -178.6 | -23.2 | -77.3 |
| ASO3682 | AluJb | -62.4 | -85.8 | 0.0 | -119.4 |
| ASO3690 | AluSx | -74.1 | -220.9 | -43.4 | -163.2 |

TABLE 9-continued

Features of lncRNAs that contain a single Alu elemen

| | | | | | |
|---|---|---|---|---|---|
| ASO3695 | AluSx | 0.0 | 0.0 | -104.4 | 0.0 |
| ASO3698 | AluSx | -12.5 | 0.0 | -124.8 | 0.0 |
| ASO3710 | FLAM_C | -99.8 | -77.7 | 0.0 | -59.6 |
| ASO3717 | AluSx | 0.0 | 0.0 | -100.3 | 0.0 |
| ASO3720 | AluJb | -155.7 | -182.1 | -11.4 | -89.8 |
| ASO3721 | AluSx | 0.0 | 0.0 | -118.6 | 0.0 |
| ASO3722 | AluSx | -65.5 | -111.8 | 0.0 | -125.0 |
| ASO3735 | AluSx | 0.0 | 0.0 | -118.6 | 0.0 |
| ASO3739 | AluSx | 0.0 | -19.8 | -207.0 | -25.6 |
| ASO3742 | AluSx | 0.0 | -29.8 | -231.9 | -16.3 |
| ASO3745 | AluSx | -86.5 | -350.5 | -25.8 | -260.7 |
| ASO3746 | AluSx | 0.0 | -34.7 | -211.3 | -20.8 |
| ASO3747 | AluJb | -50.4 | -98.4 | -11.4 | -68.1 |
| ASO3755 | FLAM_C | 0.0 | 0.0 | -98.3 | -27.2 |
| ASO3761 | AluSx | -61.3 | -109.1 | 0.0 | -119.2 |
| ASO3780 | AluSx | -66.5 | -127.9 | -20.1 | -134.0 |
| ASO3803 | AluSx | -124.7 | -308.8 | -20.4 | -202.0 |
| ASO3804 | FLAM_C | -120.1 | -124.7 | 0.0 | -75.9 |
| ASO3809 | AluSx | 0.0 | 0.0 | -118.6 | 0.0 |
| ASO3813 | AluSx | -13.9 | 0.0 | -157.2 | -13.1 |
| ASO3817 | FRAM | -60.8 | -97.6 | -22.6 | -107.7 |
| ASO3820 | AluJb | 0.0 | 0.0 | -100.4 | -18.4 |
| ASO3821 | AluJb | -82.1 | -178.7 | -16.3 | -101.7 |
| ASO3822 | AluSx | 0.0 | 0.0 | -163.3 | -18.9 |
| ASO3837 | AluJb | -122.4 | -163.1 | -8.0 | -142.8 |
| ASO3838 | AluSx | 0.0 | 0.0 | -118.6 | 0.0 |
| ASO3847 | AluY | -47.3 | -173.4 | -26.4 | -167.5 |
| ASO3851 | AluSx | -112.6 | -304.3 | -34.7 | -172.8 |
| ASO3861 | AluJb | -134.1 | -177.1 | -16.3 | -78.2 |
| ASO3864 | AluSx | -107.6 | -235.8 | -30.3 | -249.5 |
| ASO3872 | FLAM_C | 0.0 | 0.0 | -124.5 | 0.0 |
| ASO3873 | AluSx | -65.2 | -207.1 | -20.8 | -342.0 |
| ASO3874 | AluSx | 0.0 | 0.0 | -159.1 | -16.3 |
| ASO3875 | AluSx | 0.0 | 0.0 | -118.6 | 0.0 |
| ASO3876 | AluJb | 0.0 | 0.0 | -71.1 | 0.0 |
| ASO3878 | AluY | 0.0 | 0.0 | -112.6 | 0.0 |
| ASO3881 | AluJb | -99.6 | -92.1 | -19.2 | -120.7 |
| ASO3882 | FLAM_C | 0.0 | -30.9 | -68.7 | 0.0 |
| ASO3891 | AluSx | -13.5 | -17.2 | -127.7 | -17.6 |
| ASO3893 | AluY | -69.7 | -202.2 | -24.6 | -404.1 |
| ASO3900 | AluJb | -91.4 | -119.5 | 0.0 | -89.1 |
| ASO3902 | AluSx | 0.0 | -15.6 | -189.1 | -27.0 |
| ASO3906 | AluSx | 0.0 | 0.0 | -159.1 | -16.3 |
| ASO3908 | AluJb | -69.8 | -157.8 | -28.7 | -88.9 |
| ASO3911 | AluSx | 0.0 | -28.8 | -302.9 | -21.1 |
| ASO3913 | AluSx | -98.4 | -352.8 | -26.7 | -144.0 |
| ASO3946 | AluJb | -75.1 | -94.2 | -20.3 | -74.7 |
| ASO3947 | AluJb | -150.2 | -214.4 | -22.2 | -106.5 |
| ASO3948 | AluY | 0.0 | 0.0 | -115.4 | 0.0 |
| ASO3950 | FRAM | -67.6 | -103.4 | -13.6 | -64.1 |
| ASO3952 | AluSx | 0.0 | -26.9 | -105.7 | -25.0 |
| ASO3960 | AluSx | -86.5 | -350.5 | -25.8 | -260.7 |
| ASO3961 | AluSx | -111.4 | -360.3 | -39.9 | -262.4 |
| ASO3973 | AluJb | -32.0 | 0.0 | -298.5 | 0.0 |
| ASO3974 | AluSx | -99.0 | -366.7 | -36.2 | -262.2 |

\* From Antisense lncRNA Pipeline
\*\* Motif search using REPEATMASKER for Alu sequences within the specific lncRNA
\*\*\* Free energy (DG) calculation considered duplexes that contain ≥10 continuous base-pairs; otherwise, free energy was designated to be 0.
Grey highlights denote studied lncRNAs: ASO1998, ½-sbsRNA4; ASO3488, ½-sbsRNA3; ASO3667, ½-sbsRNA2; ASO3720, ½-sbsRNA1

Among them, the Alu element of lncRNA_AF087999 (NCBI) has the potential to base-pair with the Alu element within SERPINE1 and FLJ21870 3'UTRs (FIG. 3a; FIG. 4a) with ΔG values of, respectively, -151.7 kcal/mol and -182.1 kcal/mol (Table 9; where -151.7 kcal/mol defined the most stable duplex predicted to form between SERPINE1 mRNA and any of the 378 lncRNAs). lncRNA_AF087999, which for reasons that follow is designated ½-sbsRNA1, derives from chromosome 11. RT-semiquantitative (sq)PCR demonstrated that ½-sbsRNA1 is detected in cytoplasmic but not nuclear HeLa-cell fractions and is polyadenylated. Downregulating the cellular abundance of the two major isoforms of STAU1 to <10% of normal (see, e.g., below) did not affect either the cellular distribution or the abundance of ½-sbsRNA1. ½-sbsRNA1 is present in every human tissue that was examined ½-sbsRNA1 is not a substrate for Dicer or AGO2 and thus is distinct from the lncRNAs that generate endogenous siRNAs.

Two forms of ½-sbsRNA1 have been reported (NCBI). They differ at their 5' end but share a common Alu element and a common 3' end that contains a putative polyadenylation signal (AUUAAA) situated 13 nucleotides upstream of a poly(A) tract. RNase protection assays confirmed the presence of one short (S) and one long (L) form of ½-sbsRNA1 that have a different 5' end and a relative abundance in HeLa cells of 3:1 (FIG. 5a). Primer extension (FIG. 5b) and RT-sqPCR (FIG. 5c) mapped the 5' end of ½-sbsRNA1(S) to a C residue. Therefore, ½-sbsRNA1(S) consists of 688 nucleotides excluding the poly(A) tract (FIG. 5d). While some transcripts that are annotated as ncRNAs may be translated, data indicate that ½-sbsRNA1(S) is not translated.

Remarkably, not only STAU1 siRNA but also ½-sbsRNA1 siRNA increased the levels of SERPINE1 and FLJ21870 mRNAs to 2-to-4.5-fold above normal (FIG. 3b and Table 10).

TABLE 10

Comparison of RT-sqPCR shown in FIG. 1 and RT-qPCR*

| | | RT-sqPCR** | | | RT-qPCR | | |
|---|---|---|---|---|---|---|---|
| | siRNA | Control | STAU1 | ½-sbsRNA1 | Control | STAU1 | ½-sbsRNA1 |
| FIG. 1b | ½-sbsRNA1 | 100 | 103 ± 5 | 61 ± 4 | 100 | 107 ± 4 | 64 ± 3 |
| | SERPINE1 mRNA | 100 | 451 ± 5 | 308 ± 5 | 100 | 443 ± 7 | 336 ± 10 |
| | FLJ21870 mRNA | 100 | 325 ± 15 | 200 ± 10 | 100 | 303 ± 22 | 201 ± 2 |

TABLE 10-continued

Comparison of RT-sqPCR shown in FIG. 1 and RT-qPCR*

| | siRNA | RT-sqPCR** | | | RT-qPCR | | |
|---|---|---|---|---|---|---|---|
| | | Control | STAU1 | ½-sbsRNA1 | Control | STAU1 | ½-sbsRNA1 |
| FIG. 1c | FLUC-SEPRINE1 3'UTR mRNA | 13 ± 5 | 82 ± 7 | 44 ± 3 | 11 ± 7 | 82 ± 4 | 48 ± 4 |
| | FLUC-FLJ21870 3'UTR mRNA | 11 ± 3 | 93 ± 7 | 65 ± 6 | 16 ± 5 | 92 ± 6 | 68 ± 3 |

*sqPCR and qPCR used the same RT reactions
**See FIG. 3c legend for details

Furthermore, experiments that employed cycloheximide indicated that the ½-sbsRNA1-mediated reduction in SERPINE1 and FLJ21870 mRNA abundance depends on translation, as does SMD. The reduction in SERPINE1 and FLJ21870 mRNA abundance is attributable to their respective 3'UTR sequences since ½-sbsRNA1 siRNA also increased the levels of FLUC-SERPINE1 3'UTR and FLUC-FLJ21870 3'UTR reporter mRNAs relative to FLUC-No SBS mRNA (FIG. 3c and Table 10). The ½-sbsRNA1 siRNA-mediated increase in the abundance of SERPINE1 or FLJ21870 mRNA was reversed by co-expressing ½-sbsRNA1(S)R, which is resistant to siRNA, arguing against siRNA-mediated off-target effects. Significantly, ½-sbsRNA1 siRNA did not affect the expression of other FLUC reporter mRNAs that contain the 3'UTR of SMD targets not predicted to base-pair with ½-sbsRNA1.

If ½-sbsRNA1 were to create an SBS by base-pairing with the 3'UTR of SERPINE1 or FLJ21870 mRNA, then it should be possible to co-immunoprecipitate complexes of the lncRNA and each mRNA. To test this possibility, lysates of HeLa cells that transiently expressed (i)½-sbsRNA1(S)-MS2bs, which contains 12 copies of the MS2 coat protein binding site (MS2bs) upstream of the lncRNA polyadenylation signal or, as a negative control, ½-sbsRNA1(S) or FLUC-MS2bs mRNA (FIG. 3d) and (ii) FLAG-MS2-hMGFP, which consists of FLAG-tagged MS2 coat protein fused to hMGFP, were immunoprecipitated using anti-FLAG. As expected, prior to IP ½-sbsRNA1(S) as well as ½-sbsRNA1(S)-MS2bs decreased the abundance of SERPINE1 and FLJ21870 mRNAs but not SMD targets that encode interleukin 7 receptor (IL7R), CUG domain-containing protein 1 (CDCP1) or methylthioadenosine phosphorylase (MTAP) (FIG. 3e; see below). In support of the finding that ½-sbsRNA1 creates an SBS with partially complementary mRNA sequences, using lysates of cells expressing ½-sbsRNA1(S)-MS2bs, the anti-FLAG IP of FLAG-MS2-hMGFP bound to ½-sbsRNA1(S)-MS2bs co-immunoprecipitated endogenous STAU1, SERPINE1 mRNA and F1121870 mRNA as well as the UPF1 SMD factor (FIG. 3e). In contrast, irrelevant proteins, such as Calnexin, the dsRNA binding protein ILF3, the single-stranded RNA binding protein FMR1, and mRNAs that are not predicted to base-pair with ½-sbsRNA1, such as those encoding SMG7, IL7R, CDCP1 or MTAP, were not coimmunoprecipitated (FIG. 3e). STAU1 siRNA reduced the co-IP of the SERPINE1 mRNA as well as F1121870 mRNA with ½-sbsRNA1(S)-MS2bs to, respectively, ~19% or ~15% of normal (FIG. 3f), indicating that STAU1 stabilizes the duplex formed between SERPINE1 or FLJ21870 mRNA and ½-sbsRNA1.

As additional evidence that ½-sbsRNA1 creates an SBS by base-pairing with the SERPINE1 or FLJ21870 3'UTR, only STAU1-HA3 but not ILF3 or FMR1 coimmunoprecipitated with ½-sbsRNA1.

To determine if ½-sbsRNA1 is required for the co-IP of STAU1 with SERPINE1 or FLJ21870 mRNA, HeLa cells that transiently expressed STAU1-HA3 and Control siRNA or ½-sbsRNA1 siRNA in the presence or absence of ½-sbsRNA1(S)R were immunoprecipitated using anti-HA. Compared to Control siRNA, ½-sbsRNA1 siRNA, which reduced the level of ½-sbsRNA1 to ~50% of normal, reduced by ~2-fold the co-IP of STAU1-HA3 with SERPINE1 or FLJ21870 mRNA (FIG. 6a). In contrast, restoring the level of ½-sbsRNA1 to ~100% of normal by expressing ½-sbsRNA1 siRNA together with ½-sbsRNA1(S)R restored the co-IP of STAU1-HA3 with SERPINE1 or FLJ21870 mRNA to near normal (FIG. 6a). As expected, the level of IL7R mRNA, which binds STAU1 but does not contain sequences complementary to ½-sbsRNA1, was unaffected by any condition either before or after IP (FIG. 6a).

Thus, the SMD of SERPINE1 or FLJ21870 mRNA involves basepairing between their 3'UTR Alu element and the Alu element within ½-sbsRNA1 Basepairing creates an SBS that is stabilized by STAU1. Furthermore, the level of STAU1 and, thus, the efficiency of SMD does not alter the level of ½-sbsRNA1. The finding that down-regulating SERPINE1 or FLJ21870 mRNA to 50% and 25% of normal, respectively, failed to detectably decrease the co-IP of STAU1-HA3 with ½-sbsRNA1 (FIG. 7) indicates that ½-sbsRNA1 can bind to more than SERPINE1 and FLJ21870 mRNAs to recruit STAU1 if not trigger SMD.

The presence of UPF1 in the anti-FLAG IP of FLAG-MS2-hMGFP (FIG. 3e) is consistent with the idea that STAU1 that is bound to a ½-sbsRNA1-created SBS associates with UPF1, analogously to how STAU1 that is bound to the ARF1 SBS associates with UPF1. Furthermore, downregulating UPF1, like downregulating STAU1, increases the abundance of SERPINE1 mRNA, FLJ21870 mRNA and FLUCSERPINE1 3'UTR mRNA by increasing mRNA half-life. To test for UPF1 function in conjunction with ½-sbsRNA1 the effects of various siRNAs on the production of FLUC-SERPINE1 3'UTR mRNA in which the 3'UTR was intact, precisely lacked the region that was partially complementary to ½-sbsRNA1 or contained solely this region (FIG. 6b) were analyzed. Relative to Control siRNA, STAU1 siRNA, UPF1 siRNA or ½-sbsRNA1 siRNA did not affect the level of FLUC-SERPINE1 3'UTR mRNA that lacked the ½-sbsRNA1 binding site (FIG. 6c), but each siRNA increased the levels of FLUC-SERPINE1 3'UTR mRNA and FLUC mRNA that contained only the ½-sbsRNA1-BS (FIG. 6c). Thus, as indicated by its name, ½-sbsRNA1 base-pairs with the 3'UTR of SERPINE1 mRNA and, by analogy, FLJ21870 mRNA so as to recruit STAU1 and its binding partner UPF1 in a way that triggers a reduction in mRNA abundance. Consistent with previous studies of SMD, the STAU1- and ½-sbsRNA1-mediated reduction in mRNA abundance is due to a decrease in mRNA half-life. With regard to function, scrape injury repair assays revealed that ½-sbsRNA1 contributes toward reducing cell migration by targeting SERPINE1 and RAB11FIP1 mRNAs for SMD (FIG. 8).

Characterizing seven other lncRNAs that contain a single Alu element and consist of <1000 nucleotides (Table 9) confirmed that they, too, are largely cytoplasmic and polyadenylated and have the potential to base-pair with the single Alu element within at least one mRNA 3'UTR (FIG. 9a; FIGS. 4b,c,d; Table 9). Individually downregulating three of these lncRNAs—lncRNA_BCO58830 (½-sbsRNA2), lncRNA_AF075069 (½-sbsRNA3) or lncRNA_BC009800 (½-sbsRNA4)—upregulated those tested mRNAs that (i) contain a partially complementary Alu element and (ii) are upregulated upon STAU1 or UPF1 downregulation; each lncRNA failed to upregulate mRNAs that lack a partially complementary Alu element (FIG. 9b). While ½-sbsRNA2 targeted the 3'UTR Alu element of CDCP1 mRNA (FIG. 9b and Table 9, where $\Delta G=-153.7$ kcal/mol), ½-sbsRNA3 and ½-sbsRNA4 targeted the 3'UTR Alu element of MTAP mRNA (FIG. 9b and Table 9, where $\Delta G=-203.1$ and $-264.2$ kcal/mol, respectively). Furthermore, none of the three lncRNAs downregulated SERPINE1 mRNA (FIG. 9b and Table 9, where $\Delta G=0$, $-66.4$ and $-108.2$ kcal/mol, respectively) but two downregulated FLJ21870 mRNA ~2-fold (FIG. 9b and Table 9, where $\Delta G=-261.9$ and $-444.2$ kcal/mol).

These findings illustrate the potentially complex network of regulatory events that are controlled by lncRNA-mRNA duplexes that bind STAU1 and is reminiscent of the web of regulatory mechanisms that are mediated by miRNAs. Notably, both CDCP1 mRNA and MTAP mRNA were upregulated at least 2-fold upon STAU1 downregulation in experiments disclosed herein (FIG. 9b), and indeed CDCP1 mRNA is among those mRNAs that were upregulated minimally 1.8-fold upon STAU1 downregulation (Table 8). However, since MTAP mRNA was upregulated only ~1.5-fold, it is not included in Table 8.

It is important to note that $\Delta G$ values are not in themselves absolute predictors of SBS function. For example, while ½-sbsRNA2 is predicted to base-pair with the 3'UTR Alu element of BAGS mRNA with a $\Delta G$ of $-416$ kcal/mol, BAGS mRNA is not targeted for SMD in HeLa cells. The 3'UTR Alu element of BAGS mRNA may be physically inaccessible to base-pairing with ½-sbsRNA2. Nevertheless, base-pairing per se may not be sufficient for SBS function since converting the 100-nt apex of the intramolecular ARF1 SBS to a 4-nt loop that is not predicted to disrupt the adjacent 19-bp stem of the ARF1 SBS reduces STAU1 binding in vivo by 50%.

Herein is disclosed a previously unforeseen role for some of the lncRNAs that contain Alu elements: the creation of SBSs by intermolecular base-pairing with an Alu element within the 3'UTR of one or more mRNAs. Thus, SBSs can form either through intramolecular base-pairing, as exemplified by the ARF1 SBS, or intermolecular basepairing between a ½-SBS within an mRNA 3'UTR and a complementary ½-sbsRNA in the form of a largely cytoplasmic lncRNA (FIG. 9c).

There are estimated to be tens of thousands of human lncRNAs that have little or no ability to direct protein synthesis and that are distinct from rRNAs, tRNAs, snRNAs, snoRNAs, small interfering RNAs or microRNAs. Thus, the paradigm that partially complementary ncRNA-mRNA duplexes can form SBSs can extend to the creation of binding sites for other dsRNA binding proteins. Since only 23% of lncRNAs were found to contain one or more Alu elements, lncRNA-mRNA duplexes that do not involve Alu elements expand the number of ncRNAs that regulate gene expression via SMD or a different dsRNA binding protein-dependent pathway.

Example 7

Computational Analyses

The Perl program "Alu_Mask" was designed to define Alu elements within known and putative SMD targets and ncRNAs based on results obtained using REPEATMASKER.

The Perl program "RNA_RNA_anneal" was developed to predict Alu-element base-pairing between lncRNA_AF087999 (½-sbsRNA1) and the SERPINE1 or FLJ21870 mRNA 3'UTR, lncRNA_BCO58830 (½-sbsRNA2) and the CDCP1 mRNA 3'UTR, as well as lncRNA_AF075069 (½-sbsRNA3) or lncRNA_BC009800 (½-sbsRNA4) and the MTAP or FLJ21870 mRNA 3'UTR. Potential duplexes were first fixed using what was predicted to be the most stably and perfectly base-paired region and then expanded in both directions, allowing for bulges or loops of up to 10 nucleotides until base-pairing was no longer predicted. Briefly, "RNA_RNA_anneal" uses a recursive algorithm that predicts the most stable base-pairs and their $\Delta G$ value based on thermodynamic data that were extracted from RNA Structure 4.6. Duplexes between other ncRNAs and mRNA 3'UTRs were likewise predicted using this approach. All data from "RNA_RNA_anneal" were validated using RNA structure 4.6, which provides folding free energy changes.

Notably, to follow up the finding that ~13% of the ~1.6% of HeLa-cell proteinencoding transcripts that are upregulated at least 1.8-fold upon STAU1 1,2 contain a single Alu element, a random resampling of 1.6% of total-cell mRNAs (NCBI) 10,000 times revealed that the presence of one or more Alu elements in the 3'UTRs of potential SMD targets (Table 8) was enriched ~3.58-fold (p<0.001).

Example 8

Plasmid Constructions

To construct pcDNA3.1(+)/Zeo_Chr11__66193000-66191383, HeLa-cell genomic DNA was purified using DNeasy Blood & Tissue Kit (Qiagen) and PCR-amplified using the primer pair: 5'-GATGCTCGAGTGGCATTG-GCTTTCACCACCTATG-3' (sense) (SEQ ID NO: 51) and 5'-GTCAGGATCCTGCCTCAAGTCCAAAGCA-CAACTG-3' (antisense) (SEQ ID NO: 52), where underlined nucleotides specify a XhoI or BamHI site. The resulting PCR product was cleaved with XhoI and BamHI and inserted into XhoI- and BamHI-cleaved pcDNA3.1(+)/Zeo (Invitrogen).

To generate p½-sbsRNA1(S) or p½-sbsRNA1(S)-MS2bs, pcDNA3.1(+)/Zeo_Chr11__66193000-66191383 was amplified using the primer pair 5'-GAGTCAAAGCTTAAAG-GAGAGACAGTCTCACTCTG-3' (sense) (SEQ ID NO: 53) and, respectively, 5'-GTCAGCGGCCGCCAGTTGTAAG-CATATTTGGGTTAC-3' (antisense) (SEQ ID NO: 54) or 5'-GTCAGGATCCCAGTTGTAAGCATATTTGGGTTAC-3' (antisense) (SEQ ID NO: 55), where underlined nucleotides denote a HindIII, NotI or BamHI site. The resulting PCR products were cleaved with HindIII and either NotI or BamHI, respectively, and inserted into HindIII- and NotI-cleaved or HindIII— or BamHI-cleaved pcDNA3-MS2bs.

Overlap-extension PCR was used to construct p½-sbsRNA1(S)R. Two rounds of site-directed mutagenesis were performed using p½-sbsRNA1(S) and the primer pairs 5'-GATATTCATTACTAACCCCTGAAC-CCATACAGTTCAGCTTACCACTACAGTACTT CT-3' (sense) (SEQ ID NO: 56) and 5'-GAAGTACTGTAGTGG-TAAGCTGAACTGTATGGGTTCAGGGGT-TAGTAATGAATA TC-3' (antisense) in the first round, and 5'-CCTGAACCCATACAGTTCAGCTCAGAAC-TACAGTACTTCTGTAGT-3' (sense) (SEQ ID NO: 57) and 5'-ACTACAGAAGTACTGTAGTTCTGAGCT-GAACTGTATGGGTTCAGG-3' (antisense) (SEQ ID NO: 58) in the second round, where mutagenic nucleotides are underlined.

To generate pFLUC-MS2bs, pcFLUC was PCR-amplified using the primers pair 5'-GAGTCAAAGCTTATGGAA-GACGCCAAAAACATAAAGAAAGGC-3' (sense) (SEQ ID NO: 59) and 5'-GTCAGGATCCTTACAATTTG-GACTTTCCGCCCTTCTTGGC-3' (antisense) (SEQ ID NO: 60), where underlined nucleotides specify a HindIII or BamHI site. The resulting PCR product was digested with HindIII and BamHI and inserted into HindIII— and BamHI-cleaved pcDNA3-MS2bs.

To construct pFLAG-MS2-hMGFP, pMS2-HA was amplified using the primer pair 5'-GATGGCTAGCCGCCATG-GACTACAAAGACGATGACGACAAGG-GATCCGCTTCT AACTTTACTCAGTTCG-3' (sense) (SEQ ID NO: 61) and 5'-GTCAGATATCGTAGATGCCG-GAGTTTGCTGCG-3' (antisense) (SEQ ID NO: 62), where underlined nucleotides specify a NheI or EcoRV site. The resulting PCR product was digested using NheI and EcoRV and inserted into NheI- and EcoRV-cleaved phMGFP (Promega).

To create p½-sbsRNA1(S)-hMGFP, phMGFP was amplified using the primer pair 5'-GATGCCTAGGGGCGTGAT-CAAGCCCGACATG-3' (sense) (SEQ ID NO: 63) and 5'-GTCACCTAGGGCCGGCCTGGCGGGGTAGTCC-3' (antisense) (SEQ ID NO: 64), where underlined nucleotides identify the AvrII site. The resulting PCR product was digested with AvrII and inserted into the AvrII site of p½-sbsRNA1(S).

To construct pFLUC-FLJ21870 3'UTR, two fragments of the FLJ21870 3'UTR were amplified using HeLa-cell genomic DNA and the primer pair 5'-GATGTCTAGAGT-GATCAACTTCGCCAACAAACACCAG-3' (sense) (SEQ ID NO: 65) and 5'-CAGAAGGCTAGCCCGAAGAGAAC-3' (antisense) (SEQ ID NO: 66), or 5'-CTCT-TCGGGCTAGCCTTCTGG-3' (sense) (SEQ ID NO: 67) and 5'-GTCAGGGCCCGAGACAGAGTCTCCGTTGCCC-3' (antisense) (SEQ ID NO: 68), where underlined nucleotides denote a XbaI, NheI or ApaI site. The resulting PCR fragments were digested using NheI and either XbaI or ApaI, respectively, and inserted simultaneously into pFLUC-SERPINE1 3'UTR5 that had been digested with XbaI and ApaI.

To create pFLUC-SERPINE1 3'UTR Δ(½-sbsRNA1-BS), two regions of the SERPINE1 3'UTR were amplified using pFLUC-SERPINE1 3'UTR and primer pairs 5'-GAGT-CAAAGCTTGGCATTCCGGTACTGTTGG-3' (sense) (SEQ ID NO: 69) and 5'-CATCCATCTTTGTGC-CCTACCC-3' (antisense) (SEQ ID NO: 70) or 5'-TCTT-TAAAAATATATATATTTTAAATATAC-3' (sense) (SEQ ID NO: 71) and 5'-TAGAAGGCACAGTCGAGG-3' (antisense) (SEQ ID NO: 72), where underlined nucleotides denote a HindIII site. The resulting PCR fragments were phosphorylated using T4 polynucleotide kinase, digested with HindIII or ApaI, respectively, and inserted simultaneously into pFLUC-SERPINE1 3'UTR that had been digested with HindIII and ApaI.

To generate pFLUC-SERPINE1 ½-sbsRNA1-BS, the ½-sbsRNA1-BS was amplified using pFLUC-SERPINE1 3'UTR and the primer pair 5'-GATGTTTAAATAATG-CACTTTGGGAGGCCAAGG-3' (sense) (SEQ ID NO: 73) and 5'-GATGTTTAAAGACGGGGGTCTTGGTAT-GTTGC-3' (antisense) (SEQ ID NO: 74), where underlined nucleotides denote a DraI site. The resulting PCR product was then digested with DraI. Meanwhile, pFLUC No SBS was digested with HindIII and ApaI, and the released the FLUC No SBS region was subsequently digested with DraI. All three fragments from the pFLUC No SBS digestions were then ligated to the PCR product.

To generate pTRE-FLUC-SERPINE1 3'UTR or pTRE-FLUC-FLJ21870 3'UTR, FLUC-SERPINE1 3'UTR or FLUC-FLJ21870 3'UTR was amplified using, respectively, pFLUC-SERPINE1 3'UTR and the primer pair 5'-GATAC-CGCGGATGGAAGACGCCAAAAACATAAAG-3' (sense) (SEQ ID NO: 75) and 5'-GTCAGAATTCGCTTCTATTA-GATTACATTCATTTCAC-3' (antisense) (SEQ ID NO: 76), or pFLUCFLJ21870 3'UTR and the primer pair 5'-GATAC-CGCGGATGGAAGACGCCAAAAACATAAAG-3' (sense) (SEQ ID NO: 77) and 5'-GTCAGAATTCGAGACA-GAGTCTCCGTTGCCC-3' (antisense) (SEQ ID NO: 78), where underlined nucleotides denote a SacII or EcoRI site. The resulting PCR product was digested with SacII and EcoRI and inserted into SacII- and EcoRI-cleaved pTRE (Clontech).

Example 9

Cell Culture, Transient Transfection, and Formaldehyde Crosslinking

Human HeLa or HaCaT cells ($2\times10^6$/60-mm dish or $7.5\times10^7$/150-mm dish) were grown in DMEM (Gibco-BRL) containing 10% fetal bovine serum (Gibco-BRL). Cells were transiently transfected with the specified plasmids using Lipofectamine 2000 (Invitrogen) or the specified siRNA using Oligofectamine (Invitrogen). siRNAs consisted of STAU1 siRNA, ½-sbsRNA1 siRNA (5'-CCUGUACCCUU-CAGCUUACdTdT-3') (SEQ ID NO: 79), ½-sbsRNA1(A) siRNA (5'-AUGACUUUGGGCAAAGUACdTdT-3') (SEQ ID NO: 80), Dicer1 siRNA (Ambion), AGO2 siRNA (Ambion), SERPINE1 siRNA (Ambion), FLJ21870 siRNA (Ambion), RAB11FIP1 siRNA (Ambion), ½-sbsRNA2 (5'-GGUGCAAAGACAGCAUUCCdTdT-3') (SEQ ID NO: 81), ½-sbsRNA3 (5'-UAGUAGUCAAGACCAAUUCUAdTdT-3') (SEQ ID NO: 82), ½-sbsRNA4 (5'-UGGCAUUCCAG-UUGAGUUUdTdT-3') (SEQ ID NO: 83), or the nonspecific Silencer Negative Control #1 (Ambion). Notably, all lncRNA siRNAs used in this study target a sequence outside of the Alu element. For all immunoprecipitations (IPs), cells were crosslinked using 1% formaldehyde for 10 min at room temperature and subsequently quenched with 0.25 M glycine for 5 min at room temperature prior to lysis. In experiments that blocked protein synthesis, cells were incubated with 300 µg/ml of cycloheximide (Sigma) 3-hr prior to lysis.

For mRNA half-life measurements, HeLa Tet-Off cells (Clontech) were transfected with the specified siRNA in the presence of 2 µg/ml of doxycycline (Clontech). After 48-hr, the medium was replaced to remove doxycycline, and cells were transfected with the indicated reporter and reference plasmids. Four-hr later, an aliquot of cells was harvested at time 0, 2 µg/ml of doxycycline was added to the remaining cells to silence reporter-gene transcription, and aliquots of cells were harvested as a function of time thereafter.

Scrape injury repair assays were essentially as published. Briefly, two days after transfection using siRNA, monolayer cultures of HaCaT cells at 90% confluence in 100-mm dishes were scratched in nine places using a P200 pipette tip (VWR) and uniform pressure to create denuded areas that were 0.9 mm wide. Cells were washed once with growth medium, which removes scratch-generated debris and generates smooth wound edges, and cultured for an additional 16 hr with monitoring.

Example 10

Protein Purification, IP and Western Blotting

HeLa cells were lysed, and protein was isolated using hypotonic buffer that consists of 10 mM Tris-Cl (pH 7.4), 150 mM NaCl, 2 mM EDTA, 0.5% Triton X-100, 2 mM benzamidine, 1 mM PMSF and 1 tablet of protease inhibitor cocktail (Roche). If crosslinked, cells were sonicated six times for 30 sec to facilitate lysis. IP was performed. In experiments that involved formaldehyde crosslinking, crosslinks were reversed by heating at 65° C. for 45 min after IP. HeLa cells were cultured as described above but in 150-mm dishes. Transfections and immunopurifications (IPs) were performed as described. Western blotting was performed. Antibodies consisted of anti-STAU1, anti-Calnexin (Calbiochem), anti-FLAG (Sigma), anti-ILF3 (Santa Cruz), anti-FMR1 (Santa Cruz), anti-HA (Roche), anti-Dicer1 (Santa Cruz), anti-AGO2 (Santa Cruz) and anti-BAGS (Abcam).

Example 11 siRNA-Mediated Down-Regulation of Human Stau1

HeLa cells (5×10$^6$) were grown in DMEM medium (Gibco-BRL) containing 10% fetal bovine serum (Gibco-BRL) in 100-mm dishes and transiently transfected with 50 nM of in vitro-synthesized small interfering (si)RNA (Dharmacon) using Oligofectamine Reagent (Invitrogen). Stau1 was down-regulated using 5'-r(CCUAUAACUACAA-CAUGAG)d(TT)-3' (SEQ ID NO. 84). Protein was purified from half of the cells using passive lysis buffer (Promega) and used to determine the extent of down-regulation. RNA was purified from the other half using TRIzol Reagent (Invitrogen), 72 h after siRNA introduction, and analyzed using microarrays. Stau1(A) siRNA consisted of 5'-r(GU-UUGAGAUUGCACUUAAA)d(TT)-3' (SEQ ID NO. 85), and Upf1(A) siRNA consisted of 5'-r(AACGUUUGC-CGUGGAUGAG)d(TT)-3' (SEQ ID NO. 86).

Example 12

Tethering Experiments

HeLa cells (2×10$^6$) were transiently transfected using Lipofectamine Plus (Invitrogen) with 0.3 µg of the reporter plasmid pcFLuc or pcFLuc-MS2bs, 0.02 µg of the reference plasmid pRLuc, and 5 µg of one of the following effector plasmids: pMS2-HA, pMS2-HA-Stau1, pcNMS2, pcNMS2-Upf1, pcNMS2-Upf2 or pcNMS2-Upf3. Cells were harvested two days later. Protein was purified from half of the cells using passive lysis buffer (Promega), and total RNA was purified from the other half using TRIzol Reagent (Invitrogen).

Example 13

RT-PCR

FLuc-MS2bs mRNA or FLuc(UAA→CAA)-MS2bs mRNA was amplified using the primers 5'-CAACAC-CCCAACATCTTCG-3' (SEQ ID NO. 87) (sense) and 5'-CTTTCCGCCCTTCTTGGCC-3' (SEQ ID NO. 88) (antisense). G1-MS2bs or Gl(UAA→UAC)-MS2bs was amplified using the primers 5'-AATACGACTCACTATAGGGA-3' (SEQ ID NO. 89) (sense), which anneals to the T7 promoter, and 5'-GATACTTGTGGGCCAGGGCA-3' (SEQ ID NO. 90) (antisense). FLuc-Arf1 mRNA was amplified using the same T7 promoter primer (sense) and 5'-TCTAGAGGATA-GAATGGCG-3' (SEQ ID NO. 91) (antisense). PAICS mRNA was amplified using the primers 5'-AGCAGGCTG-GTACCGGTCCG-3' (SEQ ID NO. 92) (sense) and 5'-AC-CAATGTTCAGTACCTCAG-3' (SEQ ID NO. 93) (antisense).

Example 14

Microarray Analyses

HeLa-cell RNA was purified using TriZol reagent (Invitrogen) and deemed to be intact using an RNA 6000 Nano LabChip® (Agilent) together with a Bioanalyser 2100 and Biosizing software (Agilent). Biotin-labeled cRNAs were generated and hybridized to U133 Plus 2.0 Array human gene chips (comprising more than 47,000 transcripts and variants). Hybridized chips were scanned using an Affymetrix GENE-CHIP® 3000 Scanner. Results were recorded using the GENECHIP® Operating Software (GCOS) platform, which included the GENECHIP® Scanner 3000 high-resolution scanning patch that enables feature extraction (Affymetrix). Notably, the Affymetrix Gene Expression Assay identifies changes that are greater than 2-fold with 98% accuracy. Arrays were undertaken using three independently generated RNA samples. Transcripts that showed at least a 1.8-fold increase in abundance with a p value of less than 0.05 in each of the three analyses were scored as potential SMD targets.

Example 15

RNA Purification, Poly(A)+ RNA Preparation, and RT Coupled to Either Semiquantitative (sq) or Realtime (q)PCR RNA was purified from total, nuclear or cytoplasmic HeLa-cell fractions or immunoprecipitated from total-cell lysates using TRIzol (Invitrogen). Poly(A)+ RNA was extracted from total-cell RNA using the Oligotex mRNA Mini Kit (Qiagen). Alternatively, RNA derived from different human tissues (Ambion). RT-sqPCR and RT-qPCR were performed as described 1 using the designated primer pairs (Table 11).

TABLE 11

| RNA | Sense primer | Antisense primer |
|---|---|---|
| ½-sbsRNA1 | 5'-CAGCATTCTGAGTAGCTGGGATC-3' (SEQ ID NO: 94) | 5'-CAGTTGTAAGCATATTTGGGTTAC-3' (SEQ ID NO: 121) |
| Primer #1 (FIG. 5c) | 5'-CAGCATTCTGAGTAGCTGGGATC-3' (SEQ ID NO: 95) | |
| #2 | 5'-CCTTCCAACCTCAGCATTCTGAG-3' (SEQ ID NO: 96) | |
| #3 | 5'-GCTCAAGCAATCCTTCCAACCTC-3' (SEQ ID NO: 97) | |
| #4 | 5'-TCTTTTAACTCCTGGGCTCAAGC-3' (SEQ ID NO: 98) | |
| #5 | 5'-GGCTGGAATACAGTGGTGTGATC-3' (SEQ ID NO: 99) | |
| #6 | 5'-CAGTCTCACTCTGTTGCCCAGGC-3' (SEQ ID NO: 100) | |
| #7 | 5'-AAAGGAGAGACAGTCTCACTCTG-3' (SEQ ID NO: 101) | |
| #8 | 5'-AGGACAATGACCCAAGAAGTAGG-3' (SEQ ID NO: 102) | |
| #9 | 5'-CCTTTGACAAAGGACAATGACCC-3' | |

TABLE 11-continued

| | | |
|---|---|---|
| #10 | (SEQ ID NO: 103)<br>5'-GGACTTCCTCTGGCATGTAGG-3'<br>(SEQ ID NO: 104) | |
| SMG7<br>mRNA | 5'-CCAAAGGAGACCATCTGACC-3'<br>(SEQ ID NO: 105) | 5'-TTCACCTCATCTCGGCTTTCC-3'<br>(SEQ ID NO: 122) |
| SERPINE1<br>mRNA | 5'-ACCGCCAATCGCAAGGCACC-3'<br>(SEQ ID NO: 106) | 5'-GCTGATCTCATCCTTGTTCC-3'<br>(SEQ ID NO: 123) |
| FLJ21870<br>mRNA | 5'-AACGACCTGTTAAAGGCCACTC-3'<br>(SEQ ID NO: 107) | 5'-TCCTTACTTTGCAGGCATCCAG-3'<br>(SEQ ID NO: 124) |
| FLUC<br>mRNA | 5'-AATACGACTCACTATAGGGA-3'<br>(SEQ ID NO: 108) | 5'-TCTAGAGGATAGAATGGCG-3'<br>(SEQ ID NO: 125) |
| MUP mRNA | 5'-CTGATGGGGCTCTATG-3'<br>(SEQ ID NO: 109) | 5'-TCCTGGTGAGAAGTCTCC-3'<br>(SEQ ID NO: 126) |
| ½-sbsRNA1<br>(FIG. 6a only) | 5'-CAGCATTCTGAGTAGCTGGGATC-3'<br>(SEQ ID NO: 110) | 5'-GAACCTGTACCCTTCAGCTTACC-3'<br>(SEQ ID NO: 127) |
| ½-sbsRNA1$^R$<br>(FIG. 6a only) | 5'-CAGCATTCTGAGTAGCTGGGATC-3'<br>(SEQ ID NO: 111) | 5'-GAACCCATACAGTTCAGCTCAGA-3'<br>(SEQ ID NO: 128) |
| IL7R mRNA | 5'-AAGTGGCTATGCTCAAAATG-3'<br>(SEQ ID NO: 112) | 5'-TTCAGGCACTTTACCTCCAC-3'<br>(SEQ ID NO: 129) |
| ½-sbsRNA2 | 5'-GTCCAGGAAGAAGGTGCAAAG-3'<br>(SEQ ID NO: 113) | 5'-GGCTACCATATTGGACAGCAC-3'<br>(SEQ ID NO: 130) |
| ½-sbsRNA3 | 5'-CTAAATCTTCCCATGAAATAGGTG-3'<br>(SEQ ID NO: 114) | 5'-GGCCTTTGATAGAAATGTGTAGG-3'<br>(SEQ ID NO: 131) |
| ½-sbsRNA4 | 5'-GGCGTTTGTAGATCACTCCTTC-3'<br>(SEQ ID NO: 115) | 5'-ATGCGTGGTGAAACTCAACTGG-3'<br>(SEQ ID NO: 132) |
| GAPDH<br>mRNA | 5'-AAGGTCGGAGTCAACGGATTTG-3'<br>(SEQ ID NO: 116) | 5'-ATGACAAGCTTCCCGTTCTCAG-3'<br>(SEQ ID NO: 133) |
| RAB11FIP1<br>mRNA | 5'-CCTGCTGAAGACCTTGTGAGAAG-3'<br>(SEQ ID NO: 117) | 5'-AGGATGAAGTCGGGGCTTGAC-3'<br>(SEQ ID NO: 134) |
| CDCP1<br>mRNA | 5'-GCAAGGTCTACCTGAGGACC-3'<br>(SEQ ID NO: 118) | 5'-CAGTCAAGTCCACAGTCCTTGG-3'<br>(SEQ ID NO: 135) |
| MTAP<br>mRNA | 5'-TCTTGTGCCAGAGGAGTGTG-3'<br>(SEQ ID NO: 119) | 5'-CCACCGAAACTGCTTCCTCG-3'<br>(SEQ ID NO: 136) |
| BAG5<br>mRNA | 5'-CCCAGTGGGAGTGCTTGTGAAA-3'<br>(SEQ ID NO: 120) | 5'-AAGACGTTCTGTCTCCTGTGCT-3'<br>(SEQ ID NO: 137) |

In a few experiments RT primed using oligo(dT)18 rather than random hexamers. RT-sqPCR analyses situated under wedges in the leftmost lanes of figures utilized 2-fold dilutions of RNA and show that data fall in the linear range. RT-PCR values include the standard deviation obtained in the specified number of independently performed experiments.

Example 16

RNase Protection Assay (RPA) and Primer Extension

The RPA employed the RPA III RNase Protection Assay Kit (Ambion). Uniformly labeled RNA probes (107 cpm/µg) were generated by transcribing linearized pcDNA3.1(+)/Zeo_Chr11_66193000-66191383 in vitro using α-[P32]-UTP (Perkin Elmer) and the MAXIscript Kit (Ambion). Each probe (105 cpm) was incubated with poly(A)+ HeLa-cell RNA (10 µg) or yeast RNA (10 µg) in hybridization buffer (Ambion) at 42° C. overnight and subsequently cleaved using RNase A and RNase T1 (Ambion; 1:200) at 37° C. for 30 min. Input probe (1/1000) and cleaved products were resolved in a 3.5% polyacrylamide-denaturing gel and visualized using a Typhoon Phosphorimager (GE Healthcare).

Primer extension was performed using poly(A)+HeLa-cell RNA (10 µg), Superscript II (Invitrogen) and the ½-sbsRNA1-specific antisense primer 5'-GAGTTAAAAGAGGCTGCAGTG-3'(SEQ ID NO: 138). DNA sequencing was executed using the SILVER SEQUENCING DNA Sequencing System (Promega), the same antisense primer and pcDNA3.1(+)/Zeo_Chr11_66193000-66191383. Primer extension and sequencing products were resolved in an 8% polyacrylamide-denaturing gel and visualized using a Typhoon Phosphorimager.

Example 17

Fluorescence and Phase-Contrast Microscopy

Cells were visualized using a Nikon Eclipse TE2000-U inverted fluorescence microscope and, for phase microscopy, a 480-nm excitation spectra. Images were captured utilizing TILLVISION software (TILL Photonics).

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Example 18

STAU in All Classes of Vertebrates Shares a Conserved Motif N-Terminal to 'RBD'5

Using yeast two-hybrid analyses, full-length human (h)STAU1 was shown to interact with amino acids 408-496 of hSTAU1[55]. These amino acids consist of the C-terminus of hSTAU1[55] and include 'RBD'5 (FIG. 10A), which is referred to as 'RBD'5 considering it has only 18% sequence identity to the prototypical hSTAU1 RBD3 and, more to the point, fails to bind dsRNA. Using Clustal W, multiple sequence alignments of full-length hSTAU1 with hSTAU2 and STAU homologs in different species, including representatives of the five major vertebrate classes (mammals, reptiles, amphibians, birds, and fish), revealed a conserved sequence residing N-terminal to 'RBD'5 that consists of amino acids 371-390 of hSTAU1[55] (FIG. 10B). This motif is called the Staufen-swapping motif (SSM; FIG. 10B) for reasons explained below. Despite an identifiable 'RBD'5, SSM is absent from *D. melanogaster* STAU as well as some invertebrates such as *Caenorabditis elegans* (FIG. 11). However, STAU in other invertebrates, including the acorn worm *Saccoglossus kowalevskii* and the deer tick *Ixodess capularis*, contain both 'RBD'5 and SSM (FIG. 11).

SSM is interesting given its proximity to the TBD, which spans amino acids 282-372 (FIG. 10A), and its overlap with the region that recruits hUPF1 during SMD, which spans amino acids 272-405. Sequence alignments also demonstrated that, compared to hSTAU1'RBD'5, 'RBD'5 of all hSTAU2 isoforms lacks the predicted β-sheet and the N-terminus of α2 (FIG. 10B).

Example 19

SSM-'RBD'5 Forms a Homodimer in Solution and in Human Cells

Since sequence conservation generally implies function, and considering that dimerization required that one of the interacting molecules consist of full-length hSTAU1, whether SSM-'RBD'5, rather than 'RBD'5 alone, forms a homodimer was tested. The use of SSM-'RBD'5 was further justified because a search for a region of hSTAU1[55] that includes 'RBD' S, is stable in solution, and is suitable for crystallographic studies revealed that amino acids 367-476, i.e., SSM-'RBD'5, gave the best Xtal Pred score, although the score was below suboptimal. This is largely because 'RBD'5 has a higher instability index than does SSM-'RBD'5. Thus, at least theoretically, SSM provides stability to 'RBD'5.

After purifying GST-hSTAU1[55](367-476) from *E. coli* and removing the GST tag, SSM-'RBD'5 migrated during gel filtration at the size of a dimer Sedimentation velocity determinations using analytical ultracentrifugation confirmed that the average weight distribution of SSM-'RBD'5 shifted to lower Svedberg values at lower concentrations (FIG. 10C). The best-fit model for SSM-'RBD'5 (0.0090 mg/ml root mean standard deviation (rmsd) with 95% confidence limits) was one of rapid monomer (1.32+0.02/−0.03 S)–dimer (2.21±0.01 S) equilibrium where the dimer $K_d$ was 79±9 uM.

To obtain a physiologically relevant assay, 'RBD'5 was tested to determine if it is sufficient for SSM-'RBD'5 homodimer formation in human cells. 'RBD'5 was expressed with an N-terminal tag since experiments using *E. coli*-produced 'RBD'5 revealed that an N-terminal GST tag or SSM moiety was required for stability and/or solubility in vitro. Human embryonic kidney (HEK)293T cells were transiently transfected with a mixture of two plasmids: (i) pEGFP-'RBD'5, which produces monomeric enhanced green fluorescence protein (EGFP)-'RBD'5 and either pmRFP-SSM-'RBD'5 or pmRFP-'RBD'5, which produce monomeric red fluorescence protein (mRFP)—SSM-'RBD'5 or mRFP-'RBD'5, respectively; or (ii) pEGFP-SSM-'RBD'5 and either pmRFP-SSM-'RBD'5 or pmRFP-'RBD'5 (FIG. 1D, upper). Notably, EGFP and mRFP harbor mutations that disrupt dimer formation that interferes with the analyses. Cell lysates were immunoprecipitated in the presence of RNase A using anti-GFP or, to control for nonspecific immunoprecipitation (IP), mouse(m)IgG.

Western blotting demonstrated that both EGFP-tagged proteins were expressed at comparable levels prior to IP, as were both mRFP-tagged proteins (FIG. 10D, lower). Furthermore, anti-GFP immunoprecipitated comparable amounts of each EGFP-tagged protein but did not immunoprecipitate calnexin, and mIgG failed to detectably immunoprecipitate any protein (FIG. 10D, lower). EGFP-SSM-'RBD'5 co-immunoprecipitated with mRFP-SSM-'RBD' SandmRFP-'RBD'5 with comparable efficiencies, whereas EGFP-'RBD'5 co-immunoprecipitated with mRFP-SSM-'RBD'5 but not mRFP-'RBD'5 (FIG. 10D, lower). Both EGFP-'RBD'5 and EGFP-SSM-'RBD'5 also co-immunoprecipitated with endogenous hSTAU1 isoforms (FIG. 10D, lower), consistent with the finding that 'RBD'5 alone can interact with full-length hSTAU1 in yeast two-hybrid analyses. hSTAU1 'RBD'5-'RBD'5 dimerization cannot occur between two proteins that each contain only 'RBD'5 but can occur if one of two 'RBD'5-containing molecules contributes an SSM.

Example 20

Structure of hSTAU1 SSM-'RBD'5

To understand the atomic details of this dimerization interaction, the X-ray crystal structure of SSM-'RBD'5 at 1.7 Å resolution was determined (Table 12).

TABLE 12

Top matches to STAU1 'RBD'5 identified by Dali.

| PDB-Chain | Dali Z-score | Cα rmsd (A) | % ID | Protein | Organism | Binds dsRNA? | Bound to dsRNA in this structure? |
|---|---|---|---|---|---|---|---|
| *3LLH-B/A | *10.8/10.7 | *1.3/1.1 | *19/20 | TARBP2 RBD1 | *Homo sapiens* | Yes | No |
| *2NUE-A/B | *10.6/10.6 | *2.0/1.8 | *22/22 | RNase III | *Aquifex aeolicus* | Yes | Yes |
| 1YYK-A | 10.5 | 2.0 | 22 | RNase III | *Aquifex aeolicus* | Yes | Yes |

TABLE 12-continued

Top matches to STAU1 'RBD'5 identified by Dali.

| PDB-Chain | Dali Z-score | Cα rmsd (Å) | % ID | Protein | Organism | Binds dsRNA? | Bound to dsRNA in this structure? |
|---|---|---|---|---|---|---|---|
| 1DI2-A | 10.5 | 1.5 | 22 | Xlrbpa RBD2 | Xenopis laevis | Yes | Yes |
| 2NUG-B | 10.5 | 1.9 | 22 | RNase III | Aquifex aeolicus | Yes | Yes |

Results indicated that 'RBD'5 does adopt the α-β-β-β-α topology of a prototypical RBD (FIG. 12A). One molecule is present per asymmetric unit, indicating that any existing dimer in the crystal structure is derived from crystallographic symmetry mates.

SSM, which directly binds 'RBD'5 (FIGS. 12A,B), forms two α-helices (SSM α1 and α2) that are connected by a tight turn. These helices form a 'V'-shape that straddles 'RBD'5 α1 (FIGS. 12A,B). 'RBD'5 α1 and α2 pack behind the -sheet that connects the two helices in the primary sequence (FIG. 12A). The 'V'-shape created by the 'RBD'5 helices in turn straddles SSM α1 (FIGS. 12A,B).

The interactions between SSM and 'RBD'5 form a core composed of residues with hydrophobic side chains (FIG. 12B). The external solvent boundary of this core is defined by T371 of the longer of the two SSM α-helices, α1; the hydrophobic methyl group of T371 inserts into the hydrophobic core, and the T371 hydroxyl group points outward (FIG. 12B). I374, A375, L378 and L379 of SSM α1 also contribute to the hydrophobic core as do A387 of SSM α2 and 'RBD'5 α1 constituents P408 (which starts α1), L412, the ring of Y414, L415, and the β and γ carbons of the Q419 (which ends α1) (FIG. 12B). Additionally, 'RBD'5 α2 contributes A465, L469 and L472 (FIG. 12B). Of the 'RBD'5 hydrophobic core-contributing and SSM-interacting residues, P408 is absent from nearly all STAU proteins that lack an SSM. However, regardless of the presence of an SSM, L412, L415 and A465 are invariant, and Y414, L469 and L472 are generally conserved (FIG. 11).

Two polar interactions exist at the interface between SSM and 'RBD'5 and appear to position SSM and 'RBD'5 relative to one another to facilitate what is largely a hydrophobic-driven interaction. In the first, the side-chain hydroxyl group of SSM T371 and the main-chain oxygen of K367 hydrogen bond with the amine group of 'RBD'5 Q419, while the -amine of K567 interacts with the hydroxyl group of Q419 (FIG. 12B). All vertebrate STAU proteins contain a residue having similar character and position to T371 e.g., Ser replaces Thr in human and mouse STAU2 proteins (FIG. 11), and Q419 is strictly conserved. The second polar interaction involves a strongly conserved basic charge (in all vertebrate STAU proteins examined except D. rerio STAU, where the residue is Asn; FIG. 10B) contributed by SSM R376 in hSTAU1 that interacts with a citrate ligand present in the crystal structure; otherwise, R376 interacts with the main-chain oxygen of E474 near the C-terminus of 'RBD'5 α2, which is also invariant in vertebrate STAU homologs (FIG. 10B).

Interestingly, residues without strict conservation within SSM, i.e., M373, Y380, G381, T383 and P385, are positioned on its solvent-exposed side, opposite to the interface that interacts with 'RBD'5. This indicates that the conservation of SSM residues has been driven by a requirement to interact with 'RBD'5. Furthermore, 'RBD'5 Q419 and G420, the latter of which is most likely needed to end α1 and supply flexibility to the T371:Q419 interaction, are strictly conserved in all SSM-containing STAU proteins that were examined, whereas no STAU protein that lacks an SSM contained either of these residues (FIG. 11). These findings indicate that SSM and 'RBD'5 have co-evolved to interact with one another either in cis (i.e., when STAU is a monomer), in trans (i.e., when STAU is a dimer), or both.

Example 21

SSM and 'RBD'5 are Domain-Swapped Between Two Symmetry-Related Molecules in the Crystal Structure There is little-to-no electron density in the X-ray crystal structure for amino acids 397-404 in the loop that connects SSM and 'RBD'5 (FIG. 12A). This high level of disorder led to difficulties in interpreting whether SSM is bound in cis to its own 'RBD'5 or RBD'5 derives from an adjacent molecule in the crystal lattice, i.e., is the consequence of domain-swapping between two molecules.

Assuming the cis-configuration, proximal molecules in the crystal lattice were compared using PISA (FIGS. 13A,B) to define the dimer interface. The largest symmetric crystal-packing interface, which was only ~764 Å$^2$ (from each molecule), was formed between the 'RBD'5s of adjacent molecules (FIGS. 13A,B) and was defined by a PISA complexation significance score of zero (i.e., the least significant), indicating it is not biologically relevant. Furthermore, SSM-'RBD'5(E424H, D427V), which contains mutations at this interface (FIG. 13B), produced a gel-filtration chromatogram identical to that of SSM-'RBD'5(WT) (FIG. 13C), i.e., dimers and not monomers were observed.

A perfect CSS score of 1.0 was obtained for the trans configuration (FIG. 13A), in which a highly conserved SSM of one molecule binds to the 'RBD'5 of a second molecule (FIG. 12B) to create a 38-residue surface area of ~1249 Å$^2$ for each molecule (FIG. 13A). Possibly, the interaction occurs in cis when hSTAU1 is a monomer and in trans when it is a dimer.

Example 22

Comparison of 'RBD'5 to an RBD that Binds dsRNA

The structural elements that render 'RBD'5 unable to bind dsRNA were addressed. Remarkably, the three RBD structures that according to the Dali server are most similar to 'RBD'5 do bind dsRNA (Table 12). These structures are RBD1 of human TAR RNA-binding protein 2 (hTRBP2; PDB ID 3LLH; Z-score=10.8; rmsd=1.3 Å), the RBD of RNase III from the thermophilic prokaryote Aquifex aeolicus (PDB ID 2NUE; Z-score=10.6; rmsd=2.0 Å), and RBD2 of Xenopus laevis RNA-binding protein A (Xlrbpa; PDB ID 1DI2; Z-score=10.5; rmsd=1.5 Å).

hTRBP2 RBD1 is the most similar to hSTAU1 'RBD'5. To address how STAU1 'RBD'5 adopt a fold similar to that of hTRBP2 RBD1 yet fail to bind RNA, the two structures were superimposed (FIG. 14A) to create a structure-based sequence alignment (FIG. 14B). While the two structures are nearly identical, hSTAU1 'RBD'5 has a shorter loop 2 (L2) and a longer L3 compared to hTRBP2 RBD1. Furthermore, none of the key residues that typify the three RNA-binding regions of canonical RBDs and are present in hTRBP2 RBD1 are found in hSTAU1 'RBD'5. The most apparent differences reside in regions 2 and 3. L2, which is shortened and is unable to reach the minor groove of dsRNA, lacks a His residue that in hTRPB2 RBD1 interacts with the dsRNA minor grove (FIG. 14A). In hSTAU1 'RBD'5 region 3, the positively charged residues of hTRBP2 RBD1 that interact with the negatively charged phosphate backbone spanning the dsRNA major groove are negatively charged and can actually repel dsRNA (FIGS. 14A, C, and D). Consistent with this view, *D. melanogaster* STAU RBD3 and hTRBP2 RBD1 maintain a basic charge in region 3 despite having differences in the lengths of L4 and α2. In fact, *D. melanogaster* STAU RBD3 RNA binding was lost when either of the first two conserved Lys residues (K59 and K60 in hTRBP2 RBD1; FIG. 14A) of region 3 were mutated to alanine. As inferred from the NMR structure of *D. melanogaster* STAU RBD3, hSTAU1 RBD3 likewise maintains a basic charge in region 3. The absence of the conserved His residue or a functional equivalent in hSTAU1 'RBD'5 L2 of region 2 contributes to the loss of dsRNA binding as evidenced by the finding that *D. melanogaster* STAU RBD3 RNA binding was lost when this L2 His was changed to Ala.

Example 23

SSM-'RBD'5 Domain-Swapping Facilitates the Interaction Between hSTAU1-hSTAU1 as Well as hSTAU1-hSTAU2, where 'RBD'5 α1 is Key From the structure, the two α-helices of 'RBD'5 interact with the two α-helices of SSM. However, the finding that hSTAU1$^{55}$ can interact with all hSTAU2 isoforms, the smallest of which (hSTAU2$^{52}$) has a C-terminus that ends five amino acids after 'RBD'5 α1 (FIG. 10B), indicates that α1 must constitute the minimal region of 'RBD'5 necessary to interact with SSM.

To test this idea, HEK293T cells were transiently transfected with hSTAU1$^{55}$-HA$_3$ and one of three siRNA-resistant (R) plasmids that produce either hSTAU1$^{55(R)}$-FLAG, hSTAU1$^{55(R)}$Δ(C-Term)-FLAG or hSTAU1$^{55(R)}$Δ(SSM-'RBD'5)-FLAG, each of which was expressed at the level of cellular hSTAU1. hSTAU1$^{55(R)}$Δ(C-Term)-FLAG lacks all amino acids C-terminal to 'RBD'5 α1. Cell lysates were immunoprecipitated in the presence of RNaseA using anti-FLAG or, as a negative control, mIgG.

Western blotting demonstrated that the three FLAG-tagged proteins were expressed at comparable levels prior to IP, were immunoprecipitated with comparable efficiencies using anti-FLAG, and were not immunoprecipitated with mIgG. The level of hSTAU1$^{55}$-HA$_3$ or cellular hUPF1 that co-immunoprecipitated with hSTAU1$^{55(R)}$Δ(SSM-'RBD'5)-FLAG was only ~10% the level of, respectively, hSTAU1$^{55}$-HA$_3$ or cellular hUPF1 that co-immunoprecipitated with hSTAU1$^{55(R)}$-FLAG or hSTAU1$^{55(R)}$Δ(C-Term)-FLAG. IPs of the same transfections using either anti-HA, or rIgG as a negative control, revealed that the level of hSTAU1$^{55(R)}$Δ(SSM-'RBD'5)-FLAG that co-immunoprecipitated with hSTAU1$^{55}$-HA was only ~10% the level hSTAU1$^{55(R)}$-FLAG or hSTAU1$^{55(R)}$Δ(C-Term)-FLAG that co-immunoprecipitated with hSTAU1$^{55}$-HA$_3$. These results indicate that domain-swapping between SSM and 'RBD'5 is the major determinant of hSTAU1 homodimerization and that 'RBD'5 α$^1$ is necessary and sufficient to interact with SSM.

Since hSTAU1 recruits hUPF1 to SMD targets during SMD, cellular hUPF1 was also assayed. Remarkably, the co-IP of hUPF1 with each hSTAU1$^{55(R)}$-FLAG variant correlated with homodimerization ability. Consistent with this, the co-IP of hUPF1 with hSTAU1$^{55}$-HA$_3$ did not vary among transfections (FIG. 4B, lower). Assays of the three detectable cellular hSTAU2 isoforms demonstrated that hSTAU2 co-immunoprecipitates with each hSTAU1$^{55(R)}$-FLAG variant with the same relative efficiency as did hSTAU1$^{55}$-HA$_3$.

Since hSTAU1$^{55(R)}$Δ(SSM-'RBD'5)-FLAG still had residual dimerization activity (10% that of hSTAU1$^{55(R)}$-FLAG), and in view of reports that hSTAU1 'RBD'2 amino acids 37-79 can interact with full-length hSTAU1, the ability of *E. coli*-produced 'RBD'2-RBD3 amino acids 43-173 to dimerize was assayed. Gelfiltration demonstrated that 'RBD'2-RBD3 indeed migrated at the position expected of an 'RBD'2-RBD3-'RBD'2-RBD3 dimer.

Example 24

Domain-Swapping of SSM and 'RBD'5 α1 is Important for SMD

To test the importance of hSTAU1$^{55}$ dimerization to SMD, HEK293T cells were transiently transfected with: (i) STAU1 (A)siRNA; (ii) plasmid expressing one of the three hSTAU1$^{55(R)}$-FLAG variants or, as a control, no protein; (iii) three plasmids that produce a firefly luciferase (FLUC) reporter mRNA, i.e., FLUC-No SBS mRNA, which lacks an SBS, FLUC-hARF1 SBS mRNA, which contains the hARF1 SBS, and FLUC-hSERPINE1 3' UTR, which contains the 3' UTR and, thus SBS of mRNA encoding serpin peptidase inhibitor Glade e, member 1; and (iv) a reference plasmid that produces renilla luciferase (RLUC) mRNA. In parallel, cells were transfected with (i) Control siRNA, (ii) plasmid producing no hSTAU1$^{55(R)}$-FLAG protein, (iii) the three FLUC reporter plasmid DNAs, and (iv) the RLUC reference plasmid.

Western blotting of cell lysates demonstrated that STAU1 (A)siRNA reduced the abundance of cellular hSTAU1 to ~10% the level in Control siRNA-treated cells and that each hSTAU1$^{55(R)}$-FLAG variant was expressed at comparable abundance. When semiquantitative RT-PCR was used to normalize the level of each FLUC mRNA to the level of RLUC mRNA, which controls for variations in transfection efficiencies and RNA recovery, the normalized level of FLUC-No SBS mRNA, which is not an SMD target, was found to be essentially identical in all transfections, as expected. In contrast, the normalized level of FLUC-hARF1 SBS mRNA or FLUC-hSERPINE1 3' UTR mRNA was increased ~2-fold in the presence of STAU1(A) siRNA alone, consistent with an inhibition of SMD. This inhibition was reversed by 50% when hSTAU1$^{55(R)}$-FLAG or hSTAU1$^{55(R)}$Δ(C-Term)-FLAG were expressed but not when hSTAU1$^{55(R)}$Δ(SSM-'RBD'5)-FLAG was expressed. Thus, hSTAU1$^{55(R)}$—FLAG and hSTAU1$^{55(R)}$Δ(C-Term)-FLAG can functionally compensate for the siRNA-mediated down-regulation of cellular hSTAU1 more efficiently than can hSTAU1$^{55}$(R)Δ(SSM-'RBD'5)-FLAG.

hSTAU1 dimerization is important for SMD, because hSTAU1 dimers bind an SBS and/or UPF1 more efficiently than hSTAU1 monomers, but also because hSTAU1$^{55(R)}$Δ(SSM-'RBD'5)-FLAG can bind hUPF1 inefficiently. Considering that deleting the TBD and adjacent SSM of hSTAU1 ablated hUPF1 binding to an essentially undetectable level, and that 'RBD'5 alone does not bind hUPF1 (FIG. 10D), whether inhibiting hSTAU1 dimerization by expressing 'RBD'5 inhibited hSTAU1 binding to hUPF1 was tested. To this end, HEK293T cells were transiently transfected with plasmid producing hSTAU1$^{55(R)}$-FLAG, hSTAU1$^{55}$-HA$_3$, and either mRFP-'RBD'5 (from pmRFP-'RBD5') or no protein (from pmRFP). Lysates were immunoprecipitated in the presence of RNase A using anti-FLAG or, as a negative control, mIgG.

Western blotting demonstrated that comparable amounts of hSTAU1$^{55(R)}$-FLAG were expressed and immunoprecipitated using anti-FLAG in the presence or absence of 'RBD'5, and hSTAU1$^{55(R)}$—FLAG and hSTAU1$^{55}$-HA$_3$ were each expressed at a level comparable to that of cellular hSTAU1. 'RBD'5 expression reduced the amount of hSTAU1$^{55}$-HA$_3$ that co-immunoprecipitated with hSTAU1$^{55(R)}$-FLAG to 35-40% of the amount that co-immunoprecipitated in the absence of 'RBD'5 expression. The finding that 'RBD'5 expression reduced the amount of cellular hUPF1 that co-immunoprecipitated with hSTAU1$^{55(R)}$-FLAG also to 35-40% of the amount that co-immunoprecipitated in the absence of 'RBD'5 expression indicates that hUPF1 binds hSTAU1 dimers more efficiently than it binds hSTAU1 monomers.

Example 25 hSTAU1 Homodimerization Occurs Through the SSM

The hSTAU1 SSM, which is a two-helix motif that interacts with the dsRNA-binding-deficient 'RBD'5 of another hSTAU1 molecule. A complete SSM and al of 'RBD'5, which are required for this interaction, can be found in the STAU proteins of all vertebrate classes. The majority of the 'RBD'5 hydrophobic residues that contribute to SSM-'RBD'5 homodimerization via domain-swapping are generally present in other RBDs. In particular, that P408, L412, A465, L469 and L472 are conserved between hSTAU1 'RBD'5 and hTRBP2 RBD1 (FIG. 14B) most likely explains why hSTAU1 'RBD'5 and hTRBP2 RBD1 can be structurally superimposed (FIG. 14A). However, hSTAU1 'RBD'5 residues Y414 and L415, which are positioned, respectively, in or proximal to dsRNA-interacting region 1, are not conserved in other RBDs (FIG. 14B). SSM is a modular adaptation in many if not all vertebrate STAU homologs that, through its interaction with 'RBD'5, adds greater functionality to full-length protein, i.e., the potential for STAU to dimerize if not multimerize considering the 'RBD'2-'RBD'2 interaction.

Example 26 hSTAU1 Homodimerization Contributes to SMD

Compared to hSTAU1 monomers, hSTAU1 dimers bind hUPF1 more efficiently and mediate SMD more effectively. Thus, cells can regulate SMD by controlling hSTAU1 dimer formation. Since homodimers of SSM-'RBD'5 are less stable ($K_{d=79}$ µM; see also FIG. 10C) than are complexes of full-length hSTAU1 and dsRNA ($K_d=10^{-9}$ M), hSTAU1 binding to dsRNA can nucleate hSTAU1 dimerization. Proteins known to dimerize on double-stranded nucleic acid are exemplified by transcriptional activators, the adenosine deaminases ADAR1 and ADAR2, and protein kinase RNA-activated (PKR), where binding to viral dsRNA promotes PKR phosphorylation activity by allowing dimerization of the kinase domain.

Example 27

'RBD'5 has Diverged from a True RBD to Serve a New Function

Assuming 'RBD'5 evolved from a functional RBD, it not only lost the ability to bind dsRNA but gained the ability to interact with SSM. The structure together with models that compare 'RBD'5 to true RBDs, such as hTRBD2 RBD1 and RBD2 in association with dsRNA, clearly illustrate that RBD regions 2 and 3, which interact with the minor groove and bridge the proximal major groove of dsRNA, respectively, are altered in 'RBD'5 (FIG. 14D). The role of region 1 in α1, at least fortrue RBDs, determines RNA recognition specificity, where α1 can bind the major groove or possibly distinguishing features such as loops at the apex of dsRNA. In 'RBD'5, α1 specifies SSM recognition, although 'RBD'5 α1 interacts with SSM using a face that is orthogonal to the face that interacts with dsRNA in a true RBD. The data indicate that 'RBD'5 α1 is sufficient for hSTAU1 dimerization and, together with four L1 amino acids, is the only region of 'RBD'5 that exists in the smallest STAU2 isoform (FIG. 10B).

Interestingly, what remains of 'RBD'5 in the hSTAU2 isoforms with the longest C-termini corresponds to the regions of hSTAU1 'RBD'5 that contact SSM directly, i.e., 'RBD'5 α1 and the C-terminus of 'RBD'5 α2 (FIG. 10B; 12B). Due to the lack of a sufficiently sized loop residing between hSTAU2 'RBD'5 α1 and the remains of 'RBD'5 α2, details of the dimerization interaction between hSTAU2-hSTAU2 and hSTAU1-hSTAU1 can differ. However, residues of hSTAU2 'RBD'5 residing C-terminal to al are dispensable for the SSM-mediated dimerization of hSTAU2, since they are dispensable for the SSM-mediated dimerization of hSTAU1.

Example 28

The RBD Fold as a Platform for New Functions

As reported here, the combination of a modified RBD, e.g., hSTAU1 'RBD'5, within the context of an adapter region, e.g., hSTAU1 SSM, can promote greater functionality within the larger, often modular and flexible framework of proteins that contain one or more RBDs that bind dsRNA. In support of this view, modifications that consist of anL1 Cys and anL3 His within the RBD of the *Schizosaccharomyces pombe* Dicer DCR1 protein work together with a 33-amino acid region that resides C-terminal to the RBD to form a zinc-coordination motif that is required for nuclear retention. Since this RBD binds dsRNA and dsDNA, these and other changes can additionally contribute to dsDNA binding.

'RBD's that fail to bind dsRNA can acquire new functions independently of adjacent regions. As one example of this, 'RBD'5 region of *Drosophila* Staufen has adapted to bind the Miranda protein required for proper localization of prospero mRNA. As another example, hTRBP2 contains three RBDs, and the C-terminal RBD binds Dicer instead of dsRNA. Additionally, in contrast to the SSM-mediated dimerization of hSTAU1 'RBD'5, 'RBD'3 of Xlr bpa and its human homolog, p53-associated cellular protein PACT, appear to homodimerize independent of an accessory region.

Example 29

Sequence Alignments

Sequences were obtained from NCBI. Multiple protein sequence alignments were performed using Clustal W within BioEdit, which was used to generate figures.

Example 30

Protein Crystallization and Structure Determinations

Native crystal datasets were obtained using crystals produced from gel-filtration-purified hSTAU1 SSM-'RBD'5 and either the hanging-drop method for remote data collection at the Stanford Synchrotron Radiation Lightsource (SSRL) or the sitting-drop method for data collection at the Cornell High Energy Synchrotron Source (CHESS) (Table 12). An initial model was built using low-resolution experimental phases obtained from in-house single anomalous dispersion phases from an ethyl mercuric phosphate-soaked crystal. These coordinates were used for molecular-replacement and refined against a 2.2 Å native dataset (Table 12). The final model was refined against a subsequent, 1.7 Å native data set. A consistent set of reflections for the free R-factor was maintained throughout. Structure figures were generated using PyMOL (Schrödinger, LLC). See Extended Experimental Procedures for crystallization and structure determination details.

Example 31

HEK239T-Cell Transfections, and Protein and RNA Purification

Human HEK293T cells were grown in Dulbecco's-modified eagle medium (Gibco-BRL) containing 10% fetal-bovine serum (Gibco-BRL). Cells were transiently transfected with plasmids using Lipofectamine 2000 (Invitrogen) or with siRNA using Oligofectamine (Invitrogen) as indicated in the figure legends. siRNAs consisted of hSTAU1 siRNA(A) and Negative Control #1 siRNA (Ambion). Protein was isolated using passive lysis buffer (Promega), and RNA was purified using TRIzol Reagent (Invitrogen).

Example 32

Plasmid Constructions

To generate pGEX-6p-1-hSTAU1-SSM-'RBD'5, the online servers MeDor (Lieutaud et al., 2008) and XtalPred (which gave an average score of 3) were used to guide the choice of boundaries that include hSTAU1 SSM and 'RBD'5 and provide optimal protein stability and crystallization. The region of hSTAU1 cDNA that encodes amino acids 367-476 was PCR-amplified using pRSET-B hSTAU1 and the primer pair 5'-AAAA GGATCCAAGGCCACGGTAACTGCCATG-3' (sense, where the BamHI site is underlined) (SEQ ID NO: 161) and 5'-AAAA GAATTCTTATCAGTCCAACTCAGACAGCAAC-3' (antisense, where the EcoRI site is underlined) (SEQ ID NO: 162). The resulting PCR product was cleaved with BamHI and EcoRI and inserted into the BamHI and EcoRI sites of pGEX-6p-1 (GE Healthcare) to generate pGEX-6p-1-hSTAU1-SSM-'RBD'5. Notably, upon removing the GST-tag using PreScission Protease (GE Healthcare), the resulting protein contains the amino acids GPLGS N-terminal to hSTAU1 amino acids 367-476.

To construct pGEX-6p-1-hSTAU1-SSM-'RBD'5(E424H, D427V), the QuikChange™ method was used but with KOD DNA polymerase (Novagen), pGEX-6p-1-hSTAU1-SSM-'RBD'5 as template, and the primer pair 5'-GATTCCAGGTT CATTACAAAGTCTTCCCCAAAAAC-3' (sense) (SEQ ID NO: 163) and 5'-GTTTTTGGGGAAGACTTTGTAAT GAACCTGGAATC-3' (antisense) (SEQ ID NO: 164).

To construct pEGFP-hSTAU1-SSM-'RBD'5 or pEGFP-hSTAU1-'RBD'5, pRSET B-STAU1 was PCR-amplified using 5'-AAAAGAATTC TTATCA GTCCAACTCAGA-CAGCAAC-3' (antisense, EcoRI site is underlined) (SEQ ID NO: 165) and, respectively, 5'-AAAAAAGCTTAAGGC-CACGGTAACTGCCATG-3' (sense, HindIII site is underlined) (SEQ ID NO: 166) or 5'-AAAA AAGCTTAGACCCTCTGAGCAACTGGAC-3' (sense, HindIII site is underlined) (SEQ ID NO: 167). PCR products were cleaved using EcoRI and HindIII and inserted into pEGFP-C3 (BD Biosciences Clontech).

To construct pmRFP-hSTAU1-SSM-'RBD'5 or pmRFP-hSTAU1-RBD'5, pRSETB-STAU1 was PCR-amplified using the same antisense primer that was used to amplify the pEGFP plasmids and, respectively, 5'-AAAA AAGCTTCTAAGGCCACGGTAACTGCCATG-3' (sense, HindIII site is underlined) (SEQ ID NO: 168) or 5'-AAAA AAGCTTCTAGACCCTCTGAGCAACTGGAC-3' (sense, HindIII site is underlined) (SEQ ID NO: 169). PCR products were cleaved using EcoRI and HindIII and inserted into pmRFP. pmRFP derives from pDsRed-Express-C1 (Clontech Laboratories, Inc.) and contains mutations that render DsRed (i.e. mRFP) monomeric.

STAU1(A) siRNA-resistant phSTAU1$^{55(R)}$-HA$_3$ was derived from the PCR-amplification of pcDNA3/RSV-hS-TAU-HA$_3$ using two sets of primer pairs: 5'-CACCACATTG-GTGTGCACCTCCAAGCTTGG-3' (sense A) (SEQ ID NO: 170) and 5'-CCGcTTCAGGGCGATTTC GAACACTTGACTTATTTCAGATTT-3' (antisense A, where underlined nucleotides confer siRNA-resistance, and) (SEQ ID NO: 171), and 5'-AAATCTGAAATAAGTCAAGT-GTTCGAAATCGCCCTGAAgCGG-3' (sense B, where underlined nucleotides confer siRNA-resistance, and the two lower case letters were ineffective in directing a change from the wild-type sequence) (SEQ ID NO: 172) and 5'-GAAG-GCACAGTCGAGGCTGATCAGCGAG-3' (antisense B) (SEQ ID NO: 173). The resulting two PCR products were mixed and PCR-amplified using the first sense A and antisense B primers. This PCR product was cleaved with KpnI and XbaI and inserted into pcDNA3/RSV-hSTAU-HA$_3$ To generate pcI-neo-hSTAU1$^{55(R)}$-FLAG, pcI-neo-hS-TAU1$^{55(R)}$Δ(C-Term)-FLAG or pcI-neo-hSTAU1$^{55(R)}$Δ(SSM-'RBD'5)-FLAG, phSTAU1$^{55(R)}$-HA$_3$ was PCR-amplified using 5'-AAAAGCTAGCGCC ACC*ATG* AAACTTGGAAAAAAACCAATG-3' (sense, NheI site is underlined, and the Kozak sequence is bold with start codon also italicized) (SEQ ID NO: 174) and, respectively, 5'-AAAACTCGAGCTATTA*CTTGTCGT CATCGTCT TTGTAGTC* CCCCCC GCACCTCCCACA-CACAGAC-3' (antisense) (SEQ ID NO: 175), 5'-AAAA CTCGAGCTATTA*CTTGTCGT CATCGTCT TTGTAGTC* CCCCCCCTGGAATCCC TGGACTCTG-GAAAG-3' (antisense) (SEQ ID NO: 176) or 5'-AAAA CTCGAGCTATTA*CTTGTCGT CATCGTCT TTGTAGTC* CCCCCC CGGAGCTGCCCTGG-TAAAATCTTTGG-3' (antisense) (SEQ ID NO: 177), where for each antisense primer the XhoI site is underlined and the FLAG sequence introduced by the primer is bold, underlined and italicized). PCR products were digested using NheI and XhoI and inserted into pcI-neo (Promega). Each STAU1 plasmid encodes an R323K amino acid change relative to the NCBI sequence. This change derives from the original pcDNA3/RSV-hSTAU-HA$_3$ plasmid.

To generate pGEX-6p-1-hSTAU1-'RBD'2-RBD3, pRSET B-His-STAU1 was PCR-amplified using 5'-AAAA GGATCCCCTTTACTTTATCAAGTGG-3' (sense, BamHI site is underlined) (SEQ ID NO: 178) and 5'-AAAA GAATTCTTATCACGGTAACTTCTTCAGCTCCTC-3' (antisense, EcoRI site is underlined) (SEQ ID NO: 179). The PCR product was digested with BamHI and EcoRI and inserted into pGEX-6p-1 (GE Healthcare).

Example 33

Protein Expression in *E. coli* and Protein Purification

*E. coli* BL21(DE3) transformed with pGEX-6p-1-hS-TAU1-SSM-'RBD'5 was propagated in multiple 1-liter cultures of Luria Broth supplemented with ampicillin (100 mg/l), to an O.D.600 of ~0.5, at which time 300 µl of 1M isopropyl β-D-1-thiogalactopyranoside was added to each liter and the temperature was reduced from 37° C. to 30° C. The following morning, cells were collected at ~7,000×g and 4° C. and either used directly or flash-frozen in liquid N$_2$ for storage at −80° C.

Cell pellets were resuspended in ~40 ml of Buffer A (1M NaCl, 25 mMTris-HCl pH 8) to which was added 55 µl of 0.93 M dithiothreitol(DTT), 500 µl of 100 mM PMSF, 50 µl of 0.5

M EDTA pH 8, 500 μl of 80 mg/ml lysozyme, and a protease inhibitor tablet (Roche). Cells were lysed using sonication, and lysates were cleared by centrifugation at 17,000×g for 30 minutes at 4° C. The soluble portion was removed and loaded on a GSTrap™ HP column (GE Healthcare), washed with 1M NaCl, 25 mMHepes pH 8 (which was sometimes replaced with Buffer A), washed with gel-filtration (GF) buffer (100 mMNaCl, 10 mMTris-HCl pH 8, 1.3 mM DTT; this step was sometimes omitted), and then eluted with 0.3 g of glutathione (reduced, free acid) dissolved in 100 ml of GF buffer. A ~1 mg aliquot of PreScission™ Protease (GE Healthcare) was added to ~50 ml of eluted sample and left at 4° C. overnight. The following day, the sample was applied to a HiTrap™ Q HP column (GE Healthcare) to remove GST. The flow-through was concentrated to ~ml using a CORNING® SPIN-X® UF 20 5K column (MW cut-off at 5 kDa), and loaded using an ÄKTAFPLC™ system (GE Healthcare) onto a 120-ml HiLoad™Superdex™ 75 16/60 prep grade column (GE Healthcare) gel-filtration column that was pre-equilibrated with GF buffer. hSTAU1-SSM-'RBD'5 peak fractions were concentrated as above and used immediately or stored for short periods at 4° C.

Procedures for expressing pGEX-6p-1-hSTAU1-'RBD'2-RBD3 were identical to those for used for expressing hSTAU-SSM-'RBD'5. However, Buffer A contained 5% glycerol and the GSTrap™ column elution was with a solution prepared by dissolving 0.3 g glutathione (reduced, free acid), a protease inhibitor tablet (Roche) and 405 μl of 0.93 M DTT in 100 ml of GF buffer. After PreScission™ Protease treatment overnight, the solution was loaded onto a HiTrap™ SP FF column (GE Healthcare) and eluted using a linear NaCl gradient of GF buffer and glycerol-containing Buffer A using a BioLogicDuoFlow™ FPLC system. Peak fractions were collected, concentrated as above, and loaded onto a HiTrap™ Q HP column to remove contaminating RNAs. The flow-through was concentrated and loaded on a 120 ml HiLoad™Superdex™ 200 16/60 prep grade column (GE Healthcare) that was equilibrated with GF buffer containing 2.97 mM DTT using the BioLogicDuoFlow™ FPLC system.

Example 34

Analytical Ultracentrifugation hSTAU1-SSM-'RBD'5 was purified as above, except the final GF buffer contained 2.97 mM DTT, and submitted to the University of Connecticut Analytical Ultracentrifugation Facility for sedimentation velocity analysis. A Beckman-Coulter XL-I analytical ultracentrifuge with double-sector synthetic boundary cells having sapphire windows was used to take interference scans. Measuring refractive index rather than absorbance was especially useful considering the low extinction coefficient at $A_{280}$ that typifies SSM-'RBD'5; which lacks tryptophan residues. Interference scans were collected at 55,000 RPM and 20° C. every minute for 7 hours. Data were analyzed using: 1) DcDt+, version 2.0.9 (Philo, 2000; 2006), to determine the sedimentation coefficient distribution that was independent of a model, 2) Sedfit, version 10.09beta (Schuck, 2000), to produce a model-based continuous sedimentation coefficient distribution using the Lamm equation or c(s) to identify the number of species (e.g., monomers vs dimers) in solution, and 3) Sedanal, version 5.60 to combine datasets from the three highest of four concentrations tested, perform a global analysis, and determine the protein association model using the Lamm equation.

Example 36

Size Determination Using Gel-Filtration Chromatography

Size standards were prepared by dissolving dried proteins in 2 ml of GF buffer containing 2.97 mM DTT. Proteins consisted of 3.8 mg of conalbumin (75 kDa), 2.3 mg carbonic anhydrase (29 kDa) and 6.7 mg aprotinin (6.5 kDa), each from the Low Molecular Weight Gel Filtration Calibration Kit (GE Healthcare; #28-4038-41), and 6 mg of lysozyme (14.3 kDa) (Sigma; #L6876-10G). The dissolved solution (1 ml, determined using a 1 ml loop) was loaded onto a 120 ml HiLoad™Superdex™ 200 16/60 prep-grade column (GE Healthcare) and separated at a 1 ml/min flow rate using the BioLogicDuoFlow™ FPLC system. For size estimations, gel-filtration of SSM-'RBD'5 (WT), SSM-'RBD'5 (E424H, D427V) and 'RBD'2-RBD3 was performed as described for the size standards. SSM-'RBD'5 (WT) was loaded at 8 mg/ml, SSM-'RBD'5 (E424H, D427V) was loaded, and 'RBD'2-RBD3 was loaded at 6 mg/ml.

Example 37

Extended Protein Crystallization and Structure Determination Procedures

Gel-filtration-purified hSTAU1 SSM-'RBD'5 was screened for crystal formation using the JCSG Core Suites I-IV (QIAGEN; Lesley and Wilson, 2005) and a Mosquito robot. Using the sitting drop method and CrystalQuick™ (Greiner) plates, 0.2 μl of protein in GF buffer (10 mMTris-HCl pH 8, 100 mMNaCl, and 1.3 mM DTT) at 15 mg/ml (determined using the Bradford assay) was mixed with 0.2 μl of reservoir solution, which was 70 μl. Plates were covered with ClearSealFilm™ and incubated at 18° C. After four days, bi-pyrimidal shaped crystals (Figure S11) were found using JCSG Core Suite II condition #96 (or H12). The screening solution was dehydrated ~1.3 fold and therefore contained 130 mM citric acid pH 2.5 and 26% (w/v) PEG 6000 with a final pH of 4.

Using the hanging drop method and the Stanford Synchrotron Radiation Lightsource (SSRL), a native crystal dataset was generated using the conditions described above, except that drops were 3 μl and the reservoir contained 1 ml of 0.1 M citric acid pH 2.5 and 35% PEG 6000. Crystals (20-30 μl), the largest of which were on average 240 m tip-to-tip, were transferred to a 50/50 (v/v) mixture of silicon and PARATONE® N oils, moved around in the cryoprotectant with a nylon loop until free of phase-separated sweat, collected with the loop, and flash-frozen in liquid $N_2$. The native crystal dataset was collected under a cryostream remotely at the SSRL beamline 9-2 on a MAR-325 CCD detector (Table 12).

A second native dataset was collected at the Cornell High Energy Synchrotron Source (CHESS) on a crystal produced similarly to the SSRL dataset crystal, except 3 1 drops were made by mixing 1.5 μl of hSTAU1 SSM-'RBD'5 protein at a concentration of 5 mg/ml (determined at $A_{280}$ with an $ε_{280}$ of 4,470) with 1.5 μl of crystallization buffer (127 mM citric acid pH 2.5 and 25.9% PEG 6000 (final pH 4)). Drops were placed on a Micro-Bridge (Hampton Research, HR3-310) over 1 ml of 118 mM citric acid pH 2.5 and 29% PEG 6000 in the sealed wells of a 24-well plate. Data were collected under a cryostream at the CHESS beamline F1 on an ADSC Q-270 CCD detector (Table 12).

The crystal used for SAD phasing was produced similarly to the CHESS native crystal, but using a 4 ul-drop and a reservoir of 130 mM citric acid pH 2.5 and 26.5% PEG 6000. A 10 ul soaking-solution of 10 mM ethyl mercuric phosphate (EMP; Hampton Research, HR2-446) in 127 mM citric acid pH 2.5 and 28.2% PEG 6000 (final pH 4) was added directly to the drop containing the crystal, and a thick glass coverslip was placed over the Micro-Bridge. After ~45 min at room temperature, the crystal was transferred to 20 μA of cryoprotectant solution and flash-frozen. Data were collected in-house under a cryostream using a Bruker AXS X8 Prospector Ultra X-ray generator system equipped with an APEX II CCD detector (Table 12).

Data integration and scaling were performed using HKL2000 for both native synchrotron datasets. Alternatively, PROTEUM2 (Bruker AXS Inc.) was used for the in-house SAD dataset (Table 12).

CTRUNCATE within CCP4 (CCP4, 1994) was used to convert the SAD dataset intensities for input into Autosol within Phenix, where anomalous signals identified two Hg sites at each of the only two Cys residues. The resulting density-modified Resolve map and the FFFEAR and FFJOIN programs were used to locate α-helices. Combinations of Autobuild, hand-building with Coot, and rounds of refinement using Phenix at this and all subsequent stages yielded a low-resolution model of 'RBD'5 and the SSM two α-helices. A molecular-replacement (MR) search using this model, Phaser (McCoy et al., 2007), and the 1.7 Å SSRL dataset was unsuccessful. However, a solution was found using the 2.2 Å CHESS dataset (Table 12). Following further refinement assisted by placing a homology model for 'RBD'5 using I-TASSER (Roy et al., 2010), a MR solution was obtained for the 1.7 Å SSRL dataset and used the final stages of refinement. Structure figures were generated using PyMOL (Schrödinger, LLC).

Exmple 38

Western Blotting, RT-PCR and Immunoprecipitations

Protein was electrophoresed in SDS-polyacrylamide, transferred to Hybond ECL nitrocellulose (Amersham), and probed with antibodies that recognize FLAG (Sigma), HA (Roche), calnexin (StressGen), UPF1 (Gong et al. 2009), STAU1, RFP (Abcam), GFP (Abeam) or STAU2 (Sigma) Immunoreactivity was assessed using SuperSignal West Pico or Femto (Pierce Biotechnology). After autoradiography, films were quantitated using ImageQuant (Molecular Dynamics).

Reverse transcriptions (RTs) and PCR amplifications were performed as previously described. RT-PCR products were electrophoresed in 5% polyacrylamide and quantitated by PhosphorImaging (Molecular Dynamics).

Immunoprecipitations were performed using anti-GFP (Abeam), anti-HA (Roche) or anti-FLAG (Sigma).

REFERENCES

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr. D. Biol. Crystallogr. 66, 213-221.

Allison, R., Czaplinski, K., Git, A., Adegbenro, E., Stennard, F., Houliston, E., and Standart, N. (2004). Two distinct Staufen isoforms in *Xenopus* are vegetally localized during oogenesis. RNA 10, 1751-1763.

Amoutzias, G. D., Robertson, D. L., Van de Peer, Y., and Oliver, S. G. (2008). Choose your partners: dimerization in eukaryotic transcription factors. Trends Biochem Sci 33, 220-229.

Ashley, C. T., Jr., Wilkinson, K. D., Reines, D., & Warren, S. T. FMR1 protein: conserved RNP family domains and selective RNA binding. *Science* 262, 563-566 (1993).

Bachand, F., Triki, I., and Autexier, C. (2001). Human telomerase RNA-protein interactions. Nucleic Acids Res. 29, 3385-3393.

Barraud, P., Emmerth, S., Shimada, Y., Hotz, H. R., Allain, F. H., and Buhler, M. (2011). An extended dsRBD with a novel zinc-binding motif mediates nuclear retention of fission yeast Dicer. EMBO J. 30, 4223-4235.

Bartel, D. P. MicroRNAs: target recognition and regulatory functions. *Cell* 136, 215-233 (2009).

Batzer, M. A. & Deininger, P. L. Alu repeats and human genomic diversity. Nat. Rev. Genet. 3, 370-379 (2002).

Belgrader, P., and Maquat, L. E. (1994). Nonsense but not missense mutations can decrease the abundance of nuclear mRNA for the mouse major urinary protein, while both types of mutations can facilitate exon skipping. Mol. Cell. Biol. 14, 6326-6336.

Binder, B. R. & Mihaly, J. The plasminogen activator inhibitor "paradox" in cancer. *Immunol. Lett.* 118, 116-124 (2008).

Bond, C. S. (2003). TopDraw: a sketchpad for protein structure topology cartoons. Bioinformatics 19, 311-312.

Bono, F., Ebert, J., Unterholzner, L., Guttler, T., Izaurralde, E., and Conti, E. (2004). Molecular insights into the interaction of PYM with the Mago-Y14 core of the exon junction complex. EMBO Rep. 5, 304-310.

Broadus, J., Fuerstenberg, S., and Doe, C. Q. (1998). Staufen-dependent localization of prospero mRNA contributes to neuroblast daughter-cell fate. Nature 391, 792-795.

Campbell, R. E., Tour, O., Palmer, A. E., Steinbach, P. A., Baird, G. S., Zacharias, D. A., and Tsien, R. Y. (2002). A monomeric red fluorescent protein. Proc. Natl. Acad. Sci. USA 99, 7877-7882.

CCP4. (1994). The CCP4 suite: programs for protein crystallography. Acta Crystallogr. D. Biol. Crystallogr. 50, 760-763.

Chan, C. C., Dostie, J., Diem, M. D., Feng, W., Mann, M., Rappsilber, J., and Dreyfuss, G. (2004). eIF4A3 is a novel component of the exon junction complex. RNA 10, 200-209.

Chen, C. Y. & Shyu, A. B. AU-rich elements: characterization and importance in mRNA degradation. *Trends Biochem. Sci.* 20, 465-470 (1995).

Chen, L. L., DeCerbo, J. N., & Carmichael, G. G. Alu element-mediated gene silencing. *EMBO J.* 27, 1694-1705 (2008).

Chiu, S. Y., Lejeune, F., Ranganathan, A. C., and Maquat, L. E. (2004). The pioneer translation initiation complex is functionally distinct from but structurally overlaps with the steady-state translation initiation complex. Genes Dev. 18, 745-754.

Cho, D. S., Yang, W., Lee, J. T., Shiekhattar, R., Murray, J. M., and Nishikura, K. (2003). Requirement of dimerization for RNA editing activity of adenosine deaminases acting on RNA. J Biol Chem 278, 17093-17102.

Cole, J. L. (2007). Activation of PKR: an open and shut case? Trends Biochem Sci 32, 57-62.

Coller, J. M., Gray, N. K., and Wickens, M. P. (1998). mRNA stabilization by poly(A) binding protein is independent of poly(A) and requires translation. Genes Dev. 12, 3226-3235.

Cordaux, R. & Batzer, M. A. The impact of retrotransposons on human genome evolution. *Nat. Rev. Genet.* 10, 691-703 (2009).

Cowtan, K. (1998). Modified phased translation functions and their application to molecular-fragment location. Acta Crystallogr D. Biol. Crystallogr. 54, 750-756.

Curatola, A. M., Nadal, M. S. & Schneider, R. J. Rapid degradation of AU-rich element (ARE) mRNAs is activated by ribosome transit and blocked by secondary structure at any position 5' to the ARE. *Mol. Cell. Biol.* 15, 6331-6340 (1995).

Donaldson, J. G., and Jackson, C. L. (2000). Regulators and effectors of the ARF GTPases. Curr. Opin. Cell Biol. 12, 475-482.

Duchaine, T., Wang, H. J., Luo, M., Steinberg, S. V., Nabi, I. R., and DesGroseillers, L. (2000). A novel murine Staufen isoform modulates the RNA content of Staufen complexes. Mol. Cell. Biol. 20, 5592-5601.

Duchaine, T. F., Hemraj, I., Furic, L., Deitinghoff, A., Kiebler, M. A., and DesGroseillers, L. (2002). Staufen2 isoforms localize to the somatodendritic domain of neurons and interact with different organelles. J. Cell Sci. 115, 3285-3295.

Emsley, P., Lohkamp, B., Scott, W. G., and Cowtan, K. (2010). Features and development of Coot. Acta Crystallogr. D. Biol. Crystallogr. 66, 486-501.

Engstrom, P. G. et al. Complex Loci in human and mouse genomes. *PLoS Genet.* 2, e47 (2006).

Ephrussi, A., Dickinson, L. K., and Lehmann, R. (1991). Oskar organizes the germ plasm and directs localization of the posterior determinant nanos. Cell 66, 37-50.

Ferraiuolo, M. A., Lee, C. S., Ler, L. W., Hsu, J. L., Costa-Mattioli, M., Luo, M. J., Reed, R., and Sonenberg, N. (2004). A nuclear translation-like factor eIF4AIII is recruited to the mRNA during splicing and functions in nonsense-mediated decay. Proc. Natl. Acad. Sci. USA 101, 4118-4123.

Ferrandon, D., Elphick, L., Nusslein-Volhard, C. & St Johnston, D. Staufen protein associates with the 3'UTR of bicoid mRNA to form particles that move in a microtubule-dependent manner. *Cell* 79, 1221-1232 (1994).

Forch, P., Puig, O., Martinez, C., Seraphin, B. & Valcarcel, J. The splicing regulator TIA-1 interacts with U1-C to promote U1 snRNP recruitment to 5' splice sites. *EMBO J.* 21, 6882-6892 (2002).

Frischmeyer, P. A., and Dietz, H. C. (1999). Nonsense-mediated mRNA decay in health and disease. Hum. Mol. Genet. 8, 1893-1900.

Fuerstenberg, S., Peng, C. Y., Alvarez-Ortiz, P., Hor, T., and Doe, C. Q. (1998). Identification of Miranda protein domains regulating asymmetric cortical localization, cargo binding, and cortical release. Mol. Cell. Neurosci. 12, 325-339.

Furic, L., Maher-Laporte, M., and DesGroseillers, L. (2008). A genome-wide approach identifies distinct but overlapping subsets of cellular mRNAs associated with Staufen1- and Staufen2-containing ribonucleoprotein complexes. RNA 14, 324-335.

Gan, J., Shaw, G., Tropea, J. E., Waugh, D. S., Court, D. L., and Ji, X. (2008). A stepwise model for double-stranded RNA processing by ribonuclease III. Mol. Microbiol. 67, 143-154.

Gan, J., Tropea, J. E., Austin, B. P., Court, D. L., Waugh, D. S., and Ji, X. (2005). Intermediate states of ribonuclease III in complex with double-stranded RNA. Structure 13, 1435-1442.

Gatfield, D., Unterholzner, L., Ciccarelli, F. D., Bork, P., and Izaurralde, E. (2003). Nonsense-mediated mRNA decay in *Drosophila*: at the intersection of the yeast and mammalian pathways. EMBO J. 22, 3960-3970.

Gehring, N. H., Neu-Yilik, G., Schell, T., Hentze, M. W., and Kulozik, A. E. (2003). Y14 and hUpf3b form an NMD-activating complex. Mol. Cell. 11, 939-949.

Gibson, T. J., and Thompson, J. D. (1994). Detection of dsRNA-binding domains in RNA helicase A and *Drosophila* maleless: implications for monomeric RNA helicases. Nucleic Acids Res. 22, 2552-2556.

Gong, C., Kim, Y. K., Woeller, C. F., Tang, Y., & Maquat, L. E. SMD and NMD are competitive pathways that contribute to myogenesis: effects on PAX3 and myogenin mRNAs. *Genes Dev.* 23, 54-66 (2009).

Gong, C., Kim, Y. K., Woeller, C. F., Tang, Y., and Maquat, L. E. (2009). SMD and NMD are competitive pathways that contribute to myogenesis: effects on PAX3 and myogenin mRNAs. Genes Dev. 23, 54-66.

Goodrich, J. S., Clouse, K. N., and Schupbach, T. (2004). Hrb27C, Sqd and Otu cooperatively regulate gurken RNA localization and mediate nurse cell chromosome dispersion in *Drosophila* oogenesis. Development 131, 1949-1958.

Gorlach, M., Burd, C. G., and Dreyfuss, G. (1994). The mRNA poly(A)-binding protein: localization, abundance, and RNA-binding specificity. Exp. Cell Res. 211, 400-407.

Grentzmann, G., Ingram, J. A., Kelly, P. J., Gesteland, R. F., and Atkins, J. F. (1998). A dual-luciferase reporter system for studying recoding signals. RNA 4, 479-486.

Guruprasad, K., Reddy, B. V., and Pandit, M. W. (1990). Correlation between stability of a protein and its dipeptide composition: a novel approach for predicting in vivo stability of a protein from its primary sequence. Protein Eng. 4, 155-161.

Haase, A. D., Jaskiewicz, L., Zhang, H., Laine, S., Sack, R., Gatignol, A., and Filipowicz, W. (2005). TRBP, a regulator of cellular PKR and HIV-1 virus expression, interacts with Dicer and functions in RNA silencing. EMBO Rep. 6, 961-967.

Hachet, O., and Ephrussi, A. (2001). *Drosophila* Y14 shuttles to the posterior of the oocyte and is required for oskar mRNA transport. Curr. Biol. 11, 1666-1674.

Hachet, O., and Ephrussi, A. (2004). Splicing of oskar RNA in the nucleus is coupled to its cytoplasmic localization. Nature 428, 959-963.

Hall, T. A. (1999). BioEdit: a user-friendly biological sequence alignment editor and analysis program for Windows 95/98/NT. Nucl. Acids. Symp. Ser. 41, 95-98

Hammond, L. E., Rudner, D. Z., Kanaar, R., and R10, D.C. (1997). Mutations in the hrp48 gene, which encodes a *Drosophila* heterogeneous nuclear ribonucleoprotein particle protein, cause lethality and developmental defects and affect P-element third-intron splicing in vivo. Mol. Cell. Biol. 17, 7260-7267.

Hasler, J. & Strub, K. Alu elements as regulators of gene expression. Nucleic Acids Res. 34, 5491-5497 (2006).

Hentze, M. W., and Kulozik, A. E. (1999). A perfect message: RNA surveillance and nonsense-mediated decay. Cell 96, 307-310.

Hillman R T et al., 2004 An unappreciated role for RNA surveillance. Genome Biol. 5:R8.

Hitti, E. G., Sallacz, N. B., Schoft, V. K., and Jantsch, M. F. (2004). Oligomerization activity of a double-stranded RNA-binding domain. FEBS Lett 574, 25-30.

Holm, L., and Rosenstrom, P. (2010). Dali server: conservation mapping in 3D. Nucleic Acids Res. 38, W545-549.

Inoue, K., Khajavi, M., Ohyama, T., Hirabayashi, S., Wilson, J., Reggin, J. D., Mancias, P., Butler, I. J., Wilkinson, M. F., Wegner, M., and Lupski, J. R. (2004). Molecular mechanism for distinct neurological phenotypes conveyed by allelic truncating mutations. Nat. Genet. 36, 361-369.

Ishigaki, Y., L1, X., Serin, G., and Maquat, L. E. (2001). Evidence for a pioneer round of mRNA translation: mRNAs subject to nonsense-mediated decay in mammalian cells are bound by CBP80 and CBP20. *Cell* 106, 607-617.

Izaurralde, E., Lewis, J., McGuigan, C., Jankowska, M., Darzynkiewicz, E., and Mattaj, I. W. (1994). A nuclear cap binding protein complex involved in pre-mRNA splicing. Cell 78, 657-668.

Kapranov, P., Willingham, A. T., & Gingeras, T. R. Genome-wide transcription and the implications for genomic organization. *Nat. Rev. Genet.* 8, 413-423 (2007).

Kataoka, N., Yong, J., Kim, V. N., Velazquez, F., Perkinson, R. A., Wang, F., and Dreyfuss, G. (2000). Pre-mRNA splicing imprints mRNA in the nucleus with a novel RNA-binding protein that persists in the cytoplasm. Mol. Cell. 6, 673-682.

Kiebler, M. A., Hemraj, I., Verkade, P., Kohrmann, M., Fortes, P., Marion, R. M., Ortin, J., and Dotti, C. G. (1999). The mammalian staufen protein localizes to the somatodendritic domain of cultured hippocampal neurons: implications for its involvement in mRNA transport. J. Neurosci. 19, 288-297.

Kim, H. H. et al. HuR recruits let-7/RISC to repress c-Myc expression. Genes Dev. 23, 1743-1748 (2009).

Kim, V. N., Kataoka, N., and Dreyfuss, G. (2001). Role of the nonsense-mediated decay factor hUpf3 in the splicing-dependent exon-exon junction complex. Science 293, 1832-1836.

Kim, Y. K., Lee, S. H., Kim, C. S., Seol, S. K., and Jang, S. K. RNA. (2003). Long-range RNA-RNA interaction between the 5' nontranslated region and the core-coding sequences of hepatitis C virus modulates the IRES-dependent translation. RNA 9, 599-606.

Kim, Y. K. et al. Staufen1 regulates diverse classes of mammalian transcripts. EMBO J. 26, 2670-2681 (2007).

Kim, Y. K., Furic, L., Desgroseillers, L., and Maquat, L. E. (2005). Mammalian Staufen1 recruits Upf1 to specific mRNA 3'UTRs so as to elicit mRNA decay. Cell 120, 195-208.

Kim, Y. K., Furic, L., Parisien, M., Major, F., DesGroseillers, L., and Maquat, L. E. (2007). Staufen1 regulates diverse classes of mammalian transcripts. EMBO J. 26, 2670-2681.

Kim-Ha, J., Kerr, K., and Macdonald, P. M. (1995). Translational regulation of oskar mRNA by bruno, an ovarian RNA-binding protein, is essential. Cell 81, 403-412.

Kim-Ha, J., Smith, J. L., and Macdonald, P. M. (1991). oskar mRNA is localized to the posterior pole of the Drosophila oocyte. Cell 66, 23-35.

Kohrmann, M., Luo, M., Kaether, C., DesGroseillers, L., Dotti, C. G., and Kiebler, M. A. (1999). Microtubule-dependent recruitment of Staufen-green fluorescent protein into large RNA-containing granules and subsequent dendritic transport in living hippocampal neurons. Mol. Biol. Cell 10, 2945-2953.

Krause, S., Fakan, S., Weis, K., and Wahle, E. (1994) Immunodetection of poly(A) binding protein II in the cell nucleus. Exp. Cell Res. 214, 75-82.

Krichevsky, A. M., and Kosik, K. S. (2001). Neuronal RNA granules: a link between RNA localization and stimulation-dependent translation. Neuron 32, 683-696.

Krissinel, E., and Henrick, K. (2007). Inference of macromolecular assemblies from crystalline state. J. Mol. Biol. 372, 774-797.

Kuwano, Y. et al. NF90 selectively represses the translation of target mRNAs bearing an AU-rich signature motif Nucleic Acids Res. 38, 225-238.

Lau, C. K., Diem, M. D., Dreyfuss, G., and Van Duyne, G. D. (2003). Structure of the Y14-Magoh core of the exon junction complex. Curr. Biol. 13, 933-941.

Le Hir, H., Gatfield, D., Izaurralde, E., and Moore, M. J. (2001). The exon-exon junction complex provides a binding platform for factors involved in mRNA export and nonsense-mediated mRNA decay. EMBO J. 20, 4987-4997.

Le Hir, H., Izaurralde, E., Maquat, L. E., and Moore, M. J. (2000a). The spliceosome deposits multiple proteins 20-24 nucleotides upstream of mRNA exon-exon junctions. EMBO J. 19, 6860-6869.

Le Hir, H., Moore, M. J., and Maquat, L. E. (2000b). Pre-mRNA splicing alters mRNP composition: evidence for stable association of proteins at exon-exon junctions. Genes Dev. 14, 1098-1108.

Le, S., Sternglanz, R., and Greider, C. W. (2000). Identification of two RNA-binding proteins associated with human telomerase RNA. Mol. Biol. Cell 11, 999-1010.

Lee, C. M., Haun, R. S., Tsai, S. C., Moss, J., and Vaughan, M. (1992). Characterization of the human gene encoding ADP-ribosylation factor 1, a guanine nucleotide-binding activator of cholera toxin. J. Biol. Chem. 267, 9028-9034.

Lejeune, F., Ishigaki, Y., Li, X., and Maquat, L. E. (2002). The exon junction complex is detected on CBP80-bound but not eIF4E-bound mRNA in mammalian cells: dynamics of mRNP remodeling. EMBO J. 21, 3536-3545.

Lejeune, F., Li, X., and Maquat, L. E. (2003). Nonsense-mediated mRNA decay in mammalian cells involves decapping, deadenylating, and exonucleolytic activities. Mol. Cell. 12, 675-687.

Lesley, S. A., and Wilson, I. A. (2005). Protein production and crystallization at the joint center for structural genomics. J Struct Funct Genomics 6, 71-79.

Li, P., Yang, X., Wasser, M., Cai, Y., and Chia, W. (1997). Inscuteable and Staufen mediate asymmetric localization and segregation of prospero RNA during Drosophila neuroblast cell divisions. Cell 90, 437-447.

Li, S., and Wilkinson, M. F. (1998). Nonsense surveillance in lymphocytes? Immunity 8, 135-141.

Li, W., Simarro, M., Kedersha, N. & Anderson, P. FAST is a survival protein that senses mitochondrial stress and modulates TIA-1-regulated changes in protein expression. Mol. Cell. Biol. 24, 10718-10732 (2004).

Liang, C. C., Park, A. Y., & Guan, J. L. In vitro scratch assay: a convenient and inexpensive method for analysis of cell migration in vitro. Nat. Protoc. 2, 329-333 (2007).

Lieutaud, P., Canard, B., and Longhi, S. (2008). MeDor: a metaserver for predicting protein disorder. BMC Genomics 9 Suppl 2, S25.

Luo, M. L., Zhou, Z., Magni, K., Christoforides, C., Rappsilber, J., Mann, M., and Reed, R. (2001). Pre-mRNA splicing and mRNA export linked by direct interactions between UAP56 and Aly. Nature. 413, 644-647.

Luo, M., Duchaine, T. F., and DesGroseillers, L. (2002). Molecular mapping of the determinants involved in human Staufen-ribosome association. Biochem. J. 365, 817-824.

Lykke-Andersen, J., Shu, M. D., and Steitz, J. A. (2000). Human Upf proteins target an mRNA for nonsense-mediated decay when bound downstream of a termination codon. Cell 103, 1121-1131.

Lykke-Andersen, J., Shu, M. D., and Steitz, J. A. (2001). Communication of the position of exon-exon junctions to the mRNA surveillance machinery by the protein RNPS1. Science 293, 1836-1839.

Macchi, P., Kroening, S., Palacios, I. M., Baldassa, S., Grunewald, B., Ambrosino, C., Goetze, B., Lupas, A., St Johnston, D., and Kiebler, M. (2003). Barentsz, a new component of the Staufen-containing ribonucleoprotein particles in mammalian cells, interacts with Staufen in an RNA-dependent manner. J. Neurosci. 23, 5778-5788.

Mallardo, M., Deitinghoff, A., Muller, J., Goetze, B., Macchi, P., Peters, C., and Kiebler, M. A. (2003). Isolation and characterization of Staufen-containing ribonucleoprotein particles from rat brain. Proc. Natl. Acad. Sci. USA 100, 2100-2105.

Maquat, L. E. (2004a). Nonsense-mediated mRNA decay: A comparative analysis of different species. Curr. Genomics 5, 175-190.

Maquat, L. E. (2004b). Nonsense-mediated mRNA decay: splicing, translation and mRNP dynamics. Nat. Rev. Mol. Cell. Biol. 5, 89-99.

Maquat, L. E., and Gong, C. (2009). Gene expression networks: competing mRNA decay pathways in mammalian cells. Biochem Soc Trans 37, 1287-1292.

Marchler-Bauer, A., Lu, S., Anderson, J. B., Chitsaz, F., Derbyshire, M. K., DeWeese-Scott, C., Fong, J. H., Geer, L. Y., Geer, R. C., Gonzales, N. R., et al. (2011). CDD: a Conserved Domain Database for the functional annotation of proteins. Nucleic Acids Res. 39, D225-229.

Marion, R. M., Fortes, P., Beloso, A., Dotti, C., and Ortin, J. (1999). A human sequence homologue of Staufen is an RNA-binding protein that is associated with polysomes and localizes to the rough endoplasmic reticulum. Mol. Cell. Biol. 19, 2212-2219.

Martel, C., Dugre-Brisson, S., Boulay, K., Breton, B., Lapointe, G., Armando, S., Trepanier, V., Duchaine, T., Bouvier, M., and Desgroseillers, L. (2010). Multimerization of Staufen1 in live cells. RNA 16, 585-597.

Mathews, D. H., Sabina, J., Zuker, M., & Turner, D. H. Expanded sequence dependence of thermodynamic parameters improves prediction of RNA secondary structure. J. Mol. Biol. 288, 911-940 (1999).

Matsuzaki, F., Ohshiro, T., Ikeshima-Kataoka, H., and Izumi, H. (1998). miranda localizes staufen and prospero asymmetrically in mitotic neuroblasts and epithelial cells in early Drosophila embryogenesis. Development 125, 4089-4098.

McCoy, A. J., Grosse-Kunstleve, R. W., Adams, P. D., Winn, M. D., Storoni, L. C., and Read, R. J. (2007). Phaser crystallographic software. J Appl Crystallogr 40, 658-674.

Mendell, J. T., Sharifi, N. A., Meyers, J. L., Martinez-Murillo, F. & Dietz, H. C. Nonsense surveillance regulates expression of diverse classes of mammalian transcripts and mutes genomic noise. Nat. Genet. 36, 1073-1078 (2004).

Micklem, D. R., Adams, J., Grunert, S., and St Johnston, D. (2000). Distinct roles of two conserved Staufen domains in oskar mRNA localization and translation. EMBO J. 19, 1366-1377.

Miki, T., Takano, K., and Yoneda, Y. (2005). The role of mammalian Staufen on mRNA traffic: a view from its nucleocytoplasmic shuttling function. Cell Struct. Funct. 30, 51-56.

Mohr, S. E., Dillon, S. T., and Boswell, R. E. (2001). The RNA-binding protein Tsunagi interacts with Mago Nashi to establish polarity and localize oskar mRNA during Drosophila oogenesis. Genes Dev. 15, 2886-2899.

Monshausen, M., Putz, U., Rehbein, M., Schweizer, M., Des-Groseillers, L., Kuhl, D., Richter, D., and Kindler, S. (2001). Two rat brain staufen isoforms differentially bind RNA. J. Neurochem. 76, 155-165.

Moriarty, P. M., Reddy, C. C., and Maquat, L. E. (1998). Selenium deficiency reduces the abundance of mRNA for Se-dependent glutathione peroxidase 1 by a UGA-dependent mechanism likely to be nonsense codon-mediated decay of cytoplasmic mRNA. Mol. Cell. Biol. 18, 2932-2939.

Mouland, A. J., Mercier, J., Luo, M., Bernier, L., Des-Groseillers, L., and Cohen, E. A. (2000). The double-stranded RNA-binding protein Staufen is incorporated in human immunodeficiency virus type 1: evidence for a role in genomic RNA encapsidation. J. Virol. 74, 5441-5451.

Nagy, E., and Maquat, L. E. (1998). A rule for termination-codon position within intron-containing genes: when nonsense affects RNA abundance. Trends Biochem. Sci. 23, 198-199.

Ohashi, S., Koike, K., Omori, A., Ichinose, S., Ohara, S., Kobayashi, S., Sato, T. A., and Anzai, K. (2002). Identification of mRNA/protein (mRNP) complexes containing Puralpha, mStaufen, fragile X protein, and myosin Va and their association with rough endoplasmic reticulum equipped with a kinesin motor. J. Biol. Chem. 277, 37804-37810.

Otwinowski, Z., Minor, W. (1997). Processing of X-ray Diffraction Data Collected in Oscillation Mode. Method. Enzymol. 276, 307-326.

Pal, M., Ishigaki, Y., Nagy, E., and Maquat, L. E. (2001). Evidence that phosphorylation of human Upf1 protein varies with intracellular location and is mediated by a wortmannin-sensitive and rapamycin-sensitive PI 3-kinase-related kinase signaling pathway. RNA 7, 5-15.

Palacios, I. M., Gatfield, D., St Johnston, D., and Izaurralde, E. (2004). An eIF4AIII-containing complex required for mRNA localization and nonsense-mediated mRNA decay. Nature 427, 753-757.

Pang, K. C. et al. RNAdb 2.0—an expanded database of mammalian non-coding RNAs. Nucleic Acids Res. 35, D178-182 (2007).

Papworth, C., Bauer, J. C., Braman, J., and Wright, D. A. (1996). Site directed mutagenesis in one day with >80% efficiency. Strategies 3, 3-4.

Parker, G. S., Maity, T. S., and Bass, B. L. (2008). dsRNA binding properties of RDE-4 and TRBP reflect their distinct roles in RNAi. J. Mol. Biol. 384, 967-979.

Peng, S. S., Chen, C. Y. & Shyu, A. B. Functional characterization of a non-AUUUA AU-rich element from the c-jun proto-oncogene mRNA: evidence for a novel class of AU-rich elements. Mol. Cell. Biol. 16, 1490-1499 (1996).

Philo, J. S. (2000). A method for directly fitting the time derivative of sedimentation velocity data and an alternative algorithm for calculating sedimentation coefficient distribution functions. Anal Biochem 279, 151-163.

Philo, J. S. (2006). Improved methods for fitting sedimentation coefficient distributions derived by time-derivative techniques. Anal Biochem 354, 238-246.

Piecyk, M. et al. TIA-1 is a translational silencer that selectively regulates the expression of TNF-alpha. EMBO J. 19, 4154-4163 (2000).

Providence, K. M. et al. SERPINE1 (PAI-1) is deposited into keratinocyte migration "trails" and required for optimal monolayer wound repair. Arch. Dermatol. Res. 300, 303-310 (2008).

Ramos, A., Grunert, S., Adams, J., Micklem, D. R., Proctor, M. R., Freund, S., Bycroft, M., St Johnston, D., and Varani, G. (2000). RNA recognition by a Staufen double-stranded RNA-binding domain. EMBO J. 19, 997-1009.

Roy, A., Kucukural, A., and Zhang, Y. (2010). I-TASSER: a unified platform for automated protein structure and function prediction. Nat. Protoc. 5, 725-738.

Ryter, J. M., and Schultz, S. C. (1998). Molecular basis of double-stranded RNA-protein interactions: structure of a dsRNA-binding domain complexed with dsRNA. EMBO J. 17, 7505-7513.

Schuck, P. (2000). Size-distribution analysis of macromolecules by sedimentation velocity ultracentrifugation and lamm equation modeling. Biophys J 78, 1606-1619.

Schuldt, A. J., Adams, J. H., Davidson, C. M., Micklem, D. R., Haseloff, J., St Johnston, D., and Brand, A. H. (1998). Miranda mediates asymmetric protein and RNA localization in the developing nervous system. Genes Dev. 12, 1847-1857.

Serin, G., Gersappe, A., Black, J. D., Aronoff, R., and Maquat, L. E. (2001). Identification and characterization of human orthologues to Saccharomyces cerevisiae Upf2 protein and Upf3 protein (Caenorhabditis elegans SMG-4). Mol. Cell. Biol. 21, 209-223.

Shcherbo, D., Merzlyak, E. M., Chepurnykh, T. V., Fradkov, A. F., Ermakova, G. V., Solovieva, E. A., Lukyanov, K. A., Bogdanova, E. A., Zaraisky, A. G., Lukyanov, S., and Chudakov, D. M. (2007). Bright far-red fluorescent protein for whole-body imaging. Nat Methods 4, 741-746.

Shen, C. P., Knoblich, J. A., Chan, Y. M., Jiang, M. M., Jan, L. Y., and Jan, Y. N. (1998). Miranda as a multidomain adapter linking apically localized Inscuteable and basally localized Staufen and Prospero during asymmetric cell division in Drosophila. Genes Dev. 12, 1837-1846.

Shetty, S. & Idell, S. Posttranscriptional regulation of plasminogen activator inhibitor-1 in human lung carcinoma cells in vitro. Am. J. Physiol. Lung Cell Mol. Physiol. 278, L148-156 (2000).

Shibuya, T., Tange, T. O., Sonenberg, N., and Moore, M. J. (2004). eIF4AIII binds spliced mRNA in the exon junction complex and is essential for nonsense-mediated decay. Nat. Struct. Mol. Biol. 11, 346-351.

Siebel, C. W., Kanaar, R., and R10, D. C. (1994). Regulation of tissue-specific P-element pre-mRNA splicing requires the RNA-binding protein PSI. Genes Dev 8, 1713-1725.

Slabinski, L., Jaroszewski, L., Rychlewski, L., Wilson, I. A., Lesley, S. A., and Godzik, A. (2007). XtalPred: a web server for prediction of protein crystallizability. Bioinformatics 23, 3403-3405.

St Johnston, D. (1995). The intracellular localization of messenger RNAs. Cell 81, 161-170.

St Johnston, D., Beuchle, D., and Nusslein-Volhard, C. (1991). Staufen, a gene required to localize maternal RNAs in the *Drosophila* egg. Cell 66, 51-63.

St Johnston, D., Brown, N. H., Gall, J. G., and Jantsch, M. (1992). A conserved double-stranded RNA-binding domain. Proc. Natl. Acad. Sci. USA 89, 10979-10983.

Stafford, W. F., and Sherwood, P. J. (2004). Analysis of heterologous interacting systems by sedimentation velocity: curve fitting algorithms for estimation of sedimentation coefficients, equilibrium and kinetic constants. Biophys Chem 108, 231-243.

Stefl, R., Oberstrass, F. C., Hood, J. L., Jourdan, M., Zimmermann, M., Skrisovska, L., Maris, C., Peng, L., Hofr, C., Emeson, R. B., and Allain, F. H. (2010). The solution structure of the ADAR2 dsRBM-RNA complex reveals a sequence-specific readout of the minor groove. Cell 143, 225-237.

Sun, X., Perlick, H. A., Dietz, H. C., and Maquat, L. E. (1998). A mutated human homologue to yeast Upf1 protein has a dominant-negative effect on the decay of nonsense-containing mRNAs in mammalian cells. Proc. Natl. Acad. Sci. USA 95, 10009-10014.

Tange, T. O., Nott, A. & Moore, M. J. The ever-increasing complexities of the exon junction complex. *Curr. Opin. Cell Biol.* 16, 279-284 (2004).

Terwilliger, T. C. (2000). Maximum-likelihood density modification. Acta Crystallogr. D. Biol. Crystallogr. 56, 965-972.

Terwilliger, T. C., Grosse-Kunstleve, R. W., Afonine, P. V., Moriarty, N. W., Zwart, P. H., Hung, L. W., Read, R. J., and Adams, P. D. (2008). Iterative model building, structure refinement and density modification with the PHENIX AutoBuild wizard. Acta Crystallogr. D. Biol. Crystallogr. 64, 61-69.

Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res. 22, 4673-4680.

Tian, B., Bevilacqua, P. C., Diegelman-Parente, A., and Mathews, M. B. (2004). The double-stranded-RNA-binding motif: interference and much more. Nat. Rev. Mol. Cell. Biol. 5, 1013-1023.

Valente, L., and Nishikura, K. (2007). RNA binding-independent dimerization of adenosine deaminases acting on RNA and dominant negative effects of nonfunctional subunits on dimer functions. J Biol Chem 282, 16054-16061.

van Eeden, F. J., Palacios, I. M., Petronczki, M., Weston, M. J., and St Johnston, D. (2001). Barentsz is essential for the posterior localization of oskar mRNA and colocalizes with it to the posterior pole. J. Cell. Biol. 154, 511-523.

Villace, P., Marion, R. M., and Ortin, J. (2004). The composition of Staufen-containing RNA granules from human cells indicates their role in the regulated transport and translation of messenger RNAs. Nucleic Acids Res. 32, 2411-2420.

Walters, R. D., Kugel, J. F., & Goodrich, J. A. InvAluable junk: the cellular impact and function of Alu and B2 RNAs. *IUBMB Life* 61, 831-837 (2009).

Wang, Z., Jiao, X., Carr-Schmid, A. & Kiledjian, M. The hDcp2 protein is a mammalian mRNA decapping enzyme. *Proc. Natl. Acad. Sci. USA* 99, 12663-12668 (2002).

Wickham, L., Duchaine, T., Luo, M., Nabi, I. R., and Des-Groseillers, L. (1999). Mammalian staufen is a double-stranded-RNA- and tubulin-binding protein which localizes to the rough endoplasmic reticulum. Mol. Cell. Biol. 19, 2220-2230.

Wilusz, C. J., Wang, W., and Peltz, S. W. (2001). Curbing the nonsense: the activation and regulation of mRNA surveillance. Genes Dev. 15, 2781-2785.

Wilusz, J. E., Sunwoo, H., & Spector, D. L. Long noncoding RNAs: functional surprises from the RNA world. *Genes Dev.* 23, 1494-1504 (2009).

Wodicka, L., Dong, H., Mittmann, M., Ho, M. H., and Lockhart, D. J. (1997). Genome-wide expression monitoring in *Saccharomyces cerevisiae*. Nat. Biotechnol. 15, 1359-1367.

Xia, T. et al. Thermodynamic parameters for an expanded nearest-neighbor model for formation of RNA duplexes with Watson-Crick base pairs. *Biochemistry* 37, 14719-14735 (1998).

Yamashita, S., Nagata, T., Kawazoe, M., Takemoto, C., Kigawa, T., Guntert, P., Kobayashi, N., Terada, T., Shirouzu, M., Wakiyama, M., et al. Structures of the first and second double-stranded RNA-binding domains of human TAR RNA-binding protein. Protein Sci. 20, 118-130.

Yang, S. W., Chen, H. Y., Yang, J., Machida, S., Chua, N. H., and Yuan, Y. A. (2010). Structure of *Arabidopsis* HYPONASTIC LEAVES1 and its molecular implications for miRNA processing. Structure 18, 594-605.

Yulug, I. G., Yulug, A., & Fisher, E. M. The frequency and position of Alu repeats in cDNAs, as determined by database searching. *Genomics* 27, 544-548 (1995).

Zhang, J. et al. RCP is a human breast cancer-promoting gene with Ras-activating function. *J. Clin. Invest.* 119, 2171-2183 (2009).

Zhang, J., Sun, X., Qian, Y., and Maquat, L. E. (1998). Intron function in the nonsense-mediated decay of beta-globin mRNA: indications that pre-mRNA splicing in the nucleus can influence mRNA translation in the cytoplasm. RNA 4, 801-815.

Zuker, M. Mfold web server for nucleic acid folding and hybridization prediction. Nucleic Acids Res. 31, 3406-3415 (2003).

```
Staufen1 (Stau1) (Genbank No: BC050432) nucleotide sequence
                                                           SEQ ID NO: 1
  1 aaccacttaa cctctcagaa ctgaacaaag acaacattgt tcctggaacg ccctcttttt 61 aaaaaaggt  agaactttag acttcatagc actgaattaa cctgcactga aagctgttta 121 cctgcatttg ttcacttttg ttgaaagtga ccatgtctca agttcaagtg caagttcaga 181 acccatctgc tgctctctca gggagccaaa tactgaacaa gaaccagtct cttctctcac 241 agcctttgat gagtattcct tctactacta gctctctgcc ctctgaaaat gcaggtagac 301 ccattcaaan ctctgcttta ccctctgcat ctattacatc caccagtgca gctgcagaaa 361 gcataacccc tactgtagaa ctaaatgcac tgtgcatgaa acttggaaaa aaaccaatgt 421 ataagcctgt tgacccttac tctcggatgc agtccaccta taactacaac atgagaggag 481 gtgcttatcc cccgaggtac ttttacccat ttccagttcc acctttactt tatcaagtgg
```

```
541 aactttctgt gggaggacag caatttaatg gcaaaggaaa gacaagacag gctgcgaaac 601 acgatgctgc tgccaaagcg ttgaggatcc tgcagaatga gccctgcca gagaggctgg 661 aggtgaatgg aagagaatcc gaagaagaaa atctcaataa atctgaaata agtcaagtgt 721 ttgagattgc acttaaacgg aacttgcctg tgaatttcga ggtggccgg gagagtggcc 781 caccccacat gaagaacttt gtgaccaagg tttcggttgg ggagtttgtg ggggaaggtg 841 aagggaaaag caagaagatt tcaaagaaaa atgccgccat agctgttctt gaggagctga 901 agaagttacc gccctgcct gcagttgaac gagtaaagcc tagaatcaaa agaaaacaa 961 aacccatagt caagccacag acaagcccag aatatggcca ggggatcaat ccgattagcc 1021 gactggccca gatccagcag gcaaaaaagg agaaggagcc agagtacacg ctcctcacag 1081 agcgaggcct cccgcgccgc agggagtttg tgatgcaggt gaaggttgga aaccacactg 1141 cagaaggaac gggcaccaac aagaaggtgg ccaagcgcaa tgcagccgag aacatgctgg 1201 agatccttgg tttcaaagtc ccgcaggcgc agcccaccaa acccgcactc aagtcagagg 1261 agaagacacc cataaagaaa ccaggggatg aagaaaagt aaccttttt gaacctggct 1321 ctggggatga aaatgggact agtaataaag aggatgagtt caggatgcct tatctaagtc 1381 atcagcagct gcctgctgga attcttccca tggtgcccga ggtcgcccag gctgtaggag 1441 ttagtcaagg acatcacacc aaagatttta ccagggcagc tccgaatcct gccaaggcca 1501 cggtaactgc catgatagcc cgagagttgt tgtatggggg cacctcgccc acagccgaga 1561 ccatttaa gaataacatc tcttcaggcc acgtacccca tggacctctc acgagaccct 1621 ctgagcaact ggactatctt tccagagtcc agggattcca ggttgaatac aaagacttcc 1681 ccaaaaacaa caagaacgaa tttgtatctc ttatcaattg ctcctctcag ccacctctga 1741 tcagccatgg tatcggcaag gatgtggagt cctgccatga tatggctgcg ctgaacatct 1801 taaagttgct gtctgagttg gaccaacaaa gtacagagat gccaagaaca ggaaacggac 1861 caatgtctgt gtgtgggagg tgctgaacct tttctggcca tgaaccatta taaaatccca 1921 acatatatac tgaaaatact gaaactgctt tgaaaatttg gaatttctga tacctccagt 1981 gggccgagag acacggtggg taaggatgt gggcagcagc agggaagaca acagaaacac 2041 aaggaggcgg ctgtggccgg gctggactgt gcgggggttt gttgtgatgg ccactcggtg 2101 acctggcggt ccctacgcaa tagcagctgc ctgtggggaa gaggggctgc ccagccagct 2161 ggttctcccg ggacaccagc agatccacac cctgggcacc tccgtgtttg gtcttttttt 2221 tcccctgtgt gaaagaagaa acggcacgac cccttctcaa gctggctcac tcagacacat 2281 tgggacaaac cctggacagc catgccagag agaggccttt gaccggcccc agagctaaaa 2341 gcaccagaga aaatcaaatg cttcctactc agcgtgaccc aacttttcta gtgtgccacg 2401 gcccccaccac ctcctgcagt acccacacca tcaccactgc tttctcttcc aacagtgatc 2461 tgtattctta gtttcattat tttctttga ttgatatgac actatataaa at-ft-Want 2521 gagaatttct caattgtatc tagttaaata gcacagtttg gaaacttgtc tgagactgac 2581 tttatcaata atctaaccga caaagatcat atccatgtgt atgtggttag acatttttat 2641 ttcattgact aacccaggac agtttcagtg atgcaaattg tgtgccctct ggttcagctg 2701 aaacagtcct ggactttcaa aaaccttgaa taagtctccc acagttgtat aaattggaca 2761 atttaggaat tttaaacttt agatgatcat ttggttccat ttttatttca ttttattttt 2821 tgttaatgca aacaggactt aaatgaactt tgatctctgt tttaaagatt attaaaaaac 2881 attgtgtatc tatacatatg gctcttgagg acttagatt cactacacta caggatatga
```

-continued

```
2941 tctccatgta gtccatataa acctgcagag tgattttcca gagtgctcga tactgttaat 3001 tacatctcca ttagggctga aaagaatgac ctacgtttct gtatacagct gtgttgatt 3061 tgatgttgtg ttactgtaca cagaagtgtg tgcactgagg ctctgcgtgt ggtccgtatg 3121 gaaagcctgg tagccctgcg agttaagtac tgcttccatt cattgtttac gctgaatt 3181 ttctccccat ggaatgtaag taaaacttaa gtgtttgtca tcaataaatg gtaatactaa 3241 aaaaaaaaa aaa
```

Staufen1 (Stau1) (Genbank No: BC050432) amino acid sequence
SEQ ID NO: 2

MSQVQVQVQNPSAALSGSQILNKNQSLLSQPLMSIPSTTSSLPSENAGRPIQNSALPSASITSTS

AAAESITPTVELNALCMKLGKKPMYKPVDPYSRMQSTYNYNMRGGAYPPRYFYPFPVPPLL

YQVELSVGGQQFNGKGKTRQAAKHDAAAKALRILQNEPLPERLEVNGRESEEENLNKSEISQ

VFEIALKRNLPVNFEVARESGPPHMKNFVTKVSVGEFVGEGEGKSKKISKKNAAIAVLEELKK

LPPLPAVERVKPRIKKKTKPIVKPQTSPEYGQGINPISRLAQIQQAKKEKEPEYTLLTERGLPRR

REFVMQVKVGNHTAEGTGTNKKVAKRNAAENMLEILGFKVPQAQPTKPALKSEEKTPIKKP

GDGRKVTFFEPGSGDENGTSNKEDEFRMPYLSHQQLPAGILPMVPEVAQAVGVSQGHHTKD

FTRAAPNPAKATVTAMIARELLYGGTSPTAETILKNNISSGHVPHGPLTRPSEQLDYLSRVQGF

QVEYKDFPKNNKNEFVSLINCSSQPPLISHGIGKDVESCHDMAALNILKLLSELDQQSTEMPRT

GNGPMSVCGRC

ALU element consensus sequence
SEQ ID NO: 3

GCCGGGCGCGGTGGCTCACGCCTGTAATCCCAGCACTTTGGGAGGCCGAGGCGGGCGG

ATCACCTGAGGTCAGGAGTTCGAGACCAGCCTGGCCAACATGGTGAAACCCCGTCTCTA

CTAAAAATACAAAAATTAGCCGGGCGTGGTGGCGCGCGCCTGTAATCCCAGCTACTCGG

GAGGCTGAGGCAGGAGAATCGCTTGAACCCGGGAGGCGGAGGTTGCAGTGAGCCGAGA

TCGCGCCACTGCACTCCAGCCTGGGCGACAGAGCGAGACTCCGTCTCAAAAAAA

---

What is claimed is:

1. A method of screening for an agent that modulates SMD comprising
   i. incubating the agent with a stably transfected cell comprising a reporter gene with a 3' UTR ALU element; a lncRNA comprising a ALU element that base pairs with the ALU element in the mRNA of the reporter gene; and Stau1, and
   ii. assaying the amount of mRNA of the reporter gene in the cell, wherein an increase or decrease in the amount of mRNA of the reporter gene relative to the amount of mRNA of the reporter gene in the absence of the agent indicates a substance that modulates SMD activity.

2. The method of claim 1, wherein the Stau1 has at least 80% identity to the sequence set forth in SEQ ID NO: 1, or a fragment thereof.

3. The method of claim 1, wherein the reporter gene with a 3' UTR ALU element comprises at least one ALU element in its 3' UTR.

4. The method of claim 3, wherein the ALU element has at least 50% identity to the consensus ALU element set forth in SEQ ID NO: 3.

* * * * *